US011851471B2

(12) United States Patent
Seidel, III et al.

(10) Patent No.: US 11,851,471 B2
(45) Date of Patent: Dec. 26, 2023

(54) T-CELL MODULATORY MULTIMERIC POLYPEPTIDES AND METHODS OF USE THEREOF

(71) Applicant: Cue Biopharma, Inc., Cambridge, MA (US)

(72) Inventors: Ronald D. Seidel, III, Cambridge, MA (US); Rodolfo Chaparro, Cambridge, MA (US)

(73) Assignee: Cue Biopharma, Inc., Boston, MA (US)

(*) Notice: Subject to any disclaimer, the term of this patent is extended or adjusted under 35 U.S.C. 154(b) by 970 days.

(21) Appl. No.: 16/473,576

(22) PCT Filed: Jan. 8, 2018

(86) PCT No.: PCT/US2018/012830

§ 371 (c)(1),
(2) Date: Jun. 25, 2019

(87) PCT Pub. No.: WO2018/129474

PCT Pub. Date: Jul. 12, 2018

(65) Prior Publication Data

US 2020/0140519 A1 May 7, 2020

Related U.S. Application Data

(60) Provisional application No. 62/444,095, filed on Jan. 9, 2017.

(51) Int. Cl.

| | |
|---|---|
| ***C07K 14/705*** | (2006.01) |
| ***C07K 14/74*** | (2006.01) |
| ***A61K 39/00*** | (2006.01) |
| ***A61K 39/395*** | (2006.01) |
| ***A61K 35/17*** | (2015.01) |
| ***C12N 5/0783*** | (2010.01) |

(52) U.S. Cl.

CPC .. *C07K 14/70532* (2013.01); *A61K 39/00111* (2018.08); *A61K 39/39558* (2013.01); *C07K 14/70503* (2013.01); *C07K 14/70539* (2013.01); *C07K 14/70553* (2013.01); *A61K 35/17* (2013.01); *C07K 14/70596* (2013.01); *C07K 2317/31* (2013.01); *C07K 2317/40* (2013.01); *C07K 2317/52* (2013.01); *C07K 2317/73* (2013.01); *C07K 2319/30* (2013.01); *C12N 5/0636* (2013.01); *C12N 2501/51* (2013.01); *C12N 2501/585* (2013.01); *C12N 2510/00* (2013.01)

(58) Field of Classification Search

CPC ........ C07K 14/70532; C07K 14/70503; A61K 39/00111; A61K 39/39558

See application file for complete search history.

(56) References Cited

U.S. PATENT DOCUMENTS

| | | | |
|---|---|---|---|
| 5,635,363 | A | 6/1997 | Altman et al. |
| 6,197,302 | B1 | 3/2001 | Hirsch et al. |
| 6,211,342 | B1 | 4/2001 | Hirsch et al. |
| 6,268,411 | B1 | 7/2001 | Schneck et al. |
| 6,322,789 | B1 | 11/2001 | Vitiello et al. |
| 6,600,012 | B1 | 7/2003 | Agrawal et al. |
| 6,696,304 | B1 | 2/2004 | Parker |
| 7,098,306 | B2 | 8/2006 | Economou et al. |
| 7,186,804 | B2 | 3/2007 | Gillies et al. |
| 7,432,351 | B1 | 10/2008 | Chen |
| 7,670,595 | B2 | 3/2010 | Gillies et al. |
| 8,992,937 | B2 | 3/2015 | Hansen et al. |
| 9,284,349 | B2 | 3/2016 | Tsunoda et al. |
| 9,359,424 | B2 | 6/2016 | Maoult et al. |
| 9,494,588 | B2 | 11/2016 | Springer et al. |
| 10,272,042 | B2 | 4/2019 | Daftarian et al. |
| 10,501,521 | B2 | 12/2019 | Georges et al. |

(Continued)

FOREIGN PATENT DOCUMENTS

| | | |
|---|---|---|
| CN | 1791675 | 6/2006 |
| CN | 101384621 | 3/2009 |

(Continued)

OTHER PUBLICATIONS

Accession No. 1 IRL_A chain A Interleukin-2; 1 page (Aug. 25, 1995).
Huang, et al.; "Bone regeneration in a rat cranial defect with delivery of PEI-condensed plasmid DNA encoding for bone morphogenetic protein-4 (BMP-4)"; Gene Therapy; vol. 12, No. 5, p. 418 (2005).
Stamper, et al.; "Crystal structure of the B7-1/CTLA-4 complex that inhibits human immune responses"; Nature; vol. 410, pp. 608-611 (Mar. 29, 2001).
Tham, et al.; "Activation of antigen-specific T cells by artificial cell constructs having immobilized multimeric peptide-class I complexes and recombinant B7-Fc proteins"; Journal of Immunological Methods; vol. 249, pp. 111-119 (2001).

(Continued)

*Primary Examiner* — Peter J Reddig
*Assistant Examiner* — Cheng Lu
(74) *Attorney, Agent, or Firm* — BOZICEVIC FIELD & FRANCIS, LLP; Paula A. Borden

(57) ABSTRACT

The present disclosure provides variant immunomodulatory polypeptides, and fusion polypeptides comprising the variant immunomodulatory peptides. The present disclosure provides T-cell modulatory multimeric polypeptides, and compositions comprising same, where the T-cell modulatory multimeric polypeptides comprise a variant immunomodulatory polypeptide of the present disclosure. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

22 Claims, 33 Drawing Sheets

Specification includes a Sequence Listing.

(56) References Cited

U.S. PATENT DOCUMENTS

| | | | |
|---|---|---|---|
| 10,927,158 | B2 | 2/2021 | Seidel et al. |
| 10,927,161 | B2 | 2/2021 | Seidel et al. |
| 11,117,945 | B2 | 9/2021 | Seidel et al. |
| 11,370,821 | B2 | 6/2022 | Seidel et al. |
| 11,377,478 | B2 | 7/2022 | Seidel et al. |
| 11,380,821 | B2 | 7/2022 | Jia et al. |
| 11,479,595 | B2 | 10/2022 | Seidel et al. |
| 2002/0006664 | A1 | 1/2002 | Sabatini |
| 2002/0031520 | A1 | 3/2002 | Economou et al. |
| 2004/0038349 | A1 | 2/2004 | Hilbert et al. |
| 2004/0132977 | A1 | 7/2004 | Gantier et al. |
| 2004/0161817 | A1 | 8/2004 | Benton et al. |
| 2004/0209363 | A1 | 10/2004 | Watts et al. |
| 2005/0003431 | A1 | 1/2005 | Wucherpfennig et al. |
| 2005/0009012 | A1 | 1/2005 | Holzberg et al. |
| 2005/0100926 | A1 | 5/2005 | Hedley et al. |
| 2005/0142142 | A1 | 6/2005 | Burrows et al. |
| 2006/0034865 | A1 | 2/2006 | Hildebrand et al. |
| 2006/0269515 | A1 | 11/2006 | Deniz-Mize et al. |
| 2007/0036752 | A1 | 2/2007 | Gillies et al. |
| 2007/0148162 | A1 | 6/2007 | Bhardwaj et al. |
| 2007/0286843 | A1 | 12/2007 | Pfizenmaier et al. |
| 2008/0199485 | A1 | 8/2008 | Kundig et al. |
| 2008/0219947 | A1 | 9/2008 | Linette et al. |
| 2008/0269070 | A1 | 10/2008 | Ramseier et al. |
| 2010/0159594 | A1 | 6/2010 | Hansen et al. |
| 2010/0190720 | A1 | 7/2010 | Hollingsworth et al. |
| 2010/0226854 | A1 | 9/2010 | Schøller et al. |
| 2011/0002956 | A1 | 1/2011 | Weiner et al. |
| 2011/0268737 | A1 | 11/2011 | Favier et al. |
| 2011/0318380 | A1 | 12/2011 | Brix et al. |
| 2012/0003220 | A1 | 1/2012 | Chen |
| 2012/0121577 | A1 | 5/2012 | Weidanz et al. |
| 2012/0177595 | A1 | 7/2012 | Wong et al. |
| 2012/0264161 | A1 | 10/2012 | Scholler et al. |
| 2013/0017199 | A1 | 1/2013 | Langermann |
| 2013/0149305 | A1 | 6/2013 | Ostrand-Rosenberg |
| 2014/0046026 | A1 | 2/2014 | Garcia et al. |
| 2014/0162293 | A1 | 6/2014 | Springer et al. |
| 2014/0242077 | A1 | 8/2014 | Choi et al. |
| 2015/0071987 | A1 | 3/2015 | Selvaraj |
| 2015/0224186 | A1 | 8/2015 | Nakagawa |
| 2015/0232532 | A1 | 8/2015 | Ostrand-Rosenberg |
| 2015/0374788 | A1 | 12/2015 | Paulsen et al. |
| 2016/0011204 | A1 | 1/2016 | Almo et al. |
| 2016/0083477 | A1 | 3/2016 | Klein et al. |
| 2016/0090407 | A1 | 3/2016 | Hosse et al. |
| 2016/0114019 | A1 | 4/2016 | Li et al. |
| 2016/0152725 | A1 | 6/2016 | Cheung et al. |
| 2016/0175397 | A1 | 6/2016 | Umana et al. |
| 2016/0304580 | A1 | 10/2016 | Ellmark et al. |
| 2016/0362465 | A1 | 12/2016 | Nishimura et al. |
| 2017/0044229 | A1 | 2/2017 | Garcia et al. |
| 2017/0058015 | A1 | 3/2017 | Seidel, III et al. |
| 2017/0334951 | A1 | 11/2017 | O'Reilly et al. |
| 2018/0064795 | A1 | 3/2018 | Sugiyama |
| 2018/0086832 | A1 | 3/2018 | Vogelstein et al. |
| 2018/0127481 | A1 | 5/2018 | Santamaria |
| 2018/0208626 | A1 | 7/2018 | Scheinberg et al. |
| 2018/0282392 | A1 | 10/2018 | Seidel, III et al. |
| 2018/0339030 | A1 | 11/2018 | Scheinberg |
| 2019/0119377 | A1 | 4/2019 | Spirig et al. |
| 2021/0284709 | A1 | 9/2021 | Brandt et al. |
| 2022/0162314 | A1 | 5/2022 | Asher |
| 2022/0251202 | A1 | 8/2022 | Asher |
| 2023/0126199 | A1 | 4/2023 | Hanayama et al. |

FOREIGN PATENT DOCUMENTS

| | | |
|---|---|---|
| CN | 101418309 | 4/2009 |
| CN | 101448951 | 6/2009 |
| CN | 101688213 | 3/2010 |
| CN | 105121715 | 12/2015 |
| CN | 108431022 | 11/2016 |
| EP | 3596118 | 1/2020 |
| JP | 2000515363 | 11/2000 |
| JP | 2004501364 | 1/2004 |
| JP | 2005506058 | 3/2005 |
| JP | 2007530021 | 11/2007 |
| JP | 2009537175 | 10/2009 |
| JP | 2010524506 | 7/2010 |
| JP | 2012516854 | 7/2012 |
| JP | 2015537043 | 12/2015 |
| WO | WO 1997/028191 | 8/1997 |
| WO | WO 2001/090747 | 11/2001 |
| WO | WO 2002/072631 | 9/2002 |
| WO | WO 2002/087613 | 11/2002 |
| WO | WO 2002/093129 | 11/2002 |
| WO | WO 2002/102299 | 12/2002 |
| WO | WO 2003/048334 | 6/2003 |
| WO | WO 2004/029197 | 4/2004 |
| WO | WO 2004/111190 | 12/2004 |
| WO | WO 2007/136778 | 11/2007 |
| WO | WO 2008/019888 | 2/2008 |
| WO | WO 2008/113970 | 9/2008 |
| WO | WO 2008/116468 | 10/2008 |
| WO | WO 2008/134461 | 11/2008 |
| WO | WO 2009/023270 | 2/2009 |
| WO | WO 2010/037395 | 4/2010 |
| WO | WO 2010/085495 | 7/2010 |
| WO | WO 2010/091122 | 8/2010 |
| WO | WO 2011/066342 | 6/2011 |
| WO | WO 2011/066389 | 6/2011 |
| WO | WO 2012/007951 | 1/2012 |
| WO | WO 2012/127464 | 9/2012 |
| WO | WO 2012/175508 | 12/2012 |
| WO | WO 2013/003761 | 1/2013 |
| WO | WO 2013/079174 | 6/2013 |
| WO | WO 2014/083004 | 6/2014 |
| WO | WO 2014/093118 | 6/2014 |
| WO | WO 2014/145806 | 9/2014 |
| WO | WO 2015/007903 | 1/2015 |
| WO | WO 2015/112541 | 7/2015 |
| WO | WO 2015/164815 | 10/2015 |
| WO | WO 2015/195531 | 12/2015 |
| WO | WO 2016/000619 | 1/2016 |
| WO | WO 2016/014428 | 1/2016 |
| WO | WO 2016/025642 | 2/2016 |
| WO | WO 2016/029043 | 2/2016 |
| WO | WO 2016/030350 | 3/2016 |
| WO | WO 2016/141357 | 9/2016 |
| WO | WO 2016/164937 | 10/2016 |
| WO | WO 2016/168771 | 10/2016 |
| WO | WO 2016/198932 | 12/2016 |
| WO | WO 2017/008844 | 1/2017 |
| WO | WO 2017/023779 | 2/2017 |
| WO | WO 2017/059819 | 4/2017 |
| WO | WO 2017/120222 | 7/2017 |
| WO | WO 2017/151818 | 9/2017 |
| WO | WO 2017/151940 | 9/2017 |
| WO | WO 2017/201131 | 11/2017 |
| WO | WO 2017/201210 | 11/2017 |
| WO | WO 2018/119114 | 6/2018 |
| WO | WO 2018/165631 | 9/2018 |
| WO | WO 2018/170168 | 9/2018 |
| WO | WO 2019/038230 | 2/2019 |
| WO | WO 2019/051091 | 3/2019 |
| WO | WO 2019/051126 | 3/2019 |
| WO | WO 2019/051127 | 3/2019 |
| WO | WO 2019/139896 | 7/2019 |
| WO | WO 2020/243315 | 12/2020 |
| WO | WO 2020/247843 | 12/2020 |
| WO | WO 2020/257191 | 12/2020 |
| WO | WO 2021/081232 | 4/2021 |
| WO | WO 2021/081239 | 4/2021 |
| WO | WO 2021/127495 | 6/2021 |
| WO | WO 2021/172596 | 9/2021 |
| WO | WO 2021/209759 | 10/2021 |
| WO | WO 2022/015880 | 1/2022 |
| WO | WO 2022/087458 | 4/2022 |

(56) References Cited

FOREIGN PATENT DOCUMENTS

| | | |
|---|---|---|
| WO | WO 2022/125694 | 6/2022 |
| WO | WO 2022/125711 | 6/2022 |

OTHER PUBLICATIONS

Collins et al., The Interaction Properties of Costimulatory Molecules Revisited, Immunity, vol. 17, 201-210, Publication Date: Aug. 2002 (Year: 2002).*
Zheng, et al.; "B7-CTLA4 interaction enhances both production of antitumor cytotoxic T lymphocytes and resistance to tumor challenge"; PNAS; vol. 95, pp. 6284-6289 (May 1998).
Buonaguro, et al.; "Translating Tumor Antigens into Cancer Vaccines"; Clinical and Vaccine Immunology; vol. 18, No. 1, pp. 23-24 (Jan. 2011).
Celis, et al.; "Identification of Potential CTL Epitopes of Tumor-Associated Antigen Mage-1 for Five Common HLA-A Alleles"; Molecular Immunology; vol. 31, No. 18, pp. 1423-1430 (1994).
De Charette, et al.; "Turning tumour cells into antigen presenting cells: The next step to improve cancer immunotherapy?"; European Journal of Cancer; vol. 68, pp. 134-147 (2016).
HLA Nomenclature; "HLA Alleles Numbers"; 2 pages (Mar. 17, 2015).
Karin, et al.; "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production"; J. Exp. Med.; vol. 180, pp. 2227-2237 (Dec. 1994).
Martin-Orozco, et al.; "Melanoma Cells Express ICOS Ligand to Promote the Activation and Expansion of T-Regulatory Cells"; Cancer Research; vol. 70, No. 23, pp. 9581-9590 (2010).
Motz, et al.; "Tumor Endothelium FasL Establishes a Selective Immune Barrier Promoting Tolerance in Tumors"; Nat. Med.; vol. 20, No. 6, pp. 607-615 (Jun. 2014).
Ochoa-Garay, et al.; "The Ability of Peptides to Induce Cytotoxic T Cells In Vitro Does Not Strongly Correlate with Their Affinity for the H-2L$^d$ Molecule: Implications for Vaccine Design and Immunotherapy"; Molecular Immunology; vol. 34, No. 3, pp. 273-281 (1997).
Repana, et al.; "The Network of Cancer Genes (NCG): a comprehensive catalogue of known and candidate cancer genes from cancer sequencing screens"; Genome Biology; vol. 20, No. 1, 12 pages (2019).
Schumacher, et al.; "Neoantigens in cancer immunotherapy"; Science; vol. 348, No. 6230, pp. 69-74 (Apr. 2, 2015).
White, et al.; "Soluble Class I MHC with 32-MicroglobulinCovalently Linked Peptides: Specific Binding to a T Cell Hybridoma"; J Immunol; vol. 162, pp. 2671-2676 (1999).
Card, et al.; "A soluble single-chain T-cell receptor IL-2 fusion protein retains MHC-restricted peptide specificity and IL-2 bioactivity"; Cancer Immunol Immunother; vol. 53, pp. 345-357 (Nov. 11, 2003).
Engler, et al.; "Peptide vaccines against hepatitis B virus: from animal model to human studies"; Molecular Immunology; vol. 38, pp. 457-465 (Dec. 2001).
PDB:118L_A; "Chain A, T Lymphocyte Activation Antigen Cd80" 2 pages (Dec. 27, 2012).
Quayle, et al.; "Immuno-STAT(TM) (Selective Targeting and Alteration of T cells) Platform: Targeting Tumor Heterogeneity and Tumor Escape Mechanisms"; DOI:10.1158/1078-0432.CCR-19-3354; URL:https://www.cuebiopharma.com/our-appro ch/scien ific-presentatjons-publications/; 1 page (Jan. 21, 2020).
Seidel, et al.; "Peptide-HLA-based immunotherapeutics platforms for direct modulation of antigen-specific T cells"; Scientific Reports; vol. 11, No. 19220, 8 pages (Sep. 2021).
Lazar-Molnar, et al.; "The PD-1/PD-L costimulatory pathway critically affects host resistance to the pathogenic fungus *Histoplasma capsulatum*"; PNAS; vol. 105, No. 7, pp. 2658-2663 (Feb. 19, 2008).
McNally, et al.; "CD4+CD25+ regulatory T cells control CD8+ T-cell effector differentiation by modulating IL-2 homeostasis"; PNAS; vol. 108, No. 18, pp. 7529-7534 (May 3, 2011).
Tafuro, et al.; "Reconstitution of antigen presentation in HLA class I-negative cancer cells with peptide-β2m fusion molecules"; Eur. J. Immunol.; vol. 31, pp. 440-449 (2001).
Lin, et al.; "The PD-1/PD-L1 complex resembles the antigen-binding Fv domains of antibodies and T cell receptors"; PNAS; vol. 105, No. 8, pp. 3011-3016 (Feb. 26, 2008).
Büyyner; "Cell-based assays for high-throughput screening"; Expert Opin. Drug Discov..; vol. 1, No. 4, pp. 301-306 (Sep. 2006).
GENBANK:NP_068693.1; "programmed cell death 1 ligand 1 precursor [Mus musculus]"; 3 pages (Jun. 9, 2021).
GENBANK:NP_001300958.1; "programmed cell death 1 ligand 1 isoform c precursor [*Homo sapiens*]"; 3 pages (Jun. 9, 2021).
Liao, et al.; "Interleukin-2 at the Crossroads of Effector Responses, Tolerance, and Immunotherapy"; Immunity; vol. 38, No. 1, pp. 13-25 (Jan. 1, 2013).
Carey, et al.; "A soluble divalent class I MHC/IgG1 fusion protein activates CD8+ T cells in vivo"; Clinical Immunology; vol. 116, pp. 65-76 (2005).
GENEBANK:NP_001009066.1; 2 pages (2003).
Lazar-Molnar, et al.; "Crystal structure of the complex between programmed death-1 (PD-1) and its ligand PD-L2"; PNAS; vol. 105, No. 30, pp. 10483-10488 (Jul. 29, 2008).
Medina, et al.; "PD-1 Pathway Inhibitors: Immuno-Onology Agents for Restoring Anititumor Immune Responses"; Pharmacotherapy; vol. 36, No. 3, pp. 317-334 (2016).
Oliveira, et al.; "Design, Immune Responses and Anti-Tumor Potential of an HPV16 E6E7 Multi-Epitope Vaccine"; PLoS One; vol. 10, No. 9, 13 pages (Sep. 21, 2015).
Quayle, et al.; "CUE-101, a Novel HPV16 E7-pHLA-IL-2-Fc Fusion Protein, Enhances Tumor Antigen Specific T Cell Activation for the Treatment of HPV16-Driven Malignancies"; Clinical Cancer Research; vol. 26, No. 8, pp. 1953-1964 (Jan. 21, 2020).
Rocha-Zavaleta, et al.; "Interleukin-2 (IL-2) receptor-βγ signalling is activated by c-Kit in the absence of IL-2, or by exogenous IL-2 via JAK3/STAT5 in human papillomavirus-associated cervical cancer"; Cellular Signalling; vol. 16, pp. 1239-1247 (2004).
Schmittnaegel, et al.; "A New Class of Bifunctional Major Histocompatibility Class I Antibody Fusion Molecules to Redirect CDS T Cells"; Molecular Cancer Therapeutics; vol. 15, No. 9, pp. 2130-2142 (Sep. 2016).
Trolle, et al.; "The length distribution of class I restricted T cell epitopes is determined by both peptide supply and MHC allele specific binding preference"; J Immunol; vol. 196, No. 4, pp. 1480-1487 (Feb. 15, 2016).
Wang, et al.; "Molcular Modeling and Functional Mapping of B7-H1 and B7-DC Uncouple Costimulatory Function from PD-1 Interaction"; J. Exp. Med .; vol. 197, No. 9, pp. 1083-1091 (May 5, 2003).
Solinas, et al.; "The rationale behind targeting the ICOS-ICOS ligand costimulatory pathway in cancer immunotherapy"; ESMO Open; vol. 5, 7 pages (Jan. 2020).
GENBANK:AEV43323.1; "Fc IgG1 heavy chain constant region, partial [*Homo sapiens*]"; 2 pages (Jul. 25, 2016).
Kreiter, et al.; "Increased Antigen Presentation Efficiency by Coupling Antigens to MHC Class I Trafficking Signals"; The Journal of Immunology; vol. 180, No. 1, pp. 309-318 (Jan. 1, 2008).
Strohl; "Optimization of Fc-mediated effector functions of monoclonal antibodies"; Current Opinion in Biotechnology; vol. 20, pp. 685-691 (2009).
Brophy, et al.; "A yeast display system for engineering functional peptide-MHC complexes"; Journal of Immunological Methods; vol. 272, pp. 235-246 (2003).
Emboss Needle; 2 pages (Feb. 10, 2022).
GenCore AEE04235; 4 pages (2005).
Liu, et al.; "Major Histocompatibility Complex: Interaction with Peptides"; eLS; 12 pages (Aug. 15, 2011).
Mottez, et al.; "Cells Expressing a Major Histocompatibility Complex Class I Molecule with a Single Covalently Bound Peptide Are Highly Immunogenic"; J. Exp. Med .; vol. 181, pp. 493-502 (Feb. 1995).

(56) References Cited

OTHER PUBLICATIONS

Vitello, et al.; "Neoantigen prediction and the need for validation"; Nature Biotechnology; vol. 35, No. 9, pp. 815-817 (Sep. 2017).
Wieczorek, et al.; "Major Histocompatibility Complex (MHC) Class I and MHC Class II Proteins: Conformational Plasticity in Antigen Presentation"; Frontiers in Immunology; vol. 8, No. 292, pp. 1-16 (Mar. 2017).
Ackerman, et al.; "Highly Avid Magnetic Bead Capture: An Efficient Selection Method for de novo Protein Engineering Utilizing yeast Surface Display"; Biotechnol. Prog.; vol. 25, No. 3, pp. 774-783 (2009).
Aina, et al.; "Identification of novel targeting peptides for human ovarian cancer cells using 'one-bead one-compount' combinatorial libraries"; Mol. Cancer Ther.; vol. 4, No. 5, 8 pages (May 2005).
Arduin, et al.; "Highly reduced binding to high and low affinity mouse Fc gamma receptors by L234A/L235A and N297A Fc mutations engineered into mouse IgG2a"; Molecular Immunology; vol. 63, pp. 456-463 (2015).
Azuma, et al.; "B7-H1 is a ubiquitous antiapoptotic receptor on cancer cells"; Immunobiology; vol. 111, No. 7, pp. 3635-3643 (Apr. 1, 2008).
Baldi, et al.; "Recombinant protein production by large-scale transient gene expression in mammalian cells: state of the art and future perspectives"; Biotechnol. Lett.; vol. 29, pp. 677-684 (2007).
Bowers, et al.; "Coupling mammalian cell surface display with somatic hypermutation for the discovery and maturation of human antibodies"; PNAS; vol. 108, No. 51, pp. 20455-20460 (Dec. 20, 2011).
Cafri, et al.; "Development of novel genetic cancer vaccines based on membrane-attached β2 microglobulin"; Ann. N.Y. Acad. Sci.; vol. 1283, pp. 87-90 (2013).
Cebecauer, et al.; "Soluble MHC-Peptide Complexes Induce Rapid Death of CD8+ CTL"; The Journal of Immunology; vol. 174, pp. 6809-6819 (2005).
Center for Disease Control and Prevention; "How Many Cancers Are Linked with HPV Each Year?"; 4 pages (2016).
Chames, et al.; "Bispecific antibodies for cancer therapy; The light at the end of the tunnel?" mAbs; vol. 1, No. 6, pp. 539-547 (Nov.-Dec. 2009).
Cheever, et al.; "The Prioritization of Cancer Antigens: A National Cancer Institute Pilot Project for the Acceleration of Translational Research"; Clinical Cancer Research; vol. 15, No. 17, pp. 5324-5337 (Sep. 1, 2009).
Crawford, et al.; "Use of baculovirus MHC/ peptide display libraries to characterize T-cell receptor ligands"; Immunological Reviews; vol. 210, pp. 156-170 (2006).
Crisci, et al.; "Virus-like particles: The new frontier of vaccines for animal viral infections"; Veterinary Immunology and Immunopathology; vol. 148, pp. 211-225 (2012).
Czajkowsky, et al.; "Fc-fusion proteins: new developments and future perspectives"; EMBO Mol. Med.; vol. 4, pp. 1015-1028 (2012).
Das, et al.; "Generation of murine tumor cell lines deficient in MHC molecule surface expression using the CRISPR/Cas9 system"; PLoS One; vol. 12, No. 3, 19 pages (Mar. 16, 2017).
Desmond, et al.; "A systematic review of T-cell epitopes in hepatitis B virus: identification, genotypic variation and relevance to antiviral therapeutics"; Antiviral Therapy; vol. 13, pp. 161-175 (2008).
Dimasi, et al.; "The design and characterization of oligospecific antibodies for simultaneous targeting of multiple disease mediators"; Journal of Molecular Biology; 393(3): p. 672-692 (2009).
Doussal, et al.; "Phage display of peptide /major histocompatibility complex"; Journal of Immunological Methods; vol. 241, pp. 147-158 (2000).
Dulberger, et al.; "Human leukocyte antigen F (HLA-F) presents peptides and regulates immunity through interactions with NK-cell receptors"; Immunity; vol. 46, No. 6, pp. 1018-1027 (Jun. 20, 2017).
Edwards, et al.; "The Remarkable Flexibility of the Human Antibody Repertoire; Isolation of Over One Thousand Different Antibodies to a Single Protein, BLyS"; J. Mol. Biol.; vol. 334, pp. 103-118 (2003).
Engelhard; "Structure of peptides associated with MHC class I molecules"; Current Opinion in Immunology; vol. 6, pp. 13-23 (1994).
Goel, et al.; "Plasticity within the Antigen-Combining Site May Manifest as Molecufar Mimicry in the Humoral Immune Response"; The Journal of Immunology; vol. 173, pp. 7358-7367 (2004).
Gough, et al.; "The HLA Region and Autoimmune Disease: Associations and Mechanisms of Action"; Current Genomics; vol. 8, pp. 453-465 (2007).
Greten, et al.; "Peptide-β2-microglobulin-MHC fusion molecules bind antigen-specific T cells and can be used for multivalent MHC-Ig complexes"; Journal of Immunological Methods; vol. 271, pp. 125-135 (2002).
Grupp, et al.; "Adoptive Cellular Therapy"; Curr Top Microbiol Immunol.; 344: p. 149-172 (2011).
Guo, et al.; "Different length peptides bind to HLA-Aw68 similarly at their ends but bulge out in the middle"; Nature; vol. 360, pp. 364-366 (Nov. 26, 1992).
Hansen, et al.; "Phage display of peptide/major histocompatibility class I complexes"; Eur. J. Immunol.; vol. 31, pp. 32-38 (2001).
Huang, et al.; "Cancer immunotherapy using a DNA vaccine encoding a single-chain trimer of MHC class I linked to an HPV-16 E6 immunodominant CTL epitope"; Gene Ther.; vol. 12, No. 15, pp. 1180-1186 (Aug. 2005).
Hug, et al.; "T-cadherin is a receptor for hexameric and high-molecular-weight forms of Acrp30/adiponectin"; PNAS; vol. 101, No. 28, pp. 10308-10313 (Jul. 13, 2004).
Hugues, et al.; "Generation and use of alternative multimers of peptide/MHC complexes"; Journal of Immunological Methods; vol. 268, pp. 83-92 (2002).
Judkowski, et al.; "Identification of MHC Class II-Restricted Peptide Ligands, Including a Glutamic Acid Decarboxylase 65 Sequence, that Stimulate Diabetogenic T Cells from Transgenic BDC2.5 Nonobese Diabetic Mice"; The Journal of Immunology; vol. 166, pp. 908-917 (2001).
Karaki, et al.; "Is There Still Room for Cancer Vaccines at the Era of Checkpoint Inhibitors"; Vaccines; vol. 4, No. 37, 24 pages (2016).
Khan, et al.; "Adjustable Locks and Flexible Keys: Plasticity of Epitope-Paratope Interactions in Germline Antibodies"; The Journal of Immunology; vol. 192, pp. 5398-5405 (2014).
Kim, et al.; "Single chain MHC I trimer-based DNA vaccines for protection against *Listeria monocytogenes* infection"; Vaccine; vol. 30, pp. 2178-2186 (2012).
Krautwurst, et al.; "Identification of Ligands for Olfactory Receptors by Functional Expression of a Receptor Library"; Cell; vol. 95, pp. 917-926 (Dec. 23, 1998).
Kushnir, et al.; "Virus-like particles as a highly efficient vaccine platform: Diversity of targets and production systems and advances in clinical development"; Vaccine; vol. 31, pp. 58-83 (2012).
Lenormand, et al.; "HLA-DQA2 and HLA-DQB2 Genes Are Specifically Expressed in Human Langerhans Cells and Encode a New HLA Class II Molecule"; The Journal of Immunology; vol. 199, No. 8, pp. 3903-3911 (Apr. 15, 2012).
Liu, et al.; "Attaining High Transient Titers in CHO Cells"; Genetic Engineering & Biotechnology News; vol. 35, No. 17, 3 pages (Oct. 1, 2015).
Lloyd, et al.; "Modelling the human immune response: performance of a 1011 human antibody repertoire against a broad panel of therapeutically relevant antigens"; Protein Engineering, Design & Selection; vol. 22, No. 3, pp. 159-168 (2009).
Mallone, et al.; "T Cell Recognition of Autoantigens in Human Type 1 Diabetes: Clinical Perspectives"; Clinical and Developmental Immunology; vol. 2011, 16 pages (2011).
Margalit, et al.; "Induction of Antitumor Immunity by CTL Epitopes Genetically Linked to Membrane-Anchored B2-Microglobulin"; The Journal of Immunology; vol. 176, pp. 217-224 (2006).

(56) References Cited

OTHER PUBLICATIONS

McAllister, et al.; "Adaptation of Recombinant HEK-293 Cells to Growth in Serum Free Suspension"; Animal Cell Technology: Products from Cells, Cells as Products; 3 pages (1999).
Miao, et al.; "Transient expression of fluorescent fusion proteins in protoplasts of suspension cultured cells"; Nature Protocols; vol. 2, No. 10, pp. 2348-2353 (2007).
Mizukoshi, et al.; "Identification of a-fetoprotein-derived peptides recognized by cytotoxic T lymphocytes in HLA-A24+ patients with hepatocellular carcinoma"; Int. J. Cancer; vol. 118, pp. 1194-1204 (2006).
Mott, et al.; "The Solution Structure of the F42A Mutant of Human Interleukin 2"; J. Mol. Biol.; vol. 247, pp. 979-994 (1995).
Muller, et al.; "Random peptide libraries displayed on adeno-associated virus to select for targeted gene therapy vectors"; Nature Biotechnology; vol. 21, No. 9, pp. 1040-1046 (Sep. 2003).
Naidoo, et al.; "Toxicities of the anti-PD-1 and anti-PD-L1 immune checkpoint antibodies"; Annals of Oncology; vol. 26, pp. 2375-2391 (2015).
Nielsen, et al.; "MHC Class II epitope predictive algorithms"; Immunology; vol. 130, pp. 319-328 (2010).
Oates, et al.; "ImmTACs: Novel bi-specific agents for targeted cancer therapy"; OncoImmunology; vol. 2, No. 2, 3 pages (Feb. 2013).
Obermann, et al.; "Peptide-B2-microglobulin-major histocompatibility complex expressing cells are potent antigen-presenting cells that can generate specific T cells"; Immunology; vol. 122, pp. 90-97 (2007).
Oka, et al.; "Induction of WT1 (Wilms' tumor gene)-specific cytotoxic T lymphocytes by WT1 peptide vaccine and the resultant cancer regression"; PNAS; vol. 101, No. 38, pp. 13885-13890 (Sep. 21, 2004).
Peach, et al.; "Both Extracellular Immunoglobin-like Domains of CD80 Contain Residues Critical for Binding T Cell Surface Receptors CTLA-4 and CD28*"; The Journal of Biological Chemistry; vol. 270, No. 36, p. 21181-21187 (1995).
Ponstingl, et al.; "The Rule of Antibody Structure: The Primary Structure of a Monoclonal IgG1 Immunoglobulin (Myeloma Protein Nie)"; Hoppe Seylers Z Physiol Chem.; vol. 357, No. 11, pp. 1571-1604 (Nov. 1976). [English translation of Abstract Only].
Poosarla, et al.; "Computational De Novo Design of Antibodies Binding to a Peptide With High Affinity"; Biotechnology & Bioengineering; vol. 114, No. 6, pp. 1331-1342 (Jun. 2017).
Rabu, et al.; "Production of recombinant human trimeric CD137L (4-1BBL). Cross-linking is essential to its T cell co-stimulation activity"; The Journal of Biological Chemistry; vol. 280, No. 50, pp. 41472-41481 (Dec. 16, 2005).
Ramani, et al.; "A secreted protein microarray platform for extracellular protein interaction discovery"; Analytical Biochemistry: vol. 420, pp. 127-138 (2012).
Reche, et al.; "Sequence Variability Analysis of Human Class I and Class II MHC Molecules: Functional and Structural Correlates of Amino Acid Polymorphisms"; Journal of Molecular Biology; vol. 331, No. 3, pp. 623-641 (Aug. 15, 2003).
Ressing, et al.; "Human CTL epitopes encoded by human papillomavirus type 16 E6 and E7 identified through in vivo and in vitro immunogenicity studies of HLA-A*0201-binding peptides"; The Journal of Immunology; vol. 154, pp. 5934-5943 (1995).
Shah, et al.; "Bio-layer Interferometry for Measuring Kinetics of Protein-protein Interactions and Allosteric Ligand Effects"; Journal of Visualized Experiments; vol. 84, 11 pages (2014).
Sharma, et al.; "A synthetic chimeric peptide harboring human papillomavirus 16 cytotoxic T lymphocyte epitopes shows therapeutic potential in a murine model of cervical cancer"; Immunologic Research; 58(1): p. 132-138 (2014).
Spang, et al.; "Heterodimeric Barnase-Barstar Vaccine Molecules: Influence of One versus Two Targeting Units Specific for Antigen Presenting Cells"; PLoS One; vol. 7, No. 9, 11 pages (Sep. 2012).
Stadinski, et al.; "Diabetogenic T cells recognize insulin bound to IAg7 in an unexpected, weakly binding register"; PNAS; vol. 107, No. 24, pp. 10978-10983 (Jun. 15, 2010).
Taube, et al.; "Lentivirus Display: Stable Expression of Human Antibodies on the Surface of Human Cells and Virus Particles"; PLoS One; vol. 3, No. 9, 12 pages (Sep. 2008).
Torres, et al.; "The immunoglobulin constant region contributes to affinity and specificity"; Trends in Immunology; vol. 29, No. 2, pp. 91-97 (Jan. 10, 2008).
Toukam, et al.; "Targeting Antibody Responses to the Membrane Proximal External Region of the Envelope Glycoprotein of Human Immunodeficiency Virus"; PLOS One; vol. 7, No. 5, 10 pages (May 2012).
Van Der Burg, et al.; "An HLA Class I Peptide-Binding Assay Based on Competition for Binding to Class I Molecules on Intact Human B Cells Identification of Conserved HIV-1 Polymerase Peptides Binding to HLA-A*0301"; Hum. Immunol.; vol. 44, No. 4, pp. 189-198 (Dec. 1995).
Venkatakrishnan, et al.; "The Structural Biology of Hepatitis B Virus: Form and Function"; Annu. Rev. Virol.; vol. 3, No. 1, pp. 429-451 (Sep. 29, 2016).
Wang, et al.; "Using a baculovirus display library to identify MHC class I mimotopes"; PNAS; vol. 102, No. 7, pp. 2476-2481 (Feb. 15, 2005).
Wen, et al.; "Construction and screening of an antigen-derived peptide library displayed on yeast cell surface for CD4+ T cell epitope identification"; Methods Mol. Biol .; vol. 1061, pp. 245-264 (2013).
Whitehead, et al.; "Optimization of affinity, specificity and function of designed influenza inhibitors using deep sequencing"; Nat. Biotechnol .; vol. 30, No. 6, pp. 543-548 (Apr. 29, 2013).
Won, et al.; "The structure of the trimer of human 4-1BB ligand is unique among members of the tumor necrosis factor superfamily"; J Biol Chem; vol. 285, No. 12, pp. 9202-9210 (Mar. 19, 2010).
Wu, et al.; "Simultaneous targeting of multiple disease mediators by a dual-variable-domain immunoglobulin"; Nature Biotechnology; 25: p. 1290-1297 (2007).
Xu, et al.; "Cytokine release syndrome in cancer immunotherapy with chimeric antigen receptor engineered T cells"; Cancer Letters; 343(2): p. 172-178 (2014).
Ziauddin, et al.; "Microarrays of cells expressing defined cDNAs"; Nature; vol. 411, pp. 107-110 (May 3, 2011).
Stauber et al.; "Crystal structure of the IL-2 signaling complex: Paradigm for a heterotrimeric cytokine receptor"; Proc. Natl. Acad. Sci.; vol. 103, No. 8, pp. 2788-2793 (Feb. 21, 2006).
Bresson, et al.; "Anti-CD3 and nasal proinsulin combination therapy enhances remission from recent-onset autoimmune diabetes by inducing Tregs"; The Journal of Clinical Investigation; vol. 116, No. 5, pp. 1371-1381 (May 2006).
Casares, et al.; "A Peptide-Major Histocompatibility Complex II Chimera Favors Survival of Pancreatic β-Islets Grafted in Type 1 Diabetic Mice"; Transplantation; vol. 85, No. 12, pp. 1717-1725 (Jun. 27, 2008).
Durinovic-Bello, et al.; "DRB1*0401-restricted human T cell clone specific for the major proinsulin73-90 epitope expresses a down-regulatory T helper 2 phenotype"; PNAS; vol. 103, No. 31, pp. 11683-11688 (Aug. 1, 2006).
Gojanovich, et al.; "The Use of Peptide-Major-Histocompatibility-Complex Multimers in Type 1 Diabetes Mellitus"; Journal of Diabetes Science and Technology; vol. 6, No. 3, pp. 515-524 (May 2012).
Li, et al.; "Suppression of Ongoing T Cell-Mediated Autoimmunity by Peptide-MHC Class II Dimer Vaccination"; The Journal of Immunology; vol. 183, pp. 4809-4816 (Sep. 14, 2009).
Lin, et al.; "Reversal of type 1 diabetes by a new MHC II-peptide chimera: "Single-epitope-mediated suppression" to stabilize a polyclonal autoimmune T-cell process"; Eur. J. Immunol.; vol. 40, pp. 2277-2288 (2010).
Michels, et al.; "Islet-Derived CD4 T Cells Targeting Proinsulin in Human Autoimmune Diabetes"; Diabetes; vol. 66, pp. 722-734 (Mar. 2017).

(56) References Cited

OTHER PUBLICATIONS

Preda, et al.; "Soluble, dimeric HLA DR4-peptide chimeras: An approach for detection and immunoregulation of human type-1 diabetes"; Eur. J. Immunol.; vol. 35, pp. 2763-2776 (Aug. 16, 2005).
Sang, et al.; "Long-term silencing of autoimmune diabetes and improved life expectancy by a soluble pHLA-DR4 chimera in a newly-humanized NOD-DR4/B7 mouse"; Human Vaccines & Immunotherapeutics; vol. 10, No. 3, pp. 693-699 (Mar. 2014).
Tan, et al.; "Type 1 diabetes induction in humanized mice"; PNAS; vol. 114, No. 41, pp. 10954-10959 (Oct. 10, 2017).
Woodham, et al.; "In vivo detection of antigen-specific CD8T cells by immuno-positron emission tomography"; Nat Methods.; vol. 17, No. 10, pp. 1025-1032 (Oct. 2020).
Zhang, et al.; "Monoclonal antibody blocking the recognition of an insulin peptide-MHC complex modulates type 1 diabetes"; PNAS; vol. 111, No. 7, pp. 2656-2661 (Feb. 18, 2014).
Zhou, et al.; "Epitopes of MUC1 Tandem Repeats in Cancer as Revealed by Antibody Crystallography: Toward Glycopeptide Signature-Guided Therapy"; Molecules; vol. 23, No. 1326, 27 pages (2018).
Unverdorben, et al.; "Pharmacokinetic properties of IgG and various Fc fusion proteins in mice"; MABS; vol. 8, No. 1, pp. 120-128 (Oct. 29, 2015).
Fellner; "Ipilimumab (Yervoy) Prolongs Survival In Advanced Melanoma"; Drug Forecast; vol. 37, No. 9, pp. 503-530 (Sep. 2012).
Li, et al.; "Chain A, anti-connexin26 scFv,Ig heavy chain, Linker, anti-connexin26 scFv,Ig light chain"; Accession 5WYM_A, Front Mol Neurosci 10, 298, 3 pages (Jan. 13, 2017).

* cited by examiner

FIG. 2A

*Homo sapiens*
GenBank NP_787058
CD86 (B7-2)

```
  1 mdpqctmgls nilfvmafll sgaaplkiqa yfnetadlpc qfansqnqsl selvvfwqdq
 61 enlvlnevyl gkekfdsvhs kymgrtsfds dswtlrlhnl qikdkglyqc iihhkkptgm
121 irihqmnsel svlanfsqpe ivpisniten vyinltcssi hgypepkkms vllrtknsti
181 eydgimqksq dnvtelydvs islsvsfpdv tsnmtifcil etdktrllss pfsieledpq
241 pppdhipwit avlptviicv mvfclilwkw kkkkrprnsy kcgtntmere eseqtkkrek
301 ihipersdea qrvfksskts scdksdtcf (SEQ ID NO:1)
```

bold = ectodomain

FIG. 2B

Human CD86 "full" ectodomain

APLKIQAYFNETADLPCQFANSQNQSLSELVVFWQDQENLVLNEVYLGKEKFDSVHSKY
MNRTSFDSDSWTLRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:2)

FIG. 2C

Mouse CD86 "full" ectodomain

APLKIQAYFNETADLPCQFANSQNQSLSELVVFWQDQENLVLNEVYLGKEKFDSVHSKY
MGRTSFDSDSWTLRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:3)

FIG. 2D

Human
CD86 immunoglobulin V-type (IgV) domain

APLKIQAYFNETADLPCQFANSQNQSLSELVVFWQDQENLVLNEVYLGKEKFDSVHSKY
MNRTSFDSDSWTLRLHNLQIKDKGLYQCIIHHKKPTGMIRIHQMNSELSVL (SEQ ID NO:4)

FIG. 2E

Mouse CD86 IgV domain

APLKIQAYFNETADLPCQFANSQNQSLSELVVFWQDQENLVLNEVYLGKEKFDSVHSKY
MGRTSFDSDSWTLRLHNLQIKDKGLYQCIIHHKKPTGMIRIHQMNSELSVL (SEQ ID NO:5)

FIG. 2F

Human CD86 full ectodomain (N61X)

APLKIQAYFNETADLPCQFANSQNQSLSELVVFWQDQENLVLNEVYLGKEKFDSVHSKY
MXRTSFDSDSWTLRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:6)

FIG. 2G

Human CD86 full ectodomain (D66X)

APLKIQAYFNETADLPCQFANSQNQSLSELVVFWQDQENLVLNEVYLGKEKFDSVHSKY
MNRTSFXSDSWTLRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:7)

FIG. 2H

Human CD86 full ectodomain (W70X)

APLKIQAYFNETADLPCQFANSQNQSLSELVVFWQDQENLVLNEVYLGKEKFDSVHSKY
MNRTSFDSDSXTLRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:8)

FIG. 2I

Human CD86 full ectodomain (H91x)

APLKIQAYFNETADLPCQFANSQNQSLSELVVFWQDQENLVLNEVYLGKEKFDSVHSKY
MNRTSFDSDSWTLRLHNLQIKDKGLYQCIIHXKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:9)

FIG. 2J

Human CD86 IgV (N61X)

APLKIQAYFNETADLPCQFANSQNQSLSELVVFWQDQENLVLNEVYLGKEKFDSVHSKY
MXRTSFDSDSWTLRLHNLQIKDKGLYQCIIHHKKPTGMIRIHQMNSELSVL (SEQ ID NO:10)

FIG. 2K

Human CD86 IgV (D66X)

APLKIQAYFNETADLPCQFANSQNQSLSELVVFWQDQENLVLNEVYLGKEKFDSVHSKY
MNRTSFXSDSWTLRLHNLQIKDKGLYQCIIHHKKPTGMIRIHQMNSELSVL (SEQ ID NO:11)

FIG. 2L

Human CD86 IgV (W70X)

APLKIQAYFNETADLPCQFANSQNQSLSELVVFWQDQENLVLNEVYLGKEKFDSVHSKY
MNRTSFDSDSXTLRLHNLQIKDKGLYQCIIHHKKPTGMIRIHQMNSELSVL (SEQ ID NO:12)

FIG. 2M

Human CD86 IgV (H91x)

APLKIQAYFNETADLPCQFANSQNQSLSELVVFWQDQENLVLNEVYLGKEKFDSVHSKY
MNRTSFDSDSWTLRLHNLQIKDKGLYQCIIHXKKPTGMIRIHQMNSELSVL (SEQ ID NO:13)

FIG. 2N

Human CD86 "full" ectodomain (V41X)

APLKIQAYFNETADLPCQFANSQNQSLSELVVFWQDQENLXLNEVYLGKEKFDSVHSKY
MNRTSFDSDSWTLRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:14)

FIG. 2O

Human
CD86 IgV domain (V41X)

APLKIQAYFNETADLPCQFANSQNQSLSELVVFWQDQENLXLNEVYLGKEKFDSVHSKY
MNRTSFDSDSWTLRLHNLQIKDKGLYQCIIHHKKPTGMIRIHQMNSELSVL (SEQ ID NO:15)

FIG. 2P

Human CD86 "full" ectodomain (Q35X)

APLKIQAYFNETADLPCQFANSQNQSLSELVVFWXDQENLVLNEVYLGKEKFDSVHSKY
MNRTSFDSDSWTLRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:16)

FIG. 2Q

Human
CD86 IgV domain (Q35X)

APLKIQAYFNETADLPCQFANSQNQSLSELVVFWXDQENLVLNEVYLGKEKFDSVHSKY
MNRTSFDSDSWTLRLHNLQIKDKGLYQCIIHHKKPTGMIRIHQMNSELSVL (SEQ ID NO:17)

FIG. 2R

Human CD86 “full” ectodomain (F33X)

APLKIQAYFNETADLPCQFANSQNQSLSELVVXWQDQENLVLNEVYLGKEKFDSVHSKY
MNRTSFDSDSWTLRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:18)

FIG. 2S

Human
CD86 IgV domain (F33X)

APLKIQAYFNETADLPCQFANSQNQSLSELVVXWQDQENLVLNEVYLGKEKFDSVHSKY
MNRTSFDSDSWTLRLHNLQIKDKGLYQCIIHHKKPTGMIRIHQMNSELSVL (SEQ ID NO:19)

FIG. 2T

Human CD86 “full” ectodomain (L72X)

APLKIQAYFNETADLPCQFANSQNQSLSELVVFWQDQENLVLNEVYLGKEKFDSVHSKY
MNRTSFDSDSWTXRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:20)

FIG. 2U

Human
CD86 IgV domain (L72X)

APLKIQAYFNETADLPCQFANSQNQSLSELVVFWQDQENLVLNEVYLGKEKFDSVHSKY
MNRTSFDSDSWTXRLHNLQIKDKGLYQCIIHHKKPTGMIRIHQMNSELSVL (SEQ ID NO:21)

FIG. 2V

Human CD86 "full" ectodomain (Y59X)

APLKIQAYFNETADLPCQFANSQNQSLSELVVFWQDQENLVLNEVYLGKEKFDSVHSKX
MNRTSFDSDSWTLRLHNLQIKDKGLYQCIIHHKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:22)

FIG. 2W

Human
CD86 IgV domain (Y59X)

APLKIQAYFNETADLPCQFANSQNQSLSELVVFWQDQENLVLNEVYLGKEKFDSVHSKX
MNRTSFDSDSWTLRLHNLQIKDKGLYQCIIHHKKPTGMIRIHQMNSELSVL (SEQ ID NO:23)

FIG. 2X

Human CD86 "full" ectodomain (N61X; H91X)

APLKIQAYFNETADLPCQFANSQNQSLSELVVFWQDQENLVLNEVYLGKEKFDSVHSKY
MXRTSFDSDSWTLRLHNLQIKDKGLYQCIIHXKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:24)

FIG. 2Y

Human
CD86 IgV domain (N61X; H91X)

APLKIQAYFNETADLPCQFANSQNQSLSELVVFWQDQENLVLNEVYLGKEKFDSVHSKY
MXRTSFDSDSWTLRLHNLQIKDKGLYQCIIHXKKPTGMIRIHQMNSELSVL (SEQ ID NO:25)

FIG. 2Z

Human CD86 "full" ectodomain (D66X; H91X)

APLKIQAYFNETADLPCQFANSQNQSLSELVVFWQDQENLVLNEVYLGKEKFDSVHSKY
MNRTSFXSDSWTLRLHNLQIKDKGLYQCIIHXKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:26)

FIG. 2aa

Human
CD86 IgV domain (D66X; H91X)

APLKIQAYFNETADLPCQFANSQNQSLSELVVFWQDQENLVLNEVYLGKEKFDSVHSKY
MNRTSFXSDSWTLRLHNLQIKDKGLYQCIIHXKKPTGMIRIHQMNSELSVL (SEQ ID NO:27)

FIG. 2bb

Human CD86 "full" ectodomain (N61X; D66X H91X)

APLKIQAYFNETADLPCQFANSQNQSLSELVVFWQDQENLVLNEVYLGKEKFDSVHSKY
MXRTSFXSDSWTLRLHNLQIKDKGLYQCIIHXKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIP (SEQ ID NO:28)

FIG. 2cc

Human
CD86 IgV domain (N61X; D66X; H91X)

APLKIQAYFNETADLPCQFANSQNQSLSELVVFWQDQENLVLNEVYLGKEKFDSVHSKY
MXRTSFXSDSWTLRLHNLQIKDKGLYQCIIHXKKPTGMIRIHQMNSELSVL (SEQ ID NO:29)

FIG. 3A

CD28 isoform 1
*Homo sapiens*
Mature protein amino acids 19-220

```
  1  mlrlllalnl fpsiqvtgnk ilvkqspmlv aydnavnlsc kysynlfsre fraslhkgld
 61  savevcvvyg nysqqlqvys ktgfncdgkl gnesvtfylq nlyvnqtdiy fckievmypp
121  pyldneksng tiihvkgkhl cpsplfpgps kpfwvlvvvg gvlacysllv tvafiifwvr
181  skrsrllhsd ymnmtprrpg ptrkhyqpya pprdfaayrs (SEQ ID NO:30)
```

FIG. 3B

CD28 isoform 2
*Homo sapiens*
Mature protein amino acids 19-123

```
  1  mlrlllalnl fpsiqvtgnk ilvkqspmlv aydnavnlsw khlcpsplfp gpskpfwvlv
 61  vvggvlacys llvtvafiif wvrskrsrll hsdymnmtpr rpgptrkhyq pyapprdfaa
121  yrs (SEQ ID NO:31)
```

FIG. 3C

CD28 isoform 2
*Homo sapiens*
Mature protein amino acids 19-101

```
  1  mlrlllalnl fpsiqvtgkh lcpsplfpgp skpfwvlvvv ggvlacysll vtvafiifwv
 61  rskrsrllhs dymnmtprrp gptrkhyqpy apprdfaayr s (SEQ ID NO:32)
```

FIG. 4A

GenBank 3S7G_A
*Homo sapiens* IgG1 Fc (SEQ ID NO:33)
227 aa

```
  1  dkthtcppcp apellggpsv flfppkpkdt lmisrtpevt cvvvdvshed pevkfnwyvd
 61  gvevhnaktk preeqynsty rvvsvltvlh qdwlngkeyk ckvsnkalpa piektiskak
121  gqprepqvyt lppsrdeltk nqvsltclvk gfypsdiave wesngqpenn ykttppvlds
181  dgsfflyskl tvdksrwqqg nvfscsvmhe alhnhytqks lslspgk
```

GenBank AAN76044
*Homo sapiens* IgG2 Fc (amino acids 99-325) (SEQ ID NO:34)
227 aa

```
  1  stkgpsvfpl apcsrstses taalgclvkd yfpepvtvsw nsgaltsgvh tfpavlqssg
 61  lyslssvvtv pssnfgtqty tcnvdhkpsn tkvdktverk ccvecppcpa ppvagpsvfl
121  fppkpkdtlm isrtpevtcv vvdvshedpe vqfnwyvdgv evhnaktkpr eeqfnstfrv
181  vsvltvvhqd wlngkeykck vsnkglpapi ektisktkgq prepqvytlp psreemtknq
241  vsltclvkgf ypsdiavewe sngqpennyk ttppmldsdg sfflyskltv dksrwqqgnv
301  fscsvmheal hnhytqksls lspgk
```

GenBank AAW65947
*Homo sapiens* IgG3 Fc (amino acids 19-246) (SEQ ID NO:35)
238 aa

```
  1  hkpsntkvdk rvelktplgd tthtcppcpa pellggpsvf lfppkpkdtl misrtpevtc
 61  vvvdvshedp evkfnwyvdg vevhnaktkp reeqynstyr vvsvltvlhq dwlngkeykc
121  kvsnkalpap iektiskakg qprepqvytl ppsrdeltkn qvsltclvkg fypsdiavew
181  esngqpenny kttppvldsd gsfflysklt vdksrwqqgn vfscsvmhea lhnhytqksl
241  slspgk
```

FIG. 4B

GenBank AAA52770
*Homo sapiens* IgD Fc (amino acids 162-383) (SEQ ID NO:36)
222 aa

```
  1  ptkapdvfpi isgcrhpkdn spvvlaclit gyhptsvtvt wymgtqsqpq rtfpeiqrrd
 61  syymtssqls tplqqwrqge ykcvvqhtas kskkeifrwp espkaqassv ptaqpqaegs
121  lakattapat trntgrggee kkkekekeeq eeretktpec pshtqplgvy lltpavqdlw
181  lrdkatftcf vvgsdlkdah ltwevagkvp tggveeglle rhsngsqsqh srltlprslw
241  nagtsvtctl nhpslppqrl malrepaaqa pvklslnlla ssdppeaasw llcevsgfsp
301  pnillmwled qrevntsgfa parpppqprs ttfwawsvlr vpappspqpa tytcvvshed
361  srtllnasrs levsyvtdhg pmk
```

GenBank 0308221A
*Homo sapiens* IgM Fc (SEQ ID NO:37)
276 aa

```
  1  vtstltikzs dwlgesmftc rvdhrgltfq qnassmcvpd qdtairvfai ppsfasiflt
 61  kstkltclvt dlttybsvti swtreengav kthtnisesh pnatfsavge asicedbdws
121  gerftctvth tdlpsplkqt isrpkgvalh rpbvyllppa rzzlnlresa titclvtgfs
181  padvfvewmq rgeplspqky vtsapmpepq apgryfahsi ltvseeewnt ggtytcvvah
241  ealpnrvter tvdkstgkpt lynvslvmsd tagtcy
```

FIG. 4C

GenBank P01876
*Homo sapiens* IgA Fc (amino acids 120-353) (SEQ ID NO:38)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgpperdlc
181 gcysvssvlp gcaepwnhgk tftctaaype sktpltatls ksgntfrpev hllpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B
*Homo sapiens* IgE Fc (amino acids 6-222) (SEQ ID NO:39)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327) (SEQ ID NO:40)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 5A

*Homo sapiens*
GenBank NP_001229687
HLA-A
Amino acids 25-365 (SEQ ID NO:41)

```
  1  mavmaprtll lllsgalalt qtwagshsmr yfftsvsrpg rgeprfiavg yvddtqfvrf
 61  dsdaasqkme prapwieqeg peywdqetrn mkahsqtdra nlgtlrgyyn qsedgshtiq
121  imygcdvgpd grflrgyrqd aydgkdyial nedlrswtaa dmaaqitkrk weavhaaeqr
181  rvylegrcvd glrrylengk etlqrtdppk thmthhpisd heatlrcwal gfypaeitlt
241  wqrdgedqtq dtelvetrpa gdgtfqkwaa vvvpsgeeqr ytchvqhegl pkpltlrwel
301  ssqptipivg iiaglvllga vitgavvaav mwrrkssdrk ggsytqaass dsaqgsdvsl
361  tackv
```

FIG. 5B

*Homo sapiens*
GenBank NP_005505
HLA-B
Amino acids 25-362 (SEQ ID NO:42)

```
  1  mlvmaprtvl lllsaalalt etwagshsmr yfytsvsrpg rgeprfisvg yvddtqfvrf
 61  dsdaaspree prapwieqeg peywdrntqi ykaqaqtdre slrnlrgyyn qseagshtlq
121  smygcdvgpd grllrghdqy aydgkdyial nedlrswtaa dtaaqitqrk weaareaeqr
181  raylegecve wlrrylengk dkleradppk thvthhpisd heatlrcwal gfypaeitlt
241  wqrdgedqtq dtelvetrpa gdrtfqkwaa vvvpsgeeqr ytchvqhegl pkpltlrwep
301  ssqstvpivg ivaglavlav vvigavvaav mcrrkssggk ggsysqaacs dsaqgsdvsl
361  ta
```

FIG. 5C

*Homo sapiens*
GenBank NP_001229971
HLA-C
Amino acids 25-366 (SEQ ID NO:43)

```
  1   mrvmaprall lllsgglalt etwacshsmr yfdtavsrpg rgeprfisvg yvddtqfvrf
 61   dsdaasprge prapwveqeg peywdretqn ykrqaqadrv slrnlrgyyn qsedgshtlq
121   rmygcdlgpd grllrgydqs aydgkdyial nedlrswtaa dtaaqitqrk leaaraaeql
181   raylegtcve wlrrylengk etlqraeppk thvthhplsd heatlrcwal gfypaeitlt
241   wqrdgedqtq dtelvetrpa gdgtfqkwaa vvvpsgqeqr ytchmqhegl qepltlswep
301   ssqptipimg ivaglavlvv lavlgavvta mmcrrkssgg kggscsqaac snsaqgsdes
361   litcka
```

FIG. 6

```
NP_004039.1      MSRSVALAVLALLSLSGLEAIQRTPKIQVYSRHPAENGKSNFLNCYVSGFHPSDIEVDLL 60
NP_001009066.1   MSRSVALAVLALLSLSGLEAIQRTPKIQVYSRHPAENGKSNFLNCYVSGFHPSDIEVDLL 60
NP_001040602.1   MSRSVALAVLALLSLSGLEAIQRTPKIQVYSRHPPENGKPNFLNCYVSGFHPSDIEVDLL 60
NP_776318.1      MARFVALVLLGLLSLSGLDAIQRPPKIQVYSRHPPEDGKPNYLNCYVYGFHPPQIEIDLL 60
NP_033865.2      MARSVTLVFLVLVSLTGLYAIQKTPQIQVYSRHPPENGKPNILNCYVTQFHPPHIEIQML 60
                 *:* *:*..* *:**:** ***:.*:********.*:**.* *****  ***..**:::*

NP_004039.1      KNGERIEKVEHSDLSFSKDWSFYLLYYTEFTPTEKDEYACRVNHVTLSQPKIVKWDRDM 119
NP_001009066.1   KNGERIEKVEHSDLSFSKDWSFYLLYYTEFTPTEKDEYACRVNHVTLSQPKIVKWDRDM 119
NP_001040602.1   KNGEKMGKVEHSDLSFSKDWSFYLLYYTEFTPNEKDEYACRVNHVTLSGPRTVKWDRDM 119
NP_776318.1      KNGEKI-KSEQSDLSFSKDWSFYLLSHAEFTPNSKDQYSCRVKHVTLEQPRIVKWDRDL 118
NP_033865.2      KNGKKIPKVEMSDMSFSKDWSFYILAHTEFTPTETDTYACRVKHASMAEPKTVYWDRDM 119
                 ***::: * * **:*********:* ::****...* *:***:*.::  *: * ****:
```

FIG. 7

Construct 307: CD86(H91A)-(G4S)4 linker-MHC Heavy chain-linker-IgFc

APLKIQAYFNETADLPCQFANSQNQSLSELVVFWQDQENLVLNEVYLGKEKFDSVHSKY
MGRTSFDSDSWTLRLHNLQIKDKGLYQCIIHAKKPTGMIRIHQMNSELSVLGGGGSGGGG
SGGGGSGGGGSGPHSLRYFVTAVSRPGLGEPRYMEVGYVDDTEFVRFDSDAENPRYEPRA
RWMEQEGPEYWERETQKAKGNEQSFRVDLRTLLGAYNQSKGGSHTIQVISGCEVGSDGRL
LRGYQQYAYDGCDYIALNEDLKTWTAADMAALITKHKWEQAGEAERLRAYLEGTCVEWLR
RYLKNGNATLLRTDSPKAHVTHHSRPEDKVTLRCWALGFYPADITLTWQLNGEELIQDME
LVETRPCGDGTFQKWASVVVPLGKEQYYTCHVYHQGLPEPLTLRWAAAGGPRGPTIKPCP
PCKCPAPNLLGGPSVFIFPPKIKDVLMISLSPIVTCVVVDVSEDDPDVQISWFVNNVEVH
TAQTQTHREDYNSTLRVVSALPIQHQDWMSGKEFKCKVNNKDLPAPIERTISKPKGSVRA
PQVYVLPPPEEEMTKKQVTLTCMVTDFMPEDIYVEWTNNGKTELNYKNTEPVLDSDGSYF
MYSKLRVEKKNWVERNSYSCSVVHEGLHNHHTTKSFSRTPGK (SEQ ID NO:113)

Bold = CD86 (H91A) IgV
Underlined = (G4S)3 linker and AAAGG linker

FIG. 8

Construct 966: (CD86(H91A)-(G4S)4 linker) x 3 – MHC H chain – linker – IgFc

APLKIQAYFNETADLPCQFANSQNQSLSELVVFWQDQENLVLNEVYLGKEKFDSVHSKY
MGRTSFDSDSWTLRLHNLQIKDKGLYQCIIHAKKPTGMIRIHQMNSELSVLANFSQPEIV
PISNITENVYINLTCSSIHGYPEPKKMSVLLRTKNSTIEYDGIMQKSQDNVTELYDVSIS
LSVSFPDVTSNMTIFCILETDKTRLLSSPFSIELEDPQPPPDHIPGGGGSGGGGSGGGGS
GGGGSAAPLKIQAYFNETADLPCQFANSQNQSLSELVVFWQDQENLVLNEVYLGKEKFDS
VHSKYMGRTSFDSDSWTLRLHNLQIKDKGLYQCIIHAKKPTGMIRIHQMNSELSVLANFS
QPEIVPISNITENVYINLTCSSIHGYPEPKKMSVLLRTKNSTIEYDGIMQKSQDNVTELY
DVSISLSVSFPDVTSNMTIFCILETDKTRLLSSPFSIELEDPQPPPDHIPGGGGSGGGGS
GGGGSGGGGSAAPLKIQAYFNETADLPCQFANSQNQSLSELVVFWQDQENLVLNEVYLGK
EKFDSVHSKYMGRTSFDSDSWTLRLHNLQIKDKGLYQCIIHAKKPTGMIRIHQMNSELSV
LANFSQPEIVPISNITENVYINLTCSSIHGYPEPKKMSVLLRTKNSTIEYDGIMQKSQDN
VTELYDVSISLSVSFPDVTSNMTIFCILETDKTRLLSSPFSIELEDPQPPPDHIPGGGGS
GGGGSGGGGSGGGGSGPHSMRYFETAVSRPGLEEPRYISVGYVDNKEFVRFDSDAENPRY
EPRAPWMEQEGPEYWERETQKAKGQEQWFRVSLRNLLGAYNQSAGGSHTLQQMSGCDLGS
DWRLLRGYLQFAYEGRDYIALNEDLKTWTAADMAAQITRRKWEQSGAAEHYKAYLEGECV
EWLHRYLKNGNATLLRTDSPKAHVTHHPRSKGEVTLRCWALGFYPADITLTWQLNGEELT
QDMELVETRPCGDGTFQKWASVVVPLGKEQNYTCRVYHEGLPEPLTLRWAAAGGPRGPTI
KPCPPCKCPAPNLEGGPSVFIFPPKIKDVLMISLSPIVTCVVVDVSEDDPDVQISWFVNN
VEVHTAQTQTHREDYNSTLRVVSALPIQHQDWMSGKAFACAVNNKDLPAPIERTISKPKG
SVRAPQVYVLPPPEEEMTKKQVTLTCMVTDFMPEDIYVEWTNNGKTELNYKNTEPVLDSD
GSYFMYSKLRVEKKNWVERNSYSCSVVHEGLHNHHTTKSFSRTPGK (SEQ ID NO:127)

FIG. 9

Construct 1145: CD86(H91A) IgV – (G4S)4 linker – MHC H chain – linker -IgFc

APLKIQAYFNETADLPCQFANSQNQSLSELVVFWQDQENLVLNEVYLGKEKFDSVHSKY
MGRTSFDSDSWTLRLHNLQIKDKGLYQCIIHMKKPTGMIRIHQMNSELSVLAGGGGSGGG
GSGGGGSGGGGSGPHSMRYFETAVSRPGLEEPRYISVGYVDNKEFVRFDSDAENPRYEPR
APWMEQEGPEYWERETQKAKGQEQWFRVSLRNLLGAYNQSAGGSHTLQQMSGCDLGSDWR
LLRGYLQFAYEGRDYIALNEDLKTWTAADMAAQITRRKWEQSGAAEHYKAYLEGECVEWL
HRYLKNGNATLLRTDSPKAHVTHHPRSKGEVTLRCWALGFYPADITLTWQLNGEELTQDM
ELVETRPCGDGTFQKWASVVVPLGKEQNYTCRVYHEGLPEPLTLRWAAAGGPRGPTIKPC
PPCKCPAPNLEGGPSVFIFPPKIKDVLMISLSPIVTCVVVDVSEDDPDVQISWFVNNVEV
HTAQTQTHREDYNSTLRVVSALPIQHQDWMSGKAFACAVNNKDLPAPIERTISKPKGSVR
APQVYVLPPPEEEMTKKQVTLTCMVTDFMPEDIYVEWTNNGKTELNYKNTEPVLDSDGSY
FMYSKLRVEKKNWVERNSYSCSVVHEGLHNHHTTKSFSRTPGK (SEQ ID NO:175)

FIG. 10

Construct 1123: CD86(H91A) IgV – (G4S)5 linker - CD86(H91A) IgV – (G4S)4 linker – MHC H chain – linker - IgFc

APLKIQAYFNETADLPCQFANSQNQSLSELVVFWQDQENLVLNEVYLGKEKFDSVHSKY
MGRTSFDSDSWTLRLHNLQIKDKGLYQCIIHAKKPTGMIRIHQMNSELSVLAGGGGSGGG
GSGGGGSGGGGSGGGGSAAPLKIQAYFNETADLPCQFANSQNQSLSELVVFWQDQENLVL
NEVYLGKEKFDSVHSKYMGRTSFDSDSWTLRLHNLQIKDKGLYQCIIHAKKPTGMIRIHQ
MNSELSVLAGGGGSGGGGSGGGGSGGGGSGPHSMRYFETAVSRPGLEEPRYISVGYVDNK
EFVRFDSDAENPRYEPRAPWMEQEGPEYWERETQKAKGQEQWFRVSLRNLLGAYNQSAGG
SHTLQQMSGCDLGSDWRLLRGYLQFAYEGRDYIALNEDLKTWTAADMAAQITRRKWEQSG
AAEHYKAYLEGECVEWLHRYLKNGNATLLRTDSPKAHVTHHPRSKGEVTLRCWALGFYPA
DITLTWQLNGEELTQDMELVETRPCGDGTFQKWASVVVPLGKEQNYTCRVYHEGLPEPLT
LRWAAAGGPRGPTIKPCPPCKCPAPNLEGGPSVFIFPPKIKDVLMISLSPIVTCVVVDVS
EDDPDVQISWFVNNVEVHTAQTQTHREDYNSTLRVVSALPIQHQDWMSGKAFACAVNNKD
LPAPIERTISKPKGSVRAPQVYVLPPPEEEMTKKQVTLTCMVTDFMPEDIYVEWTNNGKT
ELNYKNTEPVLDSDGSYFMYSKLRVEKKNWVERNSYSCSVVHEGLHNHHTTKSFSRTPGK
(SEQ ID NO:169)

FIG. 11

| Sequence Identifier: | CD86 Construct: | Sequence Identifier: | CD86 Construct: |
|---|---|---|---|
| SEQ ID NO:94 | 249 | SEQ ID NO:140 | 1082 |
| SEQ ID NO:95 | 250 | SEQ ID NO:141 | 1083 |
| SEQ ID NO:96 | 251 | SEQ ID NO:142 | 1084 |
| SEQ ID NO:97 | 252 | SEQ ID NO:143 | 1085 |
| SEQ ID NO:98 | 253 | SEQ ID NO:144 | 1086 |
| SEQ ID NO:99 | 254 | SEQ ID NO:145 | 1087 |
| SEQ ID NO:100 | 255 | SEQ ID NO:146 | 1088 |
| SEQ ID NO:101 | 256 | SEQ ID NO:147 | 1089 |
| SEQ ID NO:102 | 257 | SEQ ID NO:148 | 1090 |
| SEQ ID NO:103 | 258 | SEQ ID NO:149 | 1091 |
| SEQ ID NO:104 | 298 | SEQ ID NO:150 | 1092 |
| SEQ ID NO:105 | 299 | SEQ ID NO:151 | 1105 |
| SEQ ID NO:106 | 300 | SEQ ID NO:152 | 1106 |
| SEQ ID NO:107 | 301 | SEQ ID NO:153 | 1107 |
| SEQ ID NO:108 | 302 | SEQ ID NO:154 | 1108 |
| SEQ ID NO:109 | 303 | SEQ ID NO:155 | 1109 |
| SEQ ID NO:110 | 304 | SEQ ID NO:156 | 1110 |
| SEQ ID NO:111 | 305 | SEQ ID NO:157 | 1111 |
| SEQ ID NO:112 | 306 | SEQ ID NO:158 | 1112 |
| SEQ ID NO:113 | 307 | SEQ ID NO:159 | 1113 |
| SEQ ID NO:114 | 953 | SEQ ID NO:160 | 1114 |
| SEQ ID NO:115 | 954 | SEQ ID NO:161 | 1115 |
| SEQ ID NO:116 | 955 | SEQ ID NO:162 | 1116 |
| SEQ ID NO:117 | 956 | SEQ ID NO:163 | 1117 |
| SEQ ID NO:118 | 957 | SEQ ID NO:164 | 1118 |
| SEQ ID NO:119 | 958 | SEQ ID NO:165 | 1119 |
| SEQ ID NO:120 | 959 | SEQ ID NO:166 | 1120 |
| SEQ ID NO:121 | 960 | SEQ ID NO:167 | 1121 |
| SEQ ID NO:122 | 961 | SEQ ID NO:168 | 1122 |
| SEQ ID NO:123 | 962 | SEQ ID NO:169 | 1123 |
| SEQ ID NO:124 | 963 | SEQ ID NO:170 | 1124 |
| SEQ ID NO:125 | 964 | SEQ ID NO:171 | 1125 |

FIG. 11 (Cont.)

| Sequence Identifier: | CD86 Construct: | Sequence Identifier: | CD86 Construct: |
|---|---|---|---|
| SEQ ID NO:126 | 965 | SEQ ID NO:172 | 1126 |
| SEQ ID NO:127 | 966 | SEQ ID NO:173 | 1143 |
| SEQ ID NO:128 | 967 | SEQ ID NO:174 | 1144 |
| SEQ ID NO:129 | 968 | SEQ ID NO:175 | 1145 |
| SEQ ID NO:130 | 969 | SEQ ID NO:176 | 1146 |
| SEQ ID NO:131 | 1073 | SEQ ID NO:177 | 1147 |
| SEQ ID NO:132 | 1074 | SEQ ID NO:178 | 1148 |
| SEQ ID NO:133 | 1075 | | |
| SEQ ID NO:134 | 1076 | | |
| SEQ ID NO:135 | 1077 | | |
| SEQ ID NO:136 | 1078 | | |
| SEQ ID NO:137 | 1079 | | |
| SEQ ID NO:138 | 1080 | | |
| SEQ ID NO:139 | 1081 | | |

LCMV-CD86v H91[X] at 3.17nM, day 2

Western blot analysis

SEQUENCE LISTING

```
<160> NUMBER OF SEQ ID NOS: 190

<210> SEQ ID NO 1
<211> LENGTH: 329
<212> TYPE: PRT
<213> ORGANISM: Artificial Sequence
<220> FEATURE:
<223> OTHER INFORMATION: Synthetic polypeptide

<400> SEQUENCE: 1

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
```

```
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325


<210> SEQ ID NO 2
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 2

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
```

```
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 3
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 3

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 4
<211> LENGTH: 110
<212> TYPE: PRT
<213> ORGANISM: Artificial Sequence
<220> FEATURE:
<223> OTHER INFORMATION: Synthetic polypeptide
```

<400> SEQUENCE: 4

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu
            100                 105                 110
```

<210> SEQ ID NO 5
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 5

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu
            100                 105                 110
```

<210> SEQ ID NO 6
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (61)..(61)
<223> OTHER INFORMATION: Xaa may be Gly, Ala, Val, Leu, Ile, Pro, Phe, Tyr, Trp, Ser, Thr, Cys, Met, Gln, Lys, Arg, His, Asp, or Glu.

<400> SEQUENCE: 6

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45
```

Lys Glu Lys Phe Asp Ser Val His Ser Lys Tyr Met Xaa Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile His His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Ile Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 7
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (66)..(66)
<223> OTHER INFORMATION: Xaa may be Gly, Ala, Val, Leu, Ile, Pro, Phe, Tyr, Trp, Ser, Thr, Cys, Met, Asn, Gln, Lys, Arg, His, or Glu.

<400> SEQUENCE: 7

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Asn Arg Thr Ser
50 55 60

Phe Xaa Ser Asp Ser Trp Thr Leu Arg Leu His Asn Leu Gln Ile Lys
65 70 75 80

Asp Lys Gly Leu Tyr Gln Cys Ile Ile His His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Ile Met Gln Lys Ser Gln Asp Asn Val Thr Glu Leu Tyr Asp Val

```
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 8
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (70)..(70)
<223> OTHER INFORMATION: Xaa may be Gly, Ala, Val, Leu, Ile, Pro, Phe,
      Tyr, Ser, Thr, Cys, Met, Asn, Gln, Lys, Arg, His, Asp, or Glu.

<400> SEQUENCE: 8

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Xaa Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 9
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (91)..(91)
<223> OTHER INFORMATION: Xaa may be Gly, Ala, Val, Leu, Ile, Pro, Phe,
```

Tyr, Trp, Ser, Thr, Cys, Met, Asn, Gln, Lys, Arg, Asp, or Glu.

<400> SEQUENCE: 9

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His Xaa Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220
```

<210> SEQ ID NO 10
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (61)..(61)
<223> OTHER INFORMATION: Xaa may be Gly, Ala, Val, Leu, Ile, Pro, Phe, Tyr, Trp, Ser, Thr, Cys, Met, Gln, Lys, Arg, His, Asp, or Glu.

<400> SEQUENCE: 10

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Xaa Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95
```

-continued

```
Met Ile Arg Ile His Gln Met Asn Ser Glu Leu Ser Val Leu
            100                 105                 110


<210> SEQ ID NO 11
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (66)..(66)
<223> OTHER INFORMATION: Xaa may be Gly, Ala, Val, Leu, Ile, Pro, Phe,
      Tyr, Trp, Ser, Thr, Cys, Met, Asn, Gln, Lys, Arg, His, or Glu.

<400> SEQUENCE: 11

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Xaa Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu
            100                 105                 110


<210> SEQ ID NO 12
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (70)..(70)
<223> OTHER INFORMATION: Xaa may be Gly, Ala, Val, Leu, Ile, Pro, Phe,
      Tyr, Ser, Thr, Cys, Met, Asn, Gln, Lys, Arg, His, Asp, or Glu.

<400> SEQUENCE: 12

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Xaa Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu
            100                 105                 110


<210> SEQ ID NO 13
<211> LENGTH: 110
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (91)..(91)
<223> OTHER INFORMATION: Xaa may be Gly, Ala, Val, Leu, Ile, Pro, Phe,
      Tyr, Trp, Ser, Thr, Cys, Met, Asn, Gln, Lys, Arg, Asp, or Glu.

<400> SEQUENCE: 13

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His Xaa Lys Lys Pro Thr Gly
                85                  90                  95

Met Ile Arg Ile His Gln Met Asn Ser Glu Leu Ser Val Leu
            100                 105                 110


<210> SEQ ID NO 14
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (41)..(41)
<223> OTHER INFORMATION: Xaa may be Gly, Ala, Leu, Ile, Pro, Phe, Tyr,
      Trp, Ser, Thr, Cys, Met, Asn, Gln, Lys, Arg, His, Asp, or Glu.

<400> SEQUENCE: 14

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Xaa Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175
```

```
Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 15
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (41)..(41)
<223> OTHER INFORMATION: Xaa may be Gly, Ala, Leu, Ile, Pro, Phe, Tyr,
      Trp, Ser, Thr, Cys, Met, Asn, Gln, Lys, Arg, His, Asp, or Glu.

<400> SEQUENCE: 15

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Xaa Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu
            100                 105                 110


<210> SEQ ID NO 16
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (35)..(35)
<223> OTHER INFORMATION: Xaa may be Gly, Ala, Val, Leu, Ile, Pro, Phe,
      Tyr, Trp, Ser, Thr, Cys, Met, Asn, Lys, Arg, His, Asp, or Glu.

<400> SEQUENCE: 16

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Xaa Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95
```

```
Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 17
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (35)..(35)
<223> OTHER INFORMATION: Xaa may be Gly, Ala, Val, Leu, Ile, Pro, Phe,
      Tyr, Trp, Ser, Thr, Cys, Met, Asn, Lys, Arg, His, Asp, or Glu.

<400> SEQUENCE: 17

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Xaa Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu
            100                 105                 110


<210> SEQ ID NO 18
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (33)..(33)
<223> OTHER INFORMATION: Xaa may be Gly, Ala, Val, Leu, Ile, Pro, Tyr,
      Trp, Ser, Thr, Cys, Met, Asn, Gln, Lys, Arg, His, Asp, or Glu.

<400> SEQUENCE: 18

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
```

```
            20                  25                  30

Xaa Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 19
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (33)..(33)
<223> OTHER INFORMATION: Xaa may be Gly, Ala, Val, Leu, Ile, Pro, Tyr,
      Trp, Ser, Thr, Cys, Met, Asn, Gln, Lys, Arg, His, Asp, or Glu.

<400> SEQUENCE: 19

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Xaa Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu
            100                 105                 110


<210> SEQ ID NO 20
<211> LENGTH: 224
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: MISC_FEATURE
<222> LOCATION: (72)..(72)
<223> OTHER INFORMATION: Xaa may be Gly, Ala, Val, Ile, Pro, Phe, Tyr,
      Trp, Ser, Thr, Cys, Met, Asn, Gln, Lys, Arg, His, Asp, or Glu.

<400> SEQUENCE: 20

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60

Phe Asp Ser Asp Ser Trp Thr Xaa Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 21
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (72)..(72)
<223> OTHER INFORMATION: Xaa may be Gly, Ala, Val, Ile, Pro, Phe, Tyr,
      Trp, Ser, Thr, Cys, Met, Asn, Gln, Lys, Arg, His, Asp, or Glu.

<400> SEQUENCE: 21

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60
```

```
Phe Asp Ser Asp Ser Trp Thr Xaa Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu
            100                 105                 110


<210> SEQ ID NO 22
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (59)..(59)
<223> OTHER INFORMATION: Xaa may be Gly, Ala, Val, Leu, Ile, Pro, Phe,
      Trp, Ser, Thr, Cys, Met, Asn, Gln, Lys, Arg, His, Asp, or Glu.

<400> SEQUENCE: 22

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Xaa Met Asn Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 23
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (59)..(59)
<223> OTHER INFORMATION: Xaa may be Gly, Ala, Val, Leu, Ile, Pro, Phe,
      Trp, Ser, Thr, Cys, Met, Asn, Gln, Lys, Arg, His, Asp, or Glu.
```

<400> SEQUENCE: 23

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Xaa Met Asn Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile His His Lys Lys Pro Thr Gly
85 90 95

Met Ile Arg Ile His Gln Met Asn Ser Glu Leu Ser Val Leu
100 105 110

<210> SEQ ID NO 24
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (61)..(61)
<223> OTHER INFORMATION: Xaa may be Gly, Ala, Val, Leu, Ile, Pro, Phe, Tyr, Trp, Ser, Thr, Cys, Met, Gln, Lys, Arg, His, Asp, or Glu.
<220> FEATURE:
<221> NAME/KEY: MISC_FEATURE
<222> LOCATION: (91)..(91)
<223> OTHER INFORMATION: Xaa may be Gly, Ala, Val, Leu, Ile, Pro, Phe, Tyr, Trp, Ser, Thr, Cys, Met, Asn, Gln, Lys, Arg, Asp, or Glu.

<400> SEQUENCE: 24

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Xaa Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile His Xaa Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Ile Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

```
Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 25
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (61)..(61)
<223> OTHER INFORMATION: Xaa may be Gly, Ala, Val, Leu, Ile, Pro, Phe,
      Tyr, Trp, Ser, Thr, Cys, Met, Gln, Lys, Arg, His, Asp, or Glu.
<220> FEATURE:
<221> NAME/KEY: MISC_FEATURE
<222> LOCATION: (91)..(91)
<223> OTHER INFORMATION: Xaa may be Gly, Ala, Val, Leu, Ile, Pro, Phe,
      Tyr, Trp, Ser, Thr, Cys, Met, Asn, Gln, Lys, Arg, Asp, or Glu.

<400> SEQUENCE: 25

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Xaa Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His Xaa Lys Lys Pro Thr Gly
                85                  90                  95

Met Ile Arg Ile His Gln Met Asn Ser Glu Leu Ser Val Leu
            100                 105                 110


<210> SEQ ID NO 26
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (66)..(66)
<223> OTHER INFORMATION: Xaa may be Gly, Ala, Val, Leu, Ile, Pro, Phe,
      Tyr, Trp, Ser, Thr, Cys, Met, Asn, Gln, Lys, Arg, His, or Glu.
<220> FEATURE:
<221> NAME/KEY: MISC_FEATURE
<222> LOCATION: (91)..(91)
<223> OTHER INFORMATION: Xaa may be Gly, Ala, Val, Leu, Ile, Pro, Phe,
      Tyr, Trp, Ser, Thr, Cys, Met, Asn, Gln, Lys, Arg, Asp, or Glu.

<400> SEQUENCE: 26

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60
```

Phe Xaa Ser Asp Ser Trp Thr Leu Arg Leu His Asn Leu Gln Ile Lys
65 70 75 80

Asp Lys Gly Leu Tyr Gln Cys Ile Ile His Xaa Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Ile Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 27
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (66)..(66)
<223> OTHER INFORMATION: Xaa may be Gly, Ala, Val, Leu, Ile, Pro, Phe, Tyr, Trp, Ser, Thr, Cys, Met, Asn, Gln, Lys, Arg, His, or Glu.
<220> FEATURE:
<221> NAME/KEY: MISC_FEATURE
<222> LOCATION: (91)..(91)
<223> OTHER INFORMATION: Xaa may be Gly, Ala, Val, Leu, Ile, Pro, Phe, Tyr, Trp, Ser, Thr, Cys, Met, Asn, Gln, Lys, Arg, Asp, or Glu.

<400> SEQUENCE: 27

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Asn Arg Thr Ser
50 55 60

Phe Xaa Ser Asp Ser Trp Thr Leu Arg Leu His Asn Leu Gln Ile Lys
65 70 75 80

Asp Lys Gly Leu Tyr Gln Cys Ile Ile His Xaa Lys Lys Pro Thr Gly
85 90 95

Met Ile Arg Ile His Gln Met Asn Ser Glu Leu Ser Val Leu
100 105 110

<210> SEQ ID NO 28
<211> LENGTH: 224
<212> TYPE: PRT
<213> ORGANISM: Artificial Sequence
<220> FEATURE:
<223> OTHER INFORMATION: Synthetic polypeptide
<220> FEATURE:

<221> NAME/KEY: MISC_FEATURE
<222> LOCATION: (61)..(61)
<223> OTHER INFORMATION: Xaa may be Gly, Ala, Val, Leu, Ile, Pro, Phe, Tyr, Trp, Ser, Thr, Cys, Met, Gln, Lys, Arg, His, Asp, or Glu.
<220> FEATURE:
<221> NAME/KEY: MISC_FEATURE
<222> LOCATION: (66)..(66)
<223> OTHER INFORMATION: Xaa may be Gly, Ala, Val, Leu, Ile, Pro, Phe, Tyr, Trp, Ser, Thr, Cys, Met, Asn, Gln, Lys, Arg, His, or Glu.
<220> FEATURE:
<221> NAME/KEY: MISC_FEATURE
<222> LOCATION: (91)..(91)
<223> OTHER INFORMATION: Xaa may be Gly, Ala, Val, Leu, Ile, Pro, Phe, Tyr, Trp, Ser, Thr, Cys, Met, Asn, Gln, Lys, Arg, Asp, or Glu.

<400> SEQUENCE: 28

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Xaa Arg Thr Ser
    50                  55                  60

Phe Xaa Ser Asp Ser Trp Thr Leu Arg Leu His Asn Leu Gln Ile Lys
65                  70                  75                  80

Asp Lys Gly Leu Tyr Gln Cys Ile Ile His Xaa Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220
```

<210> SEQ ID NO 29
<211> LENGTH: 110
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (61)..(61)
<223> OTHER INFORMATION: Xaa may be Gly, Ala, Val, Leu, Ile, Pro, Phe, Tyr, Trp, Ser, Thr, Cys, Met, Gln, Lys, Arg, His, Asp, or Glu.
<220> FEATURE:
<221> NAME/KEY: MISC_FEATURE
<222> LOCATION: (66)..(66)
<223> OTHER INFORMATION: Xaa may be Gly, Ala, Val, Leu, Ile, Pro, Phe, Tyr, Trp, Ser, Thr, Cys, Met, Asn, Gln, Lys, Arg, His, or Glu.
<220> FEATURE:
<221> NAME/KEY: MISC_FEATURE
<222> LOCATION: (91)..(91)

<223> OTHER INFORMATION: Xaa may be Gly, Ala, Val, Leu, Ile, Pro, Phe,
Tyr, Trp, Ser, Thr, Cys, Met, Asn, Gln, Lys, Arg, Asp, or Glu.

<400> SEQUENCE: 29

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Xaa Arg Thr Ser
    50                  55                  60

Phe Xaa Ser Asp Ser Trp Thr Leu Arg Leu His Asn Leu Gln Ile Lys
65                  70                  75                  80

Asp Lys Gly Leu Tyr Gln Cys Ile Ile His Xaa Lys Lys Pro Thr Gly
                85                  90                  95

Met Ile Arg Ile His Gln Met Asn Ser Glu Leu Ser Val Leu
            100                 105                 110
```

<210> SEQ ID NO 30
<211> LENGTH: 220
<212> TYPE: PRT
<213> ORGANISM: Homo sapiens

<400> SEQUENCE: 30

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 31
<211> LENGTH: 123

<212> TYPE: PRT
<213> ORGANISM: Homo sapiens

<400> SEQUENCE: 31

Met Leu Arg Leu Leu Leu Ala Leu Asn Leu Phe Pro Ser Ile Gln Val
1 5 10 15

Thr Gly Asn Lys Ile Leu Val Lys Gln Ser Pro Met Leu Val Ala Tyr
20 25 30

Asp Asn Ala Val Asn Leu Ser Trp Lys His Leu Cys Pro Ser Pro Leu
35 40 45

Phe Pro Gly Pro Ser Lys Pro Phe Trp Val Leu Val Val Val Gly Gly
50 55 60

Val Leu Ala Cys Tyr Ser Leu Leu Val Thr Val Ala Phe Ile Ile Phe
65 70 75 80

Trp Val Arg Ser Lys Arg Ser Arg Leu Leu His Ser Asp Tyr Met Asn
85 90 95

Met Thr Pro Arg Arg Pro Gly Pro Thr Arg Lys His Tyr Gln Pro Tyr
100 105 110

Ala Pro Pro Arg Asp Phe Ala Ala Tyr Arg Ser
115 120

<210> SEQ ID NO 32
<211> LENGTH: 101
<212> TYPE: PRT
<213> ORGANISM: Homo sapiens

<400> SEQUENCE: 32

Met Leu Arg Leu Leu Leu Ala Leu Asn Leu Phe Pro Ser Ile Gln Val
1 5 10 15

Thr Gly Lys His Leu Cys Pro Ser Pro Leu Phe Pro Gly Pro Ser Lys
20 25 30

Pro Phe Trp Val Leu Val Val Val Gly Gly Val Leu Ala Cys Tyr Ser
35 40 45

Leu Leu Val Thr Val Ala Phe Ile Ile Phe Trp Val Arg Ser Lys Arg
50 55 60

Ser Arg Leu Leu His Ser Asp Tyr Met Asn Met Thr Pro Arg Arg Pro
65 70 75 80

Gly Pro Thr Arg Lys His Tyr Gln Pro Tyr Ala Pro Pro Arg Asp Phe
85 90 95

Ala Ala Tyr Arg Ser
100

<210> SEQ ID NO 33
<211> LENGTH: 227
<212> TYPE: PRT
<213> ORGANISM: Homo sapiens

<400> SEQUENCE: 33

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr

```
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 34
<211> LENGTH: 325
<212> TYPE: PRT
<213> ORGANISM: Homo sapiens

<400> SEQUENCE: 34

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205
```

```
Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
                325


<210> SEQ ID NO 35
<211> LENGTH: 246
<212> TYPE: PRT
<213> ORGANISM: Homo sapiens

<400> SEQUENCE: 35

His Lys Pro Ser Asn Thr Lys Val Asp Lys Arg Val Glu Leu Lys Thr
1               5                   10                  15

Pro Leu Gly Asp Thr Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245
```

```
<210> SEQ ID NO 36
<211> LENGTH: 383
<212> TYPE: PRT
<213> ORGANISM: Homo sapiens

<400> SEQUENCE: 36

Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
            20                  25                  30

His Pro Thr Ser Val Thr Val Thr Trp Tyr Met Gly Thr Gln Ser Gln
        35                  40                  45

Pro Gln Arg Thr Phe Pro Glu Ile Gln Arg Arg Asp Ser Tyr Tyr Met
    50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Glu Lys Lys Lys Glu
    130                 135                 140

Lys Glu Lys Glu Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
    210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
            260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
    290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
            340                 345                 350

Thr Cys Val Val Ser His Glu Asp Ser Arg Thr Leu Leu Asn Ala Ser
        355                 360                 365

Arg Ser Leu Glu Val Ser Tyr Val Thr Asp His Gly Pro Met Lys
```

370 375 380

<210> SEQ ID NO 37
<211> LENGTH: 270
<212> TYPE: PRT
<213> ORGANISM: Homo sapiens

<400> SEQUENCE: 37

```
Val Thr Ser Thr Leu Thr Ile Lys Ser Asp Trp Leu Gly Glu Ser Met
1               5                   10                  15

Phe Thr Cys Arg Val Asp His Arg Gly Leu Thr Phe Gln Gln Asn Ala
            20                  25                  30

Ser Ser Met Cys Val Pro Asp Gln Asp Thr Ala Ile Arg Val Phe Ala
        35                  40                  45

Ile Pro Pro Ser Phe Ala Ser Ile Phe Leu Thr Lys Ser Thr Lys Leu
    50                  55                  60

Thr Cys Leu Val Thr Asp Leu Thr Thr Tyr Ser Val Thr Ile Ser Trp
65                  70                  75                  80

Thr Arg Glu Glu Asn Gly Ala Val Lys Thr His Thr Asn Ile Ser Glu
                85                  90                  95

Ser His Pro Asn Ala Thr Phe Ser Ala Val Gly Glu Ala Ser Ile Cys
            100                 105                 110

Glu Asp Asp Trp Ser Gly Glu Arg Phe Thr Cys Thr Val Thr His Thr
        115                 120                 125

Asp Leu Pro Ser Pro Leu Lys Gln Thr Ile Ser Arg Pro Lys Gly Val
    130                 135                 140

Ala Leu His Arg Pro Val Tyr Leu Leu Pro Pro Ala Arg Leu Asn Leu
145                 150                 155                 160

Arg Glu Ser Ala Thr Ile Thr Cys Leu Val Thr Gly Phe Ser Pro Ala
                165                 170                 175

Asp Val Phe Val Glu Trp Met Gln Arg Gly Glu Pro Leu Ser Pro Gln
            180                 185                 190

Lys Tyr Val Thr Ser Ala Pro Met Pro Glu Pro Gln Ala Pro Gly Arg
        195                 200                 205

Tyr Phe Ala His Ser Ile Leu Thr Val Ser Glu Glu Glu Trp Asn Thr
    210                 215                 220

Gly Gly Thr Tyr Thr Cys Val Val Ala His Glu Ala Leu Pro Asn Arg
225                 230                 235                 240

Val Thr Glu Arg Thr Val Asp Lys Ser Thr Gly Lys Pro Thr Leu Tyr
                245                 250                 255

Asn Val Ser Leu Val Met Ser Asp Thr Ala Gly Thr Cys Tyr
            260                 265                 270
```

<210> SEQ ID NO 38
<211> LENGTH: 353
<212> TYPE: PRT
<213> ORGANISM: Homo sapiens

<400> SEQUENCE: 38

```
Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
```

```
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr


<210> SEQ ID NO 39
<211> LENGTH: 222
<212> TYPE: PRT
<213> ORGANISM: Homo sapiens

<400> SEQUENCE: 39

Ala Asp Pro Cys Asp Ser Asn Pro Arg Gly Val Ser Ala Tyr Leu Ser
1               5                   10                  15

Arg Pro Ser Pro Phe Asp Leu Phe Ile Arg Lys Ser Pro Thr Ile Thr
            20                  25                  30

Cys Leu Val Val Asp Leu Ala Pro Ser Lys Gly Thr Val Asn Leu Thr
        35                  40                  45

Trp Ser Arg Ala Ser Gly Lys Pro Val Asn His Ser Thr Arg Lys Glu
    50                  55                  60

Glu Lys Gln Arg Asn Gly Thr Leu Thr Val Thr Ser Thr Leu Pro Val
```

-continued

```
65                  70                  75                  80

Gly Thr Arg Asp Trp Ile Glu Gly Glu Thr Tyr Gln Cys Arg Val Thr
                85                  90                  95

His Pro His Leu Pro Arg Ala Leu Met Arg Ser Thr Thr Lys Thr Ser
            100                 105                 110

Gly Pro Arg Ala Ala Pro Glu Val Tyr Ala Phe Ala Thr Pro Glu Trp
        115                 120                 125

Pro Gly Ser Arg Asp Lys Arg Thr Leu Ala Cys Leu Ile Gln Asn Phe
    130                 135                 140

Met Pro Glu Asp Ile Ser Val Gln Trp Leu His Asn Glu Val Gln Leu
145                 150                 155                 160

Pro Asp Ala Arg His Ser Thr Thr Gln Pro Arg Lys Thr Lys Gly Ser
                165                 170                 175

Gly Phe Phe Val Phe Ser Arg Leu Glu Val Thr Arg Ala Glu Trp Glu
            180                 185                 190

Gln Lys Asp Glu Phe Ile Cys Arg Ala Val His Glu Ala Ala Ser Pro
        195                 200                 205

Ser Gln Thr Val Gln Arg Ala Val Ser Val Asn Pro Gly Lys
    210                 215                 220


<210> SEQ ID NO 40
<211> LENGTH: 327
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

-continued

```
Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 41
<211> LENGTH: 365
<212> TYPE: PRT
<213> ORGANISM: Homo sapiens

<400> SEQUENCE: 41

Met Ala Val Met Ala Pro Arg Thr Leu Leu Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Lys Met Glu Pro Arg Ala Pro Trp Ile Glu Gln Glu Gly
65                  70                  75                  80

Pro Glu Tyr Trp Asp Gln Glu Thr Arg Asn Met Lys Ala His Ser Gln
                85                  90                  95

Thr Asp Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
        115                 120                 125

Pro Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Val His Ala
                165                 170                 175

Ala Glu Gln Arg Arg Val Tyr Leu Glu Gly Arg Cys Val Asp Gly Leu
            180                 185                 190

Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270
```

```
Val Pro Ser Gly Glu Glu Gln Arg Tyr Thr Cys His Val Gln His Glu
        275                 280                 285

Gly Leu Pro Lys Pro Leu Thr Leu Arg Trp Glu Leu Ser Ser Gln Pro
    290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
        355                 360                 365


<210> SEQ ID NO 42
<211> LENGTH: 362
<212> TYPE: PRT
<213> ORGANISM: Homo sapiens

<400> SEQUENCE: 42

Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asp Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
```

```
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360


<210> SEQ ID NO 43
<211> LENGTH: 366
<212> TYPE: PRT
<213> ORGANISM: Homo sapiens

<400> SEQUENCE: 43

Met Arg Val Met Ala Pro Arg Ala Leu Leu Leu Leu Leu Ser Gly Gly
1               5                   10                  15

Leu Ala Leu Thr Glu Thr Trp Ala Cys Ser His Ser Met Arg Tyr Phe
            20                  25                  30

Asp Thr Ala Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Asn Tyr Lys Arg Gln Ala Gln
                85                  90                  95

Ala Asp Arg Val Ser Leu Arg Asn Leu Arg Gly Tyr Tyr Asn Gln Ser
            100                 105                 110

Glu Asp Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Leu Glu Ala Ala Arg Ala
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu Pro
        195                 200                 205

Pro Lys Thr His Val Thr His His Pro Leu Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Met Gln His Glu
        275                 280                 285
```

```
Gly Leu Gln Glu Pro Leu Thr Leu Ser Trp Glu Pro Ser Ser Gln Pro
    290                 295                 300

Thr Ile Pro Ile Met Gly Ile Val Ala Gly Leu Ala Val Leu Val Val
305                 310                 315                 320

Leu Ala Val Leu Gly Ala Val Val Thr Ala Met Met Cys Arg Arg Lys
                325                 330                 335

Ser Ser Gly Gly Lys Gly Gly Ser Cys Ser Gln Ala Ala Cys Ser Asn
            340                 345                 350

Ser Ala Gln Gly Ser Asp Glu Ser Leu Ile Thr Cys Lys Ala
        355                 360                 365


<210> SEQ ID NO 44
<211> LENGTH: 119
<212> TYPE: PRT
<213> ORGANISM: Homo sapiens

<400> SEQUENCE: 44

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115


<210> SEQ ID NO 45
<211> LENGTH: 119
<212> TYPE: PRT
<213> ORGANISM: Pan troglodytes

<400> SEQUENCE: 45

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115
```

<210> SEQ ID NO 46
<211> LENGTH: 119
<212> TYPE: PRT
<213> ORGANISM: Macaca mulatta

<400> SEQUENCE: 46

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Pro Glu Asn Gly Lys Pro Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Lys Met Gly Lys Val Glu His Ser Asp Leu Ser Phe Ser Lys Asp Trp
65                  70                  75                  80

Ser Phe Tyr Leu Leu Tyr Tyr Thr Glu Phe Thr Pro Asn Glu Lys Asp
                85                  90                  95

Glu Tyr Ala Cys Arg Val Asn His Val Thr Leu Ser Gly Pro Arg Thr
            100                 105                 110

Val Lys Trp Asp Arg Asp Met
        115
```

<210> SEQ ID NO 47
<211> LENGTH: 118
<212> TYPE: PRT
<213> ORGANISM: Bos taurus

<400> SEQUENCE: 47

```
Met Ala Arg Phe Val Ala Leu Val Leu Leu Gly Leu Leu Ser Leu Ser
1               5                   10                  15

Gly Leu Asp Ala Ile Gln Arg Pro Pro Lys Ile Gln Val Tyr Ser Arg
            20                  25                  30

His Pro Pro Glu Asp Gly Lys Pro Asn Tyr Leu Asn Cys Tyr Val Tyr
        35                  40                  45

Gly Phe His Pro Pro Gln Ile Glu Ile Asp Leu Leu Lys Asn Gly Glu
    50                  55                  60

Lys Ile Lys Ser Glu Gln Ser Asp Leu Ser Phe Ser Lys Asp Trp Ser
65                  70                  75                  80

Phe Tyr Leu Leu Ser His Ala Glu Phe Thr Pro Asn Ser Lys Asp Gln
                85                  90                  95

Tyr Ser Cys Arg Val Lys His Val Thr Leu Glu Gln Pro Arg Ile Val
            100                 105                 110

Lys Trp Asp Arg Asp Leu
        115
```

<210> SEQ ID NO 48
<211> LENGTH: 119
<212> TYPE: PRT
<213> ORGANISM: Mus musculus

<400> SEQUENCE: 48

```
Met Ala Arg Ser Val Thr Leu Val Phe Leu Val Leu Val Ser Leu Thr
1               5                   10                  15

Gly Leu Tyr Ala Ile Gln Lys Thr Pro Gln Ile Gln Val Tyr Ser Arg
            20                  25                  30

His Pro Pro Glu Asn Gly Lys Pro Asn Ile Leu Asn Cys Tyr Val Thr
```

```
        35                  40                  45

Gln Phe His Pro Pro His Ile Glu Ile Gln Met Leu Lys Asn Gly Lys
    50                  55                  60

Lys Ile Pro Lys Val Glu Met Ser Asp Met Ser Phe Ser Lys Asp Trp
65                  70                  75                  80

Ser Phe Tyr Ile Leu Ala His Thr Glu Phe Thr Pro Thr Glu Thr Asp
                85                  90                  95

Thr Tyr Ala Cys Arg Val Lys His Ala Ser Met Ala Glu Pro Lys Thr
            100                 105                 110

Val Tyr Trp Asp Arg Asp Met
        115
```

```
<210> SEQ ID NO 49
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(5)
<223> OTHER INFORMATION: This stretch of residues may be repeated.

<400> SEQUENCE: 49

Gly Ser Gly Gly Ser
1               5


<210> SEQ ID NO 50
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(4)
<223> OTHER INFORMATION: This stretch of residues may be repeated.

<400> SEQUENCE: 50

Gly Gly Gly Ser
1


<210> SEQ ID NO 51
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 51

Gly Gly Ser Gly
1


<210> SEQ ID NO 52
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 52

Gly Gly Ser Gly Gly
1               5


<210> SEQ ID NO 53
```

```
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 53

Gly Ser Gly Ser Gly
1               5


<210> SEQ ID NO 54
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 54

Gly Ser Gly Gly Gly
1               5


<210> SEQ ID NO 55
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 55

Gly Gly Gly Ser Gly
1               5


<210> SEQ ID NO 56
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 56

Gly Ser Ser Ser Gly
1               5


<210> SEQ ID NO 57
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(5)
<223> OTHER INFORMATION: This stretch of residues may be repeated up to
      10 times.

<400> SEQUENCE: 57

Gly Ser Ser Ser Ser
1               5


<210> SEQ ID NO 58
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(5)
<223> OTHER INFORMATION: This stretch of residues may be repeated up to
```

4 times.

<400> SEQUENCE: 58

Gly Ser Ser Ser Ser
1 5

<210> SEQ ID NO 59
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(5)
<223> OTHER INFORMATION: This stretch of residues may be repeated up to 5 times.

<400> SEQUENCE: 59

Gly Ser Ser Ser Ser
1 5

<210> SEQ ID NO 60
<211> LENGTH: 50
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(50)
<223> OTHER INFORMATION: Wherein up to 9 copies of GGGGS may be omitted

<400> SEQUENCE: 60

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser
50

<210> SEQ ID NO 61
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(25)
<223> OTHER INFORMATION: Wherein up to 5 copied of GGGGS may be omitted

<400> SEQUENCE: 61

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 62
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 62

Gly Gly Gly Gly Ser Ser Ser Ser Ser
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 63

Gly Gly Gly Gly Ser Ser Ser Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 64

Gly Gly Gly Gly Ser Ser Ser
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 65

Gly Gly Gly Gly Ser Ser
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 66

Gly Gly Gly Gly Ser
1               5

<210> SEQ ID NO 67
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 67

Gly Cys Gly Ala Ser Gly Gly Gly Gly Ser Gly Gly Gly Gly Ser
1               5                   10                  15

<210> SEQ ID NO 68
<211> LENGTH: 276
<212> TYPE: PRT
<213> ORGANISM: Homo sapiens

<400> SEQUENCE: 68

Gly Ser His Ser Met Arg Tyr Phe Phe Thr Ser Val Ser Arg Pro Gly

-continued

```
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275
```

<210> SEQ ID NO 69
<211> LENGTH: 274
<212> TYPE: PRT
<213> ORGANISM: Artificial Sequence
<220> FEATURE:
<223> OTHER INFORMATION: Synthetic polypeptide

<400> SEQUENCE: 69

```
Gly Pro His Ser Leu Arg Tyr Phe Val Thr Ala Val Ser Arg Pro Gly
1               5                   10                  15

Leu Gly Glu Pro Arg Phe Ile Ala Val Gly Tyr Val Asp Asp Thr Gln
            20                  25                  30

Phe Val Arg Phe Asp Ser Asp Ala Asp Asn Pro Arg Phe Glu Pro Arg
        35                  40                  45

Ala Pro Trp Met Glu Gln Glu Gly Pro Glu Tyr Trp Glu Glu Gln Thr
    50                  55                  60

Gln Arg Ala Lys Ser Asp Glu Gln Trp Phe Arg Val Ser Leu Arg Thr
65                  70                  75                  80

Ala Gln Arg Tyr Tyr Asn Gln Ser Lys Gly Gly Ser His Thr Phe Gln
```

```
                85                  90                  95

Arg Met Phe Gly Cys Asp Val Gly Ser Asp Trp Arg Leu Leu Arg Gly
            100                 105                 110

Tyr Gln Gln Phe Ala Tyr Asp Gly Arg Asp Tyr Ile Ala Leu Asn Glu
        115                 120                 125

Asp Leu Lys Thr Trp Thr Ala Ala Asp Thr Ala Ala Leu Ile Thr Arg
    130                 135                 140

Arg Lys Trp Glu Gln Ala Gly Asp Ala Glu Tyr Tyr Arg Ala Tyr Leu
145                 150                 155                 160

Glu Gly Glu Cys Val Glu Trp Leu Arg Arg Tyr Leu Glu Leu Gly Asn
                165                 170                 175

Glu Thr Leu Leu Arg Thr Asp Ser Pro Lys Ala His Val Thr Tyr His
            180                 185                 190

Pro Arg Ser Gln Val Asp Val Thr Leu Arg Cys Trp Ala Leu Gly Phe
        195                 200                 205

Tyr Pro Ala Asp Ile Thr Leu Thr Trp Gln Leu Asn Gly Glu Asp Leu
    210                 215                 220

Thr Gln Asp Met Glu Leu Val Glu Thr Arg Pro Ala Gly Asp Gly Thr
225                 230                 235                 240

Phe Gln Lys Trp Ala Ala Val Val Val Pro Leu Gly Lys Glu Gln Asn
                245                 250                 255

Tyr Thr Cys His Val His His Lys Gly Leu Pro Glu Pro Leu Thr Leu
            260                 265                 270

Arg Trp


<210> SEQ ID NO 70
<211> LENGTH: 99
<212> TYPE: PRT
<213> ORGANISM: Artificial Sequence
<220> FEATURE:
<223> OTHER INFORMATION: Synthetic polypeptide

<400> SEQUENCE: 70

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met


<210> SEQ ID NO 71
<211> LENGTH: 99
<212> TYPE: PRT
<213> ORGANISM: Artificial Sequence
<220> FEATURE:
<223> OTHER INFORMATION: Synthetic polypeptide

<400> SEQUENCE: 71

Ile Gln Arg Thr Pro Lys Ile Gln Val Tyr Ser Cys His Pro Ala Glu
1               5                   10                  15
```

```
Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met


<210> SEQ ID NO 72
<211> LENGTH: 276
<212> TYPE: PRT
<213> ORGANISM: Artificial Sequence
<220> FEATURE:
<223> OTHER INFORMATION: Synthetic polypeptide

<400> SEQUENCE: 72

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270
```

```
Arg Trp Glu Pro
        275


<210> SEQ ID NO 73
<211> LENGTH: 276
<212> TYPE: PRT
<213> ORGANISM: Artificial Sequence
<220> FEATURE:
<223> OTHER INFORMATION: Synthetic polypeptide

<400> SEQUENCE: 73

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 74
<211> LENGTH: 99
<212> TYPE: PRT
<213> ORGANISM: Artificial Sequence
<220> FEATURE:
<223> OTHER INFORMATION: Synthetic polypeptide

<400> SEQUENCE: 74

Ile Gln Arg Thr Pro Lys Ile Gln Val Tyr Ser Cys His Pro Ala Glu
1               5                   10                  15
```

```
Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met


<210> SEQ ID NO 75
<211> LENGTH: 276
<212> TYPE: PRT
<213> ORGANISM: Artificial Sequence
<220> FEATURE:
<223> OTHER INFORMATION: Synthetic polypeptide

<400> SEQUENCE: 75

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270
```

-continued

```
Arg Trp Glu Pro
        275


<210> SEQ ID NO 76
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Xaa may be any amino acid except Pro.

<400> SEQUENCE: 76

Val Pro Gly Xaa Gly
1               5


<210> SEQ ID NO 77
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 77

Tyr Pro Tyr Asp Val Pro Asp Tyr Ala
1               5


<210> SEQ ID NO 78
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 78

Asp Tyr Lys Asp Asp Asp Asp Lys
1               5


<210> SEQ ID NO 79
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 79

Glu Gln Lys Leu Ile Ser Glu Glu Asp Leu
1               5                   10


<210> SEQ ID NO 80
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 80

His His His His His
1               5


<210> SEQ ID NO 81
<211> LENGTH: 6
<212> TYPE: PRT
<213> ORGANISM: Artificial Sequence
<220> FEATURE:
<223> OTHER INFORMATION: Synthetic polypeptide
```

<400> SEQUENCE: 81

His His His His His His
1 5

<210> SEQ ID NO 82
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 82

Trp Ser His Pro Gln Phe Glu Lys
1 5

<210> SEQ ID NO 83
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 83

Arg Tyr Ile Arg Ser
1 5

<210> SEQ ID NO 84
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 84

Phe His His Thr
1

<210> SEQ ID NO 85
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 85

Trp Glu Ala Ala Ala Arg Glu Ala Cys Cys Arg Glu Cys Cys Ala Arg
1 5 10 15

Ala

<210> SEQ ID NO 86
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 86

Leu Glu Val Leu Phe Gln Gly Pro
1 5

<210> SEQ ID NO 87
<211> LENGTH: 7
<212> TYPE: PRT
<213> ORGANISM: Artificial Sequence
<220> FEATURE:

<223> OTHER INFORMATION: Synthetic polypeptide

<400> SEQUENCE: 87

Glu Asn Leu Tyr Thr Gln Ser
1 5

<210> SEQ ID NO 88
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 88

Asp Asp Asp Asp Lys
1 5

<210> SEQ ID NO 89
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 89

Leu Val Pro Arg
1

<210> SEQ ID NO 90
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 90

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 91
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 91

Gly Ser Gly Glu Gly Arg Gly Ser Leu Leu Thr Cys Gly Asp Val Glu
1 5 10 15

Glu Asn Pro Gly Pro
20

<210> SEQ ID NO 92
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 92

Gly Ser Gly Gln Cys Thr Asn Tyr Ala Leu Leu Lys Leu Ala Gly Asp
1 5 10 15

Val Glu Ser Asn Pro Gly Pro

20

<210> SEQ ID NO 93
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 93

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 94
<211> LENGTH: 1191
<212> TYPE: DNA
<213> ORGANISM: Artificial Sequence
<220> FEATURE:
<223> OTHER INFORMATION: Synthetic polynucleotide

<400> SEQUENCE: 94
gccaccatgt ctcgctccgt ggccttagct gtgctcgcgc tactctctct ttctggcctg 60
gaggccagca tcatcaactt cgagaagctg ggcggaggcg caagcggtgg cggtggctct 120
ggtggcggtg gcagtatgat ccagaaaacc ccgcagattc aagtttacag ttgccatccg 180
ccggaaaacg gcaaaccgaa catcctgaat tgctatgtca cccagtttca tccgccgcac 240
atcgaaatcc aaatgctgaa aaacggcaag aaaattccga aagtggaaat gagtgacatg 300
agcttttcta aagattggtc cttctacatt ctggcccata ccgaattcac cccgacggaa 360
accgatacgt atgcatgtcg cgtgaaacac gcctctatgg cagaaccgaa aaccgtttac 420
tgggatcgtg acatgggtgg cggtggctcc ggtggcggtg gctcaggtgg cggtggctcg 480
ggtggcggtg gcagtggtgg cggtggcagt gctgctcctc tgaagattca agcttatttc 540
aatgagactg cagacctgcc atgccaattt gcaaactctc aaaaccaaag cctgagtgag 600
ctagtagtat tttggcagga ccaggaaaac ttggttctga atgaggtata cttaggcaaa 660
gagaaatttg acagtgttca ttccaagtat atgggccgca caagttttga ttcggacagt 720
tggaccctga gacttcacaa tcttcagatc aaggacaagg gcttgtatca atgtatcatc 780
catcacaaaa agcccacagg aatgattcgc atccaccaga tgaattctga actgtcagtg 840
cttgctaact tcagtcaacc tgaaatagta ccaatttcta atataacaga aaatgtgtac 900
ataaatttga cctgctcatc tatacacggt tacccagaac ctaagaagat gagtgttttg 960
ctaagaacca agaattcaac tatcgagtat gatggtatta tgcagaaatc tcaagataat 1020
gtcacagaac tgtacgacgt ttccatcagc ttgtctgttt cattccctga tgttacgagc 1080
aatatgacca tcttctgtat tctggaaact gacaagacgc ggcttttatc ttcacctttc 1140
tctatagagc ttgaggaccc tcagcctccc ccagaccaca ttccttaata g 1191

<210> SEQ ID NO 95
<211> LENGTH: 1191
<212> TYPE: DNA
<213> ORGANISM: Artificial Sequence
<220> FEATURE:
<223> OTHER INFORMATION: Synthetic polynucleotide

<400> SEQUENCE: 95
gccaccatgt ctcgctccgt ggccttagct gtgctcgcgc tactctctct ttctggcctg 60

```
gaggccagca tcatcaactt cgagaagctg ggcggaggcg caagcggtgg cggtggctct    120

ggtggcggtg gcagtatgat ccagaaaacc ccgcagattc aagtttacag ttgccatccg    180

ccggaaaacg gcaaaccgaa catcctgaat tgctatgtca cccagtttca tccgccgcac    240

atcgaaatcc aaatgctgaa aaacggcaag aaaattccga aagtggaaat gagtgacatg    300

agcttttcta aagattggtc cttctacatt ctggcccata ccgaattcac cccgacggaa    360

accgatacgt atgcatgtcg cgtgaaacac gcctctatgg cagaaccgaa aaccgtttac    420

tgggatcgtg acatgggtgg cggtggctcc ggtggcggtg gctcaggtgg cggtggctcg    480

ggtggcggtg gcagtggtgg cggtggcagt gctgctcctc tgaagattca agcttatttc    540

aatgagactg cagacctgcc atgccaattt gcaaactctc aaaaccaaag cctgagtgag    600

ctagtagtat tttggcagga ccaggaaaac ttggttctga atgaggtata cttaggcaaa    660

gagaaatttg acagtgttca ttccaagtat atgaaccgca caagttttga ttcggacagt    720

tggaccctga gacttcacaa tcttcagatc aaggacaagg gcttgtatca atgtatcatc    780

catcacaaaa agcccacagg aatgattcgc atccaccaga tgaattctga actgtcagtg    840

cttgctaact tcagtcaacc tgaaatagta ccaatttcta atataacaga aaatgtgtac    900

ataaatttga cctgctcatc tatacacggt tacccagaac ctaagaagat gagtgttttg    960

ctaagaacca agaattcaac tatcgagtat gatggtatta tgcagaaatc tcaagataat   1020

gtcacagaac tgtacgacgt ttccatcagc ttgtctgttt cattccctga tgttacgagc   1080

aatatgacca tcttctgtat tctggaaact gacaagacgc ggcttttatc ttcacctttc   1140

tctatagagc ttgaggaccc tcagcctccc ccagaccaca ttccttaata g            1191
```

```
<210> SEQ ID NO 96
<211> LENGTH: 1191
<212> TYPE: DNA
<213> ORGANISM: Artificial Sequence
<220> FEATURE:
<223> OTHER INFORMATION: Synthetic polynucleotide

<400> SEQUENCE: 96
```

```
gccaccatgt ctcgctccgt ggccttagct gtgctcgcgc tactctctct ttctggcctg     60

gaggccagca tcatcaactt cgagaagctg ggcggaggcg caagcggtgg cggtggctct    120

ggtggcggtg gcagtatgat ccagaaaacc ccgcagattc aagtttacag ttgccatccg    180

ccggaaaacg gcaaaccgaa catcctgaat tgctatgtca cccagtttca tccgccgcac    240

atcgaaatcc aaatgctgaa aaacggcaag aaaattccga aagtggaaat gagtgacatg    300

agcttttcta aagattggtc cttctacatt ctggcccata ccgaattcac cccgacggaa    360

accgatacgt atgcatgtcg cgtgaaacac gcctctatgg cagaaccgaa aaccgtttac    420

tgggatcgtg acatgggtgg cggtggctcc ggtggcggtg gctcaggtgg cggtggctcg    480

ggtggcggtg gcagtggtgg cggtggcagt gctgctcctc tgaagattca agcttatttc    540

aatgagactg cagacctgcc atgccaattt gcaaactctc aaaaccaaag cctgagtgag    600

ctagtagtat tttggcagga ccaggaaaac ttggttctga atgaggtata cttaggcaaa    660

gagaaatttg acagtgttca ttccaagtat atgggccgca caagttttgc ctcggacagt    720

tggaccctga gacttcacaa tcttcagatc aaggacaagg gcttgtatca atgtatcatc    780

catcacaaaa agcccacagg aatgattcgc atccaccaga tgaattctga actgtcagtg    840

cttgctaact tcagtcaacc tgaaatagta ccaatttcta atataacaga aaatgtgtac    900
```

ataaatttga cctgctcatc tatacacggt tacccagaac ctaagaagat gagtgttttg 960
ctaagaacca agaattcaac tatcgagtat gatggtatta tgcagaaatc tcaagataat 1020
gtcacagaac tgtacgacgt ttccatcagc ttgtctgttt cattccctga tgttacgagc 1080
aatatgacca tcttctgtat tctggaaact gacaagacgc ggcttttatc ttcacctttc 1140
tctatagagc ttgaggaccc tcagcctccc ccagaccaca ttccttaata g 1191

<210> SEQ ID NO 97
<211> LENGTH: 1191
<212> TYPE: DNA
<213> ORGANISM: Artificial Sequence
<220> FEATURE:
<223> OTHER INFORMATION: Synthetic polynucleotide

<400> SEQUENCE: 97
gccaccatgt ctcgctccgt ggccttagct gtgctcgcgc tactctctct ttctggcctg 60
gaggccagca tcatcaactt cgagaagctg ggcggaggcg caagcggtgg cggtggctct 120
ggtggcggtg gcagtatgat ccagaaaacc ccgcagattc aagtttacag ttgccatccg 180
ccggaaaacg gcaaaccgaa catcctgaat tgctatgtca cccagtttca tccgccgcac 240
atcgaaatcc aaatgctgaa aaacggcaag aaaattccga aagtggaaat gagtgacatg 300
agcttttcta aagattggtc cttctacatt ctggcccata ccgaattcac cccgacggaa 360
accgatacgt atgcatgtcg cgtgaaacac gcctctatgg cagaaccgaa aaccgtttac 420
tgggatcgtg acatgggtgg cggtggctcc ggtggcggtg gctcaggtgg cggtggctcg 480
ggtggcggtg gcagtggtgg cggtggcagt gctgctcctc tgaagattca agcttatttc 540
aatgagactg cagacctgcc atgccaattt gcaaactctc aaaaccaaag cctgagtgag 600
ctagtagtat tttggcagga ccaggaaaac ttggttctga atgaggtata cttaggcaaa 660
gagaaatttg acagtgttca ttccaagtat atgggccgca caagttttga ttcggacagt 720
gccaccctga gacttcacaa tcttcagatc aaggacaagg gcttgtatca atgtatcatc 780
catcacaaaa agcccacagg aatgattcgc atccaccaga tgaattctga actgtcagtg 840
cttgctaact tcagtcaacc tgaaatagta ccaatttcta atataacaga aaatgtgtac 900
ataaatttga cctgctcatc tatacacggt tacccagaac ctaagaagat gagtgttttg 960
ctaagaacca agaattcaac tatcgagtat gatggtatta tgcagaaatc tcaagataat 1020
gtcacagaac tgtacgacgt ttccatcagc ttgtctgttt cattccctga tgttacgagc 1080
aatatgacca tcttctgtat tctggaaact gacaagacgc ggcttttatc ttcacctttc 1140
tctatagagc ttgaggaccc tcagcctccc ccagaccaca ttccttaata g 1191

<210> SEQ ID NO 98
<211> LENGTH: 1191
<212> TYPE: DNA
<213> ORGANISM: Artificial Sequence
<220> FEATURE:
<223> OTHER INFORMATION: Synthetic polynucleotide

<400> SEQUENCE: 98
gccaccatgt ctcgctccgt ggccttagct gtgctcgcgc tactctctct ttctggcctg 60
gaggccagca tcatcaactt cgagaagctg ggcggaggcg caagcggtgg cggtggctct 120
ggtggcggtg gcagtatgat ccagaaaacc ccgcagattc aagtttacag ttgccatccg 180
ccggaaaacg gcaaaccgaa catcctgaat tgctatgtca cccagtttca tccgccgcac 240
atcgaaatcc aaatgctgaa aaacggcaag aaaattccga aagtggaaat gagtgacatg 300

```
agcttttcta aagattggtc cttctacatt ctggcccata ccgaattcac cccgacggaa    360

accgatacgt atgcatgtcg cgtgaaacac gcctctatgg cagaaccgaa aaccgtttac    420

tgggatcgtg acatgggtgg cggtggctcc ggtggcggtg gctcaggtgg cggtggctcg    480

ggtggcggtg gcagtggtgg cggtggcagt gctgctcctc tgaagattca agcttatttc    540

aatgagactg cagacctgcc atgccaattt gcaaactctc aaaaccaaag cctgagtgag    600

ctagtagtat tttggcagga ccaggaaaac ttggttctga atgaggtata cttaggcaaa    660

gagaaatttg acagtgttca ttccaagtat atgggccgca caagttttga ttcggacagt    720

tggaccctga gacttcacaa tcttcagatc aaggacaagg gcttgtatca atgtatcatc    780

catgccaaaa agcccacagg aatgattcgc atccaccaga tgaattctga actgtcagtg    840

cttgctaact tcagtcaacc tgaaatagta ccaatttcta atataacaga aaatgtgtac    900

ataaatttga cctgctcatc tatacacggt tacccagaac ctaagaagat gagtgttttg    960

ctaagaacca agaattcaac tatcgagtat gatggtatta tgcagaaatc tcaagataat   1020

gtcacagaac tgtacgacgt ttccatcagc ttgtctgttt cattccctga tgttacgagc   1080

aatatgacca tcttctgtat tctggaaact gacaagacgc ggcttttatc ttcacctttc   1140

tctatagagc ttgaggaccc tcagcctccc ccagaccaca ttccttaata g            1191
```

<210> SEQ ID NO 99
<211> LENGTH: 849
<212> TYPE: DNA
<213> ORGANISM: Artificial Sequence
<220> FEATURE:
<223> OTHER INFORMATION: Synthetic polynucleotide

<400> SEQUENCE: 99

```
gccaccatgt ctcgctccgt ggccttagct gtgctcgcgc tactctctct ttctggcctg     60

gaggccagca tcatcaactt cgagaagctg ggcggaggcg caagcggtgg cggtggctct    120

ggtggcggtg gcagtatgat ccagaaaacc ccgcagattc aagtttacag ttgccatccg    180

ccggaaaacg gcaaaccgaa catcctgaat tgctatgtca cccagtttca tccgccgcac    240

atcgaaatcc aaatgctgaa aaacggcaag aaaattccga aagtggaaat gagtgacatg    300

agcttttcta aagattggtc cttctacatt ctggcccata ccgaattcac cccgacggaa    360

accgatacgt atgcatgtcg cgtgaaacac gcctctatgg cagaaccgaa aaccgtttac    420

tgggatcgtg acatgggtgg cggtggctcc ggtggcggtg gctcaggtgg cggtggctcg    480

ggtggcggtg gcagtggtgg cggtggcagt gctgctcctc tgaagattca agcttatttc    540

aatgagactg cagacctgcc atgccaattt gcaaactctc aaaaccaaag cctgagtgag    600

ctagtagtat tttggcagga ccaggaaaac ttggttctga atgaggtata cttaggcaaa    660

gagaaatttg acagtgttca ttccaagtat atgggccgca caagttttga ttcggacagt    720

tggaccctga gacttcacaa tcttcagatc aaggacaagg gcttgtatca atgtatcatc    780

catcacaaaa agcccacagg aatgattcgc atccaccaga tgaattctga actgtcagtg    840

ctttaatag                                                             849
```

<210> SEQ ID NO 100
<211> LENGTH: 849
<212> TYPE: DNA
<213> ORGANISM: Artificial Sequence
<220> FEATURE:
<223> OTHER INFORMATION: Synthetic polynucleotide

<400> SEQUENCE: 100
gccaccatgt ctcgctccgt ggccttagct gtgctcgcgc tactctctct ttctggcctg 60
gaggccagca tcatcaactt cgagaagctg ggcggaggcg caagcggtgg cggtggctct 120
ggtggcggtg gcagtatgat ccagaaaacc ccgcagattc aagtttacag ttgccatccg 180
ccggaaaacg gcaaaccgaa catcctgaat tgctatgtca cccagtttca tccgccgcac 240
atcgaaatcc aaatgctgaa aaacggcaag aaaattccga aagtggaaat gagtgacatg 300
agcttttcta aagattggtc cttctacatt ctggcccata ccgaattcac cccgacggaa 360
accgatacgt atgcatgtcg cgtgaaacac gcctctatgg cagaaccgaa aaccgtttac 420
tgggatcgtg acatgggtgg cggtggctcc ggtggcggtg gctcaggtgg cggtggctcg 480
ggtggcggtg gcagtggtgg cggtggcagt gctgctcctc tgaagattca agcttatttc 540
aatgagactg cagacctgcc atgccaattt gcaaactctc aaaaccaaag cctgagtgag 600
ctagtagtat tttggcagga ccaggaaaac ttggttctga atgaggtata cttaggcaaa 660
gagaaatttg acagtgttca ttccaagtat atgaaccgca caagttttga ttcggacagt 720
tggaccctga gacttcacaa tcttcagatc aaggacaagg gcttgtatca atgtatcatc 780
catcacaaaa agcccacagg aatgattcgc atccaccaga tgaattctga actgtcagtg 840
ctttaatag 849

<210> SEQ ID NO 101
<211> LENGTH: 849
<212> TYPE: DNA
<213> ORGANISM: Artificial Sequence
<220> FEATURE:
<223> OTHER INFORMATION: Synthetic polynucleotide

<400> SEQUENCE: 101
gccaccatgt ctcgctccgt ggccttagct gtgctcgcgc tactctctct ttctggcctg 60
gaggccagca tcatcaactt cgagaagctg ggcggaggcg caagcggtgg cggtggctct 120
ggtggcggtg gcagtatgat ccagaaaacc ccgcagattc aagtttacag ttgccatccg 180
ccggaaaacg gcaaaccgaa catcctgaat tgctatgtca cccagtttca tccgccgcac 240
atcgaaatcc aaatgctgaa aaacggcaag aaaattccga aagtggaaat gagtgacatg 300
agcttttcta aagattggtc cttctacatt ctggcccata ccgaattcac cccgacggaa 360
accgatacgt atgcatgtcg cgtgaaacac gcctctatgg cagaaccgaa aaccgtttac 420
tgggatcgtg acatgggtgg cggtggctcc ggtggcggtg gctcaggtgg cggtggctcg 480
ggtggcggtg gcagtggtgg cggtggcagt gctgctcctc tgaagattca agcttatttc 540
aatgagactg cagacctgcc atgccaattt gcaaactctc aaaaccaaag cctgagtgag 600
ctagtagtat tttggcagga ccaggaaaac ttggttctga atgaggtata cttaggcaaa 660
gagaaatttg acagtgttca ttccaagtat atgggccgca caagttttgc ctcggacagt 720
tggaccctga gacttcacaa tcttcagatc aaggacaagg gcttgtatca atgtatcatc 780
catcacaaaa agcccacagg aatgattcgc atccaccaga tgaattctga actgtcagtg 840
ctttaatag 849

<210> SEQ ID NO 102
<211> LENGTH: 849
<212> TYPE: DNA
<213> ORGANISM: Artificial Sequence
<220> FEATURE:
<223> OTHER INFORMATION: Synthetic polynucleotide

<400> SEQUENCE: 102

```
gccaccatgt ctcgctccgt ggccttagct gtgctcgcgc tactctctct ttctggcctg     60
gaggccagca tcatcaactt cgagaagctg ggcggaggcg caagcggtgg cggtggctct    120
ggtggcggtg gcagtatgat ccagaaaacc ccgcagattc aagtttacag ttgccatccg    180
ccggaaaacg gcaaaccgaa catcctgaat tgctatgtca cccagtttca tccgccgcac    240
atcgaaatcc aaatgctgaa aaacggcaag aaaattccga aagtggaaat gagtgacatg    300
agcttttcta aagattggtc cttctacatt ctggcccata ccgaattcac cccgacggaa    360
accgatacgt atgcatgtcg cgtgaaacac gcctctatgg cagaaccgaa aaccgtttac    420
tgggatcgtg acatgggtgg cggtggctcc ggtggcggtg gctcaggtgg cggtggctcg    480
ggtggcggtg gcagtggtgg cggtggcagt gctgctcctc tgaagattca agcttatttc    540
aatgagactg cagacctgcc atgccaattt gcaaactctc aaaaccaaag cctgagtgag    600
ctagtagtat tttggcagga ccaggaaaac ttggttctga atgaggtata cttaggcaaa    660
gagaaatttg acagtgttca ttccaagtat atgggccgca caagttttga ttcggacagt    720
gccaccctga gacttcacaa tcttcagatc aaggacaagg gcttgtatca atgtatcatc    780
catcacaaaa agcccacagg aatgattcgc atccaccaga tgaattctga actgtcagtg    840
ctttaatag                                                            849
```

<210> SEQ ID NO 103
<211> LENGTH: 849
<212> TYPE: DNA
<213> ORGANISM: Artificial Sequence
<220> FEATURE:
<223> OTHER INFORMATION: Synthetic polynucleotide

<400> SEQUENCE: 103

```
gccaccatgt ctcgctccgt ggccttagct gtgctcgcgc tactctctct ttctggcctg     60
gaggccagca tcatcaactt cgagaagctg ggcggaggcg caagcggtgg cggtggctct    120
ggtggcggtg gcagtatgat ccagaaaacc ccgcagattc aagtttacag ttgccatccg    180
ccggaaaacg gcaaaccgaa catcctgaat tgctatgtca cccagtttca tccgccgcac    240
atcgaaatcc aaatgctgaa aaacggcaag aaaattccga aagtggaaat gagtgacatg    300
agcttttcta aagattggtc cttctacatt ctggcccata ccgaattcac cccgacggaa    360
accgatacgt atgcatgtcg cgtgaaacac gcctctatgg cagaaccgaa aaccgtttac    420
tgggatcgtg acatgggtgg cggtggctcc ggtggcggtg gctcaggtgg cggtggctcg    480
ggtggcggtg gcagtggtgg cggtggcagt gctgctcctc tgaagattca agcttatttc    540
aatgagactg cagacctgcc atgccaattt gcaaactctc aaaaccaaag cctgagtgag    600
ctagtagtat tttggcagga ccaggaaaac ttggttctga atgaggtata cttaggcaaa    660
gagaaatttg acagtgttca ttccaagtat atgggccgca caagttttga ttcggacagt    720
tggaccctga gacttcacaa tcttcagatc aaggacaagg gcttgtatca atgtatcatc    780
catgccaaaa agcccacagg aatgattcgc atccaccaga tgaattctga actgtcagtg    840
ctttaatag                                                            849
```

<210> SEQ ID NO 104
<211> LENGTH: 2373
<212> TYPE: DNA
<213> ORGANISM: Artificial Sequence
<220> FEATURE:

<223> OTHER INFORMATION: Synthetic polynucleotide

<400> SEQUENCE: 104

```
gccaccatgt ctcgctccgt ggccttagct gtgctcgcgc tactctctct ttctggcctg     60
gaggccgctg ctcctctgaa gattcaagct tatttcaatg agactgcaga cctgccatgc    120
caatttgcaa actctcaaaa ccaaagcctg agtgagctag tagtattttg gcaggaccag    180
gaaaacttgg ttctgaatga ggtatactta ggcaaagaga aatttgacag tgttcattcc    240
aagtatatgg gccgcacaag ttttgattcg gacagttgga ccctgagact tcacaatctt    300
cagatcaagg acaagggctt gtatcaatgt atcatccatc acaaaaagcc cacaggaatg    360
attcgcatcc accagatgaa ttctgaactg tcagtgcttg ctaacttcag tcaacctgaa    420
atagtaccaa tttctaatat aacagaaaat gtgtacataa atttgacctg ctcatctata    480
cacggttacc cagaacctaa gaagatgagt gttttgctaa gaaccaagaa ttcaactatc    540
gagtatgatg gtattatgca gaaatctcaa gataatgtca cagaactgta cgacgtttcc    600
atcagcttgt ctgtttcatt ccctgatgtt acgagcaata tgaccatctt ctgtattctg    660
gaaactgaca agacgcggct tttatcttca cctttctcta tagagcttga ggaccctcag    720
cctcccccag accacattcc tggaggcgga ggatctggtg gtggaggttc tggtggtggg    780
ggatctggag gcggaggatc tggcccgcat tccctgcgct actttgtgac cgctgttagc    840
cgcccgggcc tgggtgaacc gcgttacatg gaggtcggtt atgtggatga cacggagttt    900
gtgcgtttcg attcagacgc tgagaacccg cgttacgaac cgcgtgcaag atggatggaa    960
caggaaggcc cggaatattg ggaaagagag acccaaaagg caaaaggcaa cgaacaaagc   1020
ttccgtgtgg acctgcgtac cctgctgggc gcctacaacc aatcaaaagg tggctcgcac   1080
acgatccagg tgatcagcgg ctgcgaggtt ggtagcgatg gccgtctgct gcgcggctat   1140
cagcaatacg cctacgacgg ttgcgattat atcgcactga atgaagacct gaaaacctgg   1200
acggcggccg atatggcagc tctgattacg aagcacaaat gggaacaggc tggcgaggcg   1260
gaaagactgc gcgcctacct ggagggtacc tgcgtggaat ggctgcgtcg ctatctgaag   1320
aacggcaatg ccaccttgct gcgtacggat agcccgaaag cacatgttac ccaccacagc   1380
cgccccgagg acaaggttac gctgcgttgt tgggctctgg gcttttatcc ggcggatatt   1440
accctgacgt ggcagctgaa cggtgaagag ctgatccaag atatggaact ggtggaaacc   1500
cgtccgtgcg gcgatggcac gttccagaaa tgggcaagcg tggttgtccc gctgggtaaa   1560
gaacaatact acacctgtca tgtttaccac cagggtctgc cggaaccgct gacgctgcgt   1620
tgggcagctg cgggtggccc cagagggccc acaatcaagc cctgtcctcc atgcaaatgc   1680
ccagcaccta acctcttggg tggaccatcc gtcttcatct tccctccaaa gatcaaggat   1740
gtactcatga tctccctgag ccccatagtc acatgtgtgg tggtggatgt gagcgaggat   1800
gacccagatg tccagatcag ctggtttgtg aacaacgtgg aagtacacac agctcagaca   1860
caaacccata gagaggatta caacagtact ctccgggtgg tcagtgccct ccccatccag   1920
caccaggact ggatgagtgg caaggagttc aaatgcaagg tcaacaacaa agacctccca   1980
gcgcccatcg agagaaccat ctcaaaaccc aaagggtcag taagagctcc acaggtatat   2040
gtcttgcctc caccagaaga agagatgact aagaaacagg tcactctgac ctgcatggtc   2100
acagacttca tgcctgaaga catttacgtg gagtggacca acaacgggaa aacagagcta   2160
aactacaaga acactgaacc agtcctggac tctgatggtt cttacttcat gtacagcaag   2220
ctgagagtgg aaaagaagaa ctgggtggaa agaaatagct actcctgttc agtggtccac   2280
```

gagggtctgc acaatcacca cacgactaag agcttctccc ggactccggg taaaggcgga 2340
tcacatcacc atcaccatca ccatcactag tga 2373

<210> SEQ ID NO 105
<211> LENGTH: 2373
<212> TYPE: DNA
<213> ORGANISM: Artificial Sequence
<220> FEATURE:
<223> OTHER INFORMATION: Synthetic polynucleotide

<400> SEQUENCE: 105
gccaccatgt ctcgctccgt ggccttagct gtgctcgcgc tactctctct ttctggcctg 60
gaggccgctg ctcctctgaa gattcaagct tatttcaatg agactgcaga cctgccatgc 120
caatttgcaa actctcaaaa ccaaagcctg agtgagctag tagtattttg gcaggaccag 180
gaaaacttgg ttctgaatga ggtatactta ggcaaagaga aatttgacag tgttcattcc 240
aagtatatga accgcacaag ttttgattcg gacagttgga ccctgagact tcacaatctt 300
cagatcaagg acaagggctt gtatcaatgt atcatccatc acaaaaagcc cacaggaatg 360
attcgcatcc accagatgaa ttctgaactg tcagtgcttg ctaacttcag tcaacctgaa 420
atagtaccaa tttctaatat aacagaaaat gtgtacataa atttgacctg ctcatctata 480
cacggttacc cagaacctaa gaagatgagt gttttgctaa gaaccaagaa ttcaactatc 540
gagtatgatg gtattatgca gaaatctcaa gataatgtca cagaactgta cgacgtttcc 600
atcagcttgt ctgtttcatt ccctgatgtt acgagcaata tgaccatctt ctgtattctg 660
gaaactgaca agacgcggct tttatcttca cctttctcta tagagcttga ggaccctcag 720
cctcccccag accacattcc tggaggcgga ggatctggtg gtggaggttc tggtggtggg 780
ggatctggag gcggaggatc tggcccgcat tccctgcgct actttgtgac cgctgttagc 840
cgcccgggcc tgggtgaacc gcgttacatg gaggtcggtt atgtggatga cacggagttt 900
gtgcgtttcg attcagacgc tgagaacccg cgttacgaac cgcgtgcaag atggatggaa 960
caggaaggcc cggaatattg ggaaagagag acccaaaagg caaaaggcaa cgaacaaagc 1020
ttccgtgtgg acctgcgtac cctgctgggc gcctacaacc aatcaaaagg tggctcgcac 1080
acgatccagg tgatcagcgg ctgcgaggtt ggtagcgatg gccgtctgct gcgcggctat 1140
cagcaatacg cctacgacgg ttgcgattat atcgcactga atgaagacct gaaaacctgg 1200
acggcggccg atatggcagc tctgattacg aagcacaaat gggaacaggc tggcgaggcg 1260
gaaagactgc gcgcctacct ggagggtacc tgcgtggaat ggctgcgtcg ctatctgaag 1320
aacggcaatg ccaccttgct gcgtacggat agcccgaaag cacatgttac ccaccacagc 1380
cgccccgagg acaaggttac gctgcgttgt tgggctctgg gcttttatcc ggcggatatt 1440
accctgacgt ggcagctgaa cggtgaagag ctgatccaag atatggaact ggtggaaacc 1500
cgtccgtgcg gcgatggcac gttccagaaa tgggcaagcg tggttgtccc gctgggtaaa 1560
gaacaatact acacctgtca tgtttaccac cagggtctgc cggaaccgct gacgctgcgt 1620
tgggcagctg cgggtggccc cagagggccc acaatcaagc cctgtcctcc atgcaaatgc 1680
ccagcaccta acctcttggg tggaccatcc gtcttcatct tccctccaaa gatcaaggat 1740
gtactcatga tctccctgag ccccatagtc acatgtgtgg tggtggatgt gagcgaggat 1800
gacccagatg tccagatcag ctggtttgtg aacaacgtgg aagtacacac agctcagaca 1860
caaacccata gagaggatta caacagtact ctccgggtgg tcagtgccct ccccatccag 1920

-continued

```
caccaggact ggatgagtgg caaggagttc aaatgcaagg tcaacaacaa agacctccca   1980

gcgcccatcg agagaaccat ctcaaaaccc aaagggtcag taagagctcc acaggtatat   2040

gtcttgcctc caccagaaga agagatgact aagaaacagg tcactctgac ctgcatggtc   2100

acagacttca tgcctgaaga catttacgtg gagtggacca acaacgggaa aacagagcta   2160

aactacaaga acactgaacc agtcctggac tctgatggtt cttacttcat gtacagcaag   2220

ctgagagtgg aaaagaagaa ctgggtggaa agaaatagct actcctgttc agtggtccac   2280

gagggtctgc acaatcacca cacgactaag agcttctccc ggactccggg taaaggcgga   2340

tcacatcacc atcaccatca ccatcactag tga                                2373
```

```
<210> SEQ ID NO 106
<211> LENGTH: 2373
<212> TYPE: DNA
<213> ORGANISM: Artificial Sequence
<220> FEATURE:
<223> OTHER INFORMATION: Synthetic polynucleotide

<400> SEQUENCE: 106

gccaccatgt ctcgctccgt ggccttagct gtgctcgcgc tactctctct ttctggcctg     60

gaggccgctg ctcctctgaa gattcaagct tatttcaatg agactgcaga cctgccatgc    120

caatttgcaa actctcaaaa ccaaagcctg agtgagctag tagtattttg gcaggaccag    180

gaaaacttgg ttctgaatga ggtatactta ggcaaagaga aatttgacag tgttcattcc    240

aagtatatgg gccgcacaag ttttgcctcg gacagttgga ccctgagact tcacaatctt    300

cagatcaagg acaagggctt gtatcaatgt atcatccatc acaaaaagcc cacaggaatg    360

attcgcatcc accagatgaa ttctgaactg tcagtgcttg ctaacttcag tcaacctgaa    420

atagtaccaa tttctaatat aacagaaaat gtgtacataa atttgacctg ctcatctata    480

cacggttacc cagaacctaa gaagatgagt gttttgctaa gaaccaagaa ttcaactatc    540

gagtatgatg gtattatgca gaaatctcaa gataatgtca cagaactgta cgacgtttcc    600

atcagcttgt ctgtttcatt ccctgatgtt acgagcaata tgaccatctt ctgtattctg    660

gaaactgaca agacgcggct tttatcttca cctttctcta tagagcttga ggaccctcag    720

cctcccccag accacattcc tggaggcgga ggatctggtg gtggaggttc tggtggtggg    780

ggatctggag gcggaggatc tggcccgcat tccctgcgct actttgtgac cgctgttagc    840

cgcccgggcc tgggtgaacc gcgttacatg gaggtcggtt atgtggatga cacggagttt    900

gtgcgtttcg attcagacgc tgagaacccg cgttacgaac cgcgtgcaag atggatggaa    960

caggaaggcc cggaatattg ggaaagagag acccaaaagg caaaaggcaa cgaacaaagc   1020

ttccgtgtgg acctgcgtac cctgctgggc gcctacaacc aatcaaaagg tggctcgcac   1080

acgatccagg tgatcagcgg ctgcgaggtt ggtagcgatg gccgtctgct gcgcggctat   1140

cagcaatacg cctacgacgg ttgcgattat atcgcactga atgaagacct gaaaacctgg   1200

acggcggccg atatggcagc tctgattacg aagcacaaat gggaacaggc tggcgaggcg   1260

gaaagactgc gcgcctacct ggagggtacc tgcgtggaat ggctgcgtcg ctatctgaag   1320

aacggcaatg ccaccttgct gcgtacggat agcccgaaag cacatgttac ccaccacagc   1380

cgccccgagg acaaggttac gctgcgttgt tgggctctgg gcttttatcc ggcggatatt   1440

accctgacgt ggcagctgaa cggtgaagag ctgatccaag atatggaact ggtggaaacc   1500

cgtccgtgcg gcgatggcac gttccagaaa tgggcaagcg tggttgtccc gctgggtaaa   1560

gaacaatact acacctgtca tgtttaccac cagggtctgc cggaaccgct gacgctgcgt   1620
```

tgggcagctg cgggtggccc cagagggccc acaatcaagc cctgtcctcc atgcaaatgc 1680
ccagcaccta acctcttggg tggaccatcc gtcttcatct tccctccaaa gatcaaggat 1740
gtactcatga tctccctgag ccccatagtc acatgtgtgg tggtggatgt gagcgaggat 1800
gacccagatg tccagatcag ctggtttgtg aacaacgtgg aagtacacac agctcagaca 1860
caaacccata gagaggatta caacagtact ctccgggtgg tcagtgccct ccccatccag 1920
caccaggact ggatgagtgg caaggagttc aaatgcaagg tcaacaacaa agacctccca 1980
gcgcccatcg agagaaccat ctcaaaaccc aaagggtcag taagagctcc acaggtatat 2040
gtcttgcctc caccagaaga agagatgact aagaaacagg tcactctgac ctgcatggtc 2100
acagacttca tgcctgaaga catttacgtg gagtggacca acaacgggaa aacagagcta 2160
aactacaaga acactgaacc agtcctggac tctgatggtt cttacttcat gtacagcaag 2220
ctgagagtgg aaaagaagaa ctgggtggaa agaaatagct actcctgttc agtggtccac 2280
gagggtctgc acaatcacca cacgactaag agcttctccc ggactccggg taaaggcgga 2340
tcacatcacc atcaccatca ccatcactag tga 2373

<210> SEQ ID NO 107
<211> LENGTH: 2373
<212> TYPE: DNA
<213> ORGANISM: Artificial Sequence
<220> FEATURE:
<223> OTHER INFORMATION: Synthetic polynucleotide

<400> SEQUENCE: 107
gccaccatgt ctcgctccgt ggccttagct gtgctcgcgc tactctctct ttctggcctg 60
gaggccgctg ctcctctgaa gattcaagct tatttcaatg agactgcaga cctgccatgc 120
caatttgcaa actctcaaaa ccaaagcctg agtgagctag tagtattttg gcaggaccag 180
gaaaacttgg ttctgaatga ggtatactta ggcaaagaga aatttgacag tgttcattcc 240
aagtatatgg gccgcacaag ttttgattcg gacagtgcca ccctgagact tcacaatctt 300
cagatcaagg acaagggctt gtatcaatgt atcatccatc acaaaaagcc cacaggaatg 360
attcgcatcc accagatgaa ttctgaactg tcagtgcttg ctaacttcag tcaacctgaa 420
atagtaccaa tttctaatat aacagaaaat gtgtacataa atttgacctg ctcatctata 480
cacggttacc cagaacctaa gaagatgagt gttttgctaa gaaccaagaa ttcaactatc 540
gagtatgatg gtattatgca gaaatctcaa gataatgtca cagaactgta cgacgtttcc 600
atcagcttgt ctgtttcatt ccctgatgtt acgagcaata tgaccatctt ctgtattctg 660
gaaactgaca agacgcggct tttatcttca cctttctcta tagagcttga ggaccctcag 720
cctcccccag accacattcc tggaggcgga ggatctggtg gtggaggttc tggtggtggg 780
ggatctggag gcggaggatc tggcccgcat tccctgcgct actttgtgac cgctgttagc 840
cgcccgggcc tgggtgaacc gcgttacatg gaggtcggtt atgtggatga cacggagttt 900
gtgcgtttcg attcagacgc tgagaacccg cgttacgaac cgcgtgcaag atggatggaa 960
caggaaggcc cggaatattg ggaaagagag acccaaaagg caaaaggcaa cgaacaaagc 1020
ttccgtgtgg acctgcgtac cctgctgggc gcctacaacc aatcaaaagg tggctcgcac 1080
acgatccagg tgatcagcgg ctgcgaggtt ggtagcgatg gccgtctgct gcgcggctat 1140
cagcaatacg cctacgacgg ttgcgattat atcgcactga atgaagacct gaaaacctgg 1200
acggcggccg atatggcagc tctgattacg aagcacaaat gggaacaggc tggcgaggcg 1260
gaaagactgc gcgcctacct ggagggtacc tgcgtggaat ggctgcgtcg ctatctgaag 1320
aacggcaatg ccaccttgct gcgtacggat agcccgaaag cacatgttac ccaccacagc 1380
cgccccgagg acaaggttac gctgcgttgt tgggctctgg gcttttatcc ggcggatatt 1440
accctgacgt ggcagctgaa cggtgaagag ctgatccaag atatggaact ggtggaaacc 1500
cgtccgtgcg gcgatggcac gttccagaaa tgggcaagcg tggttgtccc gctgggtaaa 1560
gaacaatact acacctgtca tgtttaccac cagggtctgc cggaaccgct gacgctgcgt 1620
tgggcagctg cgggtggccc cagagggccc acaatcaagc cctgtcctcc atgcaaatgc 1680
ccagcaccta acctcttggg tggaccatcc gtcttcatct tccctccaaa gatcaaggat 1740
gtactcatga tctccctgag ccccatagtc acatgtgtgg tggtggatgt gagcgaggat 1800
gacccagatg tccagatcag ctggtttgtg aacaacgtgg aagtacacac agctcagaca 1860
caaacccata gagaggatta caacagtact ctccgggtgg tcagtgccct ccccatccag 1920
caccaggact ggatgagtgg caaggagttc aaatgcaagg tcaacaacaa agacctccca 1980
gcgcccatcg agagaaccat ctcaaaaccc aaagggtcag taagagctcc acaggtatat 2040
gtcttgcctc caccagaaga agagatgact aagaaacagg tcactctgac ctgcatggtc 2100
acagacttca tgcctgaaga catttacgtg gagtggacca acaacgggaa aacagagcta 2160
aactacaaga acactgaacc agtcctggac tctgatggtt cttacttcat gtacagcaag 2220
ctgagagtgg aaaagaagaa ctgggtggaa agaaatagct actcctgttc agtggtccac 2280
gagggtctgc acaatcacca cacgactaag agcttctccc ggactccggg taaaggcgga 2340
tcacatcacc atcaccatca ccatcactag tga 2373

<210> SEQ ID NO 108
<211> LENGTH: 2373
<212> TYPE: DNA
<213> ORGANISM: Artificial Sequence
<220> FEATURE:
<223> OTHER INFORMATION: Synthetic polynucleotide

<400> SEQUENCE: 108
gccaccatgt ctcgctccgt ggccttagct gtgctcgcgc tactctctct ttctggcctg 60
gaggccgctg ctcctctgaa gattcaagct tatttcaatg agactgcaga cctgccatgc 120
caatttgcaa actctcaaaa ccaaagcctg agtgagctag tagtattttg gcaggaccag 180
gaaaacttgg ttctgaatga ggtatactta ggcaaagaga aatttgacag tgttcattcc 240
aagtatatgg gccgcacaag ttttgattcg gacagttgga ccctgagact tcacaatctt 300
cagatcaagg acaagggctt gtatcaatgt atcatccatg ccaaaaagcc cacaggaatg 360
attcgcatcc accagatgaa ttctgaactg tcagtgcttg ctaacttcag tcaacctgaa 420
atagtaccaa tttctaatat aacagaaaat gtgtacataa atttgacctg ctcatctata 480
cacggttacc cagaacctaa gaagatgagt gttttgctaa gaaccaagaa ttcaactatc 540
gagtatgatg gtattatgca gaaatctcaa gataatgtca cagaactgta cgacgtttcc 600
atcagcttgt ctgtttcatt ccctgatgtt acgagcaata tgaccatctt ctgtattctg 660
gaaactgaca agacgcggct tttatcttca cctttctcta tagagcttga ggaccctcag 720
cctcccccag accacattcc tggaggcgga ggatctggtg gtggaggttc tggtggtggg 780
ggatctggag gcggaggatc tggcccgcat tccctgcgct actttgtgac cgctgttagc 840
cgcccgggcc tgggtgaacc gcgttacatg gaggtcggtt atgtggatga cacggagttt 900
gtgcgtttcg attcagacgc tgagaacccg cgttacgaac cgcgtgcaag atggatggaa 960

```
caggaaggcc cggaatattg ggaaagagag acccaaaagg caaaaggcaa cgaacaaagc   1020

ttccgtgtgg acctgcgtac cctgctgggc gcctacaacc aatcaaaagg tggctcgcac   1080

acgatccagg tgatcagcgg ctgcgaggtt ggtagcgatg gccgtctgct gcgcggctat   1140

cagcaatacg cctacgacgg ttgcgattat atcgcactga atgaagacct gaaaacctgg   1200

acggcggccg atatggcagc tctgattacg aagcacaaat gggaacaggc tggcgaggcg   1260

gaaagactgc gcgcctacct ggagggtacc tgcgtggaat ggctgcgtcg ctatctgaag   1320

aacggcaatg ccaccttgct gcgtacggat agcccgaaag cacatgttac ccaccacagc   1380

cgccccgagg acaaggttac gctgcgttgt tgggctctgg gcttttatcc ggcggatatt   1440

accctgacgt ggcagctgaa cggtgaagag ctgatccaag atatggaact ggtggaaacc   1500

cgtccgtgcg gcgatggcac gttccagaaa tgggcaagcg tggttgtccc gctgggtaaa   1560

gaacaatact acacctgtca tgtttaccac cagggtctgc cggaaccgct gacgctgcgt   1620

tgggcagctg cgggtggccc cagagggccc acaatcaagc cctgtcctcc atgcaaatgc   1680

ccagcaccta acctcttggg tggaccatcc gtcttcatct tccctccaaa gatcaaggat   1740

gtactcatga tctccctgag ccccatagtc acatgtgtgg tggtggatgt gagcgaggat   1800

gacccagatg tccagatcag ctggtttgtg aacaacgtgg aagtacacac agctcagaca   1860

caaacccata gagaggatta caacagtact ctccgggtgg tcagtgccct ccccatccag   1920

caccaggact ggatgagtgg caaggagttc aaatgcaagg tcaacaacaa agacctccca   1980

gcgcccatcg agagaaccat ctcaaaaccc aaagggtcag taagagctcc acaggtatat   2040

gtcttgcctc caccagaaga agagatgact aagaaacagg tcactctgac ctgcatggtc   2100

acagacttca tgcctgaaga catttacgtg gagtggacca acaacgggaa aacagagcta   2160

aactacaaga acactgaacc agtcctggac tctgatggtt cttacttcat gtacagcaag   2220

ctgagagtgg aaaagaagaa ctgggtggaa agaaatagct actcctgttc agtggtccac   2280

gagggtctgc acaatcacca cacgactaag agcttctccc ggactccggg taaaggcgga   2340

tcacatcacc atcaccatca ccatcactag tga                                2373
```

<210> SEQ ID NO 109
<211> LENGTH: 2031
<212> TYPE: DNA
<213> ORGANISM: Artificial Sequence
<220> FEATURE:
<223> OTHER INFORMATION: Synthetic polynucleotide

<400> SEQUENCE: 109

```
gccaccatgt ctcgctccgt ggccttagct gtgctcgcgc tactctctct ttctggcctg     60

gaggccgctg ctcctctgaa gattcaagct tatttcaatg agactgcaga cctgccatgc    120

caatttgcaa actctcaaaa ccaaagcctg agtgagctag tagtattttg gcaggaccag    180

gaaaacttgg ttctgaatga ggtatactta ggcaaagaga aatttgacag tgttcattcc    240

aagtatatgg gccgcacaag ttttgattcg gacagttgga ccctgagact tcacaatctt    300

cagatcaagg acaagggctt gtatcaatgt atcatccatc acaaaaagcc cacaggaatg    360

attcgcatcc accagatgaa ttctgaactg tcagtgcttg gaggcggagg atctggtggt    420

ggaggttctg gtggtggggg atctggaggc ggaggatctg gcccgcattc cctgcgctac    480

tttgtgaccg ctgttagccg cccgggcctg ggtgaaccgc gttacatgga ggtcggttat    540

gtggatgaca cggagtttgt gcgtttcgat tcagacgctg agaacccgcg ttacgaaccg    600
```

-continued

```
cgtgcaagat ggatggaaca ggaaggcccg gaatattggg aaagagagac ccaaaaggca    660
aaaggcaacg aacaaagctt ccgtgtggac ctgcgtaccc tgctgggcgc ctacaaccaa    720
tcaaaaggtg gctcgcacac gatccaggtg atcagcggct gcgaggttgg tagcgatggc    780
cgtctgctgc gcggctatca gcaatacgcc tacgacggtt gcgattatat cgcactgaat    840
gaagacctga aaacctggac ggcggccgat atggcagctc tgattacgaa gcacaaatgg    900
gaacaggctg gcgaggcgga aagactgcgc gcctacctgg agggtacctg cgtggaatgg    960
ctgcgtcgct atctgaagaa cggcaatgcc accttgctgc gtacggatag cccgaaagca   1020
catgttaccc accacagccg ccccgaggac aaggttacgc tgcgttgttg ggctctgggc   1080
ttttatccgg cggatattac cctgacgtgg cagctgaacg gtgaagagct gatccaagat   1140
atggaactgg tggaaacccg tccgtgcggc gatggcacgt tccagaaatg ggcaagcgtg   1200
gttgtcccgc tgggtaaaga acaatactac acctgtcatg tttaccacca gggtctgccg   1260
gaaccgctga cgctgcgttg ggcagctgcg ggtggcccca gagggcccac aatcaagccc   1320
tgtcctccat gcaaatgccc agcacctaac ctcttgggtg gaccatccgt cttcatcttc   1380
cctccaaaga tcaaggatgt actcatgatc tccctgagcc ccatagtcac atgtgtggtg   1440
gtggatgtga gcgaggatga cccagatgtc cagatcagct ggtttgtgaa caacgtggaa   1500
gtacacacag ctcagacaca aacccataga gaggattaca acagtactct ccgggtggtc   1560
agtgccctcc ccatccagca ccaggactgg atgagtggca aggagttcaa atgcaaggtc   1620
aacaacaaag acctcccagc gcccatcgag agaaccatct caaaacccaa agggtcagta   1680
agagctccac aggtatatgt cttgcctcca ccagaagaag agatgactaa gaaacaggtc   1740
actctgacct gcatggtcac agacttcatg cctgaagaca tttacgtgga gtggaccaac   1800
aacgggaaaa cagagctaaa ctacaagaac actgaaccag tcctggactc tgatggttct   1860
tacttcatgt acagcaagct gagagtggaa aagaagaact gggtggaaag aaatagctac   1920
tcctgttcag tggtccacga gggtctgcac aatcaccaca cgactaagag cttctcccgg   1980
actccgggta aaggcggatc acatcaccat caccatcacc atcactagtg a            2031
```

<210> SEQ ID NO 110
<211> LENGTH: 2031
<212> TYPE: DNA
<213> ORGANISM: Artificial Sequence
<220> FEATURE:
<223> OTHER INFORMATION: Synthetic polynucleotide

<400> SEQUENCE: 110

```
gccaccatgt ctcgctccgt ggccttagct gtgctcgcgc tactctctct ttctggcctg     60
gaggccgctg ctcctctgaa gattcaagct tatttcaatg agactgcaga cctgccatgc    120
caatttgcaa actctcaaaa ccaaagcctg agtgagctag tagtattttg gcaggaccag    180
gaaaacttgg ttctgaatga ggtatactta ggcaaagaga aatttgacag tgttcattcc    240
aagtatatga accgcacaag ttttgattcg gacagttgga ccctgagact tcacaatctt    300
cagatcaagg acaagggctt gtatcaatgt atcatccatc acaaaaagcc cacaggaatg    360
attcgcatcc accagatgaa ttctgaactg tcagtgcttg gaggcggagg atctggtggt    420
ggaggttctg gtggtggggg atctggaggc ggaggatctg gcccgcattc cctgcgctac    480
tttgtgaccg ctgttagccg cccgggcctg ggtgaaccgc gttacatgga ggtcggttat    540
gtggatgaca cggagtttgt gcgtttcgat tcagacgctg agaacccgcg ttacgaaccg    600
cgtgcaagat ggatggaaca ggaaggcccg gaatattggg aaagagagac ccaaaaggca    660
```

aaaggcaacg aacaaagctt ccgtgtggac ctgcgtaccc tgctgggcgc ctacaaccaa 720
tcaaaaggtg gctcgcacac gatccaggtg atcagcggct gcgaggttgg tagcgatggc 780
cgtctgctgc gcggctatca gcaatacgcc tacgacggtt gcgattatat cgcactgaat 840
gaagacctga aacctggac ggcggccgat atggcagctc tgattacgaa gcacaaatgg 900
gaacaggctg gcgaggcgga aagactgcgc gcctacctgg agggtacctg cgtggaatgg 960
ctgcgtcgct atctgaagaa cggcaatgcc accttgctgc gtacggatag cccgaaagca 1020
catgttaccc accacagccg ccccgaggac aaggttacgc tgcgttgttg ggctctgggc 1080
ttttatccgg cggatattac cctgacgtgg cagctgaacg gtgaagagct gatccaagat 1140
atggaactgg tggaaacccg tccgtgcggc gatggcacgt tccagaaatg ggcaagcgtg 1200
gttgtcccgc tgggtaaaga acaatactac acctgtcatg tttaccacca gggtctgccg 1260
gaaccgctga cgctgcgttg ggcagctgcg ggtggcccca gagggcccac aatcaagccc 1320
tgtcctccat gcaaatgccc agcacctaac ctcttgggtg gaccatccgt cttcatcttc 1380
cctccaaaga tcaaggatgt actcatgatc tccctgagcc ccatagtcac atgtgtggtg 1440
gtggatgtga gcgaggatga cccagatgtc cagatcagct ggtttgtgaa caacgtggaa 1500
gtacacacag ctcagacaca aacccataga gaggattaca acagtactct ccgggtggtc 1560
agtgccctcc ccatccagca ccaggactgg atgagtggca aggagttcaa atgcaaggtc 1620
aacaacaaag acctcccagc gcccatcgag agaaccatct caaaacccaa agggtcagta 1680
agagctccac aggtatatgt cttgcctcca ccagaagaag agatgactaa gaaacaggtc 1740
actctgacct gcatggtcac agacttcatg cctgaagaca tttacgtgga gtggaccaac 1800
aacgggaaaa cagagctaaa ctacaagaac actgaaccag tcctggactc tgatggttct 1860
tacttcatgt acagcaagct gagagtggaa aagaagaact gggtggaaag aaatagctac 1920
tcctgttcag tggtccacga gggtctgcac aatcaccaca cgactaagag cttctcccgg 1980
actccgggta aaggcggatc acatcaccat caccatcacc atcactagtg a 2031

<210> SEQ ID NO 111
<211> LENGTH: 2031
<212> TYPE: DNA
<213> ORGANISM: Artificial Sequence
<220> FEATURE:
<223> OTHER INFORMATION: Synthetic polynucleotide

<400> SEQUENCE: 111
gccaccatgt ctcgctccgt ggccttagct gtgctcgcgc tactctctct ttctggcctg 60
gaggccgctg ctcctctgaa gattcaagct tatttcaatg agactgcaga cctgccatgc 120
caatttgcaa actctcaaaa ccaaagcctg agtgagctag tagtattttg gcaggaccag 180
gaaaacttgg ttctgaatga ggtatactta ggcaaagaga aatttgacag tgttcattcc 240
aagtatatgg gccgcacaag ttttgcctcg gacagttgga ccctgagact tcacaatctt 300
cagatcaagg acaagggctt gtatcaatgt atcatccatc acaaaaagcc cacaggaatg 360
attcgcatcc accagatgaa ttctgaactg tcagtgcttg gaggcggagg atctggtggt 420
ggaggttctg gtggtggggg atctggaggc ggaggatctg gcccgcattc cctgcgctac 480
tttgtgaccg ctgttagccg cccgggcctg ggtgaaccgc gttacatgga ggtcggttat 540
gtggatgaca cggagtttgt gcgtttcgat tcagacgctg agaacccgcg ttacgaaccg 600
cgtgcaagat ggatggaaca ggaaggcccg gaatattggg aaagagagac ccaaaaggca 660

```
aaaggcaacg aacaaagctt ccgtgtggac ctgcgtaccc tgctgggcgc ctacaaccaa    720

tcaaaaggtg gctcgcacac gatccaggtg atcagcggct gcgaggttgg tagcgatggc    780

cgtctgctgc gcggctatca gcaatacgcc tacgacggtt gcgattatat cgcactgaat    840

gaagacctga aacctggac ggcggccgat atggcagctc tgattacgaa gcacaaatgg    900

gaacaggctg gcgaggcgga aagactgcgc gcctacctgg agggtacctg cgtggaatgg    960

ctgcgtcgct atctgaagaa cggcaatgcc accttgctgc gtacggatag cccgaaagca   1020

catgttaccc accacagccg ccccgaggac aaggttacgc tgcgttgttg ggctctgggc   1080

ttttatccgg cggatattac cctgacgtgg cagctgaacg gtgaagagct gatccaagat   1140

atggaactgg tggaaacccg tccgtgcggc gatggcacgt tccagaaatg ggcaagcgtg   1200

gttgtcccgc tgggtaaaga acaatactac acctgtcatg tttaccacca gggtctgccg   1260

gaaccgctga cgctgcgttg ggcagctgcg ggtggcccca gagggcccac aatcaagccc   1320

tgtcctccat gcaaatgccc agcacctaac ctcttgggtg gaccatccgt cttcatcttc   1380

cctccaaaga tcaaggatgt actcatgatc tccctgagcc ccatagtcac atgtgtggtg   1440

gtggatgtga gcgaggatga cccagatgtc cagatcagct ggtttgtgaa caacgtggaa   1500

gtacacacag ctcagacaca aacccataga gaggattaca acagtactct ccgggtggtc   1560

agtgccctcc ccatccagca ccaggactgg atgagtggca aggagttcaa atgcaaggtc   1620

aacaacaaag acctcccagc gcccatcgag agaaccatct caaaacccaa agggtcagta   1680

agagctccac aggtatatgt cttgcctcca ccagaagaag agatgactaa gaaacaggtc   1740

actctgacct gcatggtcac agacttcatg cctgaagaca tttacgtgga gtggaccaac   1800

aacgggaaaa cagagctaaa ctacaagaac actgaaccag tcctggactc tgatggttct   1860

tacttcatgt acagcaagct gagagtggaa aagaagaact gggtggaaag aaatagctac   1920

tcctgttcag tggtccacga gggtctgcac aatcaccaca cgactaagag cttctcccgg   1980

actccgggta aaggcggatc acatcaccat caccatcacc atcactagtg a            2031


<210> SEQ ID NO 112
<211> LENGTH: 2031
<212> TYPE: DNA
<213> ORGANISM: Artificial Sequence
<220> FEATURE:
<223> OTHER INFORMATION: Synthetic polynucleotide

<400> SEQUENCE: 112

gccaccatgt ctcgctccgt ggccttagct gtgctcgcgc tactctctct ttctggcctg     60

gaggccgctg ctcctctgaa gattcaagct tatttcaatg agactgcaga cctgccatgc    120

caatttgcaa actctcaaaa ccaaagcctg agtgagctag tagtattttg gcaggaccag    180

gaaaacttgg ttctgaatga ggtatactta ggcaaagaga aatttgacag tgttcattcc    240

aagtatatgg gccgcacaag ttttgattcg gacagtgcca ccctgagact tcacaatctt    300

cagatcaagg acaagggctt gtatcaatgt atcatccatc acaaaaagcc cacaggaatg    360

attcgcatcc accagatgaa ttctgaactg tcagtgcttg gaggcggagg atctggtggt    420

ggaggttctg gtggtggggg atctggaggc ggaggatctg gcccgcattc cctgcgctac    480

tttgtgaccg ctgttagccg cccgggcctg ggtgaaccgc gttacatgga ggtcggttat    540

gtggatgaca cggagtttgt gcgtttcgat tcagacgctg agaacccgcg ttacgaaccg    600

cgtgcaagat ggatggaaca ggaaggcccg gaatattggg aaagagagac ccaaaaggca    660

aaaggcaacg aacaaagctt ccgtgtggac ctgcgtaccc tgctgggcgc ctacaaccaa    720
```

tcaaaaggtg gctcgcacac gatccaggtg atcagcggct gcgaggttgg tagcgatggc 780
cgtctgctgc gcggctatca gcaatacgcc tacgacggtt gcgattatat cgcactgaat 840
gaagacctga aaacctggac ggcggccgat atggcagctc tgattacgaa gcacaaatgg 900
gaacaggctg gcgaggcgga aagactgcgc gcctacctgg agggtacctg cgtggaatgg 960
ctgcgtcgct atctgaagaa cggcaatgcc accttgctgc gtacggatag cccgaaagca 1020
catgttaccc accacagccg ccccgaggac aaggttacgc tgcgttgttg ggctctgggc 1080
ttttatccgg cggatattac cctgacgtgg cagctgaacg gtgaagagct gatccaagat 1140
atggaactgg tggaaacccg tccgtgcggc gatggcacgt tccagaaatg ggcaagcgtg 1200
gttgtcccgc tgggtaaaga acaatactac acctgtcatg tttaccacca gggtctgccg 1260
gaaccgctga cgctgcgttg ggcagctgcg ggtggcccca gagggcccac aatcaagccc 1320
tgtcctccat gcaaatgccc agcacctaac ctcttgggtg gaccatccgt cttcatcttc 1380
cctccaaaga tcaaggatgt actcatgatc tccctgagcc ccatagtcac atgtgtggtg 1440
gtggatgtga gcgaggatga cccagatgtc cagatcagct ggtttgtgaa caacgtggaa 1500
gtacacacag ctcagacaca aacccataga gaggattaca acagtactct ccgggtggtc 1560
agtgccctcc ccatccagca ccaggactgg atgagtggca aggagttcaa atgcaaggtc 1620
aacaacaaag acctcccagc gcccatcgag agaaccatct caaaacccaa agggtcagta 1680
agagctccac aggtatatgt cttgcctcca ccagaagaag agatgactaa gaaacaggtc 1740
actctgacct gcatggtcac agacttcatg cctgaagaca tttacgtgga gtggaccaac 1800
aacgggaaaa cagagctaaa ctacaagaac actgaaccag tcctggactc tgatggttct 1860
tacttcatgt acagcaagct gagagtggaa aagaagaact gggtggaaag aaatagctac 1920
tcctgttcag tggtccacga gggtctgcac aatcaccaca cgactaagag cttctcccgg 1980
actccgggta aaggcggatc acatcaccat caccatcacc atcactagtg a 2031

<210> SEQ ID NO 113
<211> LENGTH: 2031
<212> TYPE: DNA
<213> ORGANISM: Artificial Sequence
<220> FEATURE:
<223> OTHER INFORMATION: Synthetic polynucleotide

<400> SEQUENCE: 113
gccaccatgt ctcgctccgt ggccttagct gtgctcgcgc tactctctct ttctggcctg 60
gaggccgctg ctcctctgaa gattcaagct tatttcaatg agactgcaga cctgccatgc 120
caatttgcaa actctcaaaa ccaaagcctg agtgagctag tagtattttg gcaggaccag 180
gaaaacttgg ttctgaatga ggtatactta ggcaaagaga aatttgacag tgttcattcc 240
aagtatatgg gccgcacaag ttttgattcg gacagttgga ccctgagact tcacaatctt 300
cagatcaagg acaagggctt gtatcaatgt atcatccatg ccaaaaagcc cacaggaatg 360
attcgcatcc accagatgaa ttctgaactg tcagtgcttg gaggcggagg atctggtggt 420
ggaggttctg gtggtggggg atctggaggc ggaggatctg gcccgcattc cctgcgctac 480
tttgtgaccg ctgttagccg cccgggcctg ggtgaaccgc gttacatgga ggtcggttat 540
gtggatgaca cggagtttgt gcgtttcgat tcagacgctg agaacccgcg ttacgaaccg 600
cgtgcaagat ggatggaaca ggaaggcccg gaatattggg aaagagagac ccaaaaggca 660
aaaggcaacg aacaaagctt ccgtgtggac ctgcgtaccc tgctgggcgc ctacaaccaa 720

```
tcaaaaggtg gctcgcacac gatccaggtg atcagcggct gcgaggttgg tagcgatggc    780

cgtctgctgc gcggctatca gcaatacgcc tacgacggtt gcgattatat cgcactgaat    840

gaagacctga aaacctggac ggcggccgat atggcagctc tgattacgaa gcacaaatgg    900

gaacaggctg gcgaggcgga aagactgcgc gcctacctgg agggtacctg cgtggaatgg    960

ctgcgtcgct atctgaagaa cggcaatgcc accttgctgc gtacggatag cccgaaagca   1020

catgttaccc accacagccg ccccgaggac aaggttacgc tgcgttgttg ggctctgggc   1080

ttttatccgg cggatattac cctgacgtgg cagctgaacg gtgaagagct gatccaagat   1140

atggaactgg tggaaacccg tccgtgcggc gatggcacgt tccagaaatg ggcaagcgtg   1200

gttgtcccgc tgggtaaaga acaatactac acctgtcatg tttaccacca gggtctgccg   1260

gaaccgctga cgctgcgttg ggcagctgcg ggtggcccca gagggcccac aatcaagccc   1320

tgtcctccat gcaaatgccc agcacctaac ctcttgggtg gaccatccgt cttcatcttc   1380

cctccaaaga tcaaggatgt actcatgatc tccctgagcc ccatagtcac atgtgtggtg   1440

gtggatgtga gcgaggatga cccagatgtc cagatcagct ggtttgtgaa caacgtggaa   1500

gtacacacag ctcagacaca aacccataga gaggattaca acagtactct ccgggtggtc   1560

agtgccctcc ccatccagca ccaggactgg atgagtggca aggagttcaa atgcaaggtc   1620

aacaacaaag acctcccagc gcccatcgag agaaccatct caaaacccaa agggtcagta   1680

agagctccac aggtatatgt cttgcctcca ccagaagaag agatgactaa gaaacaggtc   1740

actctgacct gcatggtcac agacttcatg cctgaagaca tttacgtgga gtggaccaac   1800

aacgggaaaa cagagctaaa ctacaagaac actgaaccag tcctggactc tgatggttct   1860

tacttcatgt acagcaagct gagagtggaa aagaagaact gggtggaaag aaatagctac   1920

tcctgttcag tggtccacga gggtctgcac aatcaccaca cgactaagag cttctcccgg   1980

actccgggta aaggcggatc acatcaccat caccatcacc atcactagtg a            2031
```

```
<210> SEQ ID NO 114
<211> LENGTH: 2367
<212> TYPE: DNA
<213> ORGANISM: Artificial Sequence
<220> FEATURE:
<223> OTHER INFORMATION: Synthetic polynucleotide

<400> SEQUENCE: 114

atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catgcaaaaa agcccacagg aatgattcgc    360

atccaccaga tgaattctga actgtcagtg cttgctaact tcagtcaacc tgaaatagta    420

ccaatttcta atataacaga aaatgtgtac ataaatttga cctgctcatc tatacacggt    480

tacccagaac ctaagaagat gagtgttttg ctaagaacca agaattcaac tatcgagtat    540

gatggtatta tgcagaaatc tcaagataat gtcacagaac tgtacgacgt ttccatcagc    600

ttgtctgttt cattccctga tgttacgagc aatatgacca tcttctgtat tctggaaact    660

gacaagacgc ggcttttatc ttcacctttc tctatagagc ttgaggaccc tcagcctccc    720

ccagaccaca ttcctggagg cggaggatct ggtggtggag gttctggtgg tgggggatct    780
```

ggaggcggag gatctggccc acactcgatg cggtatttcg agaccgccgt gtcccggccc 840
ggcctcgagg agccccggta catctctgtc ggctatgtgg acaacaagga gttcgtgcgc 900
ttcgacagcg acgcggagaa tccgagatat gagccgcggg cgccgtggat ggagcaggag 960
gggccggagt attgggagcg ggaaacacag aaagccaagg gccaagagca gtggttccga 1020
gtgagcctga ggaacctgct cggcgcctac aaccagagcg cgggcggctc tcacacactc 1080
cagcagatgt ctggctgtga cttggggtcg gactggcgcc tcctccgcgg gtacctgcag 1140
ttcgcctatg aaggccgcga ttacatcgcc ctgaacgaag acctgaaaac gtggacggcg 1200
gcggacatgg cggcgcagat cacccgacgc aagtgggagc agagtggtgc tgcagagcat 1260
tacaaggcct acctggaggg cgagtgcgtg gagtggctcc acagatacct gaagaacggg 1320
aacgcgacgc tgctgcgcac agattcccca aaggcacatg tgacccatca ccccagatct 1380
aaaggtgaag tcaccctgag gtgctgggcc ctgggcttct accctgctga catcaccctg 1440
acctggcagt tgaatgggga ggagctgacc caggacatgg agcttgtgga gaccaggcct 1500
tgcggggatg gaaccttcca gaagtgggca tctgtggtgg tgcctcttgg gaaggagcag 1560
aattacacat gccgtgtgta ccatgagggg ctgcctgagc cctcaccct gagatgggca 1620 gctgcgggtg gccccagagg gcccacaatc aagccctgtc ctccatgcaa atgcccagca 1680
cctaacctcg agggtggacc atccgtcttc atcttccctc caaagatcaa ggatgtactc 1740
atgatctccc tgagccccat agtcacatgt gtggtggtgg atgtgagcga ggatgaccca 1800
gatgtccaga tcagctggtt tgtgaacaac gtggaagtac acacagctca gacacaaacc 1860
catagagagg attacaacag tactctccgg gtggtcagtg ccctccccat ccagcaccag 1920
gactggatga gtggcaaggc gttcgcatgc gcggtcaaca acaaagacct cccagcgccc 1980
atcgagagaa ccatctcaaa acccaaaggg tcagtaagag ctccacaggt atatgtcttg 2040
cctccaccag aagaagagat gactaagaaa caggtcactc tgacctgcat ggtcacagac 2100
ttcatgcctg aagacattta tgtggagtgg accaacaacg ggaaaacaga gctaaactac 2160
aagaacactg aaccagtcct ggactctgat ggttcttact tcatgtacag caagctgaga 2220
gtggaaaaga agaactgggt ggaaagaaat agctactcct gttcagtggt ccacgagggt 2280
ctgcacaatc accacacgac taagagcttc tcccggactc cgggtaaagg cggatcacat 2340
caccatcacc atcaccatca ctagtga 2367

<210> SEQ ID NO 115
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 115
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480
gagaccgccg tgtcccggcc cggcctcgag gagccccggt acatctctgt cggctatgtg 540
gacaacaagg agttcgtgcg cttcgacagc gacgcggaga atccgagata tgagccgcgg 600
gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 116
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 116
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catgcaaaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480

```
gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

<210> SEQ ID NO 117
<211> LENGTH: 3102
<212> TYPE: DNA
<213> ORGANISM: Artificial Sequence
<220> FEATURE:
<223> OTHER INFORMATION: Synthetic polynucleotide

<400> SEQUENCE: 117

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctaact tcagtcaacc tgaaatagta    420

ccaatttcta atataacaga aaatgtgtac ataaatttga cctgctcatc tatacacggt    480
```

-continued

```
tacccagaac ctaagaagat gagtgttttg ctaagaacca agaattcaac tatcgagtat    540
gatggtatta tgcagaaatc tcaagataat gtcacagaac tgtacgacgt ttccatcagc    600
ttgtctgttt cattccctga tgttacgagc aatatgacca tcttctgtat tctggaaact    660
gacaagacgc ggcttttatc ttcacctttc tctatagagc ttgaggaccc tcagcctccc    720
ccagaccaca ttcctggagg cggaggatct ggtggtggag gttctggtgg tgggggatct    780
ggaggcggag gatctgctgc tcctctgaag attcaagctt atttcaatga gactgcagac    840
ctgccatgcc aatttgcaaa ctctcaaaac caaagcctga gtgagctagt agtattttgg    900
caggaccagg aaaacttggt tctgaatgag gtatacttag gcaaagagaa atttgacagt    960
gttcattcca agtatatggg ccgcacaagt tttgattcgg acagttggac cctgagactt   1020
cacaatcttc agatcaagga caagggcttg tatcaatgta tcatccatca caaaaagccc   1080
acaggaatga ttcgcatcca ccagatgaat tctgaactgt cagtgcttgc taacttcagt   1140
caacctgaaa tagtaccaat ttctaatata acagaaaatg tgtacataaa tttgacctgc   1200
tcatctatac acggttaccc agaacctaag aagatgagtg ttttgctaag aaccaagaat   1260
tcaactatcg agtatgatgg tattatgcag aaatctcaag ataatgtcac agaactgtac   1320
gacgtttcca tcagcttgtc tgtttcattc cctgatgtta cgagcaatat gaccatcttc   1380
tgtattctgg aaactgacaa gacgcggctt ttatcttcac ctttctctat agagcttgag   1440
gaccctcagc ctcccccaga ccacattcct ggaggcggag gatctggtgg tggaggttct   1500
ggtggtgggg gatctggagg cggaggatct ggcccacact cgatgcggta tttcgagacc   1560
gccgtgtccc ggcccggcct cgaggagccc cggtacatct ctgtcggcta tgtggacaac   1620
aaggagttcg tgcgcttcga cagcgacgcg gagaatccga gatatgagcc gcgggcgccg   1680
tggatggagc aggaggggcc ggagtattgg gagcgggaaa cacagaaagc caagggccaa   1740
gagcagtggt tccgagtgag cctgaggaac ctgctcggcg cctacaacca gagcgcgggc   1800
ggctctcaca cactccagca gatgtctggc tgtgacttgg ggtcggactg gcgcctcctc   1860
cgcgggtacc tgcagttcgc ctatgaaggc cgcgattaca tcgccctgaa cgaagacctg   1920
aaaacgtgga cggcggcgga catggcggcg cagatcaccc gacgcaagtg ggagcagagt   1980
ggtgctgcag agcattacaa ggcctacctg gagggcgagt gcgtggagtg gctccacaga   2040
tacctgaaga acgggaacgc gacgctgctg cgcacagatt ccccaaaggc acatgtgacc   2100
catcacccca gatctaaagg tgaagtcacc ctgaggtgct gggccctggg cttctaccct   2160
gctgacatca ccctgacctg gcagttgaat ggggaggagc tgacccagga catggagctt   2220
gtggagacca ggccttgcgg ggatggaacc ttccagaagt gggcatctgt ggtggtgcct   2280
cttgggaagg agcagaatta cacatgccgt gtgtaccatg aggggctgcc tgagcccctc   2340
accctgagat gggcagctgc gggtggcccc agagggccca caatcaagcc ctgtcctcca   2400
tgcaaatgcc cagcacctaa cctcgagggt ggaccatccg tcttcatctt ccctccaaag   2460
atcaaggatg tactcatgat ctccctgagc cccatagtca catgtgtggt ggtggatgtg   2520
agcgaggatg acccagatgt ccagatcagc tggtttgtga acaacgtgga agtacacaca   2580
gctcagacac aaacccatag agaggattac aacagtactc tccgggtggt cagtgccctc   2640
cccatccagc accaggactg gatgagtggc aaggcgttcg catgcgcggt caacaacaaa   2700
gacctcccag cgcccatcga gagaaccatc tcaaaaccca aagggtcagt aagagctcca   2760
caggtatatg tcttgcctcc accagaagaa gagatgacta agaaacaggt cactctgacc   2820
tgcatggtca cagacttcat gcctgaagac atttatgtgg agtggaccaa caacgggaaa   2880
```

-continued

```
acagagctaa actacaagaa cactgaacca gtcctggact ctgatggttc ttacttcatg   2940

tacagcaagc tgagagtgga aaagaagaac tgggtggaaa gaaatagcta ctcctgttca   3000

gtggtccacg agggtctgca caatcaccac acgactaaga gcttctcccg gactccgggt   3060

aaaggcggat cacatcacca tcaccatcac catcactagt ga                      3102
```

<210> SEQ ID NO 118
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 118

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggtggtgga    420

ggttctggtg gtgggggatc tggaggcgga ggatctgctg ctcctctgaa gattcaagct    480

tatttcaatg agactgcaga cctgccatgc caatttgcaa actctcaaaa ccaaagcctg    540

agtgagctag tagtattttg gcaggaccag gaaaacttgg ttctgaatga ggtatactta    600

ggcaaagaga aatttgacag tgttcattcc aagtatatgg gccgcacaag ttttgattcg    660

gacagttgga ccctgagact tcacaatctt cagatcaagg acaagggctt gtatcaatgt    720

atcatccatc acaaaaagcc cacaggaatg attcgcatcc accagatgaa ttctgaactg    780

tcagtgcttg ctggaggcgg aggatctggt ggtggaggtt ctggtggtgg gggatctgga    840

ggcggaggat ctggcccaca ctcgatgcgg tatttcgaga ccgccgtgtc ccggcccggc    900

ctcgaggagc cccggtacat ctctgtcggc tatgtggaca acaaggagtt cgtgcgcttc    960

gacagcgacg cggagaatcc gagatatgag ccgcgggcgc cgtggatgga gcaggagggg   1020

ccggagtatt gggagcggga aacacagaaa gccaagggcc aagagcagtg gttccgagtg   1080

agcctgagga acctgctcgg cgcctacaac cagagcgcgg gcggctctca cacactccag   1140

cagatgtctg gctgtgactt ggggtcggac tggcgcctcc tccgcgggta cctgcagttc   1200

gcctatgaag gccgcgatta catcgccctg aacgaagacc tgaaaacgtg gacggcggcg   1260

gacatggcgg cgcagatcac ccgacgcaag tgggagcaga gtggtgctgc agagcattac   1320

aaggcctacc tggagggcga gtgcgtggag tggctccaca gatacctgaa gaacgggaac   1380

gcgacgctgc tgcgcacaga ttccccaaag gcacatgtga cccatcaccc cagatctaaa   1440

ggtgaagtca ccctgaggtg ctgggccctg ggcttctacc ctgctgacat caccctgacc   1500

tggcagttga atggggagga gctgacccag gacatggagc ttgtggagac caggccttgc   1560

ggggatggaa ccttccagaa gtgggcatct gtggtggtgc ctcttgggaa ggagcagaat   1620

tacacatgcc gtgtgtacca tgaggggctg cctgagcccc tcaccctgag atgggcagct   1680

gcgggtggcc ccagagggcc cacaatcaag ccctgtcctc catgcaaatg cccagcacct   1740

aacctcgagg gtggaccatc cgtcttcatc ttccctccaa agatcaagga tgtactcatg   1800
```

atctccctga gccccatagt cacatgtgtg gtggtggatg tgagcgagga tgacccagat 1860
gtccagatca gctggtttgt gaacaacgtg gaagtacaca cagctcagac acaaacccat 1920
agagaggatt acaacagtac tctccgggtg gtcagtgccc tccccatcca gcaccaggac 1980
tggatgagtg gcaaggcgtt cgcatgcgcg gtcaacaaca aagacctccc agcgcccatc 2040
gagagaacca tctcaaaacc caaagggtca gtaagagctc cacaggtata tgtcttgcct 2100
ccaccagaag aagagatgac taagaaacag gtcactctga cctgcatggt cacagacttc 2160
atgcctgaag acatttatgt ggagtggacc aacaacggga aaacagagct aaactacaag 2220
aacactgaac cagtcctgga ctctgatggt tcttacttca tgtacagcaa gctgagagtg 2280
gaaaagaaga actgggtgga aagaaatagc tactcctgtt cagtggtcca cgagggtctg 2340
cacaatcacc acacgactaa gagcttctcc cggactccgg gtaaaggcgg atcacatcac 2400
catcaccatc accatcacta gtga 2424

<210> SEQ ID NO 119
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 119
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catgcaaaaa agcccacagg aatgattcgc 360
atccaccaga tgaattctga actgtcagtg cttgctggag gcggaggatc tggtggtgga 420
ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg gcaggaccag gaaaacttgg ttctgaatga ggtatactta 600
ggcaaagaga aatttgacag tgttcattcc aagtatatgg gccgcacaag ttttgattcg 660
gacagttgga ccctgagact tcacaatctt cagatcaagg acaagggctt gtatcaatgt 720
atcatccatg caaaaaagcc cacaggaatg attcgcatcc accagatgaa ttctgaactg 780
tcagtgcttg ctggaggcgg aggatctggt ggtggaggtt ctggtggtgg gggatctgga 840
ggcggaggat ctggcccaca ctcgatgcgg tatttcgaga ccgccgtgtc ccggcccggc 900
ctcgaggagc cccggtacat ctctgtcggc tatgtggaca acaaggagtt cgtgcgcttc 960
gacagcgacg cggagaatcc gagatatgag ccgcgggcgc cgtggatgga gcaggagggg 1020
ccggagtatt gggagcggga aacacagaaa gccaagggcc aagagcagtg gttccgagtg 1080
agcctgagga acctgctcgg cgcctacaac cagagcgcgg gcggctctca cacactccag 1140
cagatgtctg gctgtgactt ggggtcggac tggcgcctcc tccgcgggta cctgcagttc 1200
gcctatgaag gccgcgatta catcgccctg aacgaagacc tgaaaacgtg gacggcggcg 1260
gacatggcgg cgcagatcac ccgacgcaag tgggagcaga gtggtgctgc agagcattac 1320
aaggcctacc tggagggcga gtgcgtggag tggctccaca gatacctgaa gaacgggaac 1380
gcgacgctgc tgcgcacaga ttccccaaag gcacatgtga cccatcaccc cagatctaaa 1440

```
ggtgaagtca ccctgaggtg ctgggccctg ggcttctacc ctgctgacat caccctgacc   1500
tggcagttga atggggagga gctgacccag gacatggagc ttgtggagac caggccttgc   1560
ggggatggaa ccttccagaa gtgggcatct gtggtggtgc ctcttgggaa ggagcagaat   1620
tacacatgcc gtgtgtacca tgaggggctg cctgagcccc tcaccctgag atgggcagct   1680
gcgggtggcc ccagagggcc cacaatcaag ccctgtcctc catgcaaatg cccagcacct   1740
aacctcgagg gtggaccatc cgtcttcatc ttccctccaa agatcaagga tgtactcatg   1800
atctccctga gccccatagt cacatgtgtg gtggtggatg tgagcgagga tgacccagat   1860
gtccagatca gctggtttgt gaacaacgtg gaagtacaca cagctcagac acaaacccat   1920
agagaggatt acaacagtac tctccgggtg gtcagtgccc tccccatcca gcaccaggac   1980
tggatgagtg gcaaggcgtt cgcatgcgcg gtcaacaaca aagacctccc agcgcccatc   2040
gagagaacca tctcaaaacc caaagggtca gtaagagctc cacaggtata tgtcttgcct   2100
ccaccagaag aagagatgac taagaaacag gtcactctga cctgcatggt cacagacttc   2160
atgcctgaag acatttatgt ggagtggacc aacaacggga aaacagagct aaactacaag   2220
aacactgaac cagtcctgga ctctgatggt tcttacttca tgtacagcaa gctgagagtg   2280
gaaaagaaga actgggtgga aagaaatagc tactcctgtt cagtggtcca cgagggtctg   2340
cacaatcacc acacgactaa gagcttctcc cggactccgg gtaaaggcgg atcacatcac   2400
catcaccatc accatcacta gtga                                          2424
```

<210> SEQ ID NO 120
<211> LENGTH: 3837
<212> TYPE: DNA
<213> ORGANISM: Artificial Sequence
<220> FEATURE:
<223> OTHER INFORMATION: Synthetic polynucleotide

<400> SEQUENCE: 120

```
atgtctcgct ccgtggcctt agctgtgctc gcgctactct ctctttctgg cctggaggcc     60
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
atgggccgca caagttttga ttcggacagt tggaccctga gacttcacaa tcttcagatc    300
aaggacaagg gcttgtatca atgtatcatc catcacaaaa agcccacagg aatgattcgc    360
atccaccaga tgaattctga actgtcagtg cttgctaact tcagtcaacc tgaaatagta    420
ccaatttcta atataacaga aaatgtgtac ataaatttga cctgctcatc tatacacggt    480
tacccagaac ctaagaagat gagtgttttg ctaagaacca agaattcaac tatcgagtat    540
gatggtatta tgcagaaatc tcaagataat gtcacagaac tgtacgacgt ttccatcagc    600
ttgtctgttt cattccctga tgttacgagc aatatgacca tcttctgtat tctggaaact    660
gacaagacgc ggcttttatc ttcacctttc tctatagagc ttgaggaccc tcagcctccc    720
ccagaccaca ttcctggagg cggaggatct ggtggtggag gttctggtgg tgggggatct    780
ggaggcggag gatctgctgc tcctctgaag attcaagctt atttcaatga gactgcagac    840
ctgccatgcc aatttgcaaa ctctcaaaac caaagcctga gtgagctagt agtattttgg    900
caggaccagg aaaacttggt tctgaatgag gtatacttag gcaaagagaa atttgacagt    960
gttcattcca agtatatggg ccgcacaagt tttgattcgg acagttggac cctgagactt   1020
```

-continued

```
cacaatcttc agatcaagga caagggcttg tatcaatgta tcatccatca caaaaagccc   1080
acaggaatga ttcgcatcca ccagatgaat tctgaactgt cagtgcttgc taacttcagt   1140
caacctgaaa tagtaccaat ttctaatata acagaaaatg tgtacataaa tttgacctgc   1200
tcatctatac acggttaccc agaacctaag aagatgagtg ttttgctaag aaccaagaat   1260
tcaactatcg agtatgatgg tattatgcag aaatctcaag ataatgtcac agaactgtac   1320
gacgtttcca tcagcttgtc tgtttcattc cctgatgtta cgagcaatat gaccatcttc   1380
tgtattctgg aaactgacaa gacgcggctt ttatcttcac ctttctctat agagcttgag   1440
gaccctcagc ctcccccaga ccacattcct ggaggcggag gatctggtgg tggaggttct   1500
ggtggtgggg gatctggagg cggaggatct gctgctcctc tgaagattca agcttatttc   1560
aatgagactg cagacctgcc atgccaattt gcaaactctc aaaaccaaag cctgagtgag   1620
ctagtagtat tttggcagga ccaggaaaac ttggttctga atgaggtata cttaggcaaa   1680
gagaaatttg acagtgttca ttccaagtat atgggccgca caagttttga ttcggacagt   1740
tggaccctga gacttcacaa tcttcagatc aaggacaagg gcttgtatca atgtatcatc   1800
catcacaaaa agcccacagg aatgattcgc atccaccaga tgaattctga actgtcagtg   1860
cttgctaact tcagtcaacc tgaaatagta ccaatttcta atataacaga aaatgtgtac   1920
ataaatttga cctgctcatc tatacacggt tacccagaac ctaagaagat gagtgttttg   1980
ctaagaacca agaattcaac tatcgagtat gatggtatta tgcagaaatc tcaagataat   2040
gtcacagaac tgtacgacgt ttccatcagc ttgtctgttt cattccctga tgttacgagc   2100
aatatgacca tcttctgtat tctggaaact gacaagacgc ggcttttatc ttcacctttc   2160
tctatagagc ttgaggaccc tcagcctccc ccagaccaca ttcctggagg cggaggatct   2220
ggtggtggag gttctggtgg tgggggatct ggaggcggag gatctggccc acactcgatg   2280
cggtatttcg agaccgccgt gtcccggccc ggcctcgagg agccccggta catctctgtc   2340
ggctatgtgg acaacaagga gttcgtgcgc ttcgacagcg acgcggagaa tccgagatat   2400
gagccgcggg cgccgtggat ggagcaggag gggccggagt attgggagcg ggaaacacag   2460
aaagccaagg gccaagagca gtggttccga gtgagcctga ggaacctgct cggcgcctac   2520
aaccagagcg cgggcggctc tcacacactc cagcagatgt ctggctgtga cttggggtcg   2580
gactggcgcc tcctccgcgg gtacctgcag ttcgcctatg aaggccgcga ttacatcgcc   2640
ctgaacgaag acctgaaaac gtggacggcg gcggacatgg cggcgcagat cacccgacgc   2700
aagtgggagc agagtggtgc tgcagagcat tacaaggcct acctggaggg cgagtgcgtg   2760
gagtggctcc acagatacct gaagaacggg aacgcgacgc tgctgcgcac agattcccca   2820
aaggcacatg tgacccatca ccccagatct aaaggtgaag tcaccctgag gtgctgggcc   2880
ctgggcttct accctgctga catcaccctg acctggcagt tgaatgggga ggagctgacc   2940
caggacatgg agcttgtgga gaccaggcct tgcggggatg gaaccttcca gaagtgggca   3000
tctgtggtgg tgcctcttgg gaaggagcag aattacacat gccgtgtgta ccatgagggg   3060
ctgcctgagc ccctcaccct gagatgggca gctgcgggtg gccccagagg gcccacaatc   3120
aagccctgtc ctccatgcaa atgcccagca cctaacctcg agggtggacc atccgtcttc   3180
atcttccctc caaagatcaa ggatgtactc atgatctccc tgagccccat agtcacatgt   3240
gtggtggtgg atgtgagcga ggatgaccca gatgtccaga tcagctggtt tgtgaacaac   3300
gtggaagtac acacagctca gacacaaacc catagagagg attacaacag tactctccgg   3360
gtggtcagtg ccctccccat ccagcaccag gactggatga gtggcaaggc gttcgcatgc   3420
```

```
gcggtcaaca acaaagacct cccagcgccc atcgagagaa ccatctcaaa acccaaaggg   3480

tcagtaagag ctccacaggt atatgtcttg cctccaccag aagaagagat gactaagaaa   3540

caggtcactc tgacctgcat ggtcacagac ttcatgcctg aagacattta tgtggagtgg   3600

accaacaacg ggaaaacaga gctaaactac aagaacactg aaccagtcct ggactctgat   3660

ggttcttact tcatgtacag caagctgaga gtggaaaaga agaactgggt ggaaagaaat   3720

agctactcct gttcagtggt ccacgagggt ctgcacaatc accacacgac taagagcttc   3780

tcccggactc cgggtaaagg cggatcacat caccatcacc atcaccatca ctagtga      3837
```

<210> SEQ ID NO 121
<211> LENGTH: 2820
<212> TYPE: DNA
<213> ORGANISM: Artificial Sequence
<220> FEATURE:
<223> OTHER INFORMATION: Synthetic polynucleotide

<400> SEQUENCE: 121

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggtggtgga    420

ggttctggtg gtgggggatc tggaggcgga ggatctgctg ctcctctgaa gattcaagct    480

tatttcaatg agactgcaga cctgccatgc caatttgcaa actctcaaaa ccaaagcctg    540

agtgagctag tagtattttg gcaggaccag gaaaacttgg ttctgaatga ggtatactta    600

ggcaaagaga aatttgacag tgttcattcc aagtatatgg gccgcacaag ttttgattcg    660

gacagttgga ccctgagact tcacaatctt cagatcaagg acaagggctt gtatcaatgt    720

atcatccatc acaaaaagcc cacaggaatg attcgcatcc accagatgaa ttctgaactg    780

tcagtgcttg ctggaggcgg aggatctggt ggtggaggtt ctggtggtgg gggatctgga    840

ggcggaggat ctgctgctcc tctgaagatt caagcttatt tcaatgagac tgcagacctg    900

ccatgccaat ttgcaaactc tcaaaaccaa agcctgagtg agctagtagt attttggcag    960

gaccaggaaa acttggttct gaatgaggta tacttaggca aagagaaatt tgacagtgtt   1020

cattccaagt atatgggccg cacaagtttt gattcggaca gttggaccct gagacttcac   1080

aatcttcaga tcaaggacaa gggcttgtat caatgtatca tccatcacaa aaagcccaca   1140

ggaatgattc gcatccacca gatgaattct gaactgtcag tgcttgctgg aggcggagga   1200

tctggtggtg gaggttctgg tggtggggga tctggaggcg gaggatctgg cccacactcg   1260

atgcggtatt tcgagaccgc cgtgtcccgg cccggcctcg aggagccccg gtacatctct   1320

gtcggctatg tggacaacaa ggagttcgtg cgcttcgaca gcgacgcgga gaatccgaga   1380

tatgagccgc gggcgccgtg gatggagcag gaggggccgg agtattggga gcgggaaaca   1440

cagaaagcca agggccaaga gcagtggttc cgagtgagcc tgaggaacct gctcggcgcc   1500

tacaaccaga gcgcgggcgg ctctcacaca ctccagcaga tgtctggctg tgacttgggg   1560

tcggactggc gcctcctccg cgggtacctg cagttcgcct atgaaggccg cgattacatc   1620
```

-continued gccctgaacg aagacctgaa aacgtggacg gcggcggaca tggcggcgca gatcacccga 1680
cgcaagtggg agcagagtgg tgctgcagag cattacaagg cctacctgga gggcgagtgc 1740
gtggagtggc tccacagata cctgaagaac gggaacgcga cgctgctgcg cacagattcc 1800
ccaaaggcac atgtgaccca tcaccccaga tctaaaggtg aagtcaccct gaggtgctgg 1860
gccctgggct tctaccctgc tgacatcacc ctgacctggc agttgaatgg ggaggagctg 1920
acccaggaca tggagcttgt ggagaccagg ccttgcgggg atggaacctt ccagaagtgg 1980
gcatctgtgg tggtgcctct tgggaaggag cagaattaca catgccgtgt gtaccatgag 2040
gggctgcctg agcccctcac cctgagatgg gcagctgcgg gtggccccag agggcccaca 2100
atcaagccct gtcctccatg caaatgccca gcacctaacc tcgagggtgg accatccgtc 2160
ttcatcttcc ctccaaagat caaggatgta ctcatgatct ccctgagccc catagtcaca 2220
tgtgtggtgg tggatgtgag cgaggatgac ccagatgtcc agatcagctg gtttgtgaac 2280
aacgtggaag tacacacagc tcagacacaa acccatagag aggattacaa cagtactctc 2340
cgggtggtca gtgccctccc catccagcac caggactgga tgagtggcaa ggcgttcgca 2400
tgcgcggtca acaacaaaga cctcccagcg cccatcgaga gaaccatctc aaaacccaaa 2460
gggtcagtaa gagctccaca ggtatatgtc ttgcctccac cagaagaaga gatgactaag 2520
aaacaggtca ctctgacctg catggtcaca gacttcatgc ctgaagacat ttatgtggag 2580
tggaccaaca acgggaaaac agagctaaac tacaagaaca ctgaaccagt cctggactct 2640
gatggttctt acttcatgta cagcaagctg agagtggaaa agaagaactg ggtggaaaga 2700
aatagctact cctgttcagt ggtccacgag ggtctgcaca atcaccacac gactaagagc 2760
ttctcccgga ctccgggtaa aggcggatca catcaccatc accatcacca tcactagtga 2820

<210> SEQ ID NO 122
<211> LENGTH: 2820
<212> TYPE: DNA
<213> ORGANISM: Artificial Sequence
<220> FEATURE:
<223> OTHER INFORMATION: Synthetic polynucleotide

<400> SEQUENCE: 122
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catgcaaaaa agcccacagg aatgattcgc 360
atccaccaga tgaattctga actgtcagtg cttgctggag gcggaggatc tggtggtgga 420
ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg gcaggaccag gaaaacttgg ttctgaatga ggtatactta 600
ggcaaagaga aatttgacag tgttcattcc aagtatatgg gccgcacaag ttttgattcg 660
gacagttgga ccctgagact tcacaatctt cagatcaagg acaagggctt gtatcaatgt 720
atcatccatg caaaaaagcc cacaggaatg attcgcatcc accagatgaa ttctgaactg 780
tcagtgcttg ctggaggcgg aggatctggt ggtggaggtt ctggtggtgg gggatctgga 840
ggcggaggat ctgctgctcc tctgaagatt caagcttatt tcaatgagac tgcagacctg 900
ccatgccaat ttgcaaactc tcaaaaccaa agcctgagtg agctagtagt attttggcag 960
gaccaggaaa acttggttct gaatgaggta tacttaggca aagagaaatt tgacagtgtt 1020
cattccaagt atatgggccg cacaagtttt gattcggaca gttggaccct gagacttcac 1080
aatcttcaga tcaaggacaa gggcttgtat caatgtatca tccatgcaaa aaagcccaca 1140
ggaatgattc gcatccacca gatgaattct gaactgtcag tgcttgctgg aggcggagga 1200
tctggtggtg gaggttctgg tggtggggga tctggaggcg gaggatctgg cccacactcg 1260
atgcggtatt tcgagaccgc cgtgtcccgg cccggcctcg aggagccccg gtacatctct 1320
gtcggctatg tggacaacaa ggagttcgtg cgcttcgaca gcgacgcgga gaatccgaga 1380
tatgagccgc gggcgccgtg gatggagcag gaggggccgg agtattggga gcgggaaaca 1440
cagaaagcca agggccaaga gcagtggttc cgagtgagcc tgaggaacct gctcggcgcc 1500
tacaaccaga gcgcgggcgg ctctcacaca ctccagcaga tgtctggctg tgacttgggg 1560
tcggactggc gcctcctccg cgggtacctg cagttcgcct atgaaggccg cgattacatc 1620
gccctgaacg aagacctgaa aacgtggacg gcggcggaca tggcggcgca gatcacccga 1680
cgcaagtggg agcagagtgg tgctgcagag cattacaagg cctacctgga gggcgagtgc 1740
gtggagtggc tccacagata cctgaagaac gggaacgcga cgctgctgcg cacagattcc 1800
ccaaaggcac atgtgaccca tcaccccaga tctaaaggtg aagtcaccct gaggtgctgg 1860
gccctgggct tctaccctgc tgacatcacc ctgacctggc agttgaatgg ggaggagctg 1920
acccaggaca tggagcttgt ggagaccagg ccttgcgggg atggaacctt ccagaagtgg 1980
gcatctgtgg tggtgcctct tgggaaggag cagaattaca catgccgtgt gtaccatgag 2040
gggctgcctg agcccctcac cctgagatgg gcagctgcgg gtggccccag agggcccaca 2100
atcaagccct gtcctccatg caaatgccca gcacctaacc tcgagggtgg accatccgtc 2160
ttcatcttcc ctccaaagat caaggatgta ctcatgatct ccctgagccc catagtcaca 2220
tgtgtggtgg tggatgtgag cgaggatgac ccagatgtcc agatcagctg gtttgtgaac 2280
aacgtggaag tacacacagc tcagacacaa acccatagag aggattacaa cagtactctc 2340
cgggtggtca gtgccctccc catccagcac caggactgga tgagtggcaa ggcgttcgca 2400
tgcgcggtca acaacaaaga cctcccagcg cccatcgaga gaaccatctc aaaacccaaa 2460
gggtcagtaa gagctccaca ggtatatgtc ttgcctccac cagaagaaga gatgactaag 2520
aaacaggtca ctctgacctg catggtcaca gacttcatgc ctgaagacat ttatgtggag 2580
tggaccaaca acgggaaaac agagctaaac tacaagaaca ctgaaccagt cctggactct 2640
gatggttctt acttcatgta cagcaagctg agagtggaaa agaagaactg ggtggaaaga 2700
aatagctact cctgttcagt ggtccacgag ggtctgcaca atcaccacac gactaagagc 2760
ttctcccgga ctccgggtaa aggcggatca catcaccatc accatcacca tcactagtga 2820

<210> SEQ ID NO 123
<211> LENGTH: 4572
<212> TYPE: DNA
<213> ORGANISM: Artificial Sequence
<220> FEATURE:
<223> OTHER INFORMATION: Synthetic polynucleotide

<400> SEQUENCE: 123
atgtctcgct ccgtggcctt agctgtgctc gcgctactct ctctttctgg cctggaggcc 60
gctgctcctc tgaagattca agcttatttc aatgagactg cagacctgcc atgccaattt 120

```
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
atgggccgca caagttttga ttcggacagt tggaccctga gacttcacaa tcttcagatc    300
aaggacaagg gcttgtatca atgtatcatc catcacaaaa agcccacagg aatgattcgc    360
atccaccaga tgaattctga actgtcagtg cttgctaact tcagtcaacc tgaaatagta    420
ccaatttcta atataacaga aaatgtgtac ataaatttga cctgctcatc tatacacggt    480
tacccagaac ctaagaagat gagtgttttg ctaagaacca agaattcaac tatcgagtat    540
gatggtatta tgcagaaatc tcaagataat gtcacagaac tgtacgacgt ttccatcagc    600
ttgtctgttt cattccctga tgttacgagc aatatgacca tcttctgtat tctggaaact    660
gacaagacgc ggcttttatc ttcacctttc tctatagagc ttgaggaccc tcagcctccc    720
ccagaccaca ttcctggagg cggaggatct ggtggtggag gttctggtgg tgggggatct    780
ggaggcggag gatctgctgc tcctctgaag attcaagctt atttcaatga gactgcagac    840
ctgccatgcc aatttgcaaa ctctcaaaac caaagcctga gtgagctagt agtattttgg    900
caggaccagg aaaacttggt tctgaatgag gtatacttag gcaaagagaa atttgacagt    960
gttcattcca agtatatggg ccgcacaagt tttgattcgg acagttggac cctgagactt   1020
cacaatcttc agatcaagga caagggcttg tatcaatgta tcatccatca caaaaagccc   1080
acaggaatga ttcgcatcca ccagatgaat tctgaactgt cagtgcttgc taacttcagt   1140
caacctgaaa tagtaccaat ttctaatata acagaaaatg tgtacataaa tttgacctgc   1200
tcatctatac acggttaccc agaacctaag aagatgagtg ttttgctaag aaccaagaat   1260
tcaactatcg agtatgatgg tattatgcag aaatctcaag ataatgtcac agaactgtac   1320
gacgtttcca tcagcttgtc tgtttcattc cctgatgtta cgagcaatat gaccatcttc   1380
tgtattctgg aaactgacaa gacgcggctt ttatcttcac ctttctctat agagcttgag   1440
gaccctcagc ctcccccaga ccacattcct ggaggcggag gatctggtgg tggaggttct   1500
ggtggtgggg gatctggagg cggaggatct gctgctcctc tgaagattca agcttatttc   1560
aatgagactg cagacctgcc atgccaattt gcaaactctc aaaaccaaag cctgagtgag   1620
ctagtagtat tttggcagga ccaggaaaac ttggttctga atgaggtata cttaggcaaa   1680
gagaaatttg acagtgttca ttccaagtat atgggccgca caagttttga ttcggacagt   1740
tggaccctga gacttcacaa tcttcagatc aaggacaagg gcttgtatca atgtatcatc   1800
catcacaaaa agcccacagg aatgattcgc atccaccaga tgaattctga actgtcagtg   1860
cttgctaact tcagtcaacc tgaaatagta ccaatttcta atataacaga aaatgtgtac   1920
ataaatttga cctgctcatc tatacacggt tacccagaac ctaagaagat gagtgttttg   1980
ctaagaacca agaattcaac tatcgagtat gatggtatta tgcagaaatc tcaagataat   2040
gtcacagaac tgtacgacgt ttccatcagc ttgtctgttt cattccctga tgttacgagc   2100
aatatgacca tcttctgtat tctggaaact gacaagacgc ggcttttatc ttcacctttc   2160
tctatagagc ttgaggaccc tcagcctccc ccagaccaca ttcctggagg cggaggatct   2220
ggtggtggag gttctggtgg tgggggatct ggaggcggag gatctgctgc tcctctgaag   2280
attcaagctt atttcaatga gactgcagac ctgccatgcc aatttgcaaa ctctcaaaac   2340
caaagcctga gtgagctagt agtattttgg caggaccagg aaaacttggt tctgaatgag   2400
gtatacttag gcaaagagaa atttgacagt gttcattcca agtatatggg ccgcacaagt   2460
tttgattcgg acagttggac cctgagactt cacaatcttc agatcaagga caagggcttg   2520
```

```
tatcaatgta tcatccatca caaaaagccc acaggaatga ttcgcatcca ccagatgaat   2580
tctgaactgt cagtgcttgc taacttcagt caacctgaaa tagtaccaat ttctaatata   2640
acagaaaatg tgtacataaa tttgacctgc tcatctatac acggttaccc agaacctaag   2700
aagatgagtg ttttgctaag aaccaagaat tcaactatcg agtatgatgg tattatgcag   2760
aaatctcaag ataatgtcac agaactgtac gacgtttcca tcagcttgtc tgtttcattc   2820
cctgatgtta cgagcaatat gaccatcttc tgtattctgg aaactgacaa gacgcggctt   2880
ttatcttcac ctttctctat agagcttgag gaccctcagc ctcccccaga ccacattcct   2940
ggaggcggag gatctggtgg tggaggttct ggtggtgggg gatctggagg cggaggatct   3000
ggcccacact cgatgcggta tttcgagacc gccgtgtccc ggcccggcct cgaggagccc   3060
cggtacatct ctgtcggcta tgtggacaac aaggagttcg tgcgcttcga cagcgacgcg   3120
gagaatccga gatatgagcc gcgggcgccg tggatggagc aggaggggcc ggagtattgg   3180
gagcgggaaa cacagaaagc caagggccaa gagcagtggt tccgagtgag cctgaggaac   3240
ctgctcggcg cctacaacca gagcgcgggc ggctctcaca cactccagca gatgtctggc   3300
tgtgacttgg ggtcggactg gcgcctcctc cgcgggtacc tgcagttcgc ctatgaaggc   3360
cgcgattaca tcgccctgaa cgaagacctg aaaacgtgga cggcggcgga catggcggcg   3420
cagatcaccc gacgcaagtg ggagcagagt ggtgctgcag agcattacaa ggcctacctg   3480
gagggcgagt gcgtggagtg gctccacaga tacctgaaga acgggaacgc gacgctgctg   3540
cgcacagatt ccccaaaggc acatgtgacc catcacccca gatctaaagg tgaagtcacc   3600
ctgaggtgct gggccctggg cttctaccct gctgacatca ccctgacctg gcagttgaat   3660
ggggaggagc tgacccagga catggagctt gtggagacca ggccttgcgg ggatggaacc   3720
ttccagaagt gggcatctgt ggtggtgcct cttgggaagg agcagaatta cacatgccgt   3780
gtgtaccatg aggggctgcc tgagcccctc accctgagat gggcagctgc gggtggcccc   3840
agagggccca caatcaagcc ctgtcctcca tgcaaatgcc cagcacctaa cctcgagggt   3900
ggaccatccg tcttcatctt ccctccaaag atcaaggatg tactcatgat ctccctgagc   3960
cccatagtca catgtgtggt ggtggatgtg agcgaggatg acccagatgt ccagatcagc   4020
tggtttgtga acaacgtgga agtacacaca gctcagacac aaacccatag agaggattac   4080
aacagtactc tccgggtggt cagtgccctc cccatccagc accaggactg gatgagtggc   4140
aaggcgttcg catgcgcggt caacaacaaa gacctcccag cgcccatcga gagaaccatc   4200
tcaaaaccca aagggtcagt aagagctcca caggtatatg tcttgcctcc accagaagaa   4260
gagatgacta agaaacaggt cactctgacc tgcatggtca cagacttcat gcctgaagac   4320
atttatgtgg agtggaccaa caacgggaaa acagagctaa actacaagaa cactgaacca   4380
gtcctggact ctgatggttc ttacttcatg tacagcaagc tgagagtgga aaagaagaac   4440
tgggtggaaa gaaatagcta ctcctgttca gtggtccacg agggtctgca caatcaccac   4500
acgactaaga gcttctcccg gactccgggt aaaggcggat cacatcacca tcaccatcac   4560
catcactagt ga                                                       4572
```

<210> SEQ ID NO 124
<211> LENGTH: 3216
<212> TYPE: DNA
<213> ORGANISM: Artificial Sequence
<220> FEATURE:
<223> OTHER INFORMATION: Synthetic polynucleotide

<400> SEQUENCE: 124
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggtggtgga 420
ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg gcaggaccag gaaaacttgg ttctgaatga ggtatactta 600
ggcaaagaga aatttgacag tgttcattcc aagtatatgg gccgcacaag ttttgattcg 660
gacagttgga ccctgagact tcacaatctt cagatcaagg acaagggctt gtatcaatgt 720
atcatccatc acaaaaagcc cacaggaatg attcgcatcc accagatgaa ttctgaactg 780
tcagtgcttg ctggaggcgg aggatctggt ggtggaggtt ctggtggtgg gggatctgga 840
ggcggaggat ctgctgctcc tctgaagatt caagcttatt tcaatgagac tgcagacctg 900
ccatgccaat ttgcaaactc tcaaaaccaa agcctgagtg agctagtagt attttggcag 960
gaccaggaaa acttggttct gaatgaggta tacttaggca aagagaaatt tgacagtgtt 1020
cattccaagt atatgggccg cacaagtttt gattcggaca gttggaccct gagacttcac 1080
aatcttcaga tcaaggacaa gggcttgtat caatgtatca tccatcacaa aaagcccaca 1140
ggaatgattc gcatccacca gatgaattct gaactgtcag tgcttgctgg aggcggagga 1200
tctggtggtg gaggttctgg tggtggggga tctggaggcg gaggatctgc tgctcctctg 1260
aagattcaag cttatttcaa tgagactgca gacctgccat gccaatttgc aaactctcaa 1320
aaccaaagcc tgagtgagct agtagtattt tggcaggacc aggaaaactt ggttctgaat 1380
gaggtatact taggcaaaga gaaatttgac agtgttcatt ccaagtatat gggccgcaca 1440
agttttgatt cggacagttg gaccctgaga cttcacaatc ttcagatcaa ggacaagggc 1500
ttgtatcaat gtatcatcca tcacaaaaag cccacaggaa tgattcgcat ccaccagatg 1560
aattctgaac tgtcagtgct tgctggaggc ggaggatctg gtggtggagg ttctggtggt 1620
gggggatctg gaggcggagg atctggccca cactcgatgc ggtatttcga gaccgccgtg 1680
tcccggcccg gcctcgagga gccccggtac atctctgtcg gctatgtgga caacaaggag 1740
ttcgtgcgct tcgacagcga cgcggagaat ccgagatatg agccgcgggc gccgtggatg 1800
gagcaggagg ggccggagta ttgggagcgg gaaacacaga aagccaaggg ccaagagcag 1860
tggttccgag tgagcctgag gaacctgctc ggcgcctaca accagagcgc gggcggctct 1920
cacacactcc agcagatgtc tggctgtgac ttggggtcgg actggcgcct cctccgcggg 1980
tacctgcagt tcgcctatga aggccgcgat tacatcgccc tgaacgaaga cctgaaaacg 2040
tggacggcgg cggacatggc ggcgcagatc acccgacgca agtgggagca gagtggtgct 2100
gcagagcatt acaaggccta cctggagggc gagtgcgtgg agtggctcca cagatacctg 2160
aagaacggga acgcgacgct gctgcgcaca gattccccaa aggcacatgt gacccatcac 2220
cccagatcta aaggtgaagt caccctgagg tgctgggccc tgggcttcta ccctgctgac 2280
atcaccctga cctggcagtt gaatggggag gagctgaccc aggacatgga gcttgtggag 2340
accaggcctt gcggggatgg aaccttccag aagtgggcat ctgtggtggt gcctcttggg 2400
aaggagcaga attacacatg ccgtgtgtac catgaggggc tgcctgagcc cctcaccctg 2460
agatgggcag ctgcgggtgg ccccagaggg cccacaatca agccctgtcc tccatgcaaa 2520
tgcccagcac ctaacctcga gggtggacca tccgtcttca tcttccctcc aaagatcaag 2580
gatgtactca tgatctccct gagccccata gtcacatgtg tggtggtgga tgtgagcgag 2640
gatgacccag atgtccagat cagctggttt gtgaacaacg tggaagtaca cacagctcag 2700
acacaaaccc atagagagga ttacaacagt actctccggg tggtcagtgc cctccccatc 2760
cagcaccagg actggatgag tggcaaggcg ttcgcatgcg cggtcaacaa caaagacctc 2820
ccagcgccca tcgagagaac catctcaaaa cccaaagggt cagtaagagc tccacaggta 2880
tatgtcttgc ctccaccaga agaagagatg actaagaaac aggtcactct gacctgcatg 2940
gtcacagact tcatgcctga agacatttat gtggagtgga ccaacaacgg gaaaacagag 3000
ctaaactaca agaacactga accagtcctg gactctgatg gttcttactt catgtacagc 3060
aagctgagag tggaaaagaa gaactgggtg gaaagaaata gctactcctg ttcagtggtc 3120
cacgagggtc tgcacaatca ccacacgact aagagcttct cccggactcc gggtaaaggc 3180
ggatcacatc accatcacca tcaccatcac tagtga 3216

<210> SEQ ID NO 125
<211> LENGTH: 3216
<212> TYPE: DNA
<213> ORGANISM: Artificial Sequence
<220> FEATURE:
<223> OTHER INFORMATION: Synthetic polynucleotide

<400> SEQUENCE: 125
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catgcaaaaa agcccacagg aatgattcgc 360
atccaccaga tgaattctga actgtcagtg cttgctggag gcggaggatc tggtggtgga 420
ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg gcaggaccag gaaaacttgg ttctgaatga ggtatactta 600
ggcaaagaga aatttgacag tgttcattcc aagtatatgg gccgcacaag ttttgattcg 660
gacagttgga ccctgagact tcacaatctt cagatcaagg acaagggctt gtatcaatgt 720
atcatccatg caaaaaagcc cacaggaatg attcgcatcc accagatgaa ttctgaactg 780
tcagtgcttg ctggaggcgg aggatctggt ggtggaggtt ctggtggtgg gggatctgga 840
ggcggaggat ctgctgctcc tctgaagatt caagcttatt tcaatgagac tgcagacctg 900
ccatgccaat ttgcaaactc tcaaaaccaa agcctgagtg agctagtagt attttggcag 960
gaccaggaaa acttggttct gaatgaggta tacttaggca aagagaaatt tgacagtgtt 1020
cattccaagt atatgggccg cacaagtttt gattcggaca gttggaccct gagacttcac 1080
aatcttcaga tcaaggacaa gggcttgtat caatgtatca tccatgcaaa aaagcccaca 1140

-continued

```
ggaatgattc gcatccacca gatgaattct gaactgtcag tgcttgctgg aggcggagga   1200
tctggtggtg gaggttctgg tggtggggga tctggaggcg gaggatctgc tgctcctctg   1260
aagattcaag cttatttcaa tgagactgca gacctgccat gccaatttgc aaactctcaa   1320
aaccaaagcc tgagtgagct agtagtattt tggcaggacc aggaaaactt ggttctgaat   1380
gaggtatact taggcaaaga gaaatttgac agtgttcatt ccaagtatat gggccgcaca   1440
agttttgatt cggacagttg gaccctgaga cttcacaatc ttcagatcaa ggacaagggc   1500
ttgtatcaat gtatcatcca tgcaaaaaag cccacaggaa tgattcgcat ccaccagatg   1560
aattctgaac tgtcagtgct tgctggaggc ggaggatctg gtggtggagg ttctggtggt   1620
gggggatctg gaggcggagg atctggccca cactcgatgc ggtatttcga gaccgccgtg   1680
tcccggcccg gcctcgagga gccccggtac atctctgtcg gctatgtgga caacaaggag   1740
ttcgtgcgct tcgacagcga cgcggagaat ccgagatatg agccgcgggc gccgtggatg   1800
gagcaggagg ggccggagta ttgggagcgg gaaacacaga aagccaaggg ccaagagcag   1860
tggttccgag tgagcctgag gaacctgctc ggcgcctaca accagagcgc gggcggctct   1920
cacacactcc agcagatgtc tggctgtgac ttggggtcgg actggcgcct cctccgcggg   1980
tacctgcagt tcgcctatga aggccgcgat tacatcgccc tgaacgaaga cctgaaaacg   2040
tggacggcgg cggacatggc ggcgcagatc acccgacgca agtgggagca gagtggtgct   2100
gcagagcatt acaaggccta cctggagggc gagtgcgtgg agtggctcca cagatacctg   2160
aagaacggga acgcgacgct gctgcgcaca gattccccaa aggcacatgt gacccatcac   2220
cccagatcta aaggtgaagt caccctgagg tgctgggccc tgggcttcta ccctgctgac   2280
atcaccctga cctggcagtt gaatggggag gagctgaccc aggacatgga gcttgtggag   2340
accaggcctt gcggggatgg aaccttccag aagtgggcat ctgtggtggt gcctcttggg   2400
aaggagcaga attacacatg ccgtgtgtac catgaggggc tgcctgagcc cctcaccctg   2460
agatgggcag ctgcgggtgg ccccagaggg cccacaatca agccctgtcc tccatgcaaa   2520
tgcccagcac ctaacctcga gggtggacca tccgtcttca tcttccctcc aaagatcaag   2580
gatgtactca tgatctccct gagccccata gtcacatgtg tggtggtgga tgtgagcgag   2640
gatgacccag atgtccagat cagctggttt gtgaacaacg tggaagtaca cacagctcag   2700
acacaaaccc atagagagga ttacaacagt actctccggg tggtcagtgc cctccccatc   2760
cagcaccagg actggatgag tggcaaggcg ttcgcatgcg cggtcaacaa caaagacctc   2820
ccagcgccca tcgagagaac catctcaaaa cccaaagggt cagtaagagc tccacaggta   2880
tatgtcttgc ctccaccaga agaagagatg actaagaaac aggtcactct gacctgcatg   2940
gtcacagact tcatgcctga agacatttat gtggagtgga ccaacaacgg gaaaacagag   3000
ctaaactaca agaacactga accagtcctg gactctgatg gttcttactt catgtacagc   3060
aagctgagag tggaaaagaa gaactgggtg gaaagaaata gctactcctg ttcagtggtc   3120
cacgagggtc tgcacaatca ccacacgact aagagcttct cccggactcc gggtaaaggc   3180
ggatcacatc accatcacca tcaccatcac tagtga                              3216
```

<210> SEQ ID NO 126
<211> LENGTH: 3102
<212> TYPE: DNA
<213> ORGANISM: Artificial Sequence
<220> FEATURE:
<223> OTHER INFORMATION: Synthetic polynucleotide

<400> SEQUENCE: 126

-continued

```
atgtctcgct ccgtggcctt agctgtgctc gcgctactct ctctttctgg cctggaggcc      60
gctgctcctc tgaagattca agcttatttc aatgagactg cagacctgcc atgccaattt     120
gcaaactctc aaaaccaaag cctgagtgag ctagtagtat tttggcagga ccaggaaaac     180
ttggttctga atgaggtata cttaggcaaa gagaaatttg acagtgttca ttccaagtat     240
atgggccgca caagttttga ttcggacagt tggaccctga gacttcacaa tcttcagatc     300
aaggacaagg gcttgtatca atgtatcatc catgcaaaaa agcccacagg aatgattcgc     360
atccaccaga tgaattctga actgtcagtg cttgctaact tcagtcaacc tgaaatagta     420
ccaatttcta atataacaga aaatgtgtac ataaatttga cctgctcatc tatacacggt     480
tacccagaac ctaagaagat gagtgttttg ctaagaacca agaattcaac tatcgagtat     540
gatggtatta tgcagaaatc tcaagataat gtcacagaac tgtacgacgt ttccatcagc     600
ttgtctgttt cattccctga tgttacgagc aatatgacca tcttctgtat tctggaaact     660
gacaagacgc ggcttttatc ttcacctttc tctatagagc ttgaggaccc tcagcctccc     720
ccagaccaca ttcctggagg cggaggatct ggtggtggag gttctggtgg tgggggatct     780
ggaggcggag gatctgctgc tcctctgaag attcaagctt atttcaatga gactgcagac     840
ctgccatgcc aatttgcaaa ctctcaaaac caaagcctga gtgagctagt agtattttgg     900
caggaccagg aaaacttggt tctgaatgag gtatacttag gcaaagagaa atttgacagt     960
gttcattcca agtatatggg ccgcacaagt tttgattcgg acagttggac cctgagactt    1020
cacaatcttc agatcaagga caagggcttg tatcaatgta tcatccatgc aaaaaagccc    1080
acaggaatga ttcgcatcca ccagatgaat tctgaactgt cagtgcttgc taacttcagt    1140
caacctgaaa tagtaccaat ttctaatata acagaaaatg tgtacataaa tttgacctgc    1200
tcatctatac acggttaccc agaacctaag aagatgagtg ttttgctaag aaccaagaat    1260
tcaactatcg agtatgatgg tattatgcag aaatctcaag ataatgtcac agaactgtac    1320
gacgtttcca tcagcttgtc tgtttcattc cctgatgtta cgagcaatat gaccatcttc    1380
tgtattctgg aaactgacaa gacgcggctt ttatcttcac ctttctctat agagcttgag    1440
gaccctcagc ctcccccaga ccacattcct ggaggcggag gatctggtgg tggaggttct    1500
ggtggtgggg gatctggagg cggaggatct ggcccacact cgatgcggta tttcgagacc    1560
gccgtgtccc ggcccggcct cgaggagccc cggtacatct ctgtcggcta tgtggacaac    1620
aaggagttcg tgcgcttcga cagcgacgcg gagaatccga gatatgagcc gcgggcgccg    1680
tggatggagc aggaggggcc ggagtattgg gagcgggaaa cacagaaagc caagggccaa    1740
gagcagtggt tccgagtgag cctgaggaac ctgctcggcg cctacaacca gagcgcgggc    1800
ggctctcaca cactccagca gatgtctggc tgtgacttgg ggtcggactg gcgcctcctc    1860
cgcgggtacc tgcagttcgc ctatgaaggc cgcgattaca tcgccctgaa cgaagacctg    1920
aaaacgtgga cggcggcgga catggcggcg cagatcaccc gacgcaagtg ggagcagagt    1980
ggtgctgcag agcattacaa ggcctacctg gagggcgagt gcgtggagtg gctccacaga    2040
tacctgaaga acgggaacgc gacgctgctg cgcacagatt ccccaaaggc acatgtgacc    2100
catcacccca gatctaaagg tgaagtcacc ctgaggtgct gggccctggg cttctaccct    2160
gctgacatca ccctgacctg gcagttgaat ggggaggagc tgacccagga catggagctt    2220
gtggagacca ggccttgcgg ggatggaacc ttccagaagt gggcatctgt ggtggtgcct    2280
cttgggaagg agcagaatta cacatgccgt gtgtaccatg aggggctgcc tgagcccctc    2340
```

```
accctgagat gggcagctgc gggtggcccc agagggccca caatcaagcc ctgtcctcca   2400

tgcaaatgcc cagcacctaa cctcgagggt ggaccatccg tcttcatctt ccctccaaag   2460

atcaaggatg tactcatgat ctccctgagc cccatagtca catgtgtggt ggtggatgtg   2520

agcgaggatg acccagatgt ccagatcagc tggtttgtga acaacgtgga agtacacaca   2580

gctcagacac aaacccatag agaggattac aacagtactc tccgggtggt cagtgccctc   2640

cccatccagc accaggactg gatgagtggc aaggcgttcg catgcgcggt caacaacaaa   2700

gacctcccag cgcccatcga gagaaccatc tcaaaaccca aagggtcagt aagagctcca   2760

caggtatatg tcttgcctcc accagaagaa gagatgacta agaaacaggt cactctgacc   2820

tgcatggtca cagacttcat gcctgaagac atttatgtgg agtggaccaa caacgggaaa   2880

acagagctaa actacaagaa cactgaacca gtcctggact ctgatggttc ttacttcatg   2940

tacagcaagc tgagagtgga aaagaagaac tgggtggaaa gaaatagcta ctcctgttca   3000

gtggtccacg agggtctgca caatcaccac acgactaaga gcttctcccg gactccgggt   3060

aaaggcggat cacatcacca tcaccatcac catcactagt ga                       3102
```

<210> SEQ ID NO 127
<211> LENGTH: 3837
<212> TYPE: DNA
<213> ORGANISM: Artificial Sequence
<220> FEATURE:
<223> OTHER INFORMATION: Synthetic polynucleotide

<400> SEQUENCE: 127

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catgcaaaaa agcccacagg aatgattcgc    360

atccaccaga tgaattctga actgtcagtg cttgctaact tcagtcaacc tgaaatagta    420

ccaatttcta atataacaga aaatgtgtac ataaatttga cctgctcatc tatacacggt    480

tacccagaac ctaagaagat gagtgttttg ctaagaacca agaattcaac tatcgagtat    540

gatggtatta tgcagaaatc tcaagataat gtcacagaac tgtacgacgt ttccatcagc    600

ttgtctgttt cattccctga tgttacgagc aatatgacca tcttctgtat tctggaaact    660

gacaagacgc ggcttttatc ttcacctttc tctatagagc ttgaggaccc tcagcctccc    720

ccagaccaca ttcctggagg cggaggatct ggtggtggag gttctggtgg tgggggatct    780

ggaggcggag gatctgctgc tcctctgaag attcaagctt atttcaatga gactgcagac    840

ctgccatgcc aatttgcaaa ctctcaaaac caaagcctga gtgagctagt agtattttgg    900

caggaccagg aaaacttggt tctgaatgag gtatacttag gcaaagagaa atttgacagt    960

gttcattcca agtatatggg ccgcacaagt tttgattcgg acagttggac cctgagactt   1020

cacaatcttc agatcaagga caagggcttg tatcaatgta tcatccatgc aaaaaagccc   1080

acaggaatga ttcgcatcca ccagatgaat tctgaactgt cagtgcttgc taacttcagt   1140

caacctgaaa tagtaccaat ttctaatata acagaaaatg tgtacataaa tttgacctgc   1200

tcatctatac acggttaccc agaacctaag aagatgagtg ttttgctaag aaccaagaat   1260

tcaactatcg agtatgatgg tattatgcag aaatctcaag ataatgtcac agaactgtac   1320
```

```
gacgtttcca tcagcttgtc tgtttcattc cctgatgtta cgagcaatat gaccatcttc   1380
tgtattctgg aaactgacaa gacgcggctt ttatcttcac ctttctctat agagcttgag   1440
gaccctcagc ctcccccaga ccacattcct ggaggcggag gatctggtgg tggaggttct   1500
ggtggtgggg gatctggagg cggaggatct gctgctcctc tgaagattca agcttatttc   1560
aatgagactg cagacctgcc atgccaattt gcaaactctc aaaaccaaag cctgagtgag   1620
ctagtagtat tttggcagga ccaggaaaac ttggttctga atgaggtata cttaggcaaa   1680
gagaaatttg acagtgttca ttccaagtat atgggccgca caagttttga ttcggacagt   1740
tggaccctga gacttcacaa tcttcagatc aaggacaagg gcttgtatca atgtatcatc   1800
catgcaaaaa agcccacagg aatgattcgc atccaccaga tgaattctga actgtcagtg   1860
cttgctaact tcagtcaacc tgaaatagta ccaatttcta atataacaga aaatgtgtac   1920
ataaatttga cctgctcatc tatacacggt tacccagaac ctaagaagat gagtgttttg   1980
ctaagaacca agaattcaac tatcgagtat gatggtatta tgcagaaatc tcaagataat   2040
gtcacagaac tgtacgacgt ttccatcagc ttgtctgttt cattccctga tgttacgagc   2100
aatatgacca tcttctgtat tctggaaact gacaagacgc ggcttttatc ttcacctttc   2160
tctatagagc ttgaggaccc tcagcctccc ccagaccaca ttcctggagg cggaggatct   2220
ggtggtggag gttctggtgg tgggggatct ggaggcggag gatctggccc acactcgatg   2280
cggtatttcg agaccgccgt gtcccggccc ggcctcgagg agccccggta catctctgtc   2340
ggctatgtgg acaacaagga gttcgtgcgc ttcgacagcg acgcggagaa tccgagatat   2400
gagccgcggg cgccgtggat ggagcaggag gggccggagt attgggagcg ggaaacacag   2460
aaagccaagg gccaagagca gtggttccga gtgagcctga ggaacctgct cggcgcctac   2520
aaccagagcg cgggcggctc tcacacactc cagcagatgt ctggctgtga cttggggtcg   2580
gactggcgcc tcctccgcgg gtacctgcag ttcgcctatg aaggccgcga ttacatcgcc   2640
ctgaacgaag acctgaaaac gtggacggcg gcggacatgg cggcgcagat cacccgacgc   2700
aagtgggagc agagtggtgc tgcagagcat tacaaggcct acctggaggg cgagtgcgtg   2760
gagtggctcc acagatacct gaagaacggg aacgcgacgc tgctgcgcac agattcccca   2820
aaggcacatg tgacccatca ccccagatct aaaggtgaag tcaccctgag gtgctgggcc   2880
ctgggcttct accctgctga catcaccctg acctggcagt tgaatgggga ggagctgacc   2940
caggacatgg agcttgtgga gaccaggcct tgcggggatg gaaccttcca gaagtgggca   3000
tctgtggtgg tgcctcttgg gaaggagcag aattacacat gccgtgtgta ccatgagggg   3060
ctgcctgagc ccctcaccct gagatgggca gctgcgggtg gccccagagg gcccacaatc   3120
aagccctgtc ctccatgcaa atgcccagca cctaacctcg agggtggacc atccgtcttc   3180
atcttccctc caaagatcaa ggatgtactc atgatctccc tgagccccat agtcacatgt   3240
gtggtggtgg atgtgagcga ggatgaccca gatgtccaga tcagctggtt tgtgaacaac   3300
gtggaagtac acacagctca gacacaaacc catagagagg attacaacag tactctccgg   3360
gtggtcagtg ccctccccat ccagcaccag gactggatga gtggcaaggc gttcgcatgc   3420
gcggtcaaca acaaagacct cccagcgccc atcgagagaa ccatctcaaa acccaaaggg   3480
tcagtaagag ctccacaggt atatgtcttg cctccaccag aagaagagat gactaagaaa   3540
caggtcactc tgacctgcat ggtcacagac ttcatgcctg aagacattta tgtggagtgg   3600
accaacaacg ggaaaacaga gctaaactac aagaacactg aaccagtcct ggactctgat   3660
```

ggttcttact tcatgtacag caagctgaga gtggaaaaga agaactgggt ggaaagaaat 3720
agctactcct gttcagtggt ccacgagggt ctgcacaatc accacacgac taagagcttc 3780
tcccggactc cgggtaaagg cggatcacat caccatcacc atcaccatca ctagtga 3837

<210> SEQ ID NO 128
<211> LENGTH: 4572
<212> TYPE: DNA
<213> ORGANISM: Artificial Sequence
<220> FEATURE:
<223> OTHER INFORMATION: Synthetic polynucleotide

<400> SEQUENCE: 128
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catgcaaaaa agcccacagg aatgattcgc 360
atccaccaga tgaattctga actgtcagtg cttgctaact tcagtcaacc tgaaatagta 420
ccaatttcta atataacaga aaatgtgtac ataaatttga cctgctcatc tatacacggt 480
tacccagaac ctaagaagat gagtgttttg ctaagaacca agaattcaac tatcgagtat 540
gatggtatta tgcagaaatc tcaagataat gtcacagaac tgtacgacgt ttccatcagc 600
ttgtctgttt cattccctga tgttacgagc aatatgacca tcttctgtat tctggaaact 660
gacaagacgc ggcttttatc ttcacctttc tctatagagc ttgaggaccc tcagcctccc 720
ccagaccaca ttcctggagg cggaggatct ggtggtggag gttctggtgg tgggggatct 780
ggaggcggag gatctgctgc tcctctgaag attcaagctt atttcaatga gactgcagac 840
ctgccatgcc aatttgcaaa ctctcaaaac caaagcctga gtgagctagt agtattttgg 900
caggaccagg aaaacttggt tctgaatgag gtatacttag gcaaagagaa atttgacagt 960
gttcattcca agtatatggg ccgcacaagt tttgattcgg acagttggac cctgagactt 1020
cacaatcttc agatcaagga caagggcttg tatcaatgta tcatccatgc aaaaaagccc 1080
acaggaatga ttcgcatcca ccagatgaat tctgaactgt cagtgcttgc taacttcagt 1140
caacctgaaa tagtaccaat ttctaatata acagaaaatg tgtacataaa tttgacctgc 1200
tcatctatac acggttaccc agaacctaag aagatgagtg ttttgctaag aaccaagaat 1260
tcaactatcg agtatgatgg tattatgcag aaatctcaag ataatgtcac agaactgtac 1320
gacgtttcca tcagcttgtc tgtttcattc cctgatgtta cgagcaatat gaccatcttc 1380
tgtattctgg aaactgacaa gacgcggctt ttatcttcac ctttctctat agagcttgag 1440
gaccctcagc ctcccccaga ccacattcct ggaggcggag gatctggtgg tggaggttct 1500
ggtggtgggg gatctggagg cggaggatct gctgctcctc tgaagattca agcttatttc 1560
aatgagactg cagacctgcc atgccaattt gcaaactctc aaaaccaaag cctgagtgag 1620
ctagtagtat tttggcagga ccaggaaaac ttggttctga atgaggtata cttaggcaaa 1680
gagaaatttg acagtgttca ttccaagtat atgggccgca caagttttga ttcggacagt 1740
tggaccctga gacttcacaa tcttcagatc aaggacaagg gcttgtatca atgtatcatc 1800
catgcaaaaa agcccacagg aatgattcgc atccaccaga tgaattctga actgtcagtg 1860
cttgctaact tcagtcaacc tgaaatagta ccaatttcta atataacaga aaatgtgtac 1920
ataaatttga cctgctcatc tatacacggt tacccagaac ctaagaagat gagtgttttg 1980
ctaagaacca agaattcaac tatcgagtat gatggtatta tgcagaaatc tcaagataat 2040
gtcacagaac tgtacgacgt ttccatcagc ttgtctgttt cattccctga tgttacgagc 2100
aatatgacca tcttctgtat tctggaaact gacaagacgc ggcttttatc ttcacctttc 2160
tctatagagc ttgaggaccc tcagcctccc ccagaccaca ttcctggagg cggaggatct 2220
ggtggtggag gttctggtgg tgggggatct ggaggcggag gatctgctgc tcctctgaag 2280
attcaagctt atttcaatga gactgcagac ctgccatgcc aatttgcaaa ctctcaaaac 2340
caaagcctga gtgagctagt agtattttgg caggaccagg aaaacttggt tctgaatgag 2400
gtatacttag gcaaagagaa atttgacagt gttcattcca agtatatggg ccgcacaagt 2460
tttgattcgg acagttggac cctgagactt cacaatcttc agatcaagga caagggcttg 2520
tatcaatgta tcatccatgc aaaaaagccc acaggaatga ttcgcatcca ccagatgaat 2580
tctgaactgt cagtgcttgc taacttcagt caacctgaaa tagtaccaat ttctaatata 2640
acagaaaatg tgtacataaa tttgacctgc tcatctatac acggttaccc agaacctaag 2700
aagatgagtg ttttgctaag aaccaagaat tcaactatcg agtatgatgg tattatgcag 2760
aaatctcaag ataatgtcac agaactgtac gacgtttcca tcagcttgtc tgtttcattc 2820
cctgatgtta cgagcaatat gaccatcttc tgtattctgg aaactgacaa gacgcggctt 2880
ttatcttcac ctttctctat agagcttgag gaccctcagc ctcccccaga ccacattcct 2940
ggaggcggag gatctggtgg tggaggttct ggtggtgggg gatctggagg cggaggatct 3000
ggcccacact cgatgcggta tttcgagacc gccgtgtccc ggcccggcct cgaggagccc 3060
cggtacatct ctgtcggcta tgtggacaac aaggagttcg tgcgcttcga cagcgacgcg 3120
gagaatccga gatatgagcc gcgggcgccg tggatggagc aggaggggcc ggagtattgg 3180
gagcgggaaa cacagaaagc caagggccaa gagcagtggt tccgagtgag cctgaggaac 3240
ctgctcggcg cctacaacca gagcgcgggc ggctctcaca cactccagca gatgtctggc 3300
tgtgacttgg ggtcggactg gcgcctcctc cgcgggtacc tgcagttcgc ctatgaaggc 3360
cgcgattaca tcgccctgaa cgaagacctg aaaacgtgga cggcggcgga catggcggcg 3420
cagatcaccc gacgcaagtg ggagcagagt ggtgctgcag agcattacaa ggcctacctg 3480
gagggcgagt gcgtggagtg gctccacaga tacctgaaga acgggaacgc gacgctgctg 3540
cgcacagatt ccccaaaggc acatgtgacc catcacccca gatctaaagg tgaagtcacc 3600
ctgaggtgct gggccctggg cttctaccct gctgacatca ccctgacctg gcagttgaat 3660
ggggaggagc tgacccagga catggagctt gtggagacca ggccttgcgg ggatggaacc 3720
ttccagaagt gggcatctgt ggtggtgcct cttgggaagg agcagaatta cacatgccgt 3780
gtgtaccatg aggggctgcc tgagcccctc accctgagat gggcagctgc gggtggcccc 3840
agagggccca caatcaagcc ctgtcctcca tgcaaatgcc cagcacctaa cctcgagggt 3900
ggaccatccg tcttcatctt ccctccaaag atcaaggatg tactcatgat ctccctgagc 3960
cccatagtca catgtgtggt ggtggatgtg agcgaggatg acccagatgt ccagatcagc 4020
tggtttgtga acaacgtgga agtacacaca gctcagacac aaacccatag agaggattac 4080
aacagtactc tccgggtggt cagtgccctc cccatccagc accaggactg gatgagtggc 4140
aaggcgttcg catgcgcggt caacaacaaa gacctcccag cgcccatcga gagaaccatc 4200
tcaaaaccca aagggtcagt aagagctcca caggtatatg tcttgcctcc accagaagaa 4260
gagatgacta agaaacaggt cactctgacc tgcatggtca cagacttcat gcctgaagac 4320
atttatgtgg agtggaccaa caacgggaaa acagagctaa actacaagaa cactgaacca 4380
gtcctggact ctgatggttc ttacttcatg tacagcaagc tgagagtgga aaagaagaac 4440
tgggtggaaa gaaatagcta ctcctgttca gtggtccacg agggtctgca caatcaccac 4500
acgactaaga gcttctcccg gactccgggt aaaggcggat cacatcacca tcaccatcac 4560
catcactagt ga 4572

<210> SEQ ID NO 129
<211> LENGTH: 2409
<212> TYPE: DNA
<213> ORGANISM: Artificial Sequence
<220> FEATURE:
<223> OTHER INFORMATION: Synthetic polynucleotide

<400> SEQUENCE: 129
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctaact tcagtcaacc tgaaatagta 420
ccaatttcta atataacaga agctgctcct ctgaagattc aagcttattt caatgagact 480
gcagacctgc catgccaatt tgcaaactct caaaaccaaa gcctgagtga gctagtagta 540
ttttggcagg accaggaaaa cttggttctg aatgaggtat acttaggcaa agagaaattt 600
gacagtgttc attccaagta tatgggccgc acaagttttg attcggacag ttggaccctg 660
agacttcaca atcttcagat caaggacaag ggcttgtatc aatgtatcat ccatcacaaa 720
aagcccacag gaatgattcg catccaccag atgaattctg aactgtcagt gcttgctgga 780
ggcggaggat ctggtggtgg aggttctggt ggtgggggat ctggaggcgg aggatctggc 840
ccacactcga tgcggtattt cgagaccgcc gtgtcccggc ccggcctcga ggagccccgg 900
tacatctctg tcggctatgt ggacaacaag gagttcgtgc gcttcgacag cgacgcggag 960
aatccgagat atgagccgcg ggcgccgtgg atggagcagg aggggccgga gtattgggag 1020
cgggaaacac agaaagccaa gggccaagag cagtggttcc gagtgagcct gaggaacctg 1080
ctcggcgcct acaaccagag cgcgggcggc tctcacacac tccagcagat gtctggctgt 1140
gacttggggt cggactggcg cctcctccgc gggtacctgc agttcgccta tgaaggccgc 1200
gattacatcg ccctgaacga agacctgaaa acgtggacgg cggcggacat ggcggcgcag 1260
atcacccgac gcaagtggga gcagagtggt gctgcagagc attacaaggc ctacctggag 1320
ggcgagtgcg tggagtggct ccacagatac ctgaagaacg ggaacgcgac gctgctgcgc 1380
acagattccc caaaggcaca tgtgacccat caccccagat ctaaaggtga agtcaccctg 1440
aggtgctggg ccctgggctt ctaccctgct gacatcaccc tgacctggca gttgaatggg 1500
gaggagctga cccaggacat ggagcttgtg gagaccaggc cttgcgggga tggaaccttc 1560
cagaagtggg catctgtggt ggtgcctctt gggaaggagc agaattacac atgccgtgtg 1620
taccatgagg ggctgcctga gcccctcacc ctgagatggg cagctgcggg tggccccaga 1680
gggcccacaa tcaagccctg tcctccatgc aaatgcccag cacctaacct cgagggtgga 1740
ccatccgtct tcatcttccc tccaaagatc aaggatgtac tcatgatctc cctgagcccc 1800
atagtcacat gtgtggtggt ggatgtgagc gaggatgacc cagatgtcca gatcagctgg 1860
tttgtgaaca acgtggaagt acacacagct cagacacaaa cccatagaga ggattacaac 1920
agtactctcc gggtggtcag tgccctcccc atccagcacc aggactggat gagtggcaag 1980
gcgttcgcat gcgcggtcaa caacaaagac ctcccagcgc ccatcgagag aaccatctca 2040
aaacccaaag ggtcagtaag agctccacag gtatatgtct tgcctccacc agaagaagag 2100
atgactaaga aacaggtcac tctgacctgc atggtcacag acttcatgcc tgaagacatt 2160
tatgtggagt ggaccaacaa cgggaaaaca gagctaaact acaagaacac tgaaccagtc 2220
ctggactctg atggttctta cttcatgtac agcaagctga gagtggaaaa gaagaactgg 2280
gtggaaagaa atagctactc ctgttcagtg gtccacgagg gtctgcacaa tcaccacacg 2340
actaagagct tctcccggac tccgggtaaa ggcggatcac atcaccatca ccatcaccat 2400
cactagtga 2409

<210> SEQ ID NO 130
<211> LENGTH: 2073
<212> TYPE: DNA
<213> ORGANISM: Artificial Sequence
<220> FEATURE:
<223> OTHER INFORMATION: Synthetic polynucleotide

<400> SEQUENCE: 130
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctaact tcagtcaacc tgaaatagta 420
ccaatttcta atataacaga aggaggcgga ggatctggtg gtggaggttc tggtggtggg 480
ggatctggag gcggaggatc tggcccacac tcgatgcggt atttcgagac cgccgtgtcc 540
cggcccggcc tcgaggagcc ccggtacatc tctgtcggct atgtggacaa caaggagttc 600
gtgcgcttcg acagcgacgc ggagaatccg agatatgagc cgcgggcgcc gtggatggag 660
caggaggggc cggagtattg ggagcgggaa acacagaaag ccaagggcca agagcagtgg 720
ttccgagtga gcctgaggaa cctgctcggc gcctacaacc agagcgcggg cggctctcac 780
acactccagc agatgtctgg ctgtgacttg ggtcggact ggcgcctcct ccgcgggtac 840
ctgcagttcg cctatgaagg ccgcgattac atcgccctga acgaagacct gaaaacgtgg 900
acggcggcgg acatggcggc gcagatcacc cgacgcaagt gggagcagag tggtgctgca 960
gagcattaca aggcctacct ggagggcgag tgcgtggagt ggctccacag atacctgaag 1020
aacgggaacg cgacgctgct gcgcacagat tccccaaagg cacatgtgac ccatcacccc 1080
agatctaaag gtgaagtcac cctgaggtgc tgggccctgg gcttctaccc tgctgacatc 1140
accctgacct ggcagttgaa tggggaggag ctgacccagg acatggagct tgtggagacc 1200
aggccttgcg gggatggaac cttccagaag tgggcatctg tggtggtgcc tcttgggaag 1260
gagcagaatt acacatgccg tgtgtaccat gaggggctgc ctgagcccct caccctgaga 1320

```
tgggcagctg cgggtggccc cagagggccc acaatcaagc cctgtcctcc atgcaaatgc   1380

ccagcaccta acctcgaggg tggaccatcc gtcttcatct tccctccaaa gatcaaggat   1440

gtactcatga tctccctgag ccccatagtc acatgtgtgg tggtggatgt gagcgaggat   1500

gacccagatg tccagatcag ctggtttgtg aacaacgtgg aagtacacac agctcagaca   1560

caaacccata gagaggatta caacagtact ctccgggtgg tcagtgccct ccccatccag   1620

caccaggact ggatgagtgg caaggcgttc gcatgcgcgg tcaacaacaa agacctccca   1680

gcgcccatcg agagaaccat ctcaaaaccc aaagggtcag taagagctcc acaggtatat   1740

gtcttgcctc caccagaaga agagatgact aagaaacagg tcactctgac ctgcatggtc   1800

acagacttca tgcctgaaga catttatgtg gagtggacca acaacgggaa aacagagcta   1860

aactacaaga acactgaacc agtcctggac tctgatggtt cttacttcat gtacagcaag   1920

ctgagagtgg aaaagaagaa ctgggtggaa agaaatagct actcctgttc agtggtccac   1980

gagggtctgc acaatcacca cacgactaag agcttctccc ggactccggg taaaggcgga   2040

tcacatcacc atcaccatca ccatcactag tga                                2073
```

<210> SEQ ID NO 131
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 131

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgaatcgca caagttttga ttcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320
```

```
cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

<210> SEQ ID NO 132
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 132

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttgc atcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320
```

```
cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

```
<210> SEQ ID NO 133
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 133

atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgaatcgca caagttttga ttcggacagt tggaccctga gacttcacaa tcttcagatc    300

aaggacaagg gcttgtatca atgtatcatc catgcaaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380
```

ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 134
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 134
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttgc atcggacagt tggaccctga gacttcacaa tcttcagatc 300
aaggacaagg gcttgtatca atgtatcatc catgcaaaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480
gagaccgccg tgtcccggcc cggcctcgag gagccccggt acatctctgt cggctatgtg 540
gacaacaagg agttcgtgcg cttcgacagc gacgcggaga atccgagata tgagccgcgg 600
gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 135
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 135
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccgcaa gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480
gagaccgccg tgtcccggcc cggcctcgag gagccccggt acatctctgt cggctatgtg 540
gacaacaagg agttcgtgcg cttcgacagc gacgcggaga atccgagata tgagccgcgg 600
gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440

```
gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga               2028
```

<210> SEQ ID NO 136
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 136

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccgcaa gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440
```

```
gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga               2028
```

<210> SEQ ID NO 137
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 137

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaaggca    240

atgggccgca caagttttga ttcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500
```

```
cacacagctc agacacaaac ccatagagag gattacaaca gtactctccg ggtggtcagt   1560
gccctcccca tccagcacca ggactggatg agtggcaagg cgttcgcatg cgcggtcaac   1620
aacaaagacc tcccagcgcc catcgagaga accatctcaa aacccaaagg gtcagtaaga   1680
gctccacagg tatatgtctt gcctccacca gaagaagaga tgactaagaa acaggtcact   1740
ctgacctgca tggtcacaga cttcatgcct gaagacattt atgtggagtg gaccaacaac   1800
gggaaaacag agctaaacta caagaacact gaaccagtcc tggactctga tggttcttac   1860
ttcatgtaca gcaagctgag agtggaaaag aagaactggg tggaaagaaa tagctactcc   1920
tgttcagtgg tccacgaggg tctgcacaat caccacacga ctaagagctt ctcccggact   1980
ccgggtaaag gcggatcaca tcaccatcac catcaccatc actagtga                2028
```

<210> SEQ ID NO 138
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 138

```
atgtctcgct ccgtggcctt agctgtgctc gcgctactct ctctttctgg cctggaggcc     60
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggcactga atgaggtata cttaggcaaa gagaaatttg acagtgttca ttccaagtat    240
atgggccgca caagttttga ttcggacagt tggaccctga gacttcacaa tcttcagatc    300
aaggacaagg gcttgtatca atgtatcatc catcacaaaa agcccacagg aatgattcgc    360
atccaccaga tgaattctga actgtcagtg cttgctggag gcggaggatc tggtggtgga    420
ggttctggtg gtgggggatc tggaggcgga ggatctggcc cacactcgat gcggtatttc    480
gagaccgccg tgtcccggcc cggcctcgag gagccccggt acatctctgt cggctatgtg    540
gacaacaagg agttcgtgcg cttcgacagc gacgcggaga atccgagata tgagccgcgg    600
gcgccgtgga tggagcagga ggggccggag tattgggagc gggaaacaca gaaagccaag    660
ggccaagagc agtggttccg agtgagcctg aggaacctgc tcggcgccta caaccagagc    720
gcgggcggct ctcacacact ccagcagatg tctggctgtg acttggggtc ggactggcgc    780
ctcctccgcg ggtacctgca gttcgcctat gaaggccgcg attacatcgc cctgaacgaa    840
gacctgaaaa cgtggacggc ggcggacatg gcggcgcaga tcacccgacg caagtgggag    900
cagagtggtg ctgcagagca ttacaaggcc tacctggagg gcgagtgcgt ggagtggctc    960
cacagatacc tgaagaacgg gaacgcgacg ctgctgcgca cagattcccc aaaggcacat   1020
gtgacccatc accccagatc taaaggtgaa gtcaccctga ggtgctgggc cctgggcttc   1080
taccctgctg acatcaccct gacctggcag ttgaatgggg aggagctgac ccaggacatg   1140
gagcttgtgg agaccaggcc ttgcggggat ggaaccttcc agaagtgggc atctgtggtg   1200
gtgcctcttg ggaaggagca gaattacaca tgccgtgtgt accatgaggg gctgcctgag   1260
cccctcaccc tgagatgggc agctgcgggt ggccccagag ggcccacaat caagccctgt   1320
cctccatgca aatgcccagc acctaacctc gagggtggac catccgtctt catcttccct   1380
ccaaagatca aggatgtact catgatctcc ctgagcccca tagtcacatg tgtggtggtg   1440
gatgtgagcg aggatgaccc agatgtccag atcagctggt ttgtgaacaa cgtggaagta   1500
```

```
cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga               2028
```

<210> SEQ ID NO 139
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 139

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttgggcaga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560
```

gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 140
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 140
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtag catggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480
gagaccgccg tgtcccggcc cggcctcgag gagccccggt acatctctgt cggctatgtg 540
gacaacaagg agttcgtgcg cttcgacagc gacgcggaga atccgagata tgagccgcgg 600
gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 141
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 141
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgaatcgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggtggtgga 420
ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg gcaggaccag gaaaacttgg ttctgaatga ggtatactta 600
ggcaaagaga aatttgacag tgttcattcc aagtatatga atcgcacaag ttttgattcg 660
gacagttgga ccctgagact tcacaatctt cagatcaagg acaagggctt gtatcaatgt 720
atcatccatc acaaaaagcc cacaggaatg attcgcatcc accagatgaa ttctgaactg 780
tcagtgcttg ctggaggcgg aggatctggt ggtggaggtt ctggtggtgg gggatctgga 840
ggcggaggat ctggcccaca ctcgatgcgg tatttcgaga ccgccgtgtc ccggcccggc 900
ctcgaggagc cccggtacat ctctgtcggc tatgtggaca acaaggagtt cgtgcgcttc 960
gacagcgacg cggagaatcc gagatatgag ccgcgggcgc cgtggatgga gcaggagggg 1020
ccggagtatt gggagcggga aacacagaaa gccaagggcc aagagcagtg gttccgagtg 1080
agcctgagga acctgctcgg cgcctacaac cagagcgcgg gcggctctca cacactccag 1140
cagatgtctg gctgtgactt ggggtcggac tggcgcctcc tccgcgggta cctgcagttc 1200
gcctatgaag gccgcgatta catcgccctg aacgaagacc tgaaaacgtg gacggcggcg 1260
gacatggcgg cgcagatcac ccgacgcaag tgggagcaga gtggtgctgc agagcattac 1320
aaggcctacc tggagggcga gtgcgtggag tggctccaca gatacctgaa gaacgggaac 1380
gcgacgctgc tgcgcacaga ttccccaaag gcacatgtga cccatcaccc cagatctaaa 1440
ggtgaagtca ccctgaggtg ctgggccctg ggcttctacc ctgctgacat caccctgacc 1500
tggcagttga atggggagga gctgacccag gacatggagc ttgtggagac caggccttgc 1560
ggggatggaa ccttccagaa gtgggcatct gtggtggtgc ctcttgggaa ggagcagaat 1620

```
tacacatgcc gtgtgtacca tgaggggctg cctgagcccc tcaccctgag atgggcagct   1680
gcgggtggcc ccagagggcc cacaatcaag ccctgtcctc catgcaaatg cccagcacct   1740
aacctcgagg gtggaccatc cgtcttcatc ttccctccaa agatcaagga tgtactcatg   1800
atctccctga gccccatagt cacatgtgtg gtggtggatg tgagcgagga tgacccagat   1860
gtccagatca gctggtttgt gaacaacgtg gaagtacaca cagctcagac acaaacccat   1920
agagaggatt acaacagtac tctccgggtg gtcagtgccc tccccatcca gcaccaggac   1980
tggatgagtg gcaaggcgtt cgcatgcgcg gtcaacaaca aagacctccc agcgcccatc   2040
gagagaacca tctcaaaacc caaagggtca gtaagagctc cacaggtata tgtcttgcct   2100
ccaccagaag aagagatgac taagaaacag gtcactctga cctgcatggt cacagacttc   2160
atgcctgaag acatttatgt ggagtggacc aacaacggga aaacagagct aaactacaag   2220
aacactgaac cagtcctgga ctctgatggt tcttacttca tgtacagcaa gctgagagtg   2280
gaaaagaaga actgggtgga aagaaatagc tactcctgtt cagtggtcca cgagggtctg   2340
cacaatcacc acacgactaa gagcttctcc cggactccgg gtaaaggcgg atcacatcac   2400
catcaccatc accatcacta gtga                                           2424
```

<210> SEQ ID NO 142
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 142

```
atgtctcgct ccgtggcctt agctgtgctc gcgctactct ctctttctgg cctggaggcc     60
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
atgggccgca caagttttgc atcggacagt tggaccctga gacttcacaa tcttcagatc    300
aaggacaagg gcttgtatca atgtatcatc catcacaaaa agcccacagg aatgattcgc    360
atccaccaga tgaattctga actgtcagtg cttgctggag gcggaggatc tggtggtgga    420
ggttctggtg gtgggggatc tggaggcgga ggatctgctg ctcctctgaa gattcaagct    480
tatttcaatg agactgcaga cctgccatgc caatttgcaa actctcaaaa ccaaagcctg    540
agtgagctag tagtattttg gcaggaccag gaaaacttgg ttctgaatga ggtatactta    600
ggcaaagaga aatttgacag tgttcattcc aagtatatgg gccgcacaag ttttgcatcg    660
gacagttgga ccctgagact tcacaatctt cagatcaagg acaagggctt gtatcaatgt    720
atcatccatc acaaaaagcc cacaggaatg attcgcatcc accagatgaa ttctgaactg    780
tcagtgcttg ctggaggcgg aggatctggt ggtggaggtt ctggtggtgg gggatctgga    840
ggcggaggat ctggcccaca ctcgatgcgg tatttcgaga ccgccgtgtc ccggcccggc    900
ctcgaggagc cccggtacat ctctgtcggc tatgtggaca acaaggagtt cgtgcgcttc    960
gacagcgacg cggagaatcc gagatatgag ccgcgggcgc cgtggatgga gcaggagggg   1020
ccggagtatt gggagcggga aacacagaaa gccaagggcc aagagcagtg gttccgagtg   1080
agcctgagga acctgctcgg cgcctacaac cagagcgcgg gcggctctca cacactccag   1140
cagatgtctg gctgtgactt ggggtcggac tggcgcctcc tccgcgggta cctgcagttc   1200
```

gcctatgaag gccgcgatta catcgccctg aacgaagacc tgaaaacgtg gacggcggcg 1260
gacatggcgg cgcagatcac ccgacgcaag tgggagcaga gtggtgctgc agagcattac 1320
aaggcctacc tggagggcga gtgcgtggag tggctccaca gatacctgaa gaacgggaac 1380
gcgacgctgc tgcgcacaga ttccccaaag gcacatgtga cccatcaccc cagatctaaa 1440
ggtgaagtca ccctgaggtg ctgggccctg ggcttctacc ctgctgacat caccctgacc 1500
tggcagttga atggggagga gctgacccag gacatggagc ttgtggagac caggccttgc 1560
ggggatggaa ccttccagaa gtgggcatct gtggtggtgc ctcttgggaa ggagcagaat 1620
tacacatgcc gtgtgtacca tgaggggctg cctgagcccc tcaccctgag atgggcagct 1680
gcgggtggcc ccagagggcc cacaatcaag ccctgtcctc catgcaaatg cccagcacct 1740
aacctcgagg gtggaccatc cgtcttcatc ttccctccaa agatcaagga tgtactcatg 1800
atctccctga gccccatagt cacatgtgtg gtggtggatg tgagcgagga tgacccagat 1860
gtccagatca gctggtttgt gaacaacgtg gaagtacaca cagctcagac acaaacccat 1920
agagaggatt acaacagtac tctccgggtg gtcagtgccc tccccatcca gcaccaggac 1980
tggatgagtg gcaaggcgtt cgcatgcgcg gtcaacaaca aagacctccc agcgcccatc 2040
gagagaacca tctcaaaacc caaagggtca gtaagagctc cacaggtata tgtcttgcct 2100
ccaccagaag aagagatgac taagaaacag gtcactctga cctgcatggt cacagacttc 2160
atgcctgaag acatttatgt ggagtggacc aacaacggga aaacagagct aaactacaag 2220
aacactgaac cagtcctgga ctctgatggt tcttacttca tgtacagcaa gctgagagtg 2280
gaaaagaaga actgggtgga aagaaatagc tactcctgtt cagtggtcca cgagggtctg 2340
cacaatcacc acacgactaa gagcttctcc cggactccgg gtaaaggcgg atcacatcac 2400
catcaccatc accatcacta gtga 2424

<210> SEQ ID NO 143
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 143
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgaatcgca caagttttga ttcggacagt tggaccctga gacttcacaa tcttcagatc 300
aaggacaagg gcttgtatca atgtatcatc catgcaaaaa agcccacagg aatgattcgc 360
atccaccaga tgaattctga actgtcagtg cttgctggag gcggaggatc tggtggtgga 420
ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg gcaggaccag gaaaacttgg ttctgaatga ggtatactta 600
ggcaaagaga aatttgacag tgttcattcc aagtatatga atcgcacaag ttttgattcg 660
gacagttgga ccctgagact tcacaatctt cagatcaagg acaagggctt gtatcaatgt 720
atcatccatg caaaaaagcc cacaggaatg attcgcatcc accagatgaa ttctgaactg 780
tcagtgcttg ctggaggcgg aggatctggt ggtggaggtt ctggtggtgg gggatctgga 840

```
ggcggaggat ctggcccaca ctcgatgcgg tatttcgaga ccgccgtgtc ccggcccggc    900
ctcgaggagc cccggtacat ctctgtcggc tatgtggaca acaaggagtt cgtgcgcttc    960
gacagcgacg cggagaatcc gagatatgag ccgcgggcgc cgtggatgga gcaggagggg   1020
ccggagtatt gggagcggga aacacagaaa gccaagggcc aagagcagtg gttccgagtg   1080
agcctgagga acctgctcgg cgcctacaac cagagcgcgg gcggctctca cacactccag   1140
cagatgtctg gctgtgactt ggggtcggac tggcgcctcc tccgcgggta cctgcagttc   1200
gcctatgaag gccgcgatta catcgccctg aacgaagacc tgaaaacgtg gacggcggcg   1260
gacatggcgg cgcagatcac ccgacgcaag tgggagcaga gtggtgctgc agagcattac   1320
aaggcctacc tggagggcga gtgcgtggag tggctccaca gatacctgaa gaacgggaac   1380
gcgacgctgc tgcgcacaga ttccccaaag gcacatgtga cccatcaccc cagatctaaa   1440
ggtgaagtca ccctgaggtg ctgggccctg ggcttctacc ctgctgacat caccctgacc   1500
tggcagttga atggggagga gctgacccag gacatggagc ttgtggagac caggccttgc   1560
ggggatggaa ccttccagaa gtgggcatct gtggtggtgc ctcttgggaa ggagcagaat   1620
tacacatgcc gtgtgtacca tgaggggctg cctgagcccc tcaccctgag atgggcagct   1680
gcgggtggcc ccagagggcc cacaatcaag ccctgtcctc catgcaaatg cccagcacct   1740
aacctcgagg gtggaccatc cgtcttcatc ttccctccaa agatcaagga tgtactcatg   1800
atctccctga gccccatagt cacatgtgtg gtggtggatg tgagcgagga tgacccagat   1860
gtccagatca gctggtttgt gaacaacgtg gaagtacaca cagctcagac acaaacccat   1920
agagaggatt acaacagtac tctccgggtg gtcagtgccc tccccatcca gcaccaggac   1980
tggatgagtg gcaaggcgtt cgcatgcgcg gtcaacaaca aagacctccc agcgcccatc   2040
gagagaacca tctcaaaacc caaagggtca gtaagagctc cacaggtata tgtcttgcct   2100
ccaccagaag aagagatgac taagaaacag gtcactctga cctgcatggt cacagacttc   2160
atgcctgaag acatttatgt ggagtggacc aacaacggga aaacagagct aaactacaag   2220
aacactgaac cagtcctgga ctctgatggt tcttacttca tgtacagcaa gctgagagtg   2280
gaaaagaaga actgggtgga aagaaatagc tactcctgtt cagtggtcca cgagggtctg   2340
cacaatcacc acacgactaa gagcttctcc cggactccgg gtaaaggcgg atcacatcac   2400
catcaccatc accatcacta gtga                                          2424
```

<210> SEQ ID NO 144
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 144

```
atgtctcgct ccgtggcctt agctgtgctc gcgctactct ctctttctgg cctggaggcc     60
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
atgggccgca caagttttgc atcggacagt tggaccctga gacttcacaa tcttcagatc    300
aaggacaagg gcttgtatca atgtatcatc catgcaaaaa agcccacagg aatgattcgc    360
atccaccaga tgaattctga actgtcagtg cttgctggag gcggaggatc tggtggtgga    420
```

ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg gcaggaccag gaaaacttgg ttctgaatga ggtatactta 600
ggcaaagaga aatttgacag tgttcattcc aagtatatgg gccgcacaag ttttgcatcg 660
gacagttgga ccctgagact tcacaatctt cagatcaagg acaagggctt gtatcaatgt 720
atcatccatg caaaaaagcc cacaggaatg attcgcatcc accagatgaa ttctgaactg 780
tcagtgcttg ctggaggcgg aggatctggt ggtggaggtt ctggtggtgg gggatctgga 840
ggcggaggat ctggcccaca ctcgatgcgg tatttcgaga ccgccgtgtc ccggcccggc 900
ctcgaggagc cccggtacat ctctgtcggc tatgtggaca acaaggagtt cgtgcgcttc 960
gacagcgacg cggagaatcc gagatatgag ccgcgggcgc cgtggatgga gcaggagggg 1020
ccggagtatt gggagcggga aacacagaaa gccaagggcc aagagcagtg gttccgagtg 1080
agcctgagga acctgctcgg cgcctacaac cagagcgcgg gcggctctca cacactccag 1140
cagatgtctg gctgtgactt ggggtcggac tggcgcctcc tccgcgggta cctgcagttc 1200
gcctatgaag gccgcgatta catcgccctg aacgaagacc tgaaaacgtg gacggcggcg 1260
gacatggcgg cgcagatcac ccgacgcaag tgggagcaga gtggtgctgc agagcattac 1320
aaggcctacc tggagggcga gtgcgtggag tggctccaca gatacctgaa gaacgggaac 1380
gcgacgctgc tgcgcacaga ttccccaaag gcacatgtga cccatcaccc cagatctaaa 1440
ggtgaagtca ccctgaggtg ctgggccctg ggcttctacc ctgctgacat caccctgacc 1500
tggcagttga atggggagga gctgacccag gacatggagc ttgtggagac caggccttgc 1560
ggggatggaa ccttccagaa gtgggcatct gtggtggtgc ctcttgggaa ggagcagaat 1620
tacacatgcc gtgtgtacca tgaggggctg cctgagcccc tcaccctgag atgggcagct 1680
gcgggtggcc ccagagggcc cacaatcaag ccctgtcctc catgcaaatg cccagcacct 1740
aacctcgagg gtggaccatc cgtcttcatc ttccctccaa agatcaagga tgtactcatg 1800
atctccctga gccccatagt cacatgtgtg gtggtggatg tgagcgagga tgacccagat 1860
gtccagatca gctggtttgt gaacaacgtg gaagtacaca cagctcagac acaaacccat 1920
agagaggatt acaacagtac tctccgggtg gtcagtgccc tccccatcca gcaccaggac 1980
tggatgagtg gcaaggcgtt cgcatgcgcg gtcaacaaca aagacctccc agcgcccatc 2040
gagagaacca tctcaaaacc caaagggtca gtaagagctc cacaggtata tgtcttgcct 2100
ccaccagaag aagagatgac taagaaacag gtcactctga cctgcatggt cacagacttc 2160
atgcctgaag acatttatgt ggagtggacc aacaacggga aaacagagct aaactacaag 2220
aacactgaac cagtcctgga ctctgatggt tcttacttca tgtacagcaa gctgagagtg 2280
gaaaagaaga actgggtgga aagaaatagc tactcctgtt cagtggtcca cgagggtctg 2340
cacaatcacc acacgactaa gagcttctcc cggactccgg gtaaaggcgg atcacatcac 2400
catcaccatc accatcacta gtga 2424

<210> SEQ ID NO 145
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 145
atgtctcgct ccgtggcctt agctgtgctc gcgctactct ctctttctgg cctggaggcc 60

```
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
atgaatcgca caagttttgc atcggacagt tggaccctga gacttcacaa tcttcagatc    300
aaggacaagg gcttgtatca atgtatcatc catgcaaaaa agcccacagg aatgattcgc    360
atccaccaga tgaattctga actgtcagtg cttgctggag gcggaggatc tggtggtgga    420
ggttctggtg gtgggggatc tggaggcgga ggatctgctg ctcctctgaa gattcaagct    480
tatttcaatg agactgcaga cctgccatgc caatttgcaa actctcaaaa ccaaagcctg    540
agtgagctag tagtattttg gcaggaccag gaaaacttgg ttctgaatga ggtatactta    600
ggcaaagaga aatttgacag tgttcattcc aagtatatga atcgcacaag ttttgcatcg    660
gacagttgga ccctgagact tcacaatctt cagatcaagg acaagggctt gtatcaatgt    720
atcatccatg caaaaaagcc cacaggaatg attcgcatcc accagatgaa ttctgaactg    780
tcagtgcttg ctggaggcgg aggatctggt ggtggaggtt ctggtggtgg gggatctgga    840
ggcggaggat ctggcccaca ctcgatgcgg tatttcgaga ccgccgtgtc ccggcccggc    900
ctcgaggagc cccggtacat ctctgtcggc tatgtggaca acaaggagtt cgtgcgcttc    960
gacagcgacg cggagaatcc gagatatgag ccgcgggcgc cgtggatgga gcaggagggg   1020
ccggagtatt gggagcggga aacacagaaa gccaagggcc aagagcagtg gttccgagtg   1080
agcctgagga acctgctcgg cgcctacaac cagagcgcgg gcggctctca cacactccag   1140
cagatgtctg gctgtgactt ggggtcggac tggcgcctcc tccgcgggta cctgcagttc   1200
gcctatgaag gccgcgatta catcgccctg aacgaagacc tgaaaacgtg gacggcggcg   1260
gacatggcgg cgcagatcac ccgacgcaag tgggagcaga gtggtgctgc agagcattac   1320
aaggcctacc tggagggcga gtgcgtggag tggctccaca gatacctgaa gaacgggaac   1380
gcgacgctgc tgcgcacaga ttccccaaag gcacatgtga cccatcaccc cagatctaaa   1440
ggtgaagtca ccctgaggtg ctgggccctg ggcttctacc ctgctgacat caccctgacc   1500
tggcagttga atggggagga gctgacccag gacatggagc ttgtggagac caggccttgc   1560
ggggatggaa ccttccagaa gtgggcatct gtggtggtgc ctcttgggaa ggagcagaat   1620
tacacatgcc gtgtgtacca tgaggggctg cctgagcccc tcaccctgag atgggcagct   1680
gcgggtggcc ccagagggcc cacaatcaag ccctgtcctc catgcaaatg cccagcacct   1740
aacctcgagg gtggaccatc cgtcttcatc ttccctccaa agatcaagga tgtactcatg   1800
atctccctga gccccatagt cacatgtgtg gtggtggatg tgagcgagga tgacccagat   1860
gtccagatca gctggtttgt gaacaacgtg gaagtacaca cagctcagac acaaacccat   1920
agagaggatt acaacagtac tctccgggtg gtcagtgccc tccccatcca gcaccaggac   1980
tggatgagtg gcaaggcgtt cgcatgcgcg gtcaacaaca aagacctccc agcgcccatc   2040
gagagaacca tctcaaaacc caaagggtca gtaagagctc cacaggtata tgtcttgcct   2100
ccaccagaag aagagatgac taagaaacag gtcactctga cctgcatggt cacagacttc   2160
atgcctgaag acatttatgt ggagtggacc aacaacggga aaacagagct aaactacaag   2220
aacactgaac cagtcctgga ctctgatggt tcttacttca tgtacagcaa gctgagagtg   2280
gaaaagaaga actgggtgga aagaaatagc tactcctgtt cagtggtcca cgagggtctg   2340
cacaatcacc acacgactaa gagcttctcc cggactccgg gtaaaggcgg atcacatcac   2400
```

catcaccatc accatcacta gtga 2424

<210> SEQ ID NO 146
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 146
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccgcaa gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggtggtgga 420
ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg gcaggaccag gaaaacttgg ttctgaatga ggtatactta 600
ggcaaagaga aatttgacag tgttcattcc aagtatatgg gccgcacaag ttttgattcg 660
gacagttgga ccgcaagact tcacaatctt cagatcaagg acaagggctt gtatcaatgt 720
atcatccatc acaaaaagcc cacaggaatg attcgcatcc accagatgaa ttctgaactg 780
tcagtgcttg ctggaggcgg aggatctggt ggtggaggtt ctggtggtgg gggatctgga 840
ggcggaggat ctggcccaca ctcgatgcgg tatttcgaga ccgccgtgtc ccggcccggc 900
ctcgaggagc cccggtacat ctctgtcggc tatgtggaca acaaggagtt cgtgcgcttc 960
gacagcgacg cggagaatcc gagatatgag ccgcgggcgc cgtggatgga gcaggagggg 1020
ccggagtatt gggagcggga aacacagaaa gccaagggcc aagagcagtg gttccgagtg 1080
agcctgagga acctgctcgg cgcctacaac cagagcgcgg gcggctctca cacactccag 1140
cagatgtctg gctgtgactt ggggtcggac tggcgcctcc tccgcgggta cctgcagttc 1200
gcctatgaag gccgcgatta catcgccctg aacgaagacc tgaaaacgtg gacggcggcg 1260
gacatggcgg cgcagatcac ccgacgcaag tgggagcaga gtggtgctgc agagcattac 1320
aaggcctacc tggagggcga gtgcgtggag tggctccaca gatacctgaa gaacgggaac 1380
gcgacgctgc tgcgcacaga ttccccaaag gcacatgtga cccatcaccc cagatctaaa 1440
ggtgaagtca ccctgaggtg ctgggccctg ggcttctacc ctgctgacat caccctgacc 1500
tggcagttga atggggagga gctgacccag gacatggagc ttgtggagac caggccttgc 1560
ggggatggaa ccttccagaa gtgggcatct gtggtggtgc ctcttgggaa ggagcagaat 1620
tacacatgcc gtgtgtacca tgaggggctg cctgagcccc tcaccctgag atgggcagct 1680
gcgggtggcc ccagagggcc cacaatcaag ccctgtcctc catgcaaatg cccagcacct 1740
aacctcgagg gtggaccatc cgtcttcatc ttccctccaa agatcaagga tgtactcatg 1800
atctccctga gccccatagt cacatgtgtg gtggtggatg tgagcgagga tgacccagat 1860
gtccagatca gctggtttgt gaacaacgtg gaagtacaca cagctcagac acaaacccat 1920
agagaggatt acaacagtac tctccgggtg gtcagtgccc tccccatcca gcaccaggac 1980
tggatgagtg gcaaggcgtt cgcatgcgcg gtcaacaaca aagacctccc agcgcccatc 2040

```
gagagaacca tctcaaaacc caaagggtca gtaagagctc cacaggtata tgtcttgcct   2100

ccaccagaag aagagatgac taagaaacag gtcactctga cctgcatggt cacagacttc   2160

atgcctgaag acatttatgt ggagtggacc aacaacggga aaacagagct aaactacaag   2220

aacactgaac cagtcctgga ctctgatggt tcttacttca tgtacagcaa gctgagagtg   2280

gaaaagaaga actgggtgga aagaaatagc tactcctgtt cagtggtcca cgagggtctg   2340

cacaatcacc acacgactaa gagcttctcc cggactccgg gtaaaggcgg atcacatcac   2400

catcaccatc accatcacta gtga                                           2424
```

<210> SEQ ID NO 147
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 147

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaaggca    240

atgggccgca caagttttga ttcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggtggtgga    420

ggttctggtg gtgggggatc tggaggcgga ggatctgctg ctcctctgaa gattcaagct    480

tatttcaatg agactgcaga cctgccatgc caatttgcaa actctcaaaa ccaaagcctg    540

agtgagctag tagtattttg gcaggaccag gaaaacttgg ttctgaatga ggtatactta    600

ggcaaagaga aatttgacag tgttcattcc aaggcaatgg gccgcacaag ttttgattcg    660

gacagttgga ccctgagact tcacaatctt cagatcaagg acaagggctt gtatcaatgt    720

atcatccatc acaaaaagcc cacaggaatg attcgcatcc accagatgaa ttctgaactg    780

tcagtgcttg ctggaggcgg aggatctggt ggtggaggtt ctggtggtgg gggatctgga    840

ggcggaggat ctggcccaca ctcgatgcgg tatttcgaga ccgccgtgtc ccggcccggc    900

ctcgaggagc cccggtacat ctctgtcggc tatgtggaca acaaggagtt cgtgcgcttc    960

gacagcgacg cggagaatcc gagatatgag ccgcgggcgc cgtggatgga gcaggagggg   1020

ccggagtatt gggagcggga aacacagaaa gccaagggcc aagagcagtg gttccgagtg   1080

agcctgagga acctgctcgg cgcctacaac cagagcgcgg gcggctctca cacactccag   1140

cagatgtctg gctgtgactt ggggtcggac tggcgcctcc tccgcgggta cctgcagttc   1200

gcctatgaag gccgcgatta catcgccctg aacgaagacc tgaaaacgtg gacggcggcg   1260

gacatggcgg cgcagatcac ccgacgcaag tgggagcaga gtggtgctgc agagcattac   1320

aaggcctacc tggagggcga gtgcgtggag tggctccaca gatacctgaa gaacgggaac   1380

gcgacgctgc tgcgcacaga ttccccaaag gcacatgtga cccatcaccc cagatctaaa   1440

ggtgaagtca ccctgaggtg ctgggccctg ggcttctacc ctgctgacat caccctgacc   1500

tggcagttga atggggagga gctgacccag gacatggagc ttgtggagac caggccttgc   1560

ggggatggaa ccttccagaa gtgggcatct gtggtggtgc ctcttgggaa ggagcagaat   1620
```

tacacatgcc gtgtgtacca tgaggggctg cctgagcccc tcaccctgag atgggcagct 1680
gcgggtggcc ccagagggcc cacaatcaag ccctgtcctc catgcaaatg cccagcacct 1740
aacctcgagg gtggaccatc cgtcttcatc ttccctccaa agatcaagga tgtactcatg 1800
atctccctga gccccatagt cacatgtgtg gtggtggatg tgagcgagga tgacccagat 1860
gtccagatca gctggtttgt gaacaacgtg gaagtacaca cagctcagac acaaacccat 1920
agagaggatt acaacagtac tctccgggtg gtcagtgccc tccccatcca gcaccaggac 1980
tggatgagtg gcaaggcgtt cgcatgcgcg gtcaacaaca aagacctccc agcgcccatc 2040
gagagaacca tctcaaaacc caaagggtca gtaagagctc cacaggtata tgtcttgcct 2100
ccaccagaag aagagatgac taagaaacag gtcactctga cctgcatggt cacagacttc 2160
atgcctgaag acatttatgt ggagtggacc aacaacggga aaacagagct aaactacaag 2220
aacactgaac cagtcctgga ctctgatggt tcttacttca tgtacagcaa gctgagagtg 2280
gaaaagaaga actgggtgga aagaaatagc tactcctgtt cagtggtcca cgagggtctg 2340
cacaatcacc acacgactaa gagcttctcc cggactccgg gtaaaggcgg atcacatcac 2400
catcaccatc accatcacta gtga 2424

<210> SEQ ID NO 148
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 148
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggcactga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggtggtgga 420
ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg gcaggaccag gaaaacttgg cactgaatga ggtatactta 600
ggcaaagaga aatttgacag tgttcattcc aagtatatgg gccgcacaag ttttgattcg 660
gacagttgga ccctgagact tcacaatctt cagatcaagg acaagggctt gtatcaatgt 720
atcatccatc acaaaaagcc cacaggaatg attcgcatcc accagatgaa ttctgaactg 780
tcagtgcttg ctggaggcgg aggatctggt ggtggaggtt ctggtggtgg gggatctgga 840
ggcggaggat ctggcccaca ctcgatgcgg tatttcgaga ccgccgtgtc ccggcccggc 900
ctcgaggagc cccggtacat ctctgtcggc tatgtggaca acaaggagtt cgtgcgcttc 960
gacagcgacg cggagaatcc gagatatgag ccgcgggcgc cgtggatgga gcaggagggg 1020
ccggagtatt gggagcggga aacacagaaa gccaagggcc aagagcagtg gttccgagtg 1080
agcctgagga acctgctcgg cgcctacaac cagagcgcgg gcggctctca cacactccag 1140
cagatgtctg gctgtgactt ggggtcggac tggcgcctcc tccgcgggta cctgcagttc 1200
gcctatgaag gccgcgatta catcgccctg aacgaagacc tgaaaacgtg gacggcggcg 1260
gacatggcgg cgcagatcac ccgacgcaag tgggagcaga gtggtgctgc agagcattac 1320
aaggcctacc tggagggcga gtgcgtggag tggctccaca gatacctgaa gaacgggaac 1380
gcgacgctgc tgcgcacaga ttccccaaag gcacatgtga cccatcaccc cagatctaaa 1440
ggtgaagtca ccctgaggtg ctgggccctg ggcttctacc ctgctgacat caccctgacc 1500
tggcagttga atggggagga gctgacccag gacatggagc ttgtggagac caggccttgc 1560
ggggatggaa ccttccagaa gtgggcatct gtggtggtgc ctcttgggaa ggagcagaat 1620
tacacatgcc gtgtgtacca tgaggggctg cctgagcccc tcaccctgag atgggcagct 1680
gcgggtggcc ccagagggcc cacaatcaag ccctgtcctc catgcaaatg cccagcacct 1740
aacctcgagg gtggaccatc cgtcttcatc ttccctccaa agatcaagga tgtactcatg 1800
atctccctga gccccatagt cacatgtgtg gtggtggatg tgagcgagga tgacccagat 1860
gtccagatca gctggtttgt gaacaacgtg gaagtacaca cagctcagac acaaacccat 1920
agagaggatt acaacagtac tctccgggtg gtcagtgccc tccccatcca gcaccaggac 1980
tggatgagtg gcaaggcgtt cgcatgcgcg gtcaacaaca aagacctccc agcgcccatc 2040
gagagaacca tctcaaaacc caaagggtca gtaagagctc cacaggtata tgtcttgcct 2100
ccaccagaag aagagatgac taagaaacag gtcactctga cctgcatggt cacagacttc 2160
atgcctgaag acatttatgt ggagtggacc aacaacggga aaacagagct aaactacaag 2220
aacactgaac cagtcctgga ctctgatggt tcttacttca tgtacagcaa gctgagagtg 2280
gaaaagaaga actgggtgga aagaaatagc tactcctgtt cagtggtcca cgagggtctg 2340
cacaatcacc acacgactaa gagcttctcc cggactccgg gtaaaggcgg atcacatcac 2400
catcaccatc accatcacta gtga 2424

<210> SEQ ID NO 149
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 149
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttgggcaga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggtggtgga 420
ggttctggtg gtgggggatc tggaggcgga ggatctgctg ctcctctgaa gattcaagct 480
tatttcaatg agactgcaga cctgccatgc caatttgcaa actctcaaaa ccaaagcctg 540
agtgagctag tagtattttg ggcagaccag gaaaacttgg ttctgaatga ggtatactta 600
ggcaaagaga aatttgacag tgttcattcc aagtatatgg gccgcacaag ttttgattcg 660
gacagttgga ccctgagact tcacaatctt cagatcaagg acaagggctt gtatcaatgt 720
atcatccatc acaaaaagcc cacaggaatg attcgcatcc accagatgaa ttctgaactg 780
tcagtgcttg ctggaggcgg aggatctggt ggtggaggtt ctggtggtgg gggatctgga 840

-continued

```
ggcggaggat ctggcccaca ctcgatgcgg tatttcgaga ccgccgtgtc ccggcccggc    900

ctcgaggagc cccggtacat ctctgtcggc tatgtggaca acaaggagtt cgtgcgcttc    960

gacagcgacg cggagaatcc gagatatgag ccgcgggcgc cgtggatgga gcaggagggg   1020

ccggagtatt gggagcggga aacacagaaa gccaagggcc aagagcagtg gttccgagtg   1080

agcctgagga acctgctcgg cgcctacaac cagagcgcgg gcggctctca cacactccag   1140

cagatgtctg gctgtgactt ggggtcggac tggcgcctcc tccgcgggta cctgcagttc   1200

gcctatgaag gccgcgatta catcgccctg aacgaagacc tgaaaacgtg gacggcggcg   1260

gacatggcgg cgcagatcac ccgacgcaag tgggagcaga gtggtgctgc agagcattac   1320

aaggcctacc tggagggcga gtgcgtggag tggctccaca gatacctgaa gaacgggaac   1380

gcgacgctgc tgcgcacaga ttccccaaag gcacatgtga cccatcaccc cagatctaaa   1440

ggtgaagtca ccctgaggtg ctgggccctg ggcttctacc ctgctgacat caccctgacc   1500

tggcagttga atggggagga gctgacccag gacatggagc ttgtggagac caggccttgc   1560

ggggatggaa ccttccagaa gtgggcatct gtggtggtgc ctcttgggaa ggagcagaat   1620

tacacatgcc gtgtgtacca tgaggggctg cctgagcccc tcaccctgag atgggcagct   1680

gcgggtggcc ccagagggcc cacaatcaag ccctgtcctc catgcaaatg cccagcacct   1740

aacctcgagg gtggaccatc cgtcttcatc ttccctccaa agatcaagga tgtactcatg   1800

atctccctga gccccatagt cacatgtgtg gtggtggatg tgagcgagga tgacccagat   1860

gtccagatca gctggtttgt gaacaacgtg gaagtacaca cagctcagac acaaacccat   1920

agagaggatt acaacagtac tctccgggtg gtcagtgccc tccccatcca gcaccaggac   1980

tggatgagtg gcaaggcgtt cgcatgcgcg gtcaacaaca aagacctccc agcgcccatc   2040

gagagaacca tctcaaaacc caaagggtca gtaagagctc cacaggtata tgtcttgcct   2100

ccaccagaag aagagatgac taagaaacag gtcactctga cctgcatggt cacagacttc   2160

atgcctgaag acatttatgt ggagtggacc aacaacggga aaacagagct aaactacaag   2220

aacactgaac cagtcctgga ctctgatggt tcttacttca tgtacagcaa gctgagagtg   2280

gaaaagaaga actgggtgga aagaaatagc tactcctgtt cagtggtcca cgagggtctg   2340

cacaatcacc acacgactaa gagcttctcc cggactccgg gtaaaggcgg atcacatcac   2400

catcaccatc accatcacta gtga                                          2424
```

<210> SEQ ID NO 150
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 150

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtag catggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggtggtgga    420

ggttctggtg gtgggggatc tggaggcgga ggatctgctg ctcctctgaa gattcaagct    480
```

-continued tatttcaatg agactgcaga cctgccatgc caatttgcaa actctcaaaa ccaaagcctg 540
agtgagctag tagtagcatg gcaggaccag gaaaacttgg ttctgaatga ggtatactta 600
ggcaaagaga aatttgacag tgttcattcc aagtatatgg gccgcacaag ttttgattcg 660
gacagttgga ccctgagact tcacaatctt cagatcaagg acaagggctt gtatcaatgt 720
atcatccatc acaaaaagcc cacaggaatg attcgcatcc accagatgaa ttctgaactg 780
tcagtgcttg ctggaggcgg aggatctggt ggtggaggtt ctggtggtgg gggatctgga 840
ggcggaggat ctggcccaca ctcgatgcgg tatttcgaga ccgccgtgtc ccggcccggc 900
ctcgaggagc cccggtacat ctctgtcggc tatgtggaca acaaggagtt cgtgcgcttc 960
gacagcgacg cggagaatcc gagatatgag ccgcgggcgc cgtggatgga gcaggagggg 1020
ccggagtatt gggagcggga aacacagaaa gccaagggcc aagagcagtg gttccgagtg 1080
agcctgagga acctgctcgg cgcctacaac cagagcgcgg gcggctctca cacactccag 1140
cagatgtctg gctgtgactt ggggtcggac tggcgcctcc tccgcgggta cctgcagttc 1200
gcctatgaag gccgcgatta catcgccctg aacgaagacc tgaaaacgtg gacggcggcg 1260
gacatggcgg cgcagatcac ccgacgcaag tgggagcaga gtggtgctgc agagcattac 1320
aaggcctacc tggagggcga gtgcgtggag tggctccaca gatacctgaa gaacgggaac 1380
gcgacgctgc tgcgcacaga ttccccaaag gcacatgtga cccatcaccc cagatctaaa 1440
ggtgaagtca ccctgaggtg ctgggccctg ggcttctacc ctgctgacat caccctgacc 1500
tggcagttga atggggagga gctgacccag gacatggagc ttgtggagac caggccttgc 1560
ggggatggaa ccttccagaa gtgggcatct gtggtggtgc ctcttgggaa ggagcagaat 1620
tacacatgcc gtgtgtacca tgaggggctg cctgagcccc tcaccctgag atgggcagct 1680
gcgggtggcc ccagagggcc cacaatcaag ccctgtcctc catgcaaatg cccagcacct 1740
aacctcgagg gtggaccatc cgtcttcatc ttccctccaa agatcaagga tgtactcatg 1800
atctccctga gccccatagt cacatgtgtg gtggtggatg tgagcgagga tgacccagat 1860
gtccagatca gctggtttgt gaacaacgtg gaagtacaca cagctcagac acaaacccat 1920
agagaggatt acaacagtac tctccgggtg gtcagtgccc tccccatcca gcaccaggac 1980
tggatgagtg gcaaggcgtt cgcatgcgcg gtcaacaaca aagacctccc agcgcccatc 2040
gagagaacca tctcaaaacc caaagggtca gtaagagctc cacaggtata tgtcttgcct 2100
ccaccagaag aagagatgac taagaaacag gtcactctga cctgcatggt cacagacttc 2160
atgcctgaag acatttatgt ggagtggacc aacaacggga aaacagagct aaactacaag 2220
aacactgaac cagtcctgga ctctgatggt tcttacttca tgtacagcaa gctgagagtg 2280
gaaaagaaga actgggtgga aagaaatagc tactcctgtt cagtggtcca cgagggtctg 2340
cacaatcacc acacgactaa gagcttctcc cggactccgg gtaaaggcgg atcacatcac 2400
catcaccatc accatcacta gtga 2424

<210> SEQ ID NO 151
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 151
atgtctcgct ccgtggcctt agctgtgctc gcgctactct ctctttctgg cctggaggcc 60

```
gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catcggaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

<210> SEQ ID NO 152
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 152

```
atgtctcgct ccgtggcctt agctgtgctc gcgctactct ctctttctgg cctggaggcc     60

gctgctcctc tgaagattca agcttatttc aatgagactg cagacctgcc atgccaattt    120
```

gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc cataataaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480
gagaccgccg tgtcccggcc cggcctcgag gagccccggt acatctctgt cggctatgtg 540
gacaacaagg agttcgtgcg cttcgacagc gacgcggaga atccgagata tgagccgcgg 600
gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 153
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 153
atgtctcgct ccgtggcctt agctgtgctc gcgctactct ctctttctgg cctggaggcc 60
gctgctcctc tgaagattca agcttatttc aatgagactg cagacctgcc atgccaattt 120

```
gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catgataaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

<210> SEQ ID NO 154
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 154

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180
```

```
ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc cattgtaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

<210> SEQ ID NO 155
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 155

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180
```

-continued

```
ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catcagaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

```
<210> SEQ ID NO 156
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 156

atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240
```

atgggccgca caagttttga ttcggacagt tggaccctga gacttcacaa tcttcagatc 300
aaggacaagg gcttgtatca atgtatcatc catgaaaaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480
gagaccgccg tgtcccggcc cggcctcgag gagccccggt acatctctgt cggctatgtg 540
gacaacaagg agttcgtgcg cttcgacagc gacgcggaga atccgagata tgagccgcgg 600
gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 157
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 157
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240

```
atgggccgca caagttttga ttcggacagt tggaccctga gacttcacaa tcttcagatc    300

aaggacaagg gcttgtatca atgtatcatc catggcaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

<210> SEQ ID NO 158
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 158

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300
```

aaggacaagg gcttgtatca atgtatcatc catataaaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480
gagaccgccg tgtcccggcc cggcctcgag gagccccggt acatctctgt cggctatgtg 540
gacaacaagg agttcgtgcg cttcgacagc gacgcggaga atccgagata tgagccgcgg 600
gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 159
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 159
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300

```
aaggacaagg gcttgtatca atgtatcatc catctcaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

<210> SEQ ID NO 160
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 160

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc cataagaaaa agcccacagg aatgattcgc    360
```

```
atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

<210> SEQ ID NO 161
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 161

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catatgaaaa agcccacagg aatgattcgc    360
```

```
atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028


<210> SEQ ID NO 162
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 162

atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc cattttaaaa agcccacagg aatgattcgc    360

atccaccaga tgaattctga actgtcagtg cttgctggag gcggaggatc tggtggtgga    420
```

```
ggttctggtg gtgggggatc tggaggcgga ggatctggcc cacactcgat gcggtatttc    480
gagaccgccg tgtcccggcc cggcctcgag gagccccggt acatctctgt cggctatgtg    540
gacaacaagg agttcgtgcg cttcgacagc gacgcggaga atccgagata tgagccgcgg    600
gcgccgtgga tggagcagga ggggccggag tattgggagc gggaaacaca gaaagccaag    660
ggccaagagc agtggttccg agtgagcctg aggaacctgc tcggcgccta caaccagagc    720
gcgggcggct ctcacacact ccagcagatg tctggctgtg acttggggtc ggactggcgc    780
ctcctccgcg ggtacctgca gttcgcctat gaaggccgcg attacatcgc cctgaacgaa    840
gacctgaaaa cgtggacggc ggcggacatg gcggcgcaga tcacccgacg caagtgggag    900
cagagtggtg ctgcagagca ttacaaggcc tacctggagg gcgagtgcgt ggagtggctc    960
cacagatacc tgaagaacgg gaacgcgacg ctgctgcgca cagattcccc aaaggcacat   1020
gtgacccatc accccagatc taaaggtgaa gtcaccctga ggtgctgggc cctgggcttc   1080
taccctgctg acatcaccct gacctggcag ttgaatgggg aggagctgac ccaggacatg   1140
gagcttgtgg agaccaggcc ttgcggggat ggaaccttcc agaagtgggc atctgtggtg   1200
gtgcctcttg ggaaggagca gaattacaca tgccgtgtgt accatgaggg gctgcctgag   1260
cccctcaccc tgagatgggc agctgcgggt ggccccagag ggcccacaat caagccctgt   1320
cctccatgca aatgcccagc acctaacctc gagggtggac catccgtctt catcttccct   1380
ccaaagatca aggatgtact catgatctcc ctgagcccca tagtcacatg tgtggtggtg   1440
gatgtgagcg aggatgaccc agatgtccag atcagctggt ttgtgaacaa cgtggaagta   1500
cacacagctc agacacaaac ccatagagag gattacaaca gtactctccg ggtggtcagt   1560
gccctcccca tccagcacca ggactggatg agtggcaagg cgttcgcatg cgcggtcaac   1620
aacaaagacc tcccagcgcc catcgagaga accatctcaa aacccaaagg gtcagtaaga   1680
gctccacagg tatatgtctt gcctccacca gaagaagaga tgactaagaa acaggtcact   1740
ctgacctgca tggtcacaga cttcatgcct gaagacattt atgtggagtg gaccaacaac   1800
gggaaaacag agctaaacta caagaacact gaaccagtcc tggactctga tggttcttac   1860
ttcatgtaca gcaagctgag agtggaaaag aagaactggg tggaaagaaa tagctactcc   1920
tgttcagtgg tccacgaggg tctgcacaat caccacacga ctaagagctt ctcccggact   1980
ccgggtaaag gcggatcaca tcaccatcac catcaccatc actagtga                 2028
```

<210> SEQ ID NO 163
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 163

```
atgtctcgct ccgtggcctt agctgtgctc gcgctactct ctctttctgg cctggaggcc     60
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
atgggccgca caagttttga ttcggacagt tggaccctga gacttcacaa tcttcagatc    300
aaggacaagg gcttgtatca atgtatcatc catcccaaaa agcccacagg aatgattcgc    360
atccaccaga tgaattctga actgtcagtg cttgctggag gcggaggatc tggtggtgga    420
```

```
ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga                2028
```

<210> SEQ ID NO 164
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 164

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catagcaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480
```

gagaccgccg tgtcccggcc cggcctcgag gagccccggt acatctctgt cggctatgtg 540
gacaacaagg agttcgtgcg cttcgacagc gacgcggaga atccgagata tgagccgcgg 600
gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 165
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 165
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catacaaaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480
gagaccgccg tgtcccggcc cggcctcgag gagccccggt acatctctgt cggctatgtg 540
gacaacaagg agttcgtgcg cttcgacagc gacgcggaga atccgagata tgagccgcgg 600
gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 166
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 166
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc cattggaaaa agcccacagg aatgattcgc 360
atccaccaga tgaattctga actgtcagtg cttgctggag gcggaggatc tggtggtgga 420
ggttctggtg gtgggggatc tggaggcgga ggatctggcc cacactcgat gcggtatttc 480
gagaccgccg tgtcccggcc cggcctcgag gagccccggt acatctctgt cggctatgtg 540

```
gacaacaagg agttcgtgcg cttcgacagc gacgcggaga atccgagata tgagccgcgg    600
gcgccgtgga tggagcagga ggggccggag tattgggagc gggaaacaca gaaagccaag    660
ggccaagagc agtggttccg agtgagcctg aggaacctgc tcggcgccta caaccagagc    720
gcgggcggct ctcacacact ccagcagatg tctggctgtg acttggggtc ggactggcgc    780
ctcctccgcg ggtacctgca gttcgcctat gaaggccgcg attacatcgc cctgaacgaa    840
gacctgaaaa cgtggacggc ggcggacatg gcggcgcaga tcacccgacg caagtgggag    900
cagagtggtg ctgcagagca ttacaaggcc tacctggagg gcgagtgcgt ggagtggctc    960
cacagatacc tgaagaacgg gaacgcgacg ctgctgcgca cagattcccc aaaggcacat   1020
gtgacccatc accccagatc taaaggtgaa gtcaccctga ggtgctgggc cctgggcttc   1080
taccctgctg acatcaccct gacctggcag ttgaatgggg aggagctgac ccaggacatg   1140
gagcttgtgg agaccaggcc ttgcggggat ggaaccttcc agaagtgggc atctgtggtg   1200
gtgcctcttg ggaaggagca gaattacaca tgccgtgtgt accatgaggg gctgcctgag   1260
cccctcaccc tgagatgggc agctgcgggt ggccccagag ggcccacaat caagccctgt   1320
cctccatgca aatgcccagc acctaacctc gagggtggac catccgtctt catcttccct   1380
ccaaagatca aggatgtact catgatctcc ctgagcccca tagtcacatg tgtggtggtg   1440
gatgtgagcg aggatgaccc agatgtccag atcagctggt ttgtgaacaa cgtggaagta   1500
cacacagctc agacacaaac ccatagagag gattacaaca gtactctccg ggtggtcagt   1560
gccctcccca tccagcacca ggactggatg agtggcaagg cgttcgcatg cgcggtcaac   1620
aacaaagacc tcccagcgcc catcgagaga accatctcaa aacccaaagg gtcagtaaga   1680
gctccacagg tatatgtctt gcctccacca gaagaagaga tgactaagaa acaggtcact   1740
ctgacctgca tggtcacaga cttcatgcct gaagacattt atgtggagtg gaccaacaac   1800
gggaaaacag agctaaacta caagaacact gaaccagtcc tggactctga tggttcttac   1860
ttcatgtaca gcaagctgag agtggaaaag aagaactggg tggaaagaaa tagctactcc   1920
tgttcagtgg tccacgaggg tctgcacaat caccacacga ctaagagctt ctcccggact   1980
ccgggtaaag gcggatcaca tcaccatcac catcaccatc actagtga                2028
```

<210> SEQ ID NO 167
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 167

```
atgtctcgct ccgtggcctt agctgtgctc gcgctactct ctctttctgg cctggaggcc     60
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
atgggccgca caagttttga ttcggacagt tggaccctga gacttcacaa tcttcagatc    300
aaggacaagg gcttgtatca atgtatcatc cattataaaa agcccacagg aatgattcgc    360
atccaccaga tgaattctga actgtcagtg cttgctggag gcggaggatc tggtggtgga    420
ggttctggtg gtgggggatc tggaggcgga ggatctggcc cacactcgat gcggtatttc    480
gagaccgccg tgtcccggcc cggcctcgag gagccccggt acatctctgt cggctatgtg    540
```

```
gacaacaagg agttcgtgcg cttcgacagc gacgcggaga atccgagata tgagccgcgg    600

gcgccgtgga tggagcagga ggggccggag tattgggagc gggaaacaca gaaagccaag    660

ggccaagagc agtggttccg agtgagcctg aggaacctgc tcggcgccta caaccagagc    720

gcgggcggct ctcacacact ccagcagatg tctggctgtg acttggggtc ggactggcgc    780

ctcctccgcg ggtacctgca gttcgcctat gaaggccgcg attacatcgc cctgaacgaa    840

gacctgaaaa cgtggacggc ggcggacatg gcggcgcaga tcacccgacg caagtgggag    900

cagagtggtg ctgcagagca ttacaaggcc tacctggagg gcgagtgcgt ggagtggctc    960

cacagatacc tgaagaacgg gaacgcgacg ctgctgcgca cagattcccc aaaggcacat   1020

gtgacccatc accccagatc taaaggtgaa gtcaccctga ggtgctgggc cctgggcttc   1080

taccctgctg acatcaccct gacctggcag ttgaatgggg aggagctgac ccaggacatg   1140

gagcttgtgg agaccaggcc ttgcggggat ggaaccttcc agaagtgggc atctgtggtg   1200

gtgcctcttg ggaaggagca gaattacaca tgccgtgtgt accatgaggg gctgcctgag   1260

cccctcaccc tgagatgggc agctgcgggt ggccccagag ggcccacaat caagccctgt   1320

cctccatgca aatgcccagc acctaacctc gagggtggac catccgtctt catcttccct   1380

ccaaagatca aggatgtact catgatctcc ctgagcccca tagtcacatg tgtggtggtg   1440

gatgtgagcg aggatgaccc agatgtccag atcagctggt ttgtgaacaa cgtggaagta   1500

cacacagctc agacacaaac ccatagagag gattacaaca gtactctccg ggtggtcagt   1560

gccctcccca tccagcacca ggactggatg agtggcaagg cgttcgcatg cgcggtcaac   1620

aacaaagacc tcccagcgcc catcgagaga accatctcaa aacccaaagg gtcagtaaga   1680

gctccacagg tatatgtctt gcctccacca gaagaagaga tgactaagaa acaggtcact   1740

ctgacctgca tggtcacaga cttcatgcct gaagacattt atgtggagtg gaccaacaac   1800

gggaaaacag agctaaacta caagaacact gaaccagtcc tggactctga tggttcttac   1860

ttcatgtaca gcaagctgag agtggaaaag aagaactggg tggaaagaaa tagctactcc   1920

tgttcagtgg tccacgaggg tctgcacaat caccacacga ctaagagctt ctcccggact   1980

ccgggtaaag gcggatcaca tcaccatcac catcaccatc actagtga               2028
```

<210> SEQ ID NO 168
<211> LENGTH: 2028
<212> TYPE: DNA
<213> ORGANISM: Artificial Sequence
<220> FEATURE:
<223> OTHER INFORMATION: Synthetic polynucleotide

<400> SEQUENCE: 168

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catgtgaaaa agcccacagg aatgattcgc    360

atccaccaga tgaattctga actgtcagtg cttgctggag gcggaggatc tggtggtgga    420

ggttctggtg gtgggggatc tggaggcgga ggatctggcc cacactcgat gcggtatttc    480

gagaccgccg tgtcccggcc cggcctcgag gagccccggt acatctctgt cggctatgtg    540

gacaacaagg agttcgtgcg cttcgacagc gacgcggaga atccgagata tgagccgcgg    600
```

gcgccgtgga tggagcagga ggggccggag tattgggagc gggaaacaca gaaagccaag 660
ggccaagagc agtggttccg agtgagcctg aggaacctgc tcggcgccta caaccagagc 720
gcgggcggct ctcacacact ccagcagatg tctggctgtg acttggggtc ggactggcgc 780
ctcctccgcg ggtacctgca gttcgcctat gaaggccgcg attacatcgc cctgaacgaa 840
gacctgaaaa cgtggacggc ggcggacatg gcggcgcaga tcacccgacg caagtgggag 900
cagagtggtg ctgcagagca ttacaaggcc tacctggagg gcgagtgcgt ggagtggctc 960
cacagatacc tgaagaacgg gaacgcgacg ctgctgcgca cagattcccc aaaggcacat 1020
gtgacccatc accccagatc taaaggtgaa gtcaccctga ggtgctgggc cctgggcttc 1080
taccctgctg acatcaccct gacctggcag ttgaatgggg aggagctgac ccaggacatg 1140
gagcttgtgg agaccaggcc ttgcggggat ggaaccttcc agaagtgggc atctgtggtg 1200
gtgcctcttg ggaaggagca gaattacaca tgccgtgtgt accatgaggg gctgcctgag 1260
cccctcaccc tgagatgggc agctgcgggt ggccccagag ggcccacaat caagccctgt 1320
cctccatgca aatgcccagc acctaacctc gagggtggac catccgtctt catcttccct 1380
ccaaagatca aggatgtact catgatctcc ctgagcccca tagtcacatg tgtggtggtg 1440
gatgtgagcg aggatgaccc agatgtccag atcagctggt ttgtgaacaa cgtggaagta 1500
cacacagctc agacacaaac ccatagagag gattacaaca gtactctccg ggtggtcagt 1560
gccctcccca tccagcacca ggactggatg agtggcaagg cgttcgcatg cgcggtcaac 1620
aacaaagacc tcccagcgcc catcgagaga accatctcaa aacccaaagg gtcagtaaga 1680
gctccacagg tatatgtctt gcctccacca gaagaagaga tgactaagaa acaggtcact 1740
ctgacctgca tggtcacaga cttcatgcct gaagacattt atgtggagtg gaccaacaac 1800
gggaaaacag agctaaacta caagaacact gaaccagtcc tggactctga tggttcttac 1860
ttcatgtaca gcaagctgag agtggaaaag aagaactggg tggaaagaaa tagctactcc 1920
tgttcagtgg tccacgaggg tctgcacaat caccacacga ctaagagctt ctcccggact 1980
ccgggtaaag gcggatcaca tcaccatcac catcaccatc actagtga 2028

<210> SEQ ID NO 169
<211> LENGTH: 2439
<212> TYPE: DNA
<213> ORGANISM: Artificial Sequence
<220> FEATURE:
<223> OTHER INFORMATION: Synthetic polynucleotide

<400> SEQUENCE: 169
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catgcaaaaa agcccacagg aatgattcgc 360
atccaccaga tgaattctga actgtcagtg cttgctggag gcggaggatc tggaggcgga 420
ggatctggtg gtggaggttc tggtggtggg ggatctggag gcggaggatc tgctgctcct 480
ctgaagattc aagcttattt caatgagact gcagacctgc catgccaatt tgcaaactct 540
caaaaccaaa gcctgagtga gctagtagta ttttggcagg accaggaaaa cttggttctg 600

```
aatgaggtat acttaggcaa agagaaattt gacagtgttc attccaagta tatgggccgc    660
acaagttttg attcggacag ttggaccctg agacttcaca atcttcagat caaggacaag    720
ggcttgtatc aatgtatcat ccatgcaaaa aagcccacag gaatgattcg catccaccag    780
atgaattctg aactgtcagt gcttgctgga ggcggaggat ctggtggtgg aggttctggt    840
ggtgggggat ctggaggcgg aggatctggc ccacactcga tgcggtattt cgagaccgcc    900
gtgtcccggc ccggcctcga ggagccccgg tacatctctg tcggctatgt ggacaacaag    960
gagttcgtgc gcttcgacag cgacgcggag aatccgagat atgagccgcg ggcgccgtgg   1020
atggagcagg aggggccgga gtattgggag cgggaaacac agaaagccaa gggccaagag   1080
cagtggttcc gagtgagcct gaggaacctg ctcggcgcct acaaccagag cgcgggcggc   1140
tctcacacac tccagcagat gtctggctgt gacttggggt cggactggcg cctcctccgc   1200
gggtacctgc agttcgccta tgaaggccgc gattacatcg ccctgaacga agacctgaaa   1260
acgtggacgg cggcggacat ggcggcgcag atcacccgac gcaagtggga gcagagtggt   1320
gctgcagagc attacaaggc ctacctggag ggcgagtgcg tggagtggct ccacagatac   1380
ctgaagaacg ggaacgcgac gctgctgcgc acagattccc caaaggcaca tgtgacccat   1440
caccccagat ctaaaggtga agtcaccctg aggtgctggg ccctgggctt ctaccctgct   1500
gacatcaccc tgacctggca gttgaatggg gaggagctga cccaggacat ggagcttgtg   1560
gagaccaggc cttgcgggga tggaaccttc cagaagtggg catctgtggt ggtgcctctt   1620
gggaaggagc agaattacac atgccgtgtg taccatgagg ggctgcctga gcccctcacc   1680
ctgagatggg cagctgcggg tggccccaga gggcccacaa tcaagccctg tcctccatgc   1740
aaatgcccag cacctaacct cgagggtgga ccatccgtct tcatcttccc tccaaagatc   1800
aaggatgtac tcatgatctc cctgagcccc atagtcacat gtgtggtggt ggatgtgagc   1860
gaggatgacc cagatgtcca gatcagctgg tttgtgaaca acgtggaagt acacacagct   1920
cagacacaaa cccatagaga ggattacaac agtactctcc gggtggtcag tgccctcccc   1980
atccagcacc aggactggat gagtggcaag gcgttcgcat gcgcggtcaa caacaaagac   2040
ctcccagcgc ccatcgagag aaccatctca aaacccaaag ggtcagtaag agctccacag   2100
gtatatgtct tgcctccacc agaagaagag atgactaaga aacaggtcac tctgacctgc   2160
atggtcacag acttcatgcc tgaagacatt tatgtggagt ggaccaacaa cgggaaaaca   2220
gagctaaact acaagaacac tgaaccagtc ctggactctg atggttctta cttcatgtac   2280
agcaagctga gagtggaaaa gaagaactgg gtggaaagaa atagctactc ctgttcagtg   2340
gtccacgagg gtctgcacaa tcaccacacg actaagagct tctcccggac tccgggtaaa   2400
ggcggatcac atcaccatca ccatcaccat cactagtga                          2439
```

<210> SEQ ID NO 170
<211> LENGTH: 2409
<212> TYPE: DNA
<213> ORGANISM: Artificial Sequence
<220> FEATURE:
<223> OTHER INFORMATION: Synthetic polynucleotide

<400> SEQUENCE: 170

```
atgtctcgct ccgtggcctt agctgtgctc gcgctactct ctctttctgg cctggaggcc     60
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
```

-continued

```
atgggccgca caagttttga ttcggacagt tggaccctga gacttcacaa tcttcagatc    300
aaggacaagg gcttgtatca atgtatcatc catgcaaaaa agcccacagg aatgattcgc    360
atccaccaga tgaattctga actgtcagtg cttgctggtg gtggaggttc tggtggtggg    420
ggatctggag gcggaggatc tgctgctcct ctgaagattc aagcttattt caatgagact    480
gcagacctgc catgccaatt tgcaaactct caaaaccaaa gcctgagtga gctagtagta    540
ttttggcagg accaggaaaa cttggttctg aatgaggtat acttaggcaa agagaaattt    600
gacagtgttc attccaagta tatgggccgc acaagttttg attcggacag ttggaccctg    660
agacttcaca atcttcagat caaggacaag ggcttgtatc aatgtatcat ccatgcaaaa    720
aagcccacag gaatgattcg catccaccag atgaattctg aactgtcagt gcttgctgga    780
ggcggaggat ctggtggtgg aggttctggt ggtgggggat ctggaggcgg aggatctggc    840
ccacactcga tgcggtattt cgagaccgcc gtgtcccggc ccggcctcga ggagccccgg    900
tacatctctg tcggctatgt ggacaacaag gagttcgtgc gcttcgacag cgacgcggag    960
aatccgagat atgagccgcg ggcgccgtgg atggagcagg aggggccgga gtattgggag   1020
cgggaaacac agaaagccaa gggccaagag cagtggttcc gagtgagcct gaggaacctg   1080
ctcggcgcct acaaccagag cgcgggcggc tctcacacac tccagcagat gtctggctgt   1140
gacttggggt cggactggcg cctcctccgc gggtacctgc agttcgccta tgaaggccgc   1200
gattacatcg ccctgaacga agacctgaaa acgtggacgg cggcggacat ggcggcgcag   1260
atcacccgac gcaagtggga gcagagtggt gctgcagagc attacaaggc ctacctggag   1320
ggcgagtgcg tggagtggct ccacagatac ctgaagaacg ggaacgcgac gctgctgcgc   1380
acagattccc caaaggcaca tgtgacccat caccccagat ctaaaggtga agtcaccctg   1440
aggtgctggg ccctgggctt ctaccctgct gacatcaccc tgacctggca gttgaatggg   1500
gaggagctga cccaggacat ggagcttgtg gagaccaggc cttgcgggga tggaaccttc   1560
cagaagtggg catctgtggt ggtgcctctt gggaaggagc agaattacac atgccgtgtg   1620
taccatgagg ggctgcctga gcccctcacc ctgagatggg cagctgcggg tggccccaga   1680
gggcccacaa tcaagccctg tcctccatgc aaatgcccag cacctaacct cgagggtgga   1740
ccatccgtct tcatcttccc tccaaagatc aaggatgtac tcatgatctc cctgagcccc   1800
atagtcacat gtgtggtggt ggatgtgagc gaggatgacc cagatgtcca gatcagctgg   1860
tttgtgaaca acgtggaagt acacacagct cagacacaaa cccatagaga ggattacaac   1920
agtactctcc gggtggtcag tgccctcccc atccagcacc aggactggat gagtggcaag   1980
gcgttcgcat gcgcggtcaa caacaaagac ctcccagcgc ccatcgagag aaccatctca   2040
aaacccaaag ggtcagtaag agctccacag gtatatgtct tgcctccacc agaagaagag   2100
atgactaaga aacaggtcac tctgacctgc atggtcacag acttcatgcc tgaagacatt   2160
tatgtggagt ggaccaacaa cgggaaaaca gagctaaact acaagaacac tgaaccagtc   2220
ctggactctg atggttctta cttcatgtac agcaagctga gagtggaaaa gaagaactgg   2280
gtggaaagaa atagctactc ctgttcagtg gtccacgagg gtctgcacaa tcaccacacg   2340
actaagagct tctcccggac tccgggtaaa ggcggatcac atcaccatca ccatcaccat   2400
cactagtga                                                            2409
```

<210> SEQ ID NO 171
<211> LENGTH: 2394
<212> TYPE: DNA

-continued

```
<213> ORGANISM: Artificial Sequence
<220> FEATURE:
<223> OTHER INFORMATION: Synthetic polynucleotide

<400> SEQUENCE: 171

atgtctcgct ccgtggcctt agctgtgctc gcgctactct ctctttctgg cctggaggcc      60

gctgctcctc tgaagattca agcttatttc aatgagactg cagacctgcc atgccaattt     120

gcaaactctc aaaaccaaag cctgagtgag ctagtagtat tttggcagga ccaggaaaac     180

ttggttctga atgaggtata cttaggcaaa gagaaatttg acagtgttca ttccaagtat     240

atgggccgca caagttttga ttcggacagt tggaccctga gacttcacaa tcttcagatc     300

aaggacaagg gcttgtatca atgtatcatc catgcaaaaa agcccacagg aatgattcgc     360

atccaccaga tgaattctga actgtcagtg cttgctggtg gtgggggatc tggaggcgga     420

ggatctgctg ctcctctgaa gattcaagct tatttcaatg agactgcaga cctgccatgc     480

caatttgcaa actctcaaaa ccaaagcctg agtgagctag tagtattttg gcaggaccag     540

gaaaacttgg ttctgaatga ggtatactta ggcaaagaga aatttgacag tgttcattcc     600

aagtatatgg gccgcacaag ttttgattcg gacagttgga ccctgagact tcacaatctt     660

cagatcaagg acaagggctt gtatcaatgt atcatccatg caaaaaagcc cacaggaatg     720

attcgcatcc accagatgaa ttctgaactg tcagtgcttg ctggaggcgg aggatctggt     780

ggtggaggtt ctggtggtgg gggatctgga ggcggaggat ctggcccaca ctcgatgcgg     840

tatttcgaga ccgccgtgtc ccggcccggc ctcgaggagc cccggtacat ctctgtcggc     900

tatgtggaca acaaggagtt cgtgcgcttc gacagcgacg cggagaatcc gagatatgag     960

ccgcgggcgc cgtggatgga gcaggagggg ccggagtatt gggagcggga aacacagaaa    1020

gccaagggcc aagagcagtg gttccgagtg agcctgagga acctgctcgg cgcctacaac    1080

cagagcgcgg gcggctctca cacactccag cagatgtctg gctgtgactt ggggtcggac    1140

tggcgcctcc tccgcgggta cctgcagttc gcctatgaag gccgcgatta catcgccctg    1200

aacgaagacc tgaaaacgtg gacggcggcg gacatggcgg cgcagatcac ccgacgcaag    1260

tgggagcaga gtggtgctgc agagcattac aaggcctacc tggagggcga gtgcgtggag    1320

tggctccaca gatacctgaa gaacgggaac gcgacgctgc tgcgcacaga ttccccaaag    1380

gcacatgtga cccatcaccc cagatctaaa ggtgaagtca ccctgaggtg ctgggccctg    1440

ggcttctacc ctgctgacat caccctgacc tggcagttga atggggagga gctgacccag    1500

gacatggagc ttgtggagac caggccttgc ggggatggaa ccttccagaa gtgggcatct    1560

gtggtggtgc ctcttgggaa ggagcagaat tacacatgcc gtgtgtacca tgaggggctg    1620

cctgagcccc tcaccctgag atgggcagct gcgggtggcc ccagagggcc cacaatcaag    1680

ccctgtcctc catgcaaatg cccagcacct aacctcgagg gtggaccatc cgtcttcatc    1740

ttccctccaa agatcaagga tgtactcatg atctccctga gccccatagt cacatgtgtg    1800

gtggtggatg tgagcgagga tgacccagat gtccagatca gctggtttgt gaacaacgtg    1860

gaagtacaca cagctcagac acaaacccat agagaggatt acaacagtac tctccgggtg    1920

gtcagtgccc tccccatcca gcaccaggac tggatgagtg gcaaggcgtt cgcatgcgcg    1980

gtcaacaaca aagacctccc agcgcccatc gagagaacca tctcaaaacc caaagggtca    2040

gtaagagctc cacaggtata tgtcttgcct ccaccagaag aagagatgac taagaaacag    2100

gtcactctga cctgcatggt cacagacttc atgcctgaag acatttatgt ggagtggacc    2160

aacaacggga aaacagagct aaactacaag aacactgaac cagtcctgga ctctgatggt    2220
```

```
tcttacttca tgtacagcaa gctgagagtg gaaaagaaga actgggtgga aagaaatagc   2280

tactcctgtt cagtggtcca cgagggtctg cacaatcacc acacgactaa gagcttctcc   2340

cggactccgg gtaaaggcgg atcacatcac catcaccatc accatcacta gtga         2394
```

<210> SEQ ID NO 172
<211> LENGTH: 2379
<212> TYPE: DNA
<213> ORGANISM: Artificial Sequence
<220> FEATURE:
<223> OTHER INFORMATION: Synthetic polynucleotide

<400> SEQUENCE: 172

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catgcaaaaa agcccacagg aatgattcgc    360

atccaccaga tgaattctga actgtcagtg cttgctggag gcggaggatc tgctgctcct    420

ctgaagattc aagcttattt caatgagact gcagacctgc catgccaatt tgcaaactct    480

caaaaccaaa gcctgagtga gctagtagta ttttggcagg accaggaaaa cttggttctg    540

aatgaggtat acttaggcaa agagaaattt gacagtgttc attccaagta tatgggccgc    600

acaagttttg attcggacag ttggaccctg agacttcaca atcttcagat caaggacaag    660

ggcttgtatc aatgtatcat ccatgcaaaa aagcccacag gaatgattcg catccaccag    720

atgaattctg aactgtcagt gcttgctgga ggcggaggat ctggtggtgg aggttctggt    780

ggtgggggat ctggaggcgg aggatctggc ccacactcga tgcggtattt cgagaccgcc    840

gtgtcccggc ccggcctcga ggagccccgg tacatctctg tcggctatgt ggacaacaag    900

gagttcgtgc gcttcgacag cgacgcggag aatccgagat atgagccgcg ggcgccgtgg    960

atggagcagg aggggccgga gtattgggag cgggaaacac agaaagccaa gggccaagag   1020

cagtggttcc gagtgagcct gaggaacctg ctcggcgcct acaaccagag cgcgggcggc   1080

tctcacacac tccagcagat gtctggctgt gacttggggt cggactggcg cctcctccgc   1140

gggtacctgc agttcgccta tgaaggccgc gattacatcg ccctgaacga agacctgaaa   1200

acgtggacgg cggcggacat ggcggcgcag atcacccgac gcaagtggga gcagagtggt   1260

gctgcagagc attacaaggc ctacctggag ggcgagtgcg tggagtggct ccacagatac   1320

ctgaagaacg ggaacgcgac gctgctgcgc acagattccc caaaggcaca tgtgacccat   1380

caccccagat ctaaaggtga agtcaccctg aggtgctggg ccctgggctt ctaccctgct   1440

gacatcaccc tgacctggca gttgaatggg gaggagctga cccaggacat ggagcttgtg   1500

gagaccaggc cttgcgggga tggaaccttc cagaagtggg catctgtggt ggtgcctctt   1560

gggaaggagc agaattacac atgccgtgtg taccatgagg ggctgcctga gcccctcacc   1620

ctgagatggg cagctgcggg tggccccaga gggcccacaa tcaagccctg tcctccatgc   1680

aaatgcccag cacctaacct cgagggtgga ccatccgtct tcatcttccc tccaaagatc   1740

aaggatgtac tcatgatctc cctgagcccc atagtcacat gtgtggtggt ggatgtgagc   1800

gaggatgacc cagatgtcca gatcagctgg tttgtgaaca acgtggaagt acacacagct   1860
```

-continued

```
cagacacaaa cccatagaga ggattacaac agtactctcc gggtggtcag tgccctcccc   1920
atccagcacc aggactggat gagtggcaag gcgttcgcat gcgcggtcaa caacaaagac   1980
ctcccagcgc ccatcgagag aaccatctca aaacccaaag ggtcagtaag agctccacag   2040
gtatatgtct tgcctccacc agaagaagag atgactaaga aacaggtcac tctgacctgc   2100
atggtcacag acttcatgcc tgaagacatt tatgtggagt ggaccaacaa cgggaaaaca   2160
gagctaaact acaagaacac tgaaccagtc ctggactctg atggttctta cttcatgtac   2220
agcaagctga gagtggaaaa gaagaactgg gtggaaagaa atagctactc ctgttcagtg   2280
gtccacgagg gtctgcacaa tcaccacacg actaagagct tctcccggac tccgggtaaa   2340
ggcggatcac atcaccatca ccatcaccat cactagtga                          2379
```

<210> SEQ ID NO 173
<211> LENGTH: 2865
<212> TYPE: DNA
<213> ORGANISM: Artificial Sequence
<220> FEATURE:
<223> OTHER INFORMATION: Synthetic polynucleotide

<400> SEQUENCE: 173

```
atgtctcgct ccgtggcctt agctgtgctc gcgctactct ctctttctgg cctggaggcc     60
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
atgggccgca caagttttga ttcggacagt tggaccctga gacttcacaa tcttcagatc    300
aaggacaagg gcttgtatca atgtatcatc catcacaaaa agcccacagg aatgattcgc    360
atccaccaga tgaattctga actgtcagtg cttgctggag gcggaggatc tggaggcgga    420
ggatctggtg gtggaggttc tggtggtggg ggatctggag gcggaggatc tgctgctcct    480
ctgaagattc aagcttattt caatgagact gcagacctgc catgccaatt tgcaaactct    540
caaaaccaaa gcctgagtga gctagtagta ttttggcagg accaggaaaa cttggttctg    600
aatgaggtat acttaggcaa agagaaattt gacagtgttc attccaagta tatgggccgc    660
acaagttttg attcggacag ttggaccctg agacttcaca atcttcagat caaggacaag    720
ggcttgtatc aatgtatcat ccatcacaaa aagcccacag gaatgattcg catccaccag    780
atgaattctg aactgtcagt gcttgctgga ggcggaggat ctggaggcgg aggatctggt    840
ggtggaggtt ctggtggtgg gggatctgga ggcggaggat ctgctgctcc tctgaagatt    900
caagcttatt tcaatgagac tgcagacctg ccatgccaat ttgcaaactc tcaaaaccaa    960
agcctgagtg agctagtagt attttggcag gaccaggaaa acttggttct gaatgaggta   1020
tacttaggca aagagaaatt tgacagtgtt cattccaagt atatgggccg cacaagtttt   1080
gattcggaca gttggaccct gagacttcac aatcttcaga tcaaggacaa gggcttgtat   1140
caatgtatca tccatcacaa aaagcccaca ggaatgattc gcatccacca gatgaattct   1200
gaactgtcag tgcttgctgg aggcggagga tctggtggtg gaggttctgg tggtggggga   1260
tctggaggcg gaggatctgg aggcggagga tctggcccac actcgatgcg gtatttcgag   1320
accgccgtgt cccggcccgg cctcgaggag ccccggtaca tctctgtcgg ctatgtggac   1380
aacaaggagt tcgtgcgctt cgacagcgac gcggagaatc cgagatatga gccgcgggcg   1440
ccgtggatgg agcaggaggg gccggagtat tgggagcggg aaacacagaa agccaagggc   1500
caagagcagt ggttccgagt gagcctgagg aacctgctcg gcgcctacaa ccagagcgcg   1560
```

```
ggcggctctc acacactcca gcagatgtct ggctgtgact tggggtcgga ctggcgcctc   1620
ctccgcgggt acctgcagtt cgcctatgaa ggccgcgatt acatcgccct gaacgaagac   1680
ctgaaaacgt ggacggcggc ggacatggcg gcgcagatca cccgacgcaa gtgggagcag   1740
agtggtgctg cagagcatta caaggcctac ctggagggcg agtgcgtgga gtggctccac   1800
agatacctga agaacgggaa cgcgacgctg ctgcgcacag attccccaaa ggcacatgtg   1860
acccatcacc ccagatctaa aggtgaagtc accctgaggt gctgggccct gggcttctac   1920
cctgctgaca tcaccctgac ctggcagttg aatggggagg agctgaccca ggacatggag   1980
cttgtggaga ccaggccttg cggggatgga accttccaga agtgggcatc tgtggtggtg   2040
cctcttggga aggagcagaa ttacacatgc cgtgtgtacc atgaggggct gcctgagccc   2100
ctcaccctga gatgggcagc tgcgggtggc cccagagggc ccacaatcaa gccctgtcct   2160
ccatgcaaat gcccagcacc taacctcgag ggtggaccat ccgtcttcat cttccctcca   2220
aagatcaagg atgtactcat gatctccctg agccccatag tcacatgtgt ggtggtggat   2280
gtgagcgagg atgacccaga tgtccagatc agctggtttg tgaacaacgt ggaagtacac   2340
acagctcaga cacaaaccca tagagaggat tacaacagta ctctccgggt ggtcagtgcc   2400
ctccccatcc agcaccagga ctggatgagt ggcaaggcgt tcgcatgcgc ggtcaacaac   2460
aaagacctcc cagcgcccat cgagagaacc atctcaaaac ccaaagggtc agtaagagct   2520
ccacaggtat atgtcttgcc tccaccagaa gaagagatga ctaagaaaca ggtcactctg   2580
acctgcatgg tcacagactt catgcctgaa gacatttatg tggagtggac caacaacggg   2640
aaaacagagc taaactacaa gaacactgaa ccagtcctgg actctgatgg ttcttacttc   2700
atgtacagca agctgagagt ggaaaagaag aactgggtgg aaagaaatag ctactcctgt   2760
tcagtggtcc acgagggtct gcacaatcac cacacgacta agagcttctc ccggactccg   2820
ggtaaaggcg gatcacatca ccatcaccat caccatcact agtga                   2865
```

<210> SEQ ID NO 174
<211> LENGTH: 2865
<212> TYPE: DNA
<213> ORGANISM: Artificial Sequence
<220> FEATURE:
<223> OTHER INFORMATION: Synthetic polynucleotide

<400> SEQUENCE: 174

```
atgtctcgct ccgtggcctt agctgtgctc gcgctactct ctctttctgg cctggaggcc     60
gctgctcctc tgaagattca agcttatttc aatgagactg cagacctgcc atgccaattt    120
gcaaactctc aaaaccaaag cctgagtgag ctagtagtat tttggcagga ccaggaaaac    180
ttggttctga atgaggtata cttaggcaaa gagaaatttg acagtgttca ttccaagtat    240
atgggccgca caagttttga ttcggacagt tggaccctga gacttcacaa tcttcagatc    300
aaggacaagg gcttgtatca atgtatcatc catgcaaaaa agcccacagg aatgattcgc    360
atccaccaga tgaattctga actgtcagtg cttgctggag gcggaggatc tggaggcgga    420
ggatctggtg gtggaggttc tggtggtggg ggatctggag gcggaggatc tgctgctcct    480
ctgaagattc aagcttattt caatgagact gcagacctgc catgccaatt tgcaaactct    540
caaaaccaaa gcctgagtga gctagtagta ttttggcagg accaggaaaa cttggttctg    600
aatgaggtat acttaggcaa agagaaattt gacagtgttc attccaagta tatgggccgc    660
acaagttttg attcggacag ttggaccctg agacttcaca atcttcagat caaggacaag    720
```

```
ggcttgtatc aatgtatcat ccatcacaaa aagcccacag gaatgattcg catccaccag    780
atgaattctg aactgtcagt gcttgctgga ggcggaggat ctggaggcgg aggatctggt    840
ggtggaggtt ctggtggtgg gggatctgga ggcggaggat ctgctgctcc tctgaagatt    900
caagcttatt tcaatgagac tgcagacctg ccatgccaat ttgcaaactc tcaaaaccaa    960
agcctgagtg agctagtagt attttggcag gaccaggaaa acttggttct gaatgaggta   1020
tacttaggca aagagaaatt tgacagtgtt cattccaagt atatgggccg cacaagtttt   1080
gattcggaca gttggaccct gagacttcac aatcttcaga tcaaggacaa gggcttgtat   1140
caatgtatca tccatcacaa aaagcccaca ggaatgattc gcatccacca gatgaattct   1200
gaactgtcag tgcttgctgg aggcggagga tctggtggtg gaggttctgg tggtggggga   1260
tctggaggcg gaggatctgg aggcggagga tctggcccac actcgatgcg gtatttcgag   1320
accgccgtgt cccggcccgg cctcgaggag ccccggtaca tctctgtcgg ctatgtggac   1380
aacaaggagt tcgtgcgctt cgacagcgac gcggagaatc cgagatatga gccgcgggcg   1440
ccgtggatgg agcaggaggg gccggagtat tgggagcggg aaacacagaa agccaagggc   1500
caagagcagt ggttccgagt gagcctgagg aacctgctcg gcgcctacaa ccagagcgcg   1560
ggcggctctc acacactcca gcagatgtct ggctgtgact tggggtcgga ctggcgcctc   1620
ctccgcgggt acctgcagtt cgcctatgaa ggccgcgatt acatcgccct gaacgaagac   1680
ctgaaaacgt ggacggcggc ggacatggcg gcgcagatca cccgacgcaa gtgggagcag   1740
agtggtgctg cagagcatta caaggcctac ctggagggcg agtgcgtgga gtggctccac   1800
agatacctga agaacgggaa cgcgacgctg ctgcgcacag attccccaaa ggcacatgtg   1860
acccatcacc ccagatctaa aggtgaagtc accctgaggt gctgggccct gggcttctac   1920
cctgctgaca tcaccctgac ctggcagttg aatggggagg agctgaccca ggacatggag   1980
cttgtggaga ccaggccttg cggggatgga accttccaga agtgggcatc tgtggtggtg   2040
cctcttggga aggagcagaa ttacacatgc cgtgtgtacc atgaggggct gcctgagccc   2100
ctcaccctga gatgggcagc tgcgggtggc cccagagggc ccacaatcaa gccctgtcct   2160
ccatgcaaat gcccagcacc taacctcgag ggtggaccat ccgtcttcat cttccctcca   2220
aagatcaagg atgtactcat gatctccctg agccccatag tcacatgtgt ggtggtggat   2280
gtgagcgagg atgacccaga tgtccagatc agctggtttg tgaacaacgt ggaagtacac   2340
acagctcaga cacaaaccca tagagaggat tacaacagta ctctccgggt ggtcagtgcc   2400
ctccccatcc agcaccagga ctggatgagt ggcaaggcgt tcgcatgcgc ggtcaacaac   2460
aaagacctcc cagcgcccat cgagagaacc atctcaaaac ccaaagggtc agtaagagct   2520
ccacaggtat atgtcttgcc tccaccagaa gaagagatga ctaagaaaca ggtcactctg   2580
acctgcatgg tcacagactt catgcctgaa gacatttatg tggagtggac caacaacggg   2640
aaaacagagc taaactacaa gaacactgaa ccagtcctgg actctgatgg ttcttacttc   2700
atgtacagca agctgagagt ggaaaagaag aactgggtgg aaagaaatag ctactcctgt   2760
tcagtggtcc acgagggtct gcacaatcac cacacgacta agagcttctc ccggactccg   2820
ggtaaaggcg gatcacatca ccatcaccat caccatcact agtga                   2865
```

<210> SEQ ID NO 175
<211> LENGTH: 2865
<212> TYPE: DNA
<213> ORGANISM: Artificial Sequence
<220> FEATURE:
<223> OTHER INFORMATION: Synthetic polynucleotide

<400> SEQUENCE: 175
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggaggcgga 420
ggatctggtg gtggaggttc tggtggtggg ggatctggag gcggaggatc tgctgctcct 480
ctgaagattc aagcttattt caatgagact gcagacctgc catgccaatt tgcaaactct 540
caaaaccaaa gcctgagtga gctagtagta ttttggcagg accaggaaaa cttggttctg 600
aatgaggtat acttaggcaa agagaaattt gacagtgttc attccaagta tatgggccgc 660
acaagttttg attcggacag ttggaccctg agacttcaca atcttcagat caaggacaag 720
ggcttgtatc aatgtatcat ccatgcaaaa aagcccacag gaatgattcg catccaccag 780
atgaattctg aactgtcagt gcttgctgga ggcggaggat ctggaggcgg aggatctggt 840
ggtggaggtt ctggtggtgg gggatctgga ggcggaggat ctgctgctcc tctgaagatt 900
caagcttatt tcaatgagac tgcagacctg ccatgccaat ttgcaaactc tcaaaaccaa 960
agcctgagtg agctagtagt attttggcag gaccaggaaa acttggttct gaatgaggta 1020
tacttaggca aagagaaatt tgacagtgtt cattccaagt atatgggccg cacaagtttt 1080
gattcggaca gttggaccct gagacttcac aatcttcaga tcaaggacaa gggcttgtat 1140
caatgtatca tccatcacaa aaagcccaca ggaatgattc gcatccacca gatgaattct 1200
gaactgtcag tgcttgctgg aggcggagga tctggtggtg gaggttctgg tggtggggga 1260
tctggaggcg gaggatctgg aggcggagga tctggcccac actcgatgcg gtatttcgag 1320
accgccgtgt cccggcccgg cctcgaggag ccccggtaca tctctgtcgg ctatgtggac 1380
aacaaggagt tcgtgcgctt cgacagcgac gcggagaatc cgagatatga gccgcgggcg 1440
ccgtggatgg agcaggaggg gccggagtat tgggagcggg aaacacagaa agccaagggc 1500
caagagcagt ggttccgagt gagcctgagg aacctgctcg gcgcctacaa ccagagcgcg 1560
ggcggctctc acacactcca gcagatgtct ggctgtgact tggggtcgga ctggcgcctc 1620
ctccgcgggt acctgcagtt cgcctatgaa ggccgcgatt acatcgccct gaacgaagac 1680
ctgaaaacgt ggacggcggc ggacatggcg gcgcagatca cccgacgcaa gtgggagcag 1740
agtggtgctg cagagcatta caaggcctac ctggagggcg agtgcgtgga gtggctccac 1800
agatacctga agaacgggaa cgcgacgctg ctgcgcacag attccccaaa ggcacatgtg 1860
acccatcacc ccagatctaa aggtgaagtc accctgaggt gctgggccct gggcttctac 1920
cctgctgaca tcaccctgac ctggcagttg aatggggagg agctgaccca ggacatggag 1980
cttgtggaga ccaggccttg cggggatgga accttccaga agtgggcatc tgtggtggtg 2040
cctcttggga aggagcagaa ttacacatgc cgtgtgtacc atgaggggct gcctgagccc 2100
ctcaccctga gatgggcagc tgcgggtggc cccagagggc ccacaatcaa gccctgtcct 2160
ccatgcaaat gcccagcacc taacctcgag ggtggaccat ccgtcttcat cttccctcca 2220
aagatcaagg atgtactcat gatctccctg agccccatag tcacatgtgt ggtggtggat 2280

```
gtgagcgagg atgacccaga tgtccagatc agctggtttg tgaacaacgt ggaagtacac   2340

acagctcaga cacaaaccca tagagaggat tacaacagta ctctccgggt ggtcagtgcc   2400

ctccccatcc agcaccagga ctggatgagt ggcaaggcgt tcgcatgcgc ggtcaacaac   2460

aaagacctcc cagcgcccat cgagagaacc atctcaaaac ccaaagggtc agtaagagct   2520

ccacaggtat atgtcttgcc tccaccagaa gaagagatga ctaagaaaca ggtcactctg   2580

acctgcatgg tcacagactt catgcctgaa gacatttatg tggagtggac caacaacggg   2640

aaaacagagc taaactacaa gaacactgaa ccagtcctgg actctgatgg ttcttacttc   2700

atgtacagca agctgagagt ggaaaagaag aactgggtgg aaagaaatag ctactcctgt   2760

tcagtggtcc acgagggtct gcacaatcac cacacgacta agagcttctc ccggactccg   2820

ggtaaaggcg gatcacatca ccatcaccat caccatcact agtga                  2865
```

<210> SEQ ID NO 176
<211> LENGTH: 2865
<212> TYPE: DNA
<213> ORGANISM: Artificial Sequence
<220> FEATURE:
<223> OTHER INFORMATION: Synthetic polynucleotide

<400> SEQUENCE: 176

```
atgtctcgct ccgtggcctt agctgtgctc gcgctactct ctctttctgg cctggaggcc     60

gctgctcctc tgaagattca agcttatttc aatgagactg cagacctgcc atgccaattt    120

gcaaactctc aaaaccaaag cctgagtgag ctagtagtat tttggcagga ccaggaaaac    180

ttggttctga atgaggtata cttaggcaaa gagaaatttg acagtgttca ttccaagtat    240

atgggccgca caagttttga ttcggacagt tggaccctga gacttcacaa tcttcagatc    300

aaggacaagg gcttgtatca atgtatcatc catcacaaaa agcccacagg aatgattcgc    360

atccaccaga tgaattctga actgtcagtg cttgctggag gcggaggatc tggaggcgga    420

ggatctggtg gtggaggttc tggtggtggg ggatctggag gcggaggatc tgctgctcct    480

ctgaagattc aagcttattt caatgagact gcagacctgc catgccaatt tgcaaactct    540

caaaaccaaa gcctgagtga gctagtagta ttttggcagg accaggaaaa cttggttctg    600

aatgaggtat acttaggcaa agagaaattt gacagtgttc attccaagta tatgggccgc    660

acaagttttg attcggacag ttggaccctg agacttcaca atcttcagat caaggacaag    720

ggcttgtatc aatgtatcat ccatcacaaa aagcccacag gaatgattcg catccaccag    780

atgaattctg aactgtcagt gcttgctgga ggcggaggat ctggaggcgg aggatctggt    840

ggtggaggtt ctggtggtgg gggatctgga ggcggaggat ctgctgctcc tctgaagatt    900

caagcttatt tcaatgagac tgcagacctg ccatgccaat ttgcaaactc tcaaaaccaa    960

agcctgagtg agctagtagt attttggcag gaccaggaaa acttggttct gaatgaggta   1020

tacttaggca aagagaaatt tgacagtgtt cattccaagt atatgggccg cacaagtttt   1080

gattcggaca gttggaccct gagacttcac aatcttcaga tcaaggacaa gggcttgtat   1140

caatgtatca tccatgcaaa aaagcccaca ggaatgattc gcatccacca gatgaattct   1200

gaactgtcag tgcttgctgg aggcggagga tctggtggtg gaggttctgg tggtggggga   1260

tctggaggcg gaggatctgg aggcggagga tctggcccac actcgatgcg gtatttcgag   1320

accgccgtgt cccggcccgg cctcgaggag ccccggtaca tctctgtcgg ctatgtggac   1380

aacaaggagt tcgtgcgctt cgacagcgac gcggagaatc cgagatatga gccgcgggcg   1440

ccgtggatgg agcaggaggg gccggagtat tgggagcggg aaacacagaa agccaagggc   1500
```

caagagcagt ggttccgagt gagcctgagg aacctgctcg gcgcctacaa ccagagcgcg 1560
ggcggctctc acacactcca gcagatgtct ggctgtgact tggggtcgga ctggcgcctc 1620
ctccgcgggt acctgcagtt cgcctatgaa ggccgcgatt acatcgccct gaacgaagac 1680
ctgaaaacgt ggacggcggc ggacatggcg gcgcagatca cccgacgcaa gtgggagcag 1740
agtggtgctg cagagcatta caaggcctac ctggagggcg agtgcgtgga gtggctccac 1800
agatacctga agaacgggaa cgcgacgctg ctgcgcacag attccccaaa ggcacatgtg 1860
acccatcacc ccagatctaa aggtgaagtc accctgaggt gctgggccct gggcttctac 1920
cctgctgaca tcaccctgac ctggcagttg aatggggagg agctgaccca ggacatggag 1980
cttgtggaga ccaggccttg cggggatgga accttccaga agtgggcatc tgtggtggtg 2040
cctcttggga aggagcagaa ttacacatgc cgtgtgtacc atgaggggct gcctgagccc 2100
ctcaccctga gatgggcagc tgcgggtggc cccagagggc ccacaatcaa gccctgtcct 2160
ccatgcaaat gcccagcacc taacctcgag ggtggaccat ccgtcttcat cttccctcca 2220
aagatcaagg atgtactcat gatctccctg agccccatag tcacatgtgt ggtggtggat 2280
gtgagcgagg atgacccaga tgtccagatc agctggtttg tgaacaacgt ggaagtacac 2340
acagctcaga cacaaaccca tagagaggat tacaacagta ctctccgggt ggtcagtgcc 2400
ctccccatcc agcaccagga ctggatgagt ggcaaggcgt tcgcatgcgc ggtcaacaac 2460
aaagacctcc cagcgcccat cgagagaacc atctcaaaac ccaaagggtc agtaagagct 2520
ccacaggtat atgtcttgcc tccaccagaa gaagagatga ctaagaaaca ggtcactctg 2580
acctgcatgg tcacagactt catgcctgaa gacatttatg tggagtggac caacaacggg 2640
aaaacagagc taaactacaa gaacactgaa ccagtcctgg actctgatgg ttcttacttc 2700
atgtacagca agctgagagt ggaaaagaag aactgggtgg aaagaaatag ctactcctgt 2760
tcagtggtcc acgagggtct gcacaatcac cacacgacta agagcttctc ccggactccg 2820
ggtaaaggcg gatcacatca ccatcaccat caccatcact agtga 2865

<210> SEQ ID NO 177
<211> LENGTH: 2865
<212> TYPE: DNA
<213> ORGANISM: Artificial Sequence
<220> FEATURE:
<223> OTHER INFORMATION: Synthetic polynucleotide

<400> SEQUENCE: 177
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catgcaaaaa agcccacagg aatgattcgc 360
atccaccaga tgaattctga actgtcagtg cttgctggag gcggaggatc tggaggcgga 420
ggatctggtg gtggaggttc tggtggtggg ggatctggag gcggaggatc tgctgctcct 480
ctgaagattc aagcttattt caatgagact gcagacctgc catgccaatt tgcaaactct 540
caaaaccaaa gcctgagtga gctagtagta ttttggcagg accaggaaaa cttggttctg 600
aatgaggtat acttaggcaa agagaaattt gacagtgttc attccaagta tatgggccgc 660

```
acaagttttg attcggacag ttggaccctg agacttcaca atcttcagat caaggacaag    720
ggcttgtatc aatgtatcat ccatgcaaaa aagcccacag gaatgattcg catccaccag    780
atgaattctg aactgtcagt gcttgctgga ggcggaggat ctggaggcgg aggatctggt    840
ggtggaggtt ctggtggtgg gggatctgga ggcggaggat ctgctgctcc tctgaagatt    900
caagcttatt tcaatgagac tgcagacctg ccatgccaat ttgcaaactc tcaaaaccaa    960
agcctgagtg agctagtagt attttggcag gaccaggaaa acttggttct gaatgaggta   1020
tacttaggca aagagaaatt tgacagtgtt cattccaagt atatgggccg cacaagtttt   1080
gattcggaca gttggaccct gagacttcac aatcttcaga tcaaggacaa gggcttgtat   1140
caatgtatca tccatcacaa aaagcccaca ggaatgattc gcatccacca gatgaattct   1200
gaactgtcag tgcttgctgg aggcggagga tctggtggtg gaggttctgg tggtgggga    1260
tctggaggcg gaggatctgg aggcggagga tctggcccac actcgatgcg gtatttcgag   1320
accgccgtgt cccggcccgg cctcgaggag ccccggtaca tctctgtcgg ctatgtggac   1380
aacaaggagt tcgtgcgctt cgacagcgac gcggagaatc cgagatatga gccgcgggcg   1440
ccgtggatgg agcaggaggg gccggagtat tgggagcggg aaacacagaa agccaagggc   1500
caagagcagt ggttccgagt gagcctgagg aacctgctcg gcgcctacaa ccagagcgcg   1560
ggcggctctc acacactcca gcagatgtct ggctgtgact tggggtcgga ctggcgcctc   1620
ctccgcgggt acctgcagtt cgcctatgaa ggccgcgatt acatcgccct gaacgaagac   1680
ctgaaaacgt ggacggcggc ggacatggcg gcgcagatca cccgacgcaa gtgggagcag   1740
agtggtgctg cagagcatta caaggcctac ctggagggcg agtgcgtgga gtggctccac   1800
agatacctga agaacgggaa cgcgacgctg ctgcgcacag attccccaaa ggcacatgtg   1860
acccatcacc ccagatctaa aggtgaagtc accctgaggt gctgggccct gggcttctac   1920
cctgctgaca tcaccctgac ctggcagttg aatggggagg agctgaccca ggacatggag   1980
cttgtggaga ccaggccttg cggggatgga accttccaga agtgggcatc tgtggtggtg   2040
cctcttggga aggagcagaa ttacacatgc cgtgtgtacc atgaggggct gcctgagccc   2100
ctcaccctga gatgggcagc tgcgggtggc cccagagggc ccacaatcaa gccctgtcct   2160
ccatgcaaat gcccagcacc taacctcgag ggtggaccat ccgtcttcat cttccctcca   2220
aagatcaagg atgtactcat gatctccctg agccccatag tcacatgtgt ggtggtggat   2280
gtgagcgagg atgacccaga tgtccagatc agctggtttg tgaacaacgt ggaagtacac   2340
acagctcaga cacaaaccca tagagaggat tacaacagta ctctccgggt ggtcagtgcc   2400
ctccccatcc agcaccagga ctggatgagt ggcaaggcgt tcgcatgcgc ggtcaacaac   2460
aaagacctcc cagcgcccat cgagagaacc atctcaaaac ccaaagggtc agtaagagct   2520
ccacaggtat atgtcttgcc tccaccagaa gaagagatga ctaagaaaca ggtcactctg   2580
acctgcatgg tcacagactt catgcctgaa gacatttatg tggagtggac caacaacggg   2640
aaaacagagc taaactacaa gaacactgaa ccagtcctgg actctgatgg ttcttacttc   2700
atgtacagca agctgagagt ggaaaagaag aactgggtgg aaagaaatag ctactcctgt   2760
tcagtggtcc acgagggtct gcacaatcac cacacgacta agagcttctc ccggactccg   2820
ggtaaaggcg gatcacatca ccatcaccat caccatcact agtga                   2865
```

<210> SEQ ID NO 178
<211> LENGTH: 2865
<212> TYPE: DNA
<213> ORGANISM: Artificial Sequence
<220> FEATURE:
<223> OTHER INFORMATION: Synthetic polynucleotide

<400> SEQUENCE: 178
atgtctcgct ccgtggcctt agctgtgctc gcgctactct ctctttctgg cctggaggcc 60
gctgctcctc tgaagattca agcttatttc aatgagactg cagacctgcc atgccaattt 120
gcaaactctc aaaaccaaag cctgagtgag ctagtagtat tttggcagga ccaggaaaac 180
ttggttctga atgaggtata cttaggcaaa gagaaatttg acagtgttca ttccaagtat 240
atgggccgca caagttttga ttcggacagt tggaccctga gacttcacaa tcttcagatc 300
aaggacaagg gcttgtatca atgtatcatc catcacaaaa agcccacagg aatgattcgc 360
atccaccaga tgaattctga actgtcagtg cttgctggag gcggaggatc tggaggcgga 420
ggatctggtg gtggaggttc tggtggtggg ggatctggag gcggaggatc tgctgctcct 480
ctgaagattc aagcttattt caatgagact gcagacctgc catgccaatt tgcaaactct 540
caaaaccaaa gcctgagtga gctagtagta ttttggcagg accaggaaaa cttggttctg 600
aatgaggtat acttaggcaa agagaaattt gacagtgttc attccaagta tatgggccgc 660
acaagttttg attcggacag ttggaccctg agacttcaca atcttcagat caaggacaag 720
ggcttgtatc aatgtatcat ccatgcaaaa aagcccacag gaatgattcg catccaccag 780
atgaattctg aactgtcagt gcttgctgga ggcggaggat ctggaggcgg aggatctggt 840
ggtggaggtt ctggtggtgg gggatctgga ggcggaggat ctgctgctcc tctgaagatt 900
caagcttatt tcaatgagac tgcagacctg ccatgccaat ttgcaaactc tcaaaaccaa 960
agcctgagtg agctagtagt attttggcag gaccaggaaa acttggttct gaatgaggta 1020
tacttaggca aagagaaatt tgacagtgtt cattccaagt atatgggccg cacaagtttt 1080
gattcggaca gttggaccct gagacttcac aatcttcaga tcaaggacaa gggcttgtat 1140
caatgtatca tccatgcaaa aaagcccaca ggaatgattc gcatccacca gatgaattct 1200
gaactgtcag tgcttgctgg aggcggagga tctggtggtg gaggttctgg tggtggggga 1260
tctggaggcg gaggatctgg aggcggagga tctggcccac actcgatgcg gtatttcgag 1320
accgccgtgt cccggcccgg cctcgaggag ccccggtaca tctctgtcgg ctatgtggac 1380
aacaaggagt tcgtgcgctt cgacagcgac gcggagaatc cgagatatga gccgcgggcg 1440
ccgtggatgg agcaggaggg gccggagtat tgggagcggg aaacacagaa agccaagggc 1500
caagagcagt ggttccgagt gagcctgagg aacctgctcg gcgcctacaa ccagagcgcg 1560
ggcggctctc acacactcca gcagatgtct ggctgtgact tggggtcgga ctggcgcctc 1620
ctccgcgggt acctgcagtt cgcctatgaa ggccgcgatt acatcgccct gaacgaagac 1680
ctgaaaacgt ggacggcggc ggacatggcg gcgcagatca cccgacgcaa gtgggagcag 1740
agtggtgctg cagagcatta caaggcctac ctggagggcg agtgcgtgga gtggctccac 1800
agatacctga agaacgggaa cgcgacgctg ctgcgcacag attccccaaa ggcacatgtg 1860
acccatcacc ccagatctaa aggtgaagtc accctgaggt gctgggccct gggcttctac 1920
cctgctgaca tcaccctgac ctggcagttg aatggggagg agctgaccca ggacatggag 1980
cttgtggaga ccaggccttg cggggatgga accttccaga agtgggcatc tgtggtggtg 2040
cctcttggga aggagcagaa ttacacatgc cgtgtgtacc atgaggggct gcctgagccc 2100
ctcaccctga gatgggcagc tgcgggtggc cccagagggc ccacaatcaa gccctgtcct 2160
ccatgcaaat gcccagcacc taacctcgag ggtggaccat ccgtcttcat cttccctcca 2220

```
aagatcaagg atgtactcat gatctccctg agccccatag tcacatgtgt ggtggtggat   2280

gtgagcgagg atgacccaga tgtccagatc agctggtttg tgaacaacgt ggaagtacac   2340

acagctcaga cacaaaccca tagagaggat tacaacagta ctctccgggt ggtcagtgcc   2400

ctccccatcc agcaccagga ctggatgagt ggcaaggcgt tcgcatgcgc ggtcaacaac   2460

aaagacctcc cagcgcccat cgagagaacc atctcaaaac ccaaagggtc agtaagagct   2520

ccacaggtat atgtcttgcc tccaccagaa gaagagatga ctaagaaaca ggtcactctg   2580

acctgcatgg tcacagactt catgcctgaa gacatttatg tggagtggac caacaacggg   2640

aaaacagagc taaactacaa gaacactgaa ccagtcctgg actctgatgg ttcttacttc   2700

atgtacagca agctgagagt ggaaaagaag aactgggtgg aaagaaatag ctactcctgt   2760

tcagtggtcc acgagggtct gcacaatcac cacacgacta agagcttctc ccggactccg   2820

ggtaaaggcg gatcacatca ccatcaccat caccatcact agtga                   2865
```

<210> SEQ ID NO 179
<211> LENGTH: 276
<212> TYPE: PRT
<213> ORGANISM: Homo Sapiens

<400> SEQUENCE: 179

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
```

```
            260                 265                 270

Arg Trp Glu Pro
        275


<210> SEQ ID NO 180
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 180

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Ala Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 181
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 181
```

-continued

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Cys Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Cys Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275
```

<210> SEQ ID NO 182
<211> LENGTH: 275
<212> TYPE: PRT
<213> ORGANISM: Homo Sapiens

<400> SEQUENCE: 182

```
Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Asp Gly Ser His Thr Ile Gln
                85                  90                  95
```

Ile Met Tyr Gly Cys Asp Val Gly Pro Asp Gly Arg Phe Leu Arg Gly
100 105 110

Tyr Arg Gln Asp Ala Tyr Asp Gly Lys Asp Tyr Ile Ala Leu Asn Glu
115 120 125

Asp Leu Arg Ser Trp Thr Ala Ala Asp Met Ala Ala Gln Ile Thr Lys
130 135 140

Arg Lys Trp Glu Ala Ala His Ala Ala Glu Gln Gln Arg Ala Tyr Leu
145 150 155 160

Glu Gly Thr Cys Val Glu Trp Leu Arg Arg Tyr Leu Glu Asn Gly Lys
165 170 175

Glu Thr Leu Gln Arg Thr Asp Pro Pro Lys Thr His Met Thr His His
180 185 190

Pro Ile Ser Asp His Glu Ala Thr Leu Arg Cys Trp Ala Leu Gly Phe
195 200 205

Tyr Pro Ala Glu Ile Thr Leu Thr Trp Gln Arg Asp Gly Glu Asp Gln
210 215 220

Thr Gln Asp Thr Glu Leu Val Glu Thr Arg Pro Ala Gly Asp Gly Thr
225 230 235 240

Phe Gln Lys Trp Ala Ala Val Val Val Pro Ser Gly Glu Glu Gln Arg
245 250 255

Tyr Thr Cys His Val Gln His Glu Gly Leu Pro Lys Pro Leu Thr Leu
260 265 270

Arg Trp Glu
275

<210> SEQ ID NO 183
<211> LENGTH: 275
<212> TYPE: PRT
<213> ORGANISM: Artificial Sequence
<220> FEATURE:
<223> OTHER INFORMATION: synthetic polypeptide

<400> SEQUENCE: 183

Gly Ser His Ser Met Arg Tyr Phe Tyr Thr Ser Val Ser Arg Pro Gly
1 5 10 15

Arg Gly Glu Pro Arg Phe Ile Ala Val Gly Tyr Val Asp Asp Thr Gln
20 25 30

Phe Val Arg Phe Asp Ser Asp Ala Ala Ser Gln Arg Met Glu Pro Arg
35 40 45

Ala Pro Trp Ile Glu Gln Glu Gly Pro Glu Tyr Trp Asp Gln Glu Thr
50 55 60

Arg Asn Val Lys Ala Gln Ser Gln Thr Asp Arg Val Asp Leu Gly Thr
65 70 75 80

Leu Arg Gly Ala Tyr Asn Gln Ser Glu Asp Gly Ser His Thr Ile Gln
85 90 95

Ile Met Tyr Gly Cys Asp Val Gly Pro Asp Gly Arg Phe Leu Arg Gly
100 105 110

Tyr Arg Gln Asp Ala Tyr Asp Gly Lys Asp Tyr Ile Ala Leu Asn Glu
115 120 125

Asp Leu Arg Ser Trp Thr Ala Ala Asp Met Ala Ala Gln Ile Thr Lys
130 135 140

Arg Lys Trp Glu Ala Ala His Ala Ala Glu Gln Gln Arg Ala Tyr Leu
145 150 155 160

Glu Gly Thr Cys Val Glu Trp Leu Arg Arg Tyr Leu Glu Asn Gly Lys
165 170 175

```
Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu
        275


<210> SEQ ID NO 184
<211> LENGTH: 276
<212> TYPE: PRT
<213> ORGANISM: Homo Sapiens

<400> SEQUENCE: 184

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
```

```
            260                 265                 270

Arg Trp Glu Pro
        275


<210> SEQ ID NO 185
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 185

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Ala Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 186
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 186
```

```
Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Cys Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Cys Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 187
<211> LENGTH: 276
<212> TYPE: PRT
<213> ORGANISM: Homo Sapiens

<400> SEQUENCE: 187

Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Asn Tyr Lys Arg Gln Ala Gln Ala Asp Arg Val Ser Leu Arg Asn
65                  70                  75                  80

Leu Arg Gly Tyr Tyr Asn Gln Ser Glu Asp Gly Ser His Thr Leu Gln
                85                  90                  95
```

```
Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Leu Glu Ala Ala Arg Ala Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu Pro Pro Lys Thr His Val Thr His His
            180                 185                 190

Pro Leu Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Met Gln His Glu Gly Leu Gln Glu Pro Leu Thr Leu
            260                 265                 270

Ser Trp Glu Pro
        275
```

<210> SEQ ID NO 188
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 188

```
Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Asn Tyr Lys Arg Gln Ala Gln Ala Asp Arg Val Ser Leu Arg Asn
65                  70                  75                  80

Leu Arg Gly Ala Tyr Asn Gln Ser Glu Asp Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Leu Glu Ala Ala Arg Ala Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175
```

```
Glu Thr Leu Gln Arg Ala Glu Pro Pro Lys Thr His Val Thr His His
            180                 185                 190

Pro Leu Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Met Gln His Glu Gly Leu Gln Glu Pro Leu Thr Leu
            260                 265                 270

Ser Trp Glu Pro
        275


<210> SEQ ID NO 189
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 189

Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Asn Tyr Lys Arg Gln Ala Gln Ala Asp Arg Val Ser Leu Arg Asn
65                  70                  75                  80

Leu Arg Gly Cys Tyr Asn Gln Ser Glu Asp Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Cys Ala Gln Ile Thr Gln
    130                 135                 140

Arg Lys Leu Glu Ala Ala Arg Ala Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu Pro Pro Lys Thr His Val Thr His His
            180                 185                 190

Pro Leu Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255
```

-continued

```
Tyr Thr Cys His Met Gln His Glu Gly Leu Gln Glu Pro Leu Thr Leu
            260                 265                 270

Ser Trp Glu Pro
        275


<210> SEQ ID NO 190
<211> LENGTH: 20
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(20)
<223> OTHER INFORMATION: Wherein up to 3 copies of GGGGS may be ommitted

<400> SEQUENCE: 190

Gly Gly Gly Gly Ser Gly Gly Gly Gly Ser Gly Gly Gly Gly Ser Gly
1               5                   10                  15

Gly Gly Gly Ser
            20
```

T-CELL MODULATORY MULTIMERIC POLYPEPTIDES AND METHODS OF USE THEREOF

CROSS-REFERENCE

This application claims the benefit of U.S. Provisional Patent Application No. 62/444,095, filed Jan. 9, 2017, which application is incorporated herein by reference in its entirety.

INCORPORATION BY REFERENCE OF SEQUENCE LISTING PROVIDED AS A TEXT FILE

A Sequence Listing is provided herewith as a text file, "CUEB-101_SEQ_LIST_DEC2022_EDIT_ST25.txt" created on Dec. 18, 2022 and having a size of 394 KB. The contents of the text file are incorporated by reference herein in their entirety.

INTRODUCTION

An adaptive immune response involves the engagement of the T cell receptor (TCR), present on the surface of a T cell, with a small peptide antigen non-covalently presented on the surface of an antigen presenting cell (APC) by a major histocompatibility complex (MHC; also referred to in humans as a human leukocyte antigen (HLA) complex). This engagement represents the immune system's targeting mechanism and is a requisite molecular interaction for T cell modulation (activation or inhibition) and effector function. Following epitope-specific cell targeting, the targeted T cells are activated through engagement of costimulatory proteins found on the APC with counterpart costimulatory proteins the T cells. Both signals—epitope/TCR binding and engagement of APC costimulatory proteins with T cell costimulatory proteins—are required to drive T cell specificity and activation or inhibition. The TCR is specific for a given epitope; however, the costimulatory protein not epitope specific and instead is generally expressed on all T cells or on large T cell subsets.

SUMMARY

The present disclosure provides variant immunomodulatory polypeptides, and fusion polypeptides comprising the variant immunomodulatory peptides. The present disclosure provides T-cell modulatory multimeric polypeptides, and compositions comprising same, where the T-cell modulatory multimeric polypeptides comprise a variant immunomodulatory polypeptide of the present disclosure. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

BRIEF DESCRIPTION OF THE DRAWINGS

FIG. 2A-2*cc* provide an amino acid sequence of human CD86 (FIG. 2A); "full" ectodomain of human CD86 (FIG. 2B); full ectodomain of mouse CD86 (FIG. 2C); immunoglobulin V-type (IgV) domain of the ectodomain of human CD86 (FIG. 2D); immunoglobulin V-type (IgV) domain of the ectodomain of mouse CD86 (FIG. 2E); and examples of variant CD86 polypeptides (FIG. 2F-2*cc*).

FIG. 3A-3C provide amino acid sequences of CD28.

FIG. 4A-4C provide amino acid sequences of immunoglobulin Fc polypeptides. Sequences in FIG. 4A from top to bottom, SEQ ID NOs:33-35; sequences in FIG. 4B from top to bottom, SEQ ID NOs:36-37; and sequences in FIG. 4C from top to bottom, SEQ ID NOs:38-40.

FIG. 5A-5C provide amino acid sequences of human leukocyte antigen (HLA) Class I heavy chain polypeptides. Signal sequences are underlined. Sequence in FIG. 5A, SEQ ID NO:41; sequence in FIG. 5B, SEQ ID NO:42; and sequence in FIG. 5C, SEQ ID NO:43.

FIG. 6 provides a multiple amino acid sequence alignment of beta-2 microglobulin (β2M) precursors (i.e., including the leader sequence) from *Homo sapiens* (NP_004039.1; SEQ ID NO:44), *Pan troglodytes* (NP_001009066.1; SEQ ID NO:45), *Macaca mulatta* (NP_001040602.1; SEQ ID NO:46), *Bos Taurus* (NP_776318.1; SEQ ID NO:47) and *Mus musculus* (NP_033865.2; SEQ ID NO:48). Amino acids 1-20 are a signal peptide.

FIG. 7 provides the nucleic acid sequence of the CD86 construct 307 (SEQ ID NO:113).

FIG. 8 provides the nucleic acid sequence of the CD86 construct 966 (SEQ ID NO:127).

FIG. 9 provides the nucleic acid sequence of the CD86 construct 1145 (SEQ ID NO:175).

FIG. 10 provides the nucleic acid sequence of the CD86 construct 1123 (SEQ ID NO:169).

FIG. 11 provides a table of various constructs, and the corresponding sequence identifiers.

DEFINITIONS

Figure 1A:
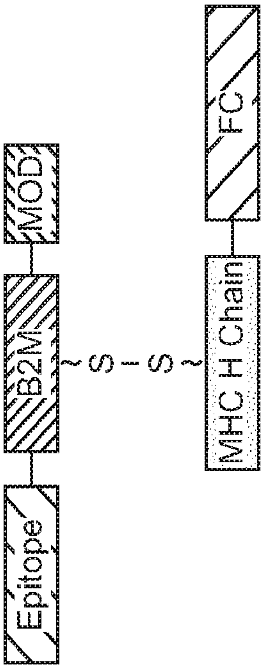
FIG. 1A-1D schematically depict various embodiments of a T-cell modulatory multimeric polypeptide of the present disclosure. In these embodiments, disulfide bonds are formed between MHC (e.g., HLA) polypeptides present in separate polypeptides.
Figure 1B:
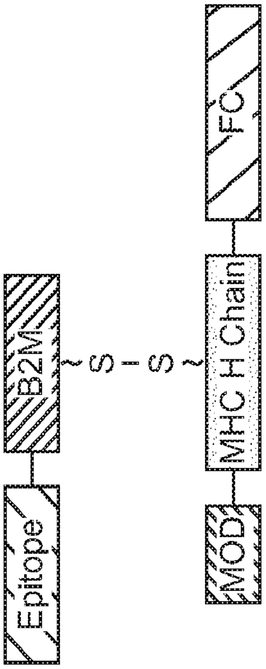
Figure 1C:
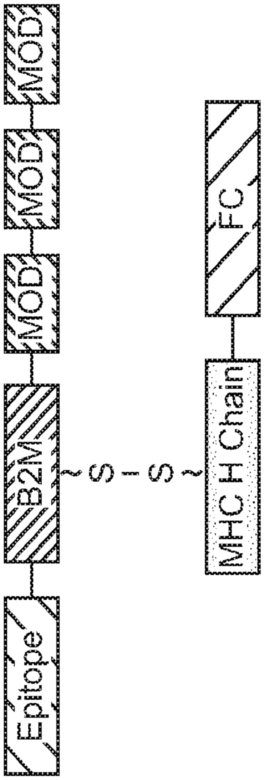
Figure 1D:
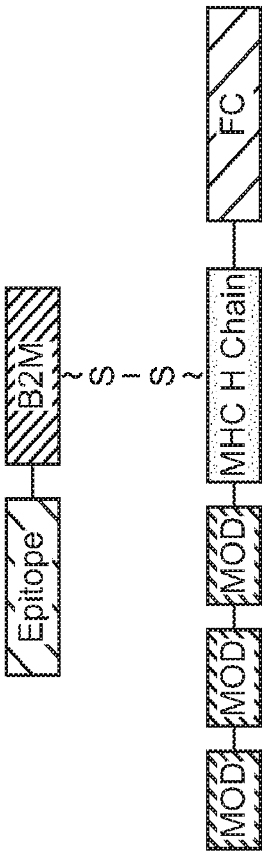

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

"Binding" as used herein (e.g. with reference to binding of a T-cell modulatory multimeric polypeptide of the present disclosure to a polypeptide (e.g., a T-cell receptor) on a T cell) refers to a non-covalent interaction between. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

The term "immunological synapse" or "immune synapse" as used herein generally refers to the natural interface between two interacting immune cells of an adaptive immune response including, e.g., the interface between an antigen-presenting cell (APC) or target cell and an effector cell, e.g., a lymphocyte, an effector T cell, a natural killer cell, and the like. An immunological synapse between an APC and a T cell is generally initiated by the interaction of a T cell antigen receptor and major histocompatibility complex molecules, e.g., as described in Bromley et al., Annu Rev Immunol. 2001; 19:375-96; the disclosure of which is incorporated herein by reference in its entirety.

"T cell" includes all types of immune cells expressing CD3, including T-helper cells ($CD4^+$ cells), cytotoxic T-cells ($CD8^+$ Cells), T-regulatory cells (Treg), and NK-T cells.

"Co-stimulatory polypeptide," as the term is used herein, includes a polypeptide on an antigen presenting cell (APC) (e.g., a dendritic cell, a B cell, and the like) that specifically binds a cognate co-stimulatory polypeptide on a T cell, thereby providing a signal which, in addition to the primary signal provided by, for instance, binding of a TCR/CD3 complex with a major histocompatibility complex (MHC) polypeptide loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, Fas ligand (FasL), inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, LIGHT, NKG2C, B7-H3, and a ligand that specifically binds to CD83.

A "modulatory domain" of a T-cell modulatory multimeric polypeptide of the present disclosure comprises a co-stimulatory polypeptide.

"Heterologous," as used herein, means a nucleotide or polypeptide that is not found in the native nucleic acid or protein, respectively.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells, for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication.

A "host cell," as used herein, denotes an in vivo or in vitro eukaryotic cell or a cell from a multicellular organism (e.g., a cell line) cultured as a unicellular entity, which eukaryotic cells can be, or have been, used as recipients for a nucleic acid (e.g., an expression vector that comprises a nucleotide sequence encoding a multimeric polypeptide of the present disclosure), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a genetically modified eukaryotic host cell is genetically modified by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a modulatory domain" includes a plurality of such modulatory domains and reference to "the HLA polypeptide" includes reference to one or more HLA polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant immunomodulatory polypeptides, and fusion polypeptides comprising the variant immunomodulatory peptides. The present disclosure provides T-cell modulatory multimeric polypeptides, and compositions comprising same, where the T-cell modulatory multimeric polypeptides comprise a variant immunomodulatory polypeptide of the present disclosure. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

A T-cell modulatory multimeric polypeptide of the present disclosure is also referred to as a "synTac polypeptide." A synTac polypeptide of the present disclosure comprises a variant modulatory domain, where the variant modulatory domain exhibits reduced binding affinity to an immunomodulatory polypeptide, compared to the affinity of a wild-type modulatory domain for the immunomodulatory polypeptide. A synTac polypeptide of the present disclosure can modulate the activity of a target T-cell. A synTac polypeptide of the present disclosure provides for enhanced target cell specificity.

Variant Immunomodulatory Polypeptides

The present disclosure provides variant CD86 modulatory polypeptides. A wild-type amino acid sequence of human CD86 is provided in FIG. 2A. The "full" ectodomain of human CD86 comprises amino acids 24-247 of the amino acid sequence provided in FIG. 2A; the amino acid sequence of the "full" ectodomain of human CD86 is provided in FIG. 2B. For comparison, an amino acid sequence of the full ectodomain of a mouse CD86 is provided in FIG. 2C. The immunoglobulin V-type (IgV) domain of the ectodomain of human CD86 comprises amino acids 24-133 of the amino acid sequence provided in FIG. 2A. The amino acid sequence of the IgV domain of a human CD86 is provided in FIG. 2D; the amino acid sequence of the IgV domain of a mouse CD86 is provided in FIG. 2E.

The amino acid sequence of the full ectodomain of a wild-type mouse CD86 can be as follows:

(SEQ ID NO: 3)

APLKIQAYFNETADLPCQFANSQNQSLSELVVFWQDQENLVLNEVYLGKEK

FDSVHSKYMGRTSFDSDSWTLRLHNLQIKDKGLYQCIIHHKKPTGMIRIHQ

MNSELSVLANFSQPEIVPISNITENVYINLTCSSIHGYPEPKKMSVLLRTK

NSTIEYDGIMQKSQDNVTELYDVSISLSVSFPDVTSNMTIFCILETDKTRL

LSSPFSIELEDPQPPPDHIP.

Amino acids G61, D66, W70, and H91 of wild-type mouse CD86 ectodomain are underlined and bolded.

The amino acid sequence of the full ectodomain of a wild-type human CD86 can be as follows:

(SEQ ID NO: 2)

APLKIQAYFNETADLPCQFANSQNQSLSELVVFWQDQENLVLNEVYLGKEK

FDSVHSKYMNRTSFDSDSWTLRLHNLQIKDKGLYQCIIHHKKPTGMIRIHQ

MNSELSVLANFSQPEIVPISNITENVYINLTCSSIHGYPEPKKMSVLLRTK

NSTIEYDGIMQKSQDNVTELYDVSISLSVSFPDVTSNMTIFCILETDKTRL

LSSPFSIELEDPQPPPDHIP.

Amino acids corresponding to G61, D66, W70, and H91 of wild-type mouse CD86 ectodomain are N61, D66, W70, and H91 in wild-type human CD86 ectodomain, and are underlined and bolded.

The amino acid sequence of the IgV domain of a wild-type mouse CD86 can be as follows:

(SEQ ID NO: 5)

APLKIQAYFNETADLPCQFANSQNQSLSELVVFWQDQENLVLNEVYLGKEK

FDSVHSKYMGRTSFDSDSWTLRLHNLQIKDKGLYQCIIHHKKPTGMIRIHQ

MNSELSVL

Amino acids G61, D66, W70, and H91 of wild-type mouse CD86 IgV domain are underlined and bolded.

The amino acid sequence of the IgV domain of a wild-type human CD86 can be as follows:

(SEQ ID NO:4)

APLKIQAYFNETADLPCQFANSQNQSLSELVVFWQDQENLVLNEVYLGKEK

FDSVHSKYMNRTSFDSDSWTLRLHNLQIKDKGLYQCIIHHKKPTGMIRIHQ

MNSELSVL.

Amino acids corresponding to G61, D66, W70, and H91 of wild-type mouse CD86 IgV domain are N61, D66, W70, and H91 in wild-type human CD86 IgV domain, and are underlined and bolded.

Wild-type CD86 binds to CD28. Amino acid sequences of CD28 are provided in FIG. 3A-3C. A variant CD86 polypeptide of the present disclosure binds to CD28 with reduced affinity compared to binding of wild-type CD86 to CD28.

In some cases, a variant CD86 polypeptide of the present disclosure exhibits reduced binding affinity to CD28, compared to the binding affinity of a CD86 polypeptide comprising the amino acid sequence depicted in FIG. 2A for CD28. For example, in some cases, a variant CD86 polypeptide of the present disclosure binds CD28 with a binding affinity that is less than the binding affinity of a CD86 polypeptide comprising the amino acid sequence depicted in FIG. 2A for a CD28 polypeptide comprising the amino acid sequence depicted in one of FIG. 3A-3C. For example, in some cases, a variant CD86 polypeptide of the present disclosure binds CD28 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a CD86 polypeptide comprising the amino acid sequence depicted in FIG. 2A for CD28 (e.g., a CD28 polypeptide comprising the amino acid sequence depicted in one of FIG. 3A-3C).

In some cases, a variant CD86 polypeptide of the present disclosure exhibits reduced binding affinity to CD28, compared to the binding affinity of a CD86 polypeptide comprising the amino acid sequence set forth in SEQ ID NO:2 for CD28. For example, in some cases, a variant CD86 polypeptide of the present disclosure binds CD28 with a binding affinity that is less than the binding affinity of a CD86 polypeptide comprising the amino acid sequence set forth in SEQ ID NO:2 for a CD28 polypeptide comprising the amino acid sequence depicted in one of FIG. 3A-3C. For example, in some cases, a variant CD86 polypeptide of the present disclosure binds CD28 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a CD86 polypeptide comprising the amino acid sequence set forth in SEQ ID NO:2 for CD28 (e.g., a CD28 polypeptide comprising the amino acid sequence depicted in one of FIG. 3A-3C).

In some cases, a variant CD86 polypeptide of the present disclosure exhibits reduced binding affinity to CD28, compared to the binding affinity of a CD86 polypeptide comprising the amino acid sequence set forth in SEQ ID NO:4 for CD28. For example, in some cases, a variant CD86 polypeptide of the present disclosure binds CD28 with a binding affinity that is less than the binding affinity of a CD86 polypeptide comprising the amino acid sequence set forth in SEQ ID NO:4 for a CD28 polypeptide comprising the amino acid sequence depicted in one of FIG. 3A-3C. For example, in some cases, a variant CD86 polypeptide of the present disclosure binds CD28 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a CD86 polypeptide comprising the amino acid sequence set forth in SEQ ID NO:4 for CD28 (e.g., a CD28 polypeptide comprising the amino acid sequence depicted in one of FIG. 3A-3C).

In some cases, a variant CD86 polypeptide of the present disclosure has a binding affinity to CD28 that is from 100 nM to 100 μM. As another example, in some cases, a variant CD86 polypeptide of the present disclosure has a binding affinity for CD28 (e.g., a CD28 polypeptide comprising the amino acid sequence depicted in one of FIG. 3A-3C) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

A variant CD86 polypeptide of the present disclosure can have a single amino acid substitution relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has from 2 to 10 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has 2 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has 3 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has 4 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has 5 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has 6 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has 7 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has 8 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has 9 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide of the present disclosure has 10 amino acid substitutions relative to a wild-type CD86 polypeptide (e.g., a CD86 polypeptide comprising the amino acid sequence depicted in FIG. 2A or as set forth in SEQ ID NO:1).

A variant CD86 polypeptide of the present disclosure can have a single amino acid substitution relative to a wild-type CD86 ectodomain polypeptide (e.g., a CD86 polypeptide comprising the amino acid set forth in SEQ ID NO:2). In some cases, a variant CD86 polypeptide of the present disclosure has from 2 to 10 amino acid substitutions relative to a wild-type CD86 polypeptide (e.g., a CD86 polypeptide comprising the amino acid set forth in SEQ ID NO:2). In some cases, a variant CD86 polypeptide of the present disclosure has 2 amino acid substitutions relative to a wild-type CD86 polypeptide (e.g., a CD86 polypeptide comprising the amino acid set forth in SEQ ID NO:2). In some cases, a variant CD86 polypeptide of the present disclosure has 3 amino acid substitutions relative to a wild-type CD86 polypeptide (e.g., a CD86 polypeptide comprising the amino acid set forth in SEQ ID NO:2). In some cases, a variant CD86 polypeptide of the present disclosure has 4 amino acid substitutions relative to a wild-type CD86 polypeptide (e.g., a CD86 polypeptide comprising the amino acid set forth in SEQ ID NO:2). In some cases, a variant CD86 polypeptide of the present disclosure has 5 amino acid substitutions relative to a wild-type CD86 polypeptide (e.g., a CD86 polypeptide comprising the amino acid set forth in SEQ ID NO:2). In some cases, a variant CD86 polypeptide of the present disclosure has 6 amino acid substitutions relative to a wild-type CD86 polypeptide (e.g., a CD86 polypeptide comprising the amino acid set forth in SEQ ID NO:2). In some cases, a variant CD86 polypeptide of the present disclosure has 7 amino acid substitutions relative to a wild-type CD86 polypeptide (e.g., a CD86 polypeptide comprising the amino acid set forth in SEQ ID NO:2). In some cases, a variant CD86 polypeptide of the present disclosure has 8 amino acid substitutions relative to a wild-type CD86 polypeptide (e.g., a CD86 polypeptide comprising the amino acid set forth in SEQ ID NO:2). In some cases, a variant CD86 polypeptide of the present disclosure has 9 amino acid substitutions relative to a wild-type CD86 polypeptide (e.g., a CD86 polypeptide comprising the amino acid set forth in SEQ ID NO:2). In some cases, a variant CD86 polypeptide of the present disclosure has 10 amino acid substitutions relative to a wild-type CD86 polypeptide (e.g., a CD86 polypeptide comprising the amino acid set forth in SEQ ID NO:2).

A variant CD86 polypeptide of the present disclosure can have a single amino acid substitution relative to a wild-type CD86 IgV polypeptide (e.g., a CD86 polypeptide comprising the amino acid set forth in SEQ ID NO:4). In some cases, a variant CD86 polypeptide of the present disclosure has from 2 to 10 amino acid substitutions relative to a wild-type CD86 polypeptide (e.g., a CD86 polypeptide comprising the amino acid set forth in SEQ ID NO:4). In some cases, a variant CD86 polypeptide of the present disclosure has 2 amino acid substitutions relative to a wild-type CD86 polypeptide (e.g., a CD86 polypeptide comprising the amino acid set forth in SEQ ID NO:4). In some cases, a variant CD86 polypeptide of the present disclosure has 3 amino acid substitutions relative to a wild-type CD86 polypeptide (e.g., a CD86 polypeptide comprising the amino acid set forth in SEQ ID NO:4). In some cases, a variant CD86 polypeptide of the present disclosure has 4 amino acid substitutions relative to a wild-type CD86 polypeptide (e.g., a CD86 polypeptide comprising the amino acid set forth in SEQ ID NO:4). In some cases, a variant CD86 polypeptide of the present disclosure has 5 amino acid substitutions relative to a wild-type CD86 polypeptide (e.g., a CD86 polypeptide comprising the amino acid set forth in SEQ ID NO:4). In some cases, a variant CD86 polypeptide of the present disclosure has 6 amino acid substitutions relative to a wild-type CD86 polypeptide (e.g., a CD86 polypeptide comprising the amino acid set forth in SEQ ID NO:4). In some cases, a variant CD86 polypeptide of the present disclosure has 7 amino acid substitutions relative to a wild-type CD86 polypeptide (e.g., a CD86 polypeptide comprising the amino acid set forth in SEQ ID NO:4). In some cases, a variant CD86 polypeptide of the present disclosure has 8 amino acid substitutions relative to a wild-type CD86 polypeptide (e.g., a CD86 polypeptide comprising the amino acid set forth in SEQ ID NO:4). In some cases, a variant CD86 polypeptide of the present disclosure has 9 amino acid substitutions relative to a wild-type CD86 polypeptide (e.g., a CD86 polypeptide comprising the amino acid set forth in SEQ ID NO:4). In some cases, a variant CD86 polypeptide of the present disclosure has 10 amino acid substitutions relative to a wild-type CD86 polypeptide (e.g., a CD86 polypeptide comprising the amino acid set forth in SEQ ID NO:4).

A variant CD86 polypeptide of the present disclosure can have a length of from 100 amino acids to 310 amino acids. For example, in some cases, a variant CD86 polypeptide of the present disclosure has a length of from 100 amino acids to 110 amino acids, from 110 amino acids to 225 amino acids, or from 225 amino acids to 310 amino acids. In some cases, a variant CD86 polypeptide of the present disclosure has a length of from 100 amino acids to 110 amino acids. In some cases, a variant CD86 polypeptide of the present disclosure has a length of from 110 amino acids to 225 amino acids. In some cases, a variant CD86 polypeptide of the present disclosure has a length of from 225 amino acids to 310 amino acids. In some cases, a variant CD86 polypeptide of the present disclosure has a length of 110 amino acids. In some cases, a variant CD86 polypeptide of the present disclosure has a length of 224 amino acids.

N61 Substitution

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2F, where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2F, where amino acid 61 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2F, where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2F, where amino acid 61 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2F, where amino acid 61 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2F, where amino acid 61 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2F, where amino acid 61 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2J, where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2J, where amino acid 61 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2J, where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2J, where amino acid 61 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2J, where amino acid 61 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2J, where amino acid 61 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2J, where amino acid 61 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

D66 Substitution

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2G, where amino acid 66 is an amino acid other than an aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2G, where amino acid 66 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2G, where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2G, where amino acid 66 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2G, where amino acid 66 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2G, where amino acid 66 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2G, where amino acid 66 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2K, where amino acid 66 is an amino acid other than an aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2K, where amino acid 66 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2K, where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2K, where amino acid 66 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2K, where amino acid 66 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2K, where amino acid 66 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2K, where amino acid 66 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10

μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

W70 Substitution

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2H, where amino acid 70 is an amino acid other than tryptophan, e.g., where amino acid 70 is Gly, Ala, Val, Leu, Ile, Pro, Phe, Tyr, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2H, where amino acid 70 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2H, where amino acid 70 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2H, where amino acid 70 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2H, where amino acid 70 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2H, where amino acid 70 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2H, where amino acid 70 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2L, where amino acid 70 is an amino acid other than tryptophan, e.g., where amino acid 70 is Gly, Ala, Val, Leu, Ile, Pro, Phe, Tyr, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2L, where amino acid 70 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2L, where amino acid 70 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2L, where amino acid 70 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2L, where amino acid 70 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2L, where amino acid 70 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2L, where amino acid 70 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

H91 Substitution

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Arg, Asn Asp, Cys, Gln, Glu, Gly, Ile, Leu, Lys, Met, Phe, Pro, Ser, Thr, Trp, Tyr, or Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Arg, Asn Asp, Cys, Gln, Glu, Lys, Met, Phe, Pro, Ser, Thr, Trp, or Tyr. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Arg. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Asn. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 isAsp. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Cys. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Gln. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Lys. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Met. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Phe. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Pro. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Ser. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Thr. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Trp. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2I, where amino acid 91 is Tyr. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Arg, Asn Asp, Cys, Gln, Glu, Gly, Ile, Leu, Lys, Met, Phe, Pro, Ser, Thr, Trp, Tyr, or Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Arg, Asn Asp, Cys, Gln, Glu, Lys, Met, Phe, Pro, Ser, Thr, Trp, or Tyr. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Arg. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Asn. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 isAsp. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Cys. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Gln. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Lys. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Met. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Phe. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Pro. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Ser. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Thr. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Trp. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2M, where amino acid 91 is Tyr. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about M, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

V41 Substitution

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2N, where amino acid 41 is an amino acid other than valine, e.g., where amino acid 41 is Gly, Ala, Leu, Ile, Pro, Phe, Tyr, Trp, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2N, where amino acid 41 is Ala, Gly, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2N, where amino acid 41 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2N, where amino acid 41 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2N, where amino acid 41 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2N, where amino acid 41 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2O, where amino acid 41 is an amino acid other than valine, e.g., where amino acid 41 is Gly, Ala, Leu, Ile, Pro, Phe, Tyr, Trp, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2O, where amino acid 41 is Ala, Gly, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2O, where amino acid 41 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2O, where amino acid 41 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2O, where amino acid 41 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2O, where amino acid 41 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

Q35 Substitution

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2P, where amino acid 53 is an amino acid other than glutamine, e.g., where amino acid 53 is Gly, Ala, Val, Leu, Ile, Pro, Phe, Tyr, Trp, Ser, Thr, Cys, Met, Asn, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2P, where amino acid 53 is Ala, Gly, Leu, Val, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2P, where amino acid 53 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2P, where amino acid 53 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2P, where amino acid 53 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2P, where amino acid 53 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2P, where amino acid 53 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Q, where amino acid 53 is an amino acid other than glutamine, e.g., where amino acid 53 is Gly, Ala, Val, Leu, Ile, Pro, Phe, Tyr, Trp, Ser, Thr, Cys, Met, Asn, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Q, where amino acid 53 is Ala, Gly, Leu, Val, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Q, where amino acid 53 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Q, where amino acid 53 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Q, where amino acid 53 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Q, where amino acid 53 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Q, where amino acid 53 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

F33 Substitution

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2R, where amino acid 33 is an amino acid other than phenylalanine, e.g., where amino acid 33 is Gly, Ala, Val, Leu, Ile, Pro, Tyr, Trp, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2R, where amino acid 33 is Ala, Gly, Leu, Val, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2R, where amino acid 33 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2R, where amino acid 33 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2R, where amino acid 33 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2R, where amino acid 33 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2R, where amino acid 33 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2S, where amino acid 33 is an amino acid other than phenylalanine, e.g., where amino acid 33 is Gly, Ala, Val, Leu, Ile, Pro, Tyr, Trp, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2S, where amino acid 33 is Ala, Gly, Leu, Val, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2S, where amino acid 33 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2S, where amino acid 33 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2S, where amino acid 33 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2S, where amino acid 33 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2S, where amino acid 33 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

L72 Substitution

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2T, where amino acid 72 is an amino acid other than leucine, e.g., where amino acid 72 is Gly, Ala, Val, Ile, Pro, Phe, Tyr, Trp, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2T, where amino acid 72 is Ala, Gly, Val, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2T, where amino acid 72 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2T, where amino acid 72 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2T, where amino acid 72 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2T, where amino acid 72 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 M, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2U, where amino acid 72 is an amino acid other than leucine, e.g., where amino acid 72 is Gly, Ala, Val, Ile, Pro, Phe, Tyr, Trp, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2U, where amino acid 72 is Ala, Gly, Val, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2U, where amino acid 72 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2U, where amino acid 72 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2U, where amino acid 72 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2U, where amino acid 72 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

Y59 Substitution

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2V, where amino acid 59 is an amino acid other than tyrosine, e.g., where amino acid 59 is Gly, Ala, Val, Leu, Ile, Pro, Phe, Trp, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2V, where amino acid 59 is Ala, Gly, Leu, Val, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2V, where amino acid 59 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2V, where amino acid 59 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2V, where amino acid 59 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2V, where amino acid 59 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2V, where amino acid 59 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2W, where amino acid 59 is an amino acid other than tyrosine, e.g., where amino acid 59 is Gly, Ala, Val, Leu, Ile, Pro, Phe, Trp, Ser, Thr, Cys, Met, Asn, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2W, where amino acid 59 is Ala, Gly, Leu, Val, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2W, where amino acid 59 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2W, where amino acid 59 is Gly. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2W, where amino acid 59 is Leu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2W, where amino acid 59 is Val. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2W, where amino acid 59 is Ile. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 M to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

Multiple Substitutions

As noted above, a variant CD86 polypeptide of the present disclosure can include a single amino acid substitution, or can include multiple (e.g., 2, 3, 4, 5, 6, 7, 8, 9, 10, or more than 10) amino acid substitutions. The following are non-limiting examples of variant CD86 polypeptides comprising multiple amino acid substitutions.

N61 and H91 Substitutions

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2X, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; and where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2X, where amino acid 91 is Ala, Gly, Val, Leu, or Ile, and where amino acid 61 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2X, where amino acid 91 is Ala, and where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2X, where amino acid 91 is Gly, and where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2X, where amino acid 91 is Val, and where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2X, where amino acid 91 is Leu, and where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2X, where amino acid 91 is Ile, and where amino acid 61 is Ala. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Y, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; and where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Ala, Gly, Val, Leu, or Ile, and where amino acid 61 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Ala, and where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Gly, and where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Val, and where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Y where amino acid 91 is Leu, and where amino acid 61 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Ile, and where amino acid 61 is Ala. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

D66 and H91 Substitutions

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Z, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; and where amino acid 66 is other than aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Ala, Gly, Val, Leu, or Ile, and where amino acid 66 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Ala, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Gly, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Val, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Leu, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Ile, and where amino acid 66 is Ala. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 M, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; and where amino acid 66 is other than aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Ala, Gly, Val, Leu, or Ile, and where amino acid 66 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Ala, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Gly, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Val, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Leu, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Ile, and where amino acid 66 is Ala. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

N61, D66, and H91 Substitutions

In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu; and where amino acid 66 is other than aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Ala, Gly, Val, Leu, or Ile; where amino acid 61 is Ala, Gly, Val, Leu, or Ile; and where amino acid 66 is Ala, Gly, Val, Leu, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Ala, where amino acid 61 is Ala, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Gly, where amino acid 61 is Ala, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Val, where amino acid 61 is Ala, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Leu, where amino acid 61 is Ala, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Ile, where amino acid 61 is Ala, and where amino acid 66 is Ala. In some cases, the variant CD86 polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 M, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

Fusion Polypeptides

The present disclosure provides CD86 fusion polypeptides. A fusion polypeptide of the present disclosure comprises: a) a variant CD86 polypeptide of the present disclosure; and b) a heterologous fusion partner. In some cases, the heterologous fusion partner is fused to the N-terminus of the variant CD86 polypeptide. In some cases, the heterologous fusion partner is fused to the C-terminus of the variant CD86 polypeptide. In some cases, a CD86 fusion polypeptide of the present disclosure comprises a first heterologous fusion partner fused to the N-terminus of the variant CD86 polypeptide, and a second heterologous fusion partner fused to the C-terminus of the variant CD86 polypeptide.

The total length of a CD86 fusion polypeptide of the present disclosure can range from 115 amino acids to 2000 amino acids. For example, a CD86 fusion polypeptide of the present disclosure can range from 115 amino acids to 150 amino acids, from 150 amino acids to 175 amino acids, from 175 amino acids to 200 amino acids, from 200 amino acids to 225 amino acids, from 225 amino acids to 250 amino acids, from 250 amino acids to 275 amino acids, from 275 amino acids to 300 amino acids, from 300 amino acids to 350 amino acids, from 350 amino acids, from 350 amino acids to 400 amino acids, from 400 amino acids, from 400 amino acids to 450 amino acids, from 450 amino acids to 500 amino acids, from 500 amino acids to 600 amino acids, from 600 amino acids to 700 amino acids, from 700 amino acids to 800 amino acids, from 800 amino acids to 900 amino acids, from 900 amino acids to 1000 amino acids, from 1000 amino acids to 1250 amino acids, from 1250 amino acids to 1500 amino acids, from 1500 amino acids to 1750 amino acids, or from 1750 amino acids to 2000 amino acids.

Suitable fusion partners include, but are not limited to, a transmembrane domain; an antibody Fc region; an antigen-binding region of an antibody; a cytokine; an immunomodulatory domain; an intracellular signaling domain; and the like.

T-Cell Modulatory Multimeric Polypeptides

The present disclosure provides multimeric (e.g., heterodimeric, heterotrimeric) polypeptides. The multimeric polypeptides are T cell modulatory polypeptides, and are also referred to herein as "T-cell modulatory multimeric polypeptides," or "synTac" (for "immunological synapse for T cell activation"). FIGS. 1A-1D provide schematic depictions of T-cell modulatory multimeric polypeptides of the present disclosure. A T-cell modulatory multimeric polypeptide of the present disclosure is also referred to as a "synTac polypeptide" or a "multimeric polypeptide."

In some cases, a synTac polypeptide of the present disclosure comprises a wild-type CD86 polypeptide. In some cases, a synTac polypeptide of the present disclosure comprises a variant CD86 polypeptide of the present disclosure. As noted above, a variant CD86 polypeptide present in a multimeric polypeptide of the present disclosure exhibits reduced binding affinity to CD28, compared to the binding affinity of wild-type CD86 to CD28. A multimeric polypeptide of the present disclosure that comprises a variant CD86 polypeptide of the present disclosure also exhibits reduced binding affinity to CD28, compared to a control multimeric polypeptide comprising a wild-type CD86 (e.g., a CD86 polypeptide comprising the amino acid sequence depicted in FIG. 2A, or comprising the CD86 ectodomain amino acid sequence depicted in FIG. 2B, or comprising the CD86 IgV amino acid sequence depicted in FIG. 2D).

In some cases, a synTac polypeptide of the present disclosure exhibits reduced binding affinity to CD28, compared to the binding affinity of a CD86 polypeptide comprising the amino acid sequence depicted in FIG. 2A for CD28. For example, in some cases, a synTac polypeptide of the present disclosure binds CD28 with a binding affinity that is less than the binding affinity of a control synTac polypeptide comprising a CD86 polypeptide comprising the amino acid sequence depicted in FIG. 2A for a CD28 polypeptide comprising the amino acid sequence depicted in one of FIG. 3A-3C. For example, in some cases, a synTac polypeptide of the present disclosure binds CD28 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a CD86 polypeptide comprising the amino acid sequence depicted in FIG. 2A for CD28 (e.g., a CD28 polypeptide comprising the amino acid sequence depicted in one of FIG. 3A-3C).

In some cases, a synTac polypeptide of the present disclosure exhibits reduced binding affinity to CD28, compared to the binding affinity of a CD86 polypeptide comprising the amino acid sequence depicted in FIG. 2B for CD28. For example, in some cases, a synTac polypeptide of the present disclosure binds CD28 with a binding affinity that is less than the binding affinity of a control synTac polypeptide comprising a CD86 polypeptide comprising the amino acid sequence depicted in FIG. 2B for a CD28 polypeptide comprising the amino acid sequence depicted in one of FIG. 3A-3C. For example, in some cases, a synTac polypeptide of the present disclosure binds CD28 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a CD86 polypeptide comprising the amino acid sequence depicted in FIG. 2B for CD28 (e.g., a CD28 polypeptide comprising the amino acid sequence depicted in one of FIG. 3A-3C).

In some cases, a synTac polypeptide of the present disclosure exhibits reduced binding affinity to CD28, compared to the binding affinity of a CD86 polypeptide comprising the amino acid sequence depicted in FIG. 2D for CD28. For example, in some cases, a synTac polypeptide of the present disclosure binds CD28 with a binding affinity that is less than the binding affinity of a control synTac polypeptide comprising a CD86 polypeptide comprising the amino acid sequence depicted in FIG. 2D for a CD28 polypeptide comprising the amino acid sequence depicted in one of FIG. 3A-3C. For example, in some cases, a synTac polypeptide of the present disclosure binds CD28 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a CD86 polypeptide comprising the amino acid sequence depicted in FIG.

2D for CD28 (e.g., a CD28 polypeptide comprising the amino acid sequence depicted in one of FIG. 3A-3C).

In some cases, a synTac polypeptide of the present disclosure has a binding affinity for CD28 that is from 100 nm to about 100 μM. In some cases, a synTac polypeptide of the present disclosure has a binding affinity for CD28 that is from about 100 nM to 500 nM. For example, in some cases, a synTac polypeptide of the present disclosure has a binding affinity for CD28 (e.g., a CD28 polypeptide comprising the amino acid sequence depicted in one of FIG. 3A-3C) that is from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, or from about 450 nM to about 500 nM. In some cases, a synTac polypeptide of the present disclosure has a binding affinity for CD28 (e.g., a CD28 polypeptide comprising the amino acid sequence depicted in one of FIG. 3A-3C) that is from about 500 nM to 1 M. For example, in some cases, a synTac polypeptide of the present disclosure has a binding affinity for CD28 (e.g., a CD28 polypeptide comprising the amino acid sequence depicted in one of FIG. 3A-3C) that is from about 500 nM to about 600 nM, from about 600 nM to about 700 nM, from about 700 nM to about 800 nM, from about 800 nM to about 900 nM, or from about 900 nM to about 1 μM. In some cases, a synTac polypeptide of the present disclosure has a binding affinity for CD28 (e.g., a CD28 polypeptide comprising the amino acid sequence depicted in one of FIG. 3A-3C) that is from about 1 μM to 10 μM. For example, in some cases, a synTac polypeptide of the present disclosure has a binding affinity for CD28 (e.g., a CD28 polypeptide comprising the amino acid sequence depicted in one of FIG. 3A-3C) that is from about 1 μM to 2 μM, from about 2 μM to about 3 μM, from about 3 μM to about 4 μM, from about 4 μM to about 5 μM, from about 5 μM to about 6 μM, from about 6 μM to about 7 μM, from about 7 μM to about 8 μM, from about 8 μM to about 9 μM, or from about 9 μM to about 10 μM. In some cases, a synTac polypeptide of the present disclosure has a binding affinity for CD28 (e.g., a CD28 polypeptide comprising the amino acid sequence depicted in one of FIG. 3A-3C) that is from about 10 μM to 100 μM. For example, in some cases, a synTac polypeptide of the present disclosure has a binding affinity for CD28 (e.g., a CD28 polypeptide comprising the amino acid sequence depicted in one of FIG. 3A-3C) that is from about 10 μM to about 20 μM, from about 20 μM to about 30 μM, from about M to about 40 μM, from about 40 μM to about 50 μM, from about 50 μM to about 60 μM, from about 60 μM to about 70 μM, from about 70 μM to about 80 μM, from about 80 μM to about 90 μM, or from about 90 μM to about 100 μM.

Determining Binding Affinity

Binding affinity between an immunomodulatory polypeptide and its cognate co-immunomodulatory polypeptide can be determined by bio-layer interferometry (BLI) using purified immunomodulatory polypeptide and purified cognate co-immunomodulatory polypeptide. Binding affinity between a synTac of the present disclosure and its cognate co-immunomodulatory polypeptide can also be determined by BLI using purified synTac and the cognate co-immunomodulatory polypeptide. BLI methods are well known to those skilled in the art. See, e.g., Lad et al. (2015) *J. Biomol. Screen.* 20(4):498-507; and Shah and Duncan (2014) *J. Vis. Exp.* 18:e51383. The specific and relative binding affinities described in this disclosure between an immunomodulatory polypeptide and its cognate co-immunomodulatory polypeptide, or between a synTac and its cognate co-immunomodulatory polypeptide, can be determined using the following procedures.

To determine binding affinity between a synTac of the present disclosure and its cognate co-immunomodulatory polypeptide, a BLI assay can be carried out using an Octet RED 96 (Pal FortéBio) instrument, or a similar instrument, as follows. To determinine binding affinity of a T-cell modulatory multimeric polypeptide (e.g., a synTac of the present disclosure; or a control T-cell modulatory multimeric polypeptide (where a control T-cell modulatory multimeric polypeptide comprises a wild-type immunomodulatory polypeptide)), the T-cell modulatory multimeric polypeptide is immobilized onto an insoluble support (a "biosensor"). The immobilized T-cell modulatory multimeric polypeptide is the "target." Immobilization can be effected by immobilizing a capture antibody onto the insoluble support, where the capture antibody immobilizes the T-cell modulatory multimeric polypeptide. For example, immobilization can be effected by immobilizing anti-Fc (e.g., anti-human IgG Fc) antibodies onto the insoluble support, where the immobilized anti-Fc antibodies bind to and immobilize the T-cell modulatory multimeric polypeptide (where the T-cell modulatory multimeric polypeptide comprises an IgFc polypeptide). A co-immunomodulatory polypeptide is applied, at several different concentrations, to the immobilized T-cell modulatory multimeric polypeptide, and the instrument's response recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-immunomodulatory polypeptide to the immobilized T-cell modulatory multimeric polypeptide is conducted at 30° C. As a positive control for binding affinity, an anti-MHC Class I monoclonal antibody can be used. For example, anti-HLA Class I monoclonal antibody W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The co-immunomodulatory polypeptide, or the anti-MHC Class I mAb, is the "analyte." BLI analyzes the interference pattern of white light reflected from two surfaces: i) from the immobilized polypeptide ("target"); and ii) an internal reference layer. A change in the number of molecules ("analyte"; e.g., co-immunomodulatory polypeptide; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_d/_a$) gives rise to the affinity constant $K_D$.

As noted above, determining binding affinity between an immunomodulatory polypeptide (e.g., CD86 or a CD86 variant) and its cognate co-immunomodulatory polypeptide (e.g., CD28) also can be determined by BLI. The assay is similar to that described above for the synTac multimeric polypeptide. A BLI assay can be carried out using an Octet RED 96 (Pal FortéBio) instrument, or a similar instrument, as follows. A component immunomodulatory polypeptide of a synTac of the present disclosure (e.g., a variant CD86 polypeptide of the present disclosure); and a control immunomodulatory polypeptide (where a control immunomodulatory polypeptide comprises a wild-type immunomodulatory polypeptide, e.g. wild-type CD86)) are immobilized onto an insoluble support (a "biosensor"). The immunomodulatory polypeptide is the "target." Immobilization can be effected by immobilizing a capture antibody onto the insoluble support, where the capture antibody immobilizes the immunomodulatory polypeptide. For example, if the target is fused to an immuno-affinity tag (e.g. FLAG, human IgG Fc) immobilization can be effected by immobilizing with the appropriate antibody to the immuno-affinity tag (e.g. anti-human IgG Fc) onto the insoluble support, where the immobilized antibodies bind to and immobilize the immunomodulatory polypeptide (where the immunomodulatory polypeptide comprises an IgFc polypeptide). A co-immunomodulatory polypeptide (or polypeptides) is applied, at several different concentrations, to the immobilized immunomodulatory polypeptide, and the instrument's response recorded. Alternatively, a co-immunomodulatory polypeptide (or polypeptides) is immobilized to the biosensor and the immunomodulatory polypeptide is applied, at several different concentrations, to the immoobilized coimmunomodulatory polypeptide(s), and the instrument's response is recorded. Assays are conducted in a liquid medium comprising 25 mM HEPES pH 6.8, 5% poly (ethylene glycol) 6000, 50 mM KCl, 0.1% bovine serum albumin, and 0.02% Tween 20 nonionic detergent. Binding of the co-immunomodulatory polypeptide to the immobilized immunomodulatory polypeptide is conducted at 30° C. As a positive control for binding affinity, an anti-MHC Class I monoclonal antibody can be used. For example, anti-HLA Class I monoclonal antibody W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The co-immunomodulatory polypeptide, or the anti-MHC Class I mAb, is the "analyte." BLI analyzes the interference pattern of white light reflected from two surfaces: i) from the immobilized polypeptide ("target"); and ii) an internal reference layer. A change in the number of molecules ("analyte"; e.g., co-immunomodulatory polypeptide; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_d/_a$) gives rise to the affinity constant $K_D$. Determining the binding affinity of both a wild-type immunomodulatory polypeptide (e.g., CD86) for its cognate co-immunomodulatory polypeptide (e.g., CD28) and a variant immunomodulatory polypeptide (e.g., a CD86 variant as disclosed herein) for the cognate co-immunomodulatory polypeptide (e.g., CD28) thus allows one to determine the relative binding affinity of the variant co-immunomodulatory polypeptide, as compared to the wild-type co-immunomodulatory polypeptide, for the cognate co-immunomodulatory polypeptide. That is, one can determine whether the binding affinity of a variant immunomodulatory polypetpide for its receptor (its cognate co-immunomodulatory polypeptide) is reduced as compared to the binding affinity of the wild-type immunomodulatory polypeptide for the same cognate co-immunomodulatory polypeptide, and, if so, what is the percentage reduction from the binding affinity of the wild-type co-immunomodulatory polypeptide.

The BLI assay is carried out in a multi-well plate. To run the assay, the plate layout is defined, the assay steps are defined, and biosensors are assigned in Octet Data Acquisition software. The biosensor assembly is hydrated. The hydrated biosensor assembly and the assay plate are equilibrated for 10 minutes on the Octet instrument. Once the data are acquired, the acquired data are loaded into the Octet Data Analysis software. The data are processed in the Processing window by specifying method for reference subtraction, y-axis alignment, inter-step correction, and Savitzky-Golay filtering. Data are analyzed in the Analysis window by specifying steps to analyze (Association and Dissociation), selecting curve fit model (1:1), fitting method (global), and window of interest (in seconds). The quality of fit is evaluated. $K_D$ values for each data trace (analyte concentration) can be averaged if within a 3-fold range. $K_D$ error values should be within one order of magnitude of the affinity constant values; $R^2$ values should be above 0.95. See, e.g., Abdiche et al. (2008) *J. Anal. Biochem.* 377:209.

In some cases, the ratio of:i) the binding affinity of a control T-cell modulatory multimeric polypeptide (where the control comprises a wild-type immunomodulatory polypeptide, e.g., wild-type CD86) to a cognate co-immunomodulatory polypeptide (e.g., CD28) to ii) the binding affinity of a T-cell modulatory multimeric polypeptide of the present disclosure comprising a variant of the wild-type immunomodulatory polypeptide (e.g., variant CD86) to the cognate co-immunomodulatory polypeptide (e.g., CD28), when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, the ratio of:i) the binding affinity of a control T-cell modulatory multimeric polypeptide (where the control comprises a wild-type immunomodulatory polypeptide) to a cognate co-immunomodulatory polypeptide to ii) the binding affinity of a T-cell modulatory multimeric polypeptide of the present disclosure comprising a variant of the wild-type immunomodulatory polypeptide to the cognate co-immunomodulatory polypeptide, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

In some cases, the ratio of:i) the binding affinity of a control immunomodulatory polypeptide (where the control comprises a wild-type immunomodulatory polypeptide, e.g., wild-type CD86) to a cognate co-immunomodulatory polypeptide (e.g., CD28) to ii) the binding affinity of an immunomodulatory polypeptide of the present disclosure comprising a variant of the wild-type immunomodulatory polypeptide (e.g., variant CD86) to the cognate co-immunomodulatory polypeptide (e.g., CD28), when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, the ratio of:i) the binding affinity of a control immunomodulatory polypeptide (where the control comprises a wild-type immunomodulatory polypeptide) to a cognate co-immunomodulatory polypeptide to ii) the binding affinity of a immunomodulatory polypeptide of the present disclosure comprising a variant of the wild-type immunomodulatory polypeptide to the cognate co-immunomodulatory polypeptide, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

For conducting affinity measurements, wild-type CD86 can be a CD86 polypeptide comprising the amino acid sequence depicted in FIG. 2A, or comprising the CD86 ectodomain amino acid sequence depicted in FIG. 2B, or comprising the CD86 IgV amino acid sequence depicted in FIG. 2D; and wild-type CD28 can be a CD28 polypeptide comprising the amino acid sequence depicted in one of FIG. 3A-3C.

A variant CD86 polypeptide present in a synTac polypeptide of the present disclosure can have a single amino acid substitution relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has from 2 to 10 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has 2 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has 3 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has 4 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has 5 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has 6 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has 7 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has 8 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has 9 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). In some cases, a variant CD86 polypeptide present in a synTac polypeptide of the present disclosure has 10 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4).

In some cases, a variant CD86 polypeptide present in a synTac polypeptide of the present disclosure has from 11 to 50 amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4). For example, in some cases, a variant CD86 polypeptide present in a synTac polypeptide of the present disclosure has from 11 to 15, from 15 to 20, from 20 to 25, from 25 to 30, from 30 to 35, from 35 to 40, from 40 to 45, or from 45 to 50, amino acid substitutions relative to a wild-type CD86 polypeptide (e.g., a CD86 polypeptide comprising the amino acid sequence depicted in FIG. 2A; or as set forth in SEQ ID NO:1; or a CD86 polypeptide comprising the amino acid sequence depicted in FIG. 2B and set forth in SEQ ID NO:2; or a CD86 polypeptide comprising the amino acid sequence depicted in FIG. 2D and set forth in SEQ ID NO:4).

In some cases, a multimeric polypeptide of the present disclosure comprises a first polypeptide and a second polypeptide, where the first polypeptide comprises, in order from amino terminus (N-terminus) to carboxyl terminus (C-terminus): a) an epitope (e.g., a T-cell epitope); b) a first major histocompatibility complex (MHC) polypeptide and c) an immunomodulatory polypeptide (e.g., a variant CD86 polypeptide of the present disclosure); and where the second polypeptide comprises, in order from N-terminus to C-terminus: a) a second MHC polypeptide; and b) an immunoglobulin (Ig) Fc polypeptide. In other cases, a multimeric polypeptide of the present disclosure comprises a first polypeptide and a second polypeptide, where the first polypeptide comprises, in order from N-terminus to C-terminus: a) an epitope (e.g., a T-cell epitope); and b) a first MHC polypeptide; and where the second polypeptide comprises, in order from N-terminus to C-terminus: a) an immunomodulatory polypeptide (e.g., a variant CD86 polypeptide of the present disclosure); b) a second MHC polypeptide; and c) an Ig Fc polypeptide. In some instances, the first and the second MHC polypeptides are Class I MHC polypeptides; e.g., in some cases, the first MHC polypeptide is an MHC Class I β2-microglobulin (B2M or β2M) polypeptide, and the second MHC polypeptide is an MHC Class I heavy chain (H chain); or the first MHC polypeptide is an MHC Class I H chain, and the second MHC polypeptide is an MHC Class I β2M polypeptide). In other cases, the first and the second MHC polypeptides are Class II MHC polypeptides; e.g., in some cases, the first MHC polypeptide is an MHC Class II α-chain polypeptide, and the second MHC polypeptide is an MHC Class II β-chain polypeptide. In other cases, the first polypeptide is an MHC Class II β-chain polypeptide, and the second MHC polypeptide is an MHC Class II α-chain polypeptide. In some cases, the multimeric polypeptide includes two or more immunomodulatory polypeptides, where at least one of the immunomodulatory polypeptides is a variant CD86 immunomodulatory polypeptide of the present disclosure. Where a multimeric polypeptide of the present disclosure includes two or more immunomodulatory polypeptides, in some cases, the two or more immunomodulatory polypeptides are present in the same polypeptide chain, and may be in tandem. Where a multimeric polypeptide of the present disclosure includes two or more immunomodulatory polypeptides, in some cases, the two or more immunomodulatory polypeptides are present in separate polypeptides. In some cases, a multimeric polypeptide of the present disclosure is a heterodimer. In some cases, a multimeric polypeptide of the present disclosure is a trimeric polypeptide.

In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an Ig Fc polypeptide; and iii) an immunomodulatory domain (e.g., a variant CD86 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an immunomodulatory domain (e.g., a variant CD86 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) an immunomodulatory domain (e.g., a variant CD86 polypeptide of the present disclosure); and ii) a second MHC polypeptide. In some cases, a multimeric polypeptide of the present disclosure comprises: a) a first polypeptide comprising, in order from N-terminus to C-terminus: i) an epitope; ii) a first MHC polypeptide; and iii) an immunomodulatory domain (e.g., a variant CD86 polypeptide of the present disclosure); and b) a second polypeptide comprising, in order from N-terminus to C-terminus: i) a second MHC polypeptide. In some cases, where a multimeric polypeptide of the present disclosure comprises a non-Ig scaffold, the non-Ig scaffold is an XTEN peptide, a transferrin polypeptide, an Fc receptor polypeptide, an elastin-like polypeptide, a silk-like polypeptide, or a silk-elastin-like polypeptide.

In some cases, a multimeric polypeptide of the present disclosure is monovalent. In some cases, a multimeric polypeptide of the present disclosure is multivalent. In some cases, a multivalent multimeric polypeptide of the present disclosure comprises an immunoglobulin Fc polypeptide on one of the first or the second polypeptide. For example, depending on the Fc polypeptide present in a multimeric polypeptide of the present disclosure, the multimeric polypeptide can be a homodimer, where two molecules of the multimeric polypeptide are present in the homodimer, where the two molecules of the multimeric polypeptide can be disulfide linked to one another, e.g., via the Fc polypeptide present in the two molecules. As another example, a multimeric polypeptide of the present disclosure can comprise three, four, or five molecules of the multimeric polypeptide, where the molecules of the multimeric polypeptide can be disulfide linked to one another, e.g., via the Fc polypeptide present in the molecules.

In some cases, a multimeric polypeptide of the present disclosure comprises: a) a first polypeptide comprising, in order from N-terminus to C-terminus: i) an epitope; ii) a β2M polypeptide; and iii) a variant CD86 polypeptide of the present disclosure; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant CD86 polypeptide of the present disclosure; ii) a Class I MHC heavy chain; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant CD86 polypeptide of the present disclosure; iv) a second variant CD86 polypeptide of the present disclosure; and v) a third variant CD86 polypeptide of the present disclosure; and b) a second polypeptide comprising, in order from N-terminus to C-terminus: i) a Class I MHC heavy chain; and ii) an Fc polypeptide. In some cases, the first, second, and third variant CD86 polypeptides have the same amino acid sequence. In some cases, the first, second, and third variant CD86 polypeptides differ from one another in amino acid sequence. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant CD86 polypeptide of the present disclosure; ii) a second variant CD86 polypeptide of the present disclosure; and iii) a third variant CD86 polypeptide of the present disclosure; iv) a Class I MHC heavy chain; and v) an Fc polypeptide. In some cases, the first, second, and third variant CD86 polypeptides have the same amino acid sequence. In some cases, the first, second, and third variant CD86 polypeptides differ from one another in amino acid sequence.

Linkers

A multimeric polypeptide of the present disclosure can include linker peptides interposed between, e.g., an epitope and an MHC polypeptide; between an MHC polypeptide and an immunomodulatory polypeptide; between an MHC polypeptide and an Ig Fc polypeptide; between a first variant CD86 polypeptide and a second variant CD86 polypeptide; or a between a second variant CD86 polypeptide and a third variant CD86 polypeptide.

A linker between an MHC polypeptide and an IgFc can be referred to as "L1"; a linker between an MHC polypeptide and a MOD (immunomodulatory polypeptide) can be referred to as "L2"; and a linker between two tandem immunomodulatory polypeptides can be referred to as "L3".

Suitable linkers (also referred to as "spacers") can be readily selected and can be of any of a number of suitable lengths, such as from 1 amino acid to 25 amino acids, from 3 amino acids to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids. A suitable linker can be 1, 2, 3, 4, 5, 6, 7, 8, 9, 10, 11, 12, 13, 14, 15, 16, 17, 18, 19, 20, 21, 22, 23, 24, or 25 amino acids in length. Suitable linkers can range from 25 amino acids to 50 amino acids in length, e.g., from 25 amino acids to 30 amino acids, from 30 amino acids to 35 amino acids, from 35 amino acids to 40 amino acids, from 40 amino acids to 45 amino acids, or from 45 amino acids to 50 amino acids in length.

Exemplary linkers include glycine polymers $(G)_n$, glycine-serine polymers (including, for example, $(GS)_n$, $(GSGGS)_n$ (SEQ ID NO:49) and $(GGGS)_n$ (SEQ ID NO:50), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, *Rev. Computational Chem.* 11173-142 (1992)). Exemplary linkers can comprise amino acid sequences including, but not limited to, GGSG (SEQ ID NO:51), GGSGG (SEQ ID NO:52), GSGSG (SEQ ID NO:53), GSGGG (SEQ ID NO:54), GGGSG (SEQ ID NO:55), GSSSG (SEQ ID NO:56), and the like. Exemplary linkers can include, e.g., Gly($Ser_4$)n (SEQ ID NO:57), where n is 1, 2, 3, 4, 5, 6, 7, 8, 9, or 10. In some cases, a linker comprises the amino acid sequence (GSSSS)n (SEQ ID NO:58), where n is 4. In some cases, a linker comprises the amino acid sequence (GSSSS)n (SEQ ID NO:59), where n is 5. In some cases, a linker comprises the amino acid sequence $(GGGGS)_5$ ("G4S5"; SEQ ID NO:62). In some cases, a linker comprises the amino acid sequence $(GGGGS)_4$ ("G4S4"; SEQ ID NO:63). In some cases, a linker comprises the amino acid sequence $(GGGGS)_3$ ("G4S3"; SEQ ID NO:64). In some cases, a linker comprises the amino acid sequence GGGGSGGGGS ("G4S2"; SEQ ID NO:65).

In some cases, a linker comprises the amino acid sequence GGGGS ("G4S"; SEQ ID NO:66). In some cases, a linker comprises the amino acid sequence (GGGGS)n (SEQ ID NO:60), where n is 1. In some cases, a linker comprises the amino acid sequence (GGGGS)n (SEQ ID NO:60), where n is 2. In some cases, a linker comprises the amino acid sequence (GGGGS)n (SEQ ID NO:60), where n is 3. In some cases, a linker comprises the amino acid sequence (GGGGS)n (SEQ ID NO:60), where n is 4. In some cases, a linker comprises the amino acid sequence (GGGGS)n (SEQ ID NO:61), where n is 5. In some cases, a linker comprises the amino acid sequence (GGGGS)n (SEQ ID NO:60), where n is 6. In some cases, a linker comprises the amino acid sequence (GGGGS)n (SEQ ID NO:60), where n is 7. In some cases, a linker comprises the amino acid sequence (GGGGS)n (SEQ ID NO:60), where n is 8. In some cases, a linker comprises the amino acid sequence (GGGGS)n (SEQ ID NO:60), where n is 9. In some cases, a linker comprises the amino acid sequence (GGGGS)n (SEQ ID NO:60), where n is 10.

As noted above, a linker between an MHC polypeptide and an IgFc can be referred to as "L1"; a linker between an MHC polypeptide and a MOD (immunomodulatory polypeptide) can be referred to as "L2"; and a linker between two tandem immunomodulatory polypeptides can be referred to as "L3". In some cases, L1 comprises the amino acid sequence GGGGS ("G4S"; SEQ ID NO:66). In some cases, L1 comprises the amino acid sequence (GGGGS)n (SEQ ID NO:60), where n is 1. In some cases, L1 comprises the amino acid sequence (GGGGS)n (SEQ ID NO:60), where n is 2. In some cases, L1 comprises the amino acid sequence (GGGGS)n (SEQ ID NO:60), where n is 3. In some cases, L1 comprises the amino acid sequence (GGGGS)n (SEQ ID NO:60), where n is 4. In some cases, L1 comprises the amino acid sequence (GGGGS)n (SEQ ID NO:61), where n is 5. In some cases, L1 comprises the amino acid sequence (GGGGS)n (SEQ ID NO:60), where n is 6. In some cases, L1 comprises the amino acid sequence (GGGGS)n (SEQ ID NO:60), where n is 7. In some cases, L1 comprises the amino acid sequence (GGGGS)n (SEQ ID NO:60), where n is 8. In some cases, L1 comprises the amino acid sequence (GGGGS)n (SEQ ID NO:60), where n is 9. In some cases, L1 comprises the amino acid sequence (GGGGS)n (SEQ ID NO:60), where n is 10.

In some cases, L2 comprises the amino acid sequence GGGGS ("G4S"; SEQ ID NO:60). In some cases, L2 comprises the amino acid sequence (GGGGS)n (SEQ ID NO:60), where n is 1. In some cases, L2 comprises the amino acid sequence (GGGGS)n (SEQ ID NO:60), where n is 2. In some cases, L2 comprises the amino acid sequence (GGGGS)n (SEQ ID NO:60), where n is 3. In some cases, L2 comprises the amino acid sequence (GGGGS)n (SEQ ID NO:60), where n is 4. In some cases, L2 comprises the amino acid sequence (GGGGS)n (SEQ ID NO:61), where n is 5. In some cases, L2 comprises the amino acid sequence (GGGGS)n (SEQ ID NO:60), where n is 6. In some cases, L2 comprises the amino acid sequence (GGGGS)n (SEQ ID NO:60), where n is 7. In some cases, L2 comprises the amino acid sequence (GGGGS)n (SEQ ID NO:60), where n is 8. In some cases, L2 comprises the amino acid sequence (GGGGS)n (SEQ ID NO:60), where n is 9. In some cases, L2 comprises the amino acid sequence (GGGGS)n (SEQ ID NO:60), where n is 10.

In some cases, L3 comprises the amino acid sequence GGGGS ("G4S"; SEQ ID NO:60). In some cases, L3 comprises the amino acid sequence (GGGGS)n (SEQ ID NO:60), where n is 1. In some cases, L3 comprises the amino acid sequence (GGGGS)n (SEQ ID NO:60), where n is 2. In some cases, L3 comprises the amino acid sequence (GGGGS)n (SEQ ID NO:60), where n is 3. In some cases, L3 comprises the amino acid sequence (GGGGS)n (SEQ ID NO:60), where n is 4. In some cases, L3 comprises the amino acid sequence (GGGGS)n (SEQ ID NO:61), where n is 5. In some cases, L3 comprises the amino acid sequence (GGGGS)n (SEQ ID NO:60), where n is 6. In some cases, L3 comprises the amino acid sequence (GGGGS)n (SEQ ID NO:60), where n is 7. In some cases, L3 comprises the amino acid sequence (GGGGS)n (SEQ ID NO:60), where n is 8. In some cases, L3 comprises the amino acid sequence (GGGGS)n (SEQ ID NO:60), where n is 9. In some cases, L3 comprises the amino acid sequence (GGGGS)n (SEQ ID NO:60), where n is 10.

In some cases, a linker polypeptide, present in a first polypeptide of a multimeric polypeptide of the present disclosure, includes a cysteine residue that can form a disulfide bond with a cysteine residue present in a second polypeptide of a multimeric polypeptide of the present disclosure. In some cases, for example, a suitable linker comprises the amino acid sequence GCGASGGGGSGGGGS (SEQ ID NO:67).

Epitopes

An epitope present in a multimeric polypeptide of the present disclosure can have a length of from about 4 amino acids to about 25 amino acids, e.g., the epitope can have a length of from 4 amino acids (aa) to 10 aa, from 10 aa to 15 aa, from 15 aa to 20 aa, or from 20 aa to 25 aa. For example, an epitope present in a multimeric polypeptide of the present disclosure can have a length of 4 amino acids (aa), 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, an epitope present in a multimeric polypeptide of the present disclosure has a length of from 5 amino acids to 10 amino acids, e.g., 5 aa, 6 aa, 7 aa, 8 aa, 9 aa, or 10 aa.

An epitope present in a multimeric polypeptide of the present disclosure is specifically bound by a T-cell, i.e., the epitope is specifically bound by an epitope-specific T cell. An epitope-specific T cell binds an epitope having a reference amino acid sequence, but does not substantially bind an epitope that differs from the reference amino acid sequence. For example, an epitope-specific T cell binds an epitope having a reference amino acid sequence, and binds an epitope that differs from the reference amino acid sequence, if at all, with an affinity that is less than $10^{-6}$ M, less than $10^{-5}$ M, or less than $10^{-4}$ M. An epitope-specific T cell can bind an epitope for which it is specific with an affinity of at least $10^{-7}$ M, at least $10^{-8}$ M, at least $10^{-9}$ M, or at least $10^{-10}$ M.

Suitable epitopes include, but are not limited to, epitopes present in a cancer-associated antigen. Cancer-associated antigens include, but are not limited to, α-folate receptor; carbonic anhydrase IX (CAIX); CD19; CD20; CD22; CD30; CD33; CD44v7/8; carcinoembryonic antigen (CEA); epithelial glycoprotein-2 (EGP-2); epithelial glycoprotein-40 (EGP-40); folate binding protein (FBP); fetal acetylcholine receptor; ganglioside antigen GD2; Her2/neu; IL-13R-a2; kappa light chain; LeY; L1 cell adhesion molecule; melanoma-associated antigen (MAGE); MAGE-A1; mesothelin; MUC1; NKG2D ligands; oncofetal antigen (h5T4); prostate stem cell antigen (PSCA); prostate-specific membrane antigen (PSMA); tumor-associate glycoprotein-72 (TAG-72); and vascular endothelial growth factor receptor-2 (VEGF-R2). See, e.g., Vigneron et al. (2013) *Cancer Immunity* 13:15; and Vigneron (2015) *BioMed Res. Int'l* Article ID 948501.

MHC Polypeptides

As noted above, a multimeric polypeptide of the present disclosure includes MHC polypeptides. For the purposes of the instant disclosure, the term "major histocompatibility complex (MHC) polypeptides" is meant to include MHC polypeptides of various species, including human MHC (also referred to as human leukocyte antigen (HLA)) polypeptides, rodent (e.g., mouse, rat, etc.) MHC polypeptides, and MHC polypeptides of other mammalian species (e.g., lagomorphs, non-human primates, canines, felines, ungulates (e.g., equines, bovines, ovines, caprines, etc.), and the like. The term "MHC polypeptide" is meant to include Class I MHC polypeptides (e.g., β-2 microglobulin and MHC class I heavy chain) and MHC Class II polypeptides (e.g., MHC Class II α polypeptide and MHC Class II β polypeptide).

As noted above, in some embodiments of a multimeric polypeptide of the present disclosure, the first and the second MHC polypeptides are Class I MHC polypeptides; e.g., in some cases, the first MHC polypeptide is an MHC Class I β2-microglobulin (β2M) polypeptide, and the second MHC polypeptide is an MHC Class I heavy chain (H chain). In other cases, the first and the second MHC polypeptides are Class II MHC polypeptides; e.g., in some cases, the first MHC polypeptide is an MHC Class II α-chain polypeptide, and the second MHC polypeptide is an MHC Class II β-chain polypeptide. In other cases, the first polypeptide is an MHC Class II β-chain polypeptide, and the second MHC polypeptide is an MHC Class II α-chain polypeptide.

In some cases, an MHC polypeptide of a multimeric polypeptide of the present disclosure is a human MHC polypeptide, where human MHC polypeptides are also referred to as "human leukocyte antigen" ("HLA") polypeptides. In some cases, an MHC polypeptide of a multimeric polypeptide of the present disclosure is a Class I HLA polypeptide, e.g., a β2-microglobulin polypeptide, or a Class I HLA heavy chain polypeptide. Class I HLA heavy chain polypeptides include HLA-A heavy chain polypeptides, HLA-B heavy chain polypeptides, HLA-C heavy chain polypeptides, HLA-E heavy chain polypeptides, HLA-F heavy chain polypeptides, and HLA-G heavy chain polypeptides. In some cases, an MHC polypeptide of a multimeric polypeptide of the present disclosure is a Class II HLA polypeptide, e.g., a Class II HLA α chain or a Class II HLA β chain. MHC Class II polypeptides include MCH Class II DP a and β polypeptides, DM α and β polypeptides, DOA a and R polypeptides, DOB α and β polypeptides, DQ α and β polypeptides, and DR α and β polypeptides.

As an example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-365 of the amino acid sequence of the human HLA-A heavy chain polypeptide depicted in FIG. 5A.

As an example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-365 of the amino acid sequence of the following human HLA-A heavy chain amino acid sequence:

```
                                        (SEQ ID NO: 68)
GSHSMRYFFTSVSRPGRGEPRFIAVGYVDDTQFVRFDSDAASQRMEPRAPW

IEQEGPEYWDGETRKVKAHSQTHRVDLGTLRGYYNQSEAGSHTVQRMYGCD

VGSDWRFLRGYHQYAYDGKDYIALKEDLRSWTAADMAAQTTKHKWEAAHVA

EQLRAYLEGTCVEWLRRYLENGKETLQRTDAPKTHMTHHAVSDHEATLRCW

ALSFYPAEITLTWQRDGEDQTQDTELVETRPAGDGTFQKWAAVVVPSGQEQ

RYTCHVQHEGLPKPLTLRWEP.
```

HLA-A

As an example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-A heavy chain amino acid sequence:

```
                                                 (SEQ ID NO: 179)
GSHSMRYFFTSVSRPGRGEPRFIAVGYVDDTQFVRFDSDAASQRMEPRAPW
IEQEGPEYWDGETRKVKAHSQTHRVDLGTLRGYYNQSEAGSHTVQRMYGCD
VGSDWRFLRGYHQYAYDGKDYIALKEDLRSWTAADMAAQTTKHKWEAAHVA
EQLRAYLEGTCVEWLRRYLENGKETLQRTDAPKTHMTHHAVSDHEATLRCW
ALSFYPAEITLTWQRDGEDQTQDTELVETRPAGDGTFQKWAAVVVPSGQEQ
RYTCHVQHEGLPKPLTLRWEP.
```

HLA-A (Y84A; A236C)

In some cases, the MHC Class I heavy chain polypeptide comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A heavy chain (Y84A; A236C) amino acid sequence:

```
                                                 (SEQ ID NO: 180)
GSHSMRYFFTSVSRPGRGEPRFIAVGYVDDTQFVRFDSDAASQRMEPRAPW
IEQEGPEYWDGETRKVKAHSQTHRVDLGTLRGAYNQSEAGSHTVQRMYGCD
VGSDWRFLRGYHQYAYDGKDYIALKEDLRSWTAADMAAQTTKHKWEAAHVA
EQLRAYLEGTCVEWLRRYLENGKETLQRTDAPKTHMTHHAVSDHEATLRCW
ALSFYPAEITLTWQRDGEDQTQDTELVETRPCGDGTFQKWAAVVVPSGQEQ
RYTCHVQHEGLPKPLTLRWEP,
```

where amino acid 84 is Ala and amino acid 236 is Cys. In some cases, the Cys-236 forms an interchain disulfide bond with Cys-12 of a variant β2M polypeptide that comprises an R12C substitution.

HLA-A (Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A heavy chain (Y84C; A139C) amino acid sequence:

```
                                                 (SEQ ID NO: 181)
GSHSMRYFFTSVSRPGRGEPRFIAVGYVDDTQFVRFDSDAASQRMEPRAPW
IEQEGPEYWDGETRKVKAHSQTHRVDLGTLRGCYNQSEAGSHTVQRMYGCD
VGSDWRFLRGYHQYAYDGKDYIALKEDLRSWTAADMCAQTTKHKWEAAHVA
EQLRAYLEGTCVEWLRRYLENGKETLQRTDAPKTHMTHHAVSDHEATLRCW
ALSFYPAEITLTWQRDGEDQTQDTELVETRPAGDGTFQKWAAVVVPSGQEQ
RYTCHVQHEGLPKPLTLRWEP,
```

where amino acid 84 is Cys and amino acid 139 is Cys. In some cases, Cys-84 forms an intrachain disulfide bond with Cys-139.

HLA-A A11

As one non-limiting example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-A All heavy chain amino acid sequence:

```
                                                 (SEQ ID NO: 182)
GSHSMRYFYTSVSRPGRGEPRFIAVGYVDDTQFVRFDSDAASQRMEPRAP
WIEQEGPEYWDQETRNVKAQSQTDRVDLGTLRGYYNQSEDGSHTIQIMYG
CDVGPDGRFLRGYRQDAYDGKDYIALNEDLRSWTAADMAAQITKRKWEAA
HAAEQQRAYLEGTCVEWLRRYLENGKETLQRTDPPKTHMTHHPISDHEAT
LRCWALGFYPAEITLTWQRDGEDQTQDTELVETRPAGDGTFQKWAAVVVP
SGEEQRYTCHVQHEGLPKPLTLRWE.
```

Such an MHC Class I heavy chain may be prominent in Asian populations, including populations of individuals of Asian descent.

HLA-A All (Y84A; A236C)

As one non-limiting example, in some cases, the MHC Class I heavy chain polypeptide is an HLA-A All allele that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A All heavy chain (Y84A; A236C) amino acid sequence:

```
                                                 (SEQ ID NO: 183)
GSHSMRYFYTSVSRPGRGEPRFIAVGYVDDTQFVRFDSDAASQRMEPRAP
WIEQEGPEYWDQETRNVKAQSQTDRVDLGTLRGAYNQSEDGSHTIQIMYG
CDVGPDGRFLRGYRQDAYDGKDYIALNEDLRSWTAADMAAQITKRKWEAA
HAAEQQRAYLEGTCVEWLRRYLENGKETLQRTDPPKTHMTHHPISDHEAT
LRCWALGFYPAEITLTWQRDGEDQTQDTELVETRPCGDGTFQKWAAVVVP
SGEEQRYTCHVQHEGLPKPLTLRWE,
```

where amino acid 84 is Ala and amino acid 236 is Cys. In some cases, the Cys-236 forms an interchain disulfide bond with Cys-12 of a variant β2M polypeptide that comprises an R12C substitution.

HLA-B

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-B heavy chain amino acid sequence:

```
                                                 (SEQ ID NO: 184)
GSHSMRYFYTSVSRPGRGEPRFISVGYVDDTQFVRFDSDAASPREEPRAP
WIEQEGPEYWDRNTQIYKAQAQTDRESLRNLRGYYNQSEAGSHTLQSMYG
CDVGPDGRLLRGHDQYAYDGKDYIALNEDLRSWTAADTAAQITQRKWEAA
REAEQRRAYLEGECVEWLRRYLENGKDKLERADPPKTHVTHHPISDHEAT
```

-continued

LRCWALGFYPAEITLTWQRDGEDQTQDTELVETRPAGDRTFQKWAAVVVP

SGEEQRYTCHVQHEGLPKPLTLRWEP.

HLA-B (Y84A; A236C)

As one non-limiting example, in some cases, the MHC Class I heavy chain polypeptide is an HLA-B polypeptide that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-B heavy chain (Y84A; A236C) amino acid sequence:

(SEQ ID NO: 185)

GSHSMRYFYTSVSRPGRGEPRFISVGYVDDTQFVRFDSDAASPREEPRAP

WIEQEGPEYWDRNTQIYKAQAQTDRESLRNLRGAYNQSEAGSHTLQSMYG

CDVGPDGRLLRGHDQYAYDGKDYIALNEDLRSWTAADTAAQITQRKWEAA

REAEQRRAYLEGECVEWLRRYLENGKDKLERADPPKTHVTHHPISDHEAT

LRCWALGFYPAEITLTWQRDGEDQTQDTELVETRPCGDRTFQKWAAVVVP

SGEEQRYTCHVQHEGLPKPLTLRWEP, where amino acid 84 is Ala and amino acid 236 is Cys. In some cases, the Cys-236 forms an interchain disulfide bond with Cys-12 of a variant β2M polypeptide that comprises an R12C substitution.

HLA-B (Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-B heavy chain (Y84C; A139C) amino acid sequence:

(SEQ ID NO: 186)

GSHSMRYFYTSVSRPGRGEPRFISVGYVDDTQFVRFDSDAASPREEPRAP

WIEQEGPEYWDRNTQIYKAQAQTDRESLRNLRGCYNQSEAGSHTLQSMYG

CDVGPDGRLLRGHDQYAYDGKDYIALNEDLRSWTAADTCAQITQRKWEAA

REAEQRRAYLEGECVEWLRRYLENGKDKLERADPPKTHVTHHPISDHEAT

LRCWALGFYPAEITLTWQRDGEDQTQDTELVETRPAGDRTFQKWAAVVVP

SGEEQRYTCHVQHEGLPKPLTLRWEP, where amino acid 84 is Cys and amino acid 139 is Cys. In some cases, Cys-84 forms an intrachain disulfide bond with Cys-139.

HLA-C

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-C heavy chain amino acid sequence:

(SEQ ID NO: 187)

CSHSMRYFDTAVSRPGRGEPRFISVGYVDDTQFVRFDSDAASPRGEPRAP

WVEQEGPEYWDRETQNYKRQAQADRVSLRNLRGYYNQSEDGSHTLQRMYG

-continued

CDLGPDGRLLRGYDQSAYDGKDYIALNEDLRSWTAADTAAQITQRKLEAA

RAAEQLRAYLEGTCVEWLRRYLENGKETLQRAEPPKTHVTHHPLSDHEAT

LRCWALGFYPAEITLTWQRDGEDQTQDTELVETRPAGDGTFQKWAAVVVP

SGQEQRYTCHMQHEGLQEPLTLSWEP.

HLA-C(Y84A; A236C)

As one non-limiting example, in some cases, the MHC Class I heavy chain polypeptide is an HLA-C polypeptide that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-C heavy chain (Y84A; A236C) amino acid sequence:

(SEQ ID NO: 188)

CSHSMRYFDTAVSRPGRGEPRFISVGYVDDTQFVRFDSDAASPRGEPRAP

WVEQEGPEYWDRETQNYKRQAQADRVSLRNLRGAYNQSEDGSHTLQRMYG

CDLGPDGRLLRGYDQSAYDGKDYIALNEDLRSWTAADTAAQITQRKLEAA

RAAEQLRAYLEGTCVEWLRRYLENGKETLQRAEPPKTHVTHHPLSDHEAT

LRCWALGFYPAEITLTWQRDGEDQTQDTELVETRPCGDGTFQKWAAVVVP

SGQEQRYTCHMQHEGLQEPLTLSWEP, where amino acid 84 is Ala and amino acid 236 is Cys. In some cases, the Cys-236 forms an interchain disulfide bond with Cys-12 of a variant β2M polypeptide that comprises an R12C substitution.

HLA-C(Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-C heavy chain (Y84C; A139C) amino acid sequence:

(SEQ ID NO: 189)

CSHSMRYFDTAVSRPGRGEPRFISVGYVDDTQFVRFDSDAASPRGEPRAP

WVEQEGPEYWDRETQNYKRQAQADRVSLRNLRGCYNQSEDGSHTLQRMYG

CDLGPDGRLLRGYDQSAYDGKDYIALNEDLRSWTAADTCAQITQRKLEAA

RAAEQLRAYLEGTCVEWLRRYLENGKETLQRAEPPKTHVTHHPLSDHEAT

LRCWALGFYPAEITLTWQRDGEDQTQDTELVETRPAGDGTFQKWAAVVVP

SGQEQRYTCHMQHEGLQEPLTLSWEP, where amino acid 84 is Cys and amino acid 139 is Cys. In some cases, Cys-84 forms an intrachain disulfide bond with Cys-139.

As another example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-B heavy chain polypeptide depicted in FIG. 5B.

As another example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-C heavy chain polypeptide depicted in FIG. 5C.

As another example, an MHC Class I heavy chain polypeptide of a multimeric polypeptide of the present disclosure can comprise an amino acid sequence having at least 75%, at least 80%, at least 85%, at least 90%, at least 95%, at least 98%, at least 99%, or 100%, amino acid sequence identity to the following amino acid sequence:

```
                                            (SEQ ID NO: 69)
GPHSLRYFVTAVSRPGLGEPRFIAVGYVDDTQFVRFDSDADNPRFEPRAP
WMEQEGPEYWEEQTQRAKSDEQWFRVSLRTAQRYYNQSKGGSHTFQRMFG
CDVGSDWRLLRGYQQFAYDGRDYIALNEDLKTWTAADTAALITRRKWEQA
GDAEYYRAYLEGECVEWLRRYLELGNETLLRTDSPKAHVTYHPRSQVDVT
LRCWALGFYPADITLTWQLNGEDLTQDMELVETRPAGDGTFQKWAAVVVP
LGKEQNYTCHVHHKGLPEPLTLRW.
```

A β2-microglobulin (β2M) polypeptide of a multimeric polypeptide of the present disclosure can be a human β2M polypeptide, a non-human primate β2M polypeptide, a murine β2M polypeptide, and the like. In some instances, a β2M polypeptide comprises an amino acid sequence having at least 75%, at least 80%, at least 85%, at least 90%, at least 95%, at least 98%, at least 99%, or 100%, amino acid sequence identity to a β2M amino acid sequence depicted in FIG. 6. In some instances, a β2M polypeptide comprises an amino acid sequence having at least 75%, at least 80%, at least 85%, at least 90%, at least 95%, at least 98%, at least 99%, or 100%, amino acid sequence identity to amino acids 21 to 119 of a β2M amino acid sequence depicted in FIG. 6.

In some cases, an MHC polypeptide comprises a single amino acid substitution relative to a reference MHC polypeptide (where a reference MHC polypeptide can be a wild-type MHC polypeptide), where the single amino acid substitution substitutes an amino acid with a cysteine (Cys) residue. Such cysteine residues, when present in an MHC polypeptide of a first polypeptide of a multimeric polypeptide of the present disclosure, can form a disulfide bond with a cysteine residue present in a second polypeptide chain of a multimeric polypeptide of the present disclosure.

In some cases, a first MHC polypeptide in a first polypeptide of a multimeric polypeptide of the present disclosure, and/or the second MHC polypeptide in the second polypeptide of a multimeric polypeptide of the present disclosure, includes an amino acid substitution to substitute an amino acid with a cysteine, where the substituted cysteine in the first MHC polypeptide forms a disulfide bond with a cysteine in the second MHC polypeptide, where a cysteine in the first MHC polypeptide forms a disulfide bond with the substituted cysteine in the second MHC polypeptide, or where the substituted cysteine in the first MHC polypeptide forms a disulfide bond with the substituted cysteine in the second MHC polypeptide.

For example, in some cases, one of following pairs of residues in an HLA β2-microglobulin and an HLA Class I heavy chain is substituted with cysteines (where residue numbers are those of the mature polypeptide): 1) β2M residue 12, HLA Class I heavy chain residue 236; 2) β2M residue 12, HLA Class I heavy chain residue 237; 3) β2M residue 8, HLA Class I heavy chain residue 234; 4) β2M residue 10, HLA Class I heavy chain residue 235; 5) β2M residue 24, HLA Class I heavy chain residue 236; 6) β2M residue 28, HLA Class I heavy chain residue 232; 7) β2M residue 98, HLA Class I heavy chain residue 192; 8) β2M residue 99, HLA Class I heavy chain residue 234; 9) β2M residue 3, HLA Class I heavy chain residue 120; 10) β2M residue 31, HLA Class I heavy chain residue 96; 11) β2M residue 53, HLA Class I heavy chain residue 35; 12) β2M residue 60, HLA Class I heavy chain residue 96; 13) β2M residue 60, HLA Class I heavy chain residue 122; 14) β2M residue 63, HLA Class I heavy chain residue 27; 15) β2M residue Arg3, HLA Class I heavy chain residue Gly120; 16) β2M residue His31, HLA Class I heavy chain residue Gln96; 17) β2M residue Asp53, HLA Class I heavy chain residue Arg35; 18) β2M residue Trp60, HLA Class I heavy chain residue Gln96; 19) β2M residue Trp60, HLA Class I heavy chain residue Asp122; 20) β2M residue Tyr63, HLA Class I heavy chain residue Tyr27; 21) β2M residue Lys6, HLA Class I heavy chain residue Glu232; 22) β2M residue Gln8, HLA Class I heavy chain residue Arg234; 23) β2M residue Tyr10, HLA Class I heavy chain residue Pro235; 24) β2M residue Ser11, HLA Class I heavy chain residue Gln242; 25) β2M residue Asn24, HLA Class I heavy chain residue Ala236; 26) β2M residue Ser28, HLA Class I heavy chain residue Glu232; 27) β2M residue Asp98, HLA Class I heavy chain residue His192; and 28) β2M residue Met99, HLA Class I heavy chain residue Arg234. The amino acid numbering of the MHC/HLA Class I heavy chain is in reference to the mature MHC/HLA Class I heavy chain, without a signal peptide. For example, in the amino acid sequence depicted in FIG. 5A, which includes a signal peptide, Gly120 is Gly144; Gln96 is Gln120; etc. In some cases, the β2M polypeptide comprises an R12C substitution, and the HLA Class I heavy chain comprises an A236C substitution; in such cases, a disulfide bond forms between Cys-12 of the β2M polypeptide and Cys-236 of the HLA Class I heavy chain. For example, in some cases, residue 236 of the mature HLA-A amino acid sequence (i.e., residue 260 of the amino acid sequence depicted in FIG. 5A) is substituted with a Cys. In some cases, residue 236 of the mature HLA-B amino acid sequence (i.e., residue 260 of the amino acid sequence depicted in FIG. 5B) is substituted with a Cys. In some cases, residue 236 of the mature HLA-C amino acid sequence (i.e., residue 260 of the amino acid sequence depicted in FIG. 5C) is substituted with a Cys. In some cases, residue 32 (corresponding to Arg-12 of mature β2M) of an amino acid sequence depicted in FIG. 6 is substituted with a Cys.

In some cases, a β2M polypeptide comprises the amino acid sequence:

```
                                        (SEQ ID NO: 70)
IQRTPKIQVY SRHPAENGKS NFLNCYVSGF
HPSDIEVDLLKNGERIEKVE HSDLSFSKDW
SFYLLYYTEF TPTEKDEYAC RVNHVTLSQP KIVKWDRDM.
```

In some cases, a β2M polypeptide comprises the amino acid sequence:

```
                                        (SEQ ID NO: 71)
IQRTPKIQVY SCHPAENGKS NFLNCYVSGF
HPSDIEVDLLKNGERIEKVE HSDLSFSKDW SFYLLYYTEF
TPTEKDEYAC RVNHVTLSQP KIVKWDRDM.
```

In some cases, an HLA Class I heavy chain polypeptide comprises the amino acid sequence:

(SEQ ID NO: 72)
GSHSMRYFFTSVSRPGRGEPRFIAVGYVDDTQFVRFDSDAASQRMEPRAP
WIEQEGPEYWDGETRKVKAHSQTHRVDLGTLRGYYNQSEAGSHTVQRMYG
CDVGSDWRFLRGYHQYAYDGKDYIALKEDLRSWTAADMAAQTTKHKWEAA
HVAEQLRAYLEGTCVEWLRRYLENGKETLQRTDAPKTHMTHHAVSDHEAT
LRCWALSFYPAEITLTWQRDGEDQTQDTELVETRPAGDGTFQKWAAVVVP
SGQEQRYTCHVQHEGLPKPLTLRWEP.

In some cases, an HLA Class I heavy chain polypeptide comprises the amino acid sequence:

(SEQ ID NO: 73)
GSHSMRYFFTSVSRPGRGEPRFIAVGYVDDTQFVRFDSDAASQRMEPRAP
WIEQEGPEYWDGETRKVKAHSQTHRVDLGTLRGYYNQSEAGSHTVQRMYG
CDVGSDWRFLRGYHQYAYDGKDYIALKEDLRSWTAADMAAQTTKHKWEAA
HVAEQLRAYLEGTCVEWLRRYLENGKETLQRTDAPKTHMTHHAVSDHEAT
LRCWALSFYPAEITLTWQRDGEDQTQDTELVETRPCGDGTFQKWAAVVVP
SGQEQRYTCHVQHEGLPKPLTLRWEP.

In some cases, the β2M polypeptide comprises the following amino acid sequence:

IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:74); and the HLA Class I heavy chain polypeptide of a multimeric polypeptide of the present disclosure comprises the following amino acid sequence:

(SEQ ID NO: 75)
GSHSMRYFFTSVSRPGRGEPRFIAVGYVDDTQFVRFDSDAASQRMEPRAP
WIEQEGPEYWDGETRKVKAHSQTHRVDLGTLRGYYNQSEAGSHTVQRMYG
CDVGSDWRFLRGYHQYAYDGKDYIALKEDLRSWTAADMAAQTTKHKWEAA
HVAEQLRAYLEGTCVEWLRRYLENGKETLQRTDAPKTHMTHHAVSDHEAT
LRCWALSFYPAEITLTWQRDGEDQTQDTELVETRPCGDGTFQKWAAVVVP
SGQEQRYTCHVQHEGLPKPLTLRWEP, where the Cys residues that are underlined and in bold form a disulfide bond with one another in the multimeric polypeptide.

Immunomodulatory Polypeptides

A multimeric polypeptide of the present disclosure comprises a variant immunomodulatory polypeptide, as described above. Thus, a multimeric polypeptide of the present disclosure comprises the variant CD86 polypeptide present in a multimeric polypeptide of the present disclosure.

In some cases, a variant CD86 polypeptide present in a multimeric polypeptide of the present disclosure has a binding affinity to CD28 that is from 100 nM to 100 μM. As another example, in some cases, a variant CD86 polypeptide present in a multimeric polypeptide of the present disclosure has a binding affinity for CD28 (e.g., a CD28 polypeptide comprising the amino acid sequence depicted in one of FIG. 3A-3C) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

A variant CD86 polypeptide present in a multimeric polypeptide of the present disclosure can have a single amino acid substitution relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has from 2 to 10 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has 2 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has 3 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has 4 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has 5 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has 6 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has 7 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has 8 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has 9 amino acid substitutions relative to a wild-type CD86 polypeptide (e.g., a CD86 polypeptide comprising the amino acid sequence depicted in FIG. 2A or as set forth in SEQ ID NO:1). In some cases, a variant CD86 polypeptide present in a multimeric polypeptide of the present disclosure has 10 amino acid substitutions relative to a wild-type CD86 polypeptide (e.g., a CD86 polypeptide comprising the amino acid sequence depicted in FIG. 2A or as set forth in SEQ ID NO:1).

A variant CD86 polypeptide present in a multimeric polypeptide of the present disclosure can have a single amino acid substitution relative to a wild-type CD86 ectodomain polypeptide (e.g., a CD86 polypeptide comprising the amino acid set forth in SEQ ID NO:2). In some cases, a variant CD86 polypeptide present in a multimeric polypeptide of the present disclosure has from 2 to 10 amino acid substitutions relative to a wild-type CD86 polypeptide (e.g., a CD86 polypeptide comprising the amino acid set forth in SEQ ID NO:2). In some cases, a variant CD86 polypeptide present in a multimeric polypeptide of the present disclosure has 2 amino acid substitutions relative to a wild-type CD86 polypeptide (e.g., a CD86 polypeptide comprising the amino acid set forth in SEQ ID NO:2). In some cases, a variant CD86 polypeptide present in a multimeric polypeptide of the present disclosure has 3 amino acid substitutions relative to a wild-type CD86 polypeptide (e.g., a CD86 polypeptide comprising the amino acid set forth in SEQ ID NO:2). In some cases, a variant CD86 polypeptide present in a multimeric polypeptide of the present disclosure has 4 amino acid substitutions relative to a wild-type CD86 polypeptide (e.g., a CD86 polypeptide comprising the amino acid set forth in SEQ ID NO:2). In some cases, a variant CD86 polypeptide present in a multimeric polypeptide of the present disclosure has 5 amino acid substitutions relative to a wild-type CD86 polypeptide (e.g., a CD86 polypeptide comprising the amino acid set forth in SEQ ID NO:2). In some cases, a variant CD86 polypeptide present in a multimeric polypeptide of the present disclosure has 6 amino acid substitutions relative to a wild-type CD86 polypeptide (e.g., a CD86 polypeptide comprising the amino acid set forth in SEQ ID NO:2). In some cases, a variant CD86 polypeptide present in a multimeric polypeptide of the present disclosure has 7 amino acid substitutions relative to a wild-type CD86 polypeptide (e.g., a CD86 polypeptide comprising the amino acid set forth in SEQ ID NO:2). In some cases, a variant CD86 polypeptide present in a multimeric polypeptide of the present disclosure has 8 amino acid substitutions relative to a wild-type CD86 polypeptide (e.g., a CD86 polypeptide comprising the amino acid set forth in SEQ ID NO:2). In some cases, a variant CD86 polypeptide present in a multimeric polypeptide of the present disclosure has 9 amino acid substitutions relative to a wild-type CD86 polypeptide (e.g., a CD86 polypeptide comprising the amino acid set forth in SEQ ID NO:2). In some cases, a variant CD86 polypeptide present in a multimeric polypeptide of the present disclosure has 10 amino acid substitutions relative to a wild-type CD86 polypeptide (e.g., a CD86 polypeptide comprising the amino acid set forth in SEQ ID NO:2).

A variant CD86 polypeptide present in a multimeric polypeptide of the present disclosure can have a single amino acid substitution relative to a wild-type CD86 IgV polypeptide (e.g., a CD86 polypeptide comprising the amino acid set forth in SEQ ID NO:4). In some cases, a variant CD86 polypeptide present in a multimeric polypeptide of the present disclosure has from 2 to 10 amino acid substitutions relative to a wild-type CD86 polypeptide (e.g., a CD86 polypeptide comprising the amino acid set forth in SEQ ID NO:4). In some cases, a variant CD86 polypeptide present in a multimeric polypeptide of the present disclosure has 2 amino acid substitutions relative to a wild-type CD86 polypeptide (e.g., a CD86 polypeptide comprising the amino acid set forth in SEQ ID NO:4). In some cases, a variant CD86 polypeptide present in a multimeric polypeptide of the present disclosure has 3 amino acid substitutions relative to a wild-type CD86 polypeptide (e.g., a CD86 polypeptide comprising the amino acid set forth in SEQ ID NO:4). In some cases, a variant CD86 polypeptide present in a multimeric polypeptide of the present disclosure has 4 amino acid substitutions relative to a wild-type CD86 polypeptide (e.g., a CD86 polypeptide comprising the amino acid set forth in SEQ ID NO:4). In some cases, a variant CD86 polypeptide present in a multimeric polypeptide of the present disclosure has 5 amino acid substitutions relative to a wild-type CD86 polypeptide (e.g., a CD86 polypeptide comprising the amino acid set forth in SEQ ID NO:4). In some cases, a variant CD86 polypeptide present in a multimeric polypeptide of the present disclosure has 6 amino acid substitutions relative to a wild-type CD86 polypeptide (e.g., a CD86 polypeptide comprising the amino acid set forth in SEQ ID NO:4). In some cases, a variant CD86 polypeptide present in a multimeric polypeptide of the present disclosure has 7 amino acid substitutions relative to a wild-type CD86 polypeptide (e.g., a CD86 polypeptide comprising the amino acid set forth in SEQ ID NO:4). In some cases, a variant CD86 polypeptide present in a multimeric polypeptide of the present disclosure has 8 amino acid substitutions relative to a wild-type CD86 polypeptide (e.g., a CD86 polypeptide comprising the amino acid set forth in SEQ ID NO:4). In some cases, a variant CD86 polypeptide present in a multimeric polypeptide of the present disclosure has 9 amino acid substitutions relative to a wild-type CD86 polypeptide (e.g., a CD86 polypeptide comprising the amino acid set forth in SEQ ID NO:4). In some cases, a variant CD86 polypeptide present in a multimeric polypeptide of the present disclosure has 10 amino acid substitutions relative to a wild-type CD86 polypeptide (e.g., a CD86 polypeptide comprising the amino acid set forth in SEQ ID NO:4).

A variant CD86 polypeptide present in a multimeric polypeptide of the present disclosure can have a length of from 100 amino acids to 310 amino acids. For example, in some cases, a variant CD86 polypeptide present in a multimeric polypeptide of the present disclosure has a length of from 100 amino acids to 110 amino acids, from 110 amino acids to 225 amino acids, or from 225 amino acids to 310 amino acids. In some cases, a variant CD86 polypeptide of the present disclosure has a length of from 100 amino acids to 110 amino acids. In some cases, a variant CD86 polypeptide of the present disclosure has a length of from 110 amino acids to 225 amino acids. In some cases, a variant CD86 polypeptide present in a multimeric polypeptide of the present disclosure has a length of from 225 amino acids to 310 amino acids. In some cases, a variant CD86 polypeptide present in a multimeric polypeptide of the present disclosure has a length of 110 amino acids. In some cases, a variant CD86 polypeptide present in a multimeric polypeptide of the present disclosure has a length of 224 amino acids.

N61 Substitution

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 61 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 61 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 61 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 61 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 61 is Ile. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 61 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 61 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 61 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 61 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 61 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about M, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide has a length of 110 amino acids.

D66 Substitution

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 66 is an amino acid other than an aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 66 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 66 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 66 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 66 is Leu. In some cases, a variant CD86 polypeptide o present in a multimeric polypeptide f the present disclosure comprises an amino acid sequence having at least 90%, at least 95%, at least 98%, or at least 99%, amino acid sequence identity to the amino acid sequence depicted in FIG. 2G, where amino acid 66 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 66 is an amino acid other than an aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 66 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 66 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 66 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 66 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 66 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

W70 Substitution

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 70 is an amino acid other than tryptophan, e.g., where amino acid 70 is Gly, Ala, Val, Leu, Ile, Pro, Phe, Tyr, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 70 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 70 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 70 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 70 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 70 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 70 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 70 is an amino acid other than tryptophan, e.g., where amino acid 70 is Gly, Ala, Val, Leu, Ile, Pro, Phe, Tyr, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 70 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 70 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 70 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 70 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 70 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 70 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

H91 Substitution

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Arg, Asn Asp, Cys, Gln, Glu, Gly, Ile, Leu, Lys, Met, Phe, Pro, Ser, Thr, Trp, Tyr, or Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Arg, Asn Asp, Cys, Gln, Glu, Lys, Met, Phe, Pro, Ser, Thr, Trp, or Tyr. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Arg. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Asn. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 isAsp. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Cys. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Gln. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Lys. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Met. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Phe. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Pro. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Ser. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Thr. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Trp. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 91 is Tyr. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Arg, Asn Asp, Cys, Gln, Glu, Gly, Ile, Leu, Lys, Met, Phe, Pro, Ser, Thr, Trp, Tyr, or Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Arg, Asn Asp, Cys, Gln, Glu, Lys, Met, Phe, Pro, Ser, Thr, Trp, or Tyr. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Arg. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Asn. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 isAsp. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Cys. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Gln. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Lys. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Met. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Phe. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Pro. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Ser. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Thr. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Trp. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 91 is Tyr. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

V41 Substitution

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 41 is an amino acid other than valine, e.g., where amino acid 41 is Gly, Ala, Leu, Ile, Pro, Phe, Tyr, Trp, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 41 is Ala, Gly, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 41 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 41 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 41 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 41 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 41 is an amino acid other than valine, e.g., where amino acid 41 is Gly, Ala, Leu, Ile, Pro, Phe, Tyr, Trp, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 41 is Ala, Gly, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 41 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 41 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 41 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 41 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

Q35 Substitution

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 35 is an amino acid other than glutamine, e.g., where amino acid 35 is Gly, Ala, Val, Leu, Ile, Pro, Phe, Tyr, Trp, Ser, Thr, Cys, Met, Asn, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 35 is Ala, Gly, Leu, Val, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 35 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 35 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 35 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 35 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 35 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 35 is an amino acid other than glutamine, e.g., where amino acid 35 is Gly, Ala, Val, Leu, Ile, Pro, Phe, Tyr, Trp, Ser, Thr, Cys, Met, Asn, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 35 is Ala, Gly, Leu, Val, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 35 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 35 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 35 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 35 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 35 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

F33 Substitution

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2R, where amino acid 33 is an amino acid other than phenylalanine, e.g., where amino acid 33 is Gly, Ala, Val, Leu, Ile, Pro, Tyr, Trp, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2R, where amino acid 33 is Ala, Gly, Leu, Val, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2R, where amino acid 33 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2R, where amino acid 33 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2R, where amino acid 33 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2R, where amino acid 33 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2R, where amino acid 33 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2S, where amino acid 33 is an amino acid other than phenylalanine, e.g., where amino acid 33 is Gly, Ala, Val, Leu, Ile, Pro, Tyr, Trp, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2S, where amino acid 33 is Ala, Gly, Leu, Val, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2S, where amino acid 33 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2S, where amino acid 33 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2S, where amino acid 33 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2S, where amino acid 33 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2S, where amino acid 33 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

L72 Substitution

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2T, where amino acid 72 is an amino acid other than leucine, e.g., where amino acid 72 is Gly, Ala, Val, Ile, Pro, Phe, Tyr, Trp, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2T, where amino acid 72 is Ala, Gly, Val, or Ile. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2T, where amino acid 72 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2T, where amino acid 72 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2T, where amino acid 72 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2T, where amino acid 72 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2U, where amino acid 72 is an amino acid other than leucine, e.g., where amino acid 72 is Gly, Ala, Val, Ile, Pro, Phe, Tyr, Trp, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2U, where amino acid 72 is Ala, Gly, Val, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2U, where amino acid 72 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2U, where amino acid 72 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2U, where amino acid 72 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2U, where amino acid 72 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

Y59 Substitution

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2V, where amino acid 59 is an amino acid other than tyrosine, e.g., where amino acid 59 is Gly, Ala, Val, Leu, Ile, Pro, Phe, Trp, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2V, where amino acid 59 is Ala, Gly, Leu, Val, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2V, where amino acid 59 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2V, where amino acid 59 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2V, where amino acid 59 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2V, where amino acid 59 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2V, where amino acid 59 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2W, where amino acid 59 is an amino acid other than tyrosine, e.g., where amino acid 59 is Gly, Ala, Val, Leu, Ile, Pro, Phe, Trp, Ser, Thr, Cys, Met, Asn, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2W, where amino acid 59 is Ala, Gly, Leu, Val, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2W, where amino acid 59 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2W, where amino acid 59 is Gly. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2W, where amino acid 59 is Leu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2W, where amino acid 59 is Val. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2W, where amino acid 59 is Ile. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

Multiple Substitutions

As noted above, a variant CD86 polypeptide present in a multimeric polypeptide of the present disclosure can include a single amino acid substitution, or can include multiple (e.g., 2, 3, 4, 5, 6, 7, 8, 9, 10, or more than 10) amino acid substitutions. The following are non-limiting examples of variant CD86 polypeptides, comprising multiple amino acid substitutions, that are suitable for inclusion in a multimeric polypeptide of the present disclosure.

N61 and H91 Substitutions

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2X, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; and where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2X, where amino acid 91 is Ala, Gly, Val, Leu, or Ile, and where amino acid 61 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2X, where amino acid 91 is Ala, and where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2X, where amino acid 91 is Gly, and where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2X, where amino acid 91 is Val, and where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2X, where amino acid 91 is Leu, and where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2X, where amino acid 91 is Ile, and where amino acid 61 is Ala. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Y, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; and where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Ala, Gly, Val, Leu, or Ile, and where amino acid 61 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Ala, and where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Gly, and where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Val, and where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Y where amino acid 91 is Leu, and where amino acid 61 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Y, where amino acid 91 is Ile, and where amino acid 61 is Ala. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

D66 and H91 Substitutions

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Z, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; and where amino acid 66 is other than aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Ala, Gly, Val, Leu, or Ile, and where amino acid 66 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Gly, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Val, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Leu, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Z, where amino acid 91 is Ile, and where amino acid 66 is Ala. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; and where amino acid 66 is other than aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Ala, Gly, Val, Leu, or Ile, and where amino acid 66 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Gly, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Val, and where amino acid 66 is Ala. In some cases, a variant CD86 polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Leu, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*aa*, where amino acid 91 is Ile, and where amino acid 66 is Ala. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

N61, D66, and H91 Substitutions

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu; and where amino acid 66 is other than aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Ala, Gly, Val, Leu, or Ile; where amino acid 61 is Ala, Gly, Val, Leu, or Ile; and where amino acid 66 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Ala, where amino acid 61 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Gly, where amino acid 61 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Val, where amino acid 61 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Leu, where amino acid 61 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*bb*, where amino acid 91 is Ile, where amino acid 61 is Ala, and where amino acid 66 is Ala. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 224 amino acids.

In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*cc*, where amino acid 91 is an amino acid other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu; where amino acid 61 is an amino acid other than an asparagine, e.g., where amino acid 61 is Gly, Ala, Val, Leu, Ile, Pro, Phe, Tyr, Trp, Ser, Thr, Cys, Met, Gln, Lys, Arg, His, Asp, or Glu; and where amino acid 66 is other than aspartic acid, e.g., where amino acid 66 is Gly, Ala, Val, Leu, Ile, Pro, Phe, Tyr, Trp, Ser, Thr, Cys, Met, Asn, Gln, Lys, Arg, His, or Glu. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*cc*, where amino acid 91 is Ala, Gly, Val, Leu, or Ile; where amino acid 61 is Ala, Gly, Val, Leu, or Ile; and where amino acid 66 is Ala, Gly, Val, Leu, or Ile. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*cc*, where amino acid 91 is Ala, where amino acid 61 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*cc*, where amino acid 91 is Gly, where amino acid 61 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*cc*, where amino acid 91 is Val, where amino acid 61 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*cc*, where amino acid 91 is Leu, where amino acid 61 is Ala, and where amino acid 66 is Ala. In some cases, a variant CD86 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2*cc*, where amino acid 91 is Ile, where amino acid 61 is Ala, and where amino acid 66 is Ala. In some cases, a multimeric polypeptide of the present disclosure comprises two copies of the variant CD86 polypeptide, e.g., where the two copies are in tandem with no linker between the two copies, or are in tandem and separated by a linker peptide. In some cases, a multimeric polypeptide of the present disclosure comprises three copies of the variant CD86 polypeptide, e.g., where the three copies are in tandem with no linker between the three copies, or are in tandem and separated by a linker peptide. In some cases, where a CD86/synTac of the present disclosure comprises HLA Class I heavy chain and β2M, the CD86 polypeptide(s) is/are on the polypeptide chain comprising the HLA Class I heavy chain. In some cases, where an CD86/synTac of the present disclosure comprises HLA Class I heavy chain and β2M, the CD86 polypeptide(s) is/are on the polypeptide chain comprising the β2M polypeptide. In some cases, the variant CD86 polypeptide present in a multimeric polypeptide of the present disclosure has a binding affinity for CD28 that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant CD86 polypeptide present in a multimeric polypeptide of the present disclosure has a length of 110 amino acids.

Multiple Immunomodulatory Domains

As noted above, in some cases, a multimeric polypeptide of the present disclosure comprises two or more immunomodulatory polypeptides, where at least one of the two or more immunomodulatory polypeptide is a variant CD86 polypeptide of the present disclosure.

In some cases, a multimeric polypeptide of the present disclosure comprises two or more copies of a variant CD86 polypeptide of the present disclosure. In some cases, the two or more variant CD86 polypeptides are on the same polypeptide chain of a multimeric polypeptide of the present disclosure. In some cases, the two or more variant CD86 polypeptides are on separate polypeptide chains of a multimeric polypeptide of the present disclosure.

In some cases, a multimeric polypeptide of the present disclosure comprises a first immunomodulatory polypeptide, and at least a second immunomodulatory polypeptide, where the first immunomodulatory polypeptide is a variant CD86 polypeptide of the present disclosure, and the second immunomodulatory polypeptide is not a CD86 polypeptide. For example, in some cases, the second immunomodulatory polypeptide is a member of the tumor necrosis factor (TNF) superfamily; e.g., a FasL polypeptide, a 4-1BBL polypeptide, a CD40 polypeptide, an OX40L polypeptide, a CD30L polypeptide, a CD70 polypeptide, etc. In some cases, the second immunomodulatory polypeptide of a multimeric polypeptide of the present disclosure is a T-cell co-stimulatory polypeptide and is a member of the immunoglobulin (Ig) superfamily; e.g., a CD7 polypeptide, a CD80 polypeptide, an ICAM polypeptide, etc. In some cases, the second immunomodulatory polypeptide is 4-1BBL, OX40L, ICOS-L, ICAM, PD-L1, FasL, and PD-L2. Suitable immunomodulatory polypeptides of a multimeric polypeptide of the present disclosure include, e.g., CD7, CD30L, CD40, CD70, CD83, HLA-G, MICA, MICB, HVEM, lymphotoxin beta receptor, 3/TR6, ILT3, ILT4, or HVEM.

Further T cell modulatory domains (MODs) that can be included in a multimeric polypeptide of the present disclosure include naturally occurring or synthetic human gene products (protein), affinity reagents (e.g., an antibody, antibody fragment, single chain Fvs, aptamers, nanobody) targeting a human gene product, including, but not limited to all secreted proteins arising from classical and non-classical (e.g., FGF2, IL1, S100A4) secretion mechanisms, and ecto-domains of all cell surface proteins anchored by naturally occurring genetically encoded protein segments (single or multiple membrane spans) or post-translational modifications such as GPI linkages). Any naturally occurring or synthetic affinity reagent (e.g., antibody, antibody fragment, single chain Fvs, aptamer, nanobody, lectin, etc) targeting a cell surface glycan or other post-translational modification (e.g., sulfation). Examples include, but are not limited to, members of the TNF/TNFR family (OX40L, ICOSL, FASL, LTA, LTB TRAIL, CD153, TNFSF9, RANKL, TWEAK, TNFSF13, TNFSF13b, TNFSF14, TNFSF15, TNFSF18, CD40LG, CD70) or affinity reagents directed at the TNF/TNFR family members; members of the Immunoglobulin superfamily (VISTA, PD1, PD-L1, PD-L2, B71, B72, CTLA4, CD28, TIM3, CD4, CD8, CD19, T cell receptor chains, ICOS, ICOS ligand, HHLA2, butyrophilins, BTLA, B7-H3, B7-H4, CD3, CD79a, CD79b, IgSF CAMS (including CD2, CD58, CD48, CD150, CD229, CD244, ICAM-1), Leukocyte immunoglobulin like receptors (LILR), killer cell immunoglobulin like receptors (KIR)), lectin superfamily members, selectins, cytokines/chemokine and cytokine/chemokine receptors, growth factors and growth factor receptors), adhesion molecules (integrins, fibronectins, cadherins), or ecto-domains of multi-span integral membrane protein, or affinity reagents directed at the Immunoglobulin superfamily and listed gene products. In addition, active homologs/orthologs of these gene products, including but not limited to, viral sequences (e.g., CMV, EBV), bacterial sequences, fungal sequences, eukaryotic pathogens (e.g., *Schistosoma, Plasmodium, Babesia, Eimeria, Theileria, Toxoplasma, Entamoeba, Leishmania*, and *Trypanosoma*), and mammalian-derived coding regions. In addition. a MOD may comprise a small molecules drug targeting a human gene product.

Scaffold Polypeptides

A T-cell modulatory multimeric polypeptide of the present disclosure comprises an Fc polypeptide, or another suitable scaffold polypeptide.

Suitable scaffold polypeptides include antibody-based scaffold polypeptides and non-antibody-based scaffolds. Non-antibody-based scaffolds include, e.g., albumin, an XTEN (extended recombinant) polypeptide, transferrin, an Fc receptor polypeptide, an elastin-like polypeptide (see, e.g., Hassouneh et al. (2012) *Methods Enzymol.* 502:215; e.g., a polypeptide comprising a pentapeptide repeat unit of (Val-Pro-Gly-X-Gly; (SEQ ID NO:76)), where X is any amino acid other than proline), an albumin-binding polypeptide, a silk-like polypeptide (see, e.g., Valluzzi et al. (2002) *Philos Trans R Soc Lond B Biol Sci.* 357:165), a silk-elastin-like polypeptide (SELP; see, e.g., Megeed et al. (2002) *Adv Drug Deliv Rev.* 54:1075), and the like. Suitable XTEN polypeptides include, e.g., those disclosed in WO 2009/023270, WO 2010/091122, WO 2007/103515, US 2010/0189682, and US 2009/0092582; see also Schellenberger et al. (2009) *Nat Biotechnol.* 27:1186). Suitable albumin polypeptides include, e.g., human serum albumin.

Suitable scaffold polypeptides will in some cases be a half-life extending polypeptides. Thus, in some cases, a suitable scaffold polypeptide increases the in vivo half-life (e.g., the serum half-life) of the multimeric polypeptide, compared to a control multimeric polypeptide lacking the scaffold polypeptide. For example, in some cases, a scaffold polypeptide increases the in vivo half-life (e.g., the serum half-life) of the multimeric polypeptide, compared to a control multimeric polypeptide lacking the scaffold polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. As an example, in some cases, an Fc polypeptide increases the in vivo half-life (e.g., the serum half-life) of the multimeric polypeptide, compared to a control multimeric polypeptide lacking the Fc polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold.

Fc Polypeptides

In some cases, the first and/or the second polypeptide chain of a multimeric polypeptide of the present disclosure comprises an Fc polypeptide. The Fc polypeptide of a multimeric polypeptide of the present disclosure can be a human IgG1 Fc, a human IgG2 Fc, a human IgG3 Fc, a human IgG4 Fc, etc. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIGS. 4A-C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A; and comprises a substitution of N77; e.g., the Fc polypeptide comprises an N77A substitution. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgM Fc polypeptide depicted in FIG. 4B; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-276 to the human IgM Fc polypeptide depicted in FIG. 4B. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgA Fc polypeptide depicted in FIG. 4C; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-234 to the human IgA Fc polypeptide depicted in FIG. 4C.

Additional Polypeptides

A polypeptide chain of a multimeric polypeptide of the present disclosure can include one or more polypeptides in addition to those described above. Suitable additional polypeptides include epitope tags and affinity domains. The one or more additional polypeptide can be included at the N-terminus of a polypeptide chain of a multimeric polypeptide of the present disclosure, at the C-terminus of a polypeptide chain of a multimeric polypeptide of the present disclosure, or internally within a polypeptide chain of a multimeric polypeptide of the present disclosure.

Epitope Tag

Suitable epitope tags include, but are not limited to, hemagglutinin (HA; e.g., YPYDVPDYA (SEQ ID NO:77); FLAG (e.g., DYKDDDDK (SEQ ID NO:78); c-myc (e.g., EQKLISEEDL; SEQ ID NO:79), and the like.

Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:80), HisX6 (HHHHHH) (SEQ ID NO:81), C-myc (EQKLISEEDL) (SEQ ID NO:79), Flag (DYKDDDDK) (SEQ ID NO:78), StrepTag (WSHPQFEK) (SEQ ID NO:82), hemagglutinin, e.g., HA Tag (YPYDVPDYA) (SEQ ID NO:77), glutathione-S-transferase (GST), thioredoxin, cellulose binding domain, RYIRS (SEQ ID NO:83), Phe-His-His-Thr (SEQ ID NO:84), chitin binding domain, S-peptide, T7 peptide, SH2 domain, C-end RNA tag, WEAAAREACCRECCARA (SEQ ID NO:85), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, 5100 proteins, parvalbumin, calbindin D9K, calbindin D28K, and calretinin, inteins, biotin, streptavidin, MyoD, Id, leucine zipper sequences, and maltose binding protein.

Exemplary Multimeric Polypeptides

Exemplary multimeric polypeptides of the present disclosure are described below.

In some cases, a multimeric polypeptide of the present disclosure comprises: a) a first polypeptide comprising, in order from N-terminus to C-terminus: i) an epitope; ii) a β2M polypeptide; and iii) a variant CD86 polypeptide comprising an amino acid sequence having at least 90%, at least 95%, at least 98%, or at least 99%, amino acid sequence identity to the amino acid sequence depicted in SEQ ID NO:2 (FIG. 2B) or SEQ ID NO:4 (FIG. 2D), where amino acid 91 is other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu, or where amino acid 91 is Ala, Gly, Val, Leu, or Ile, or where amino acid 91 is Arg, Asn Asp, Cys, Gln, Glu, Gly, Ile, Leu, Lys, Met, Phe, Pro, Ser, Thr, Trp, Tyr, or Val, or where amino acid 91 is Arg, Asn Asp, Cys, Gln, Glu, Lys, Met, Phe, Pro, Ser, Thr, Trp, or Tyr, where the variant CD86 polypeptide has a length of from 110 amino acids to 224 amino acids; and b) a second polypeptide comprising, in order from N-terminus to C-terminus: i) a variant CD86 polypeptide; ii) a Class I HLA heavy chain; and iii) an Ig Fc polypeptide. In some cases, both the β2M and the Class I HLA heavy chain comprise amino acid substitutions that provide for a Cys such that the β2M and the Class I HLA heavy chain are disulfide linked to one another. In some of these embodiments, the variant CD86 polypeptide comprises an H91A substitution, comprises an amino acid sequence having at least 90%, at least 95%, at least 98%, or at least 99%, amino acid sequence identity to the amino acid sequence set forth in SEQ ID NO:2, and has a length of 224 amino acids. In some of these embodiments, the variant CD86 polypeptide comprises an H91A substitution, comprises an amino acid sequence having at least 90%, at least 95%, at least 98%, or at least 99%, amino acid sequence identity to the amino acid sequence set forth in SEQ ID NO:4, and has a length of 110 amino acids.

In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant CD86 polypeptide; ii) a second variant CD86 polypeptide; iii) a third variant CD86 polypeptide, wherein each of the first, second, and third variant CD86 polypeptides independently comprises an amino acid sequence having at least 90%, at least 95%, at least 98%, or at least 99%, amino acid sequence identity to the amino acid sequence depicted in SEQ ID NO:2 (FIG. 2B) or SEQ ID NO:4 (FIG. 2D), where amino acid 91 is other than histidine, e.g., where amino acid 91 is Gly, Ala, Val, Leu, Ile, Pro, Phe, Tyr, Trp, Ser, Thr, Cys, Met, Asn, Gln, Lys, Arg, Asp, or Glu, or where amino acid 91 is Ala, Gly, Val, Leu, or Ile, or where amino acid 91 is Arg, Asn Asp, Cys, Gln, Glu, Gly, Ile, Leu, Lys, Met, Phe, Pro, Ser, Thr, Trp, Tyr, or Val, or where amino acid 91 is Arg, Asn Asp, Cys, Gln, Glu, Lys, Met, Phe, Pro, Ser, Thr, Trp, or Tyr, where the variant CD86 polypeptide has a length of from 110 amino acids to 224 amino acids; ivi) a Class I HLA heavy chain; and v) an Ig Fc polypeptide. In some cases, both the β2M and the Class I HLA heavy chain comprise amino acid substitutions that provide for a Cys such that the β2M and the Class I HLA heavy chain are disulfide linked to one another. In some of these embodiments, at least one of the variant CD86 polypeptides comprises an H91A substitution, comprises an amino acid sequence having at least 90%, at least 95%, at least 98%, or at least 99%, amino acid sequence identity to the amino acid sequence set forth in SEQ ID NO:2, and has a length of 224 amino acids. In some of these embodiments, at least one of the variant CD86 polypeptide comprises an H91A substitution, comprises an amino acid sequence having at least 90%, at least 95%, at least 98%, or at least 99%, amino acid sequence identity to the amino acid sequence set forth in SEQ ID NO:4, and has a length of 110 amino acids. In some of these embodiments, the first, second, and third CD86 variants are in tandem and are not separated by a linker. In some embodiments, a linker is interposed between the first and the second CD86 variants, between the second and the third CD86 variants, and between the third CD86 variant and the Class I HLA heavy chain polypeptide. In some cases, the linker is $(GGGGS)_5$ ("G4S5"; SEQ ID NO:62).

Examples of polypeptide chains suitable for inclusion in a multimeric polypeptide of the present disclosure are those encoded by the nucleotide sequences set forth in SEQ ID NOs:94-178. FIG. 11 provides the construct names corresponding to SEQ ID NOs:94-178. In some cases, a polypeptide chain of a multimeric polypeptide of the present disclosure is encoded by one of SEQ ID NOs:94-178. In some cases, a polypeptide chain of a multimeric polypeptide of the present disclosure is encoded by a nucleotide sequence having at least 80%, at least 85%, at least 90%, at least 95%, at least 98%, or at least 99%, nucleotide sequence identity to one of SEQ ID NOs:94-178.

In some cases, a polypeptide chain of a multimeric polypeptide of the present disclosure is encoded by SEQ ID NO:94. In some cases, a polypeptide chain of a multimeric polypeptide of the present disclosure is encoded by SEQ ID NO:95. In some cases, a polypeptide chain of a multimeric polypeptide of the present disclosure is encoded by SEQ ID NO:96. In some cases, a polypeptide chain of a multimeric polypeptide of the present disclosure is encoded by SEQ ID NO:97. In some cases, a polypeptide chain of a multimeric polypeptide of the present disclosure is encoded by SEQ ID NO:98. In some cases, a polypeptide chain of a multimeric polypeptide of the present disclosure is encoded by SEQ ID NO:99. In some cases, a polypeptide chain of a multimeric polypeptide of the present disclosure is encoded by SEQ ID NO:100.

In some cases, a polypeptide chain of a multimeric polypeptide of the present disclosure is encoded by SEQ ID NO:101. In some cases, a polypeptide chain of a multimeric polypeptide of the present disclosure is encoded by SEQ ID NO:102. In some cases, a polypeptide chain of a multimeric polypeptide of the present disclosure is encoded by SEQ ID NO:103. In some cases, a polypeptide chain of a multimeric polypeptide of the present disclosure is encoded by SEQ ID NO:104. In some cases, a polypeptide chain of a multimeric polypeptide of the present disclosure is encoded by SEQ ID NO:105. In some cases, a polypeptide chain of a multimeric polypeptide of the present disclosure is encoded by SEQ ID NO:106. In some cases, a polypeptide chain of a multimeric polypeptide of the present disclosure is encoded by SEQ ID NO:107. In some cases, a polypeptide chain of a multimeric polypeptide of the present disclosure is encoded by SEQ ID NO:108. In some cases, a polypeptide chain of a multimeric polypeptide of the present disclosure is encoded by SEQ ID NO:109. In some cases, a polypeptide chain of a multimeric polypeptide of the present disclosure is encoded by SEQ ID NO:110.

In some cases, a polypeptide chain of a multimeric polypeptide of the present disclosure is encoded by SEQ ID NO:111. In some cases, a polypeptide chain of a multimeric polypeptide of the present disclosure is encoded by SEQ ID NO:112. In some cases, a polypeptide chain of a multimeric polypeptide of the present disclosure is encoded by SEQ ID NO:113. In some cases, a polypeptide chain of a multimeric polypeptide of the present disclosure is encoded by SEQ ID NO:114. In some cases, a polypeptide chain of a multimeric polypeptide of the present disclosure is encoded by SEQ ID NO:115. In some cases, a polypeptide chain of a multimeric polypeptide of the present disclosure is encoded by SEQ ID NO:116. In some cases, a polypeptide chain of a multimeric polypeptide of the present disclosure is encoded by SEQ ID NO:117. In some cases, a polypeptide chain of a multimeric polypeptide of the present disclosure is encoded by SEQ ID NO:118. In some cases, a polypeptide chain of a multimeric polypeptide of the present disclosure is encoded by SEQ ID NO:119. In some cases, a polypeptide chain of a multimeric polypeptide of the present disclosure is encoded by SEQ ID NO:120.

In some cases, a polypeptide chain of a multimeric polypeptide of the present disclosure is encoded by SEQ ID NO:121. In some cases, a polypeptide chain of a multimeric polypeptide of the present disclosure is encoded by SEQ ID NO:122. In some cases, a polypeptide chain of a multimeric polypeptide of the present disclosure is encoded by SEQ ID NO:123. In some cases, a polypeptide chain of a multimeric polypeptide of the present disclosure is encoded by SEQ ID NO:124. In some cases, a polypeptide chain of a multimeric polypeptide of the present disclosure is encoded by SEQ ID NO:125. In some cases, a polypeptide chain of a multimeric polypeptide of the present disclosure is encoded by SEQ ID NO:126. In some cases, a polypeptide chain of a multimeric polypeptide of the present disclosure is encoded by SEQ ID NO:127. In some cases, a polypeptide chain of a multimeric polypeptide of the present disclosure is encoded by SEQ ID NO:128. In some cases, a polypeptide chain of a multimeric polypeptide of the present disclosure is encoded by SEQ ID NO:129. In some cases, a polypeptide chain of a multimeric polypeptide of the present disclosure is encoded by SEQ ID NO:130.

In some cases, a polypeptide chain of a multimeric polypeptide of the present disclosure is encoded by SEQ ID NO:131. In some cases, a polypeptide chain of a multimeric polypeptide of the present disclosure is encoded by SEQ ID NO:132. In some cases, a polypeptide chain of a multimeric polypeptide of the present disclosure is encoded by SEQ ID NO:133. In some cases, a polypeptide chain of a multimeric polypeptide of the present disclosure is encoded by SEQ ID NO:134. In some cases, a polypeptide chain of a multimeric polypeptide of the present disclosure is encoded by SEQ ID NO:135. In some cases, a polypeptide chain of a multimeric polypeptide of the present disclosure is encoded by SEQ ID NO:136. In some cases, a polypeptide chain of a multimeric polypeptide of the present disclosure is encoded by SEQ ID NO:137. In some cases, a polypeptide chain of a multimeric polypeptide of the present disclosure is encoded by SEQ ID NO:138. In some cases, a polypeptide chain of a multimeric polypeptide of the present disclosure is encoded by SEQ ID NO:139. In some cases, a polypeptide chain of a multimeric polypeptide of the present disclosure is encoded by SEQ ID NO:140.

In some cases, a polypeptide chain of a multimeric polypeptide of the present disclosure is encoded by SEQ ID NO:141. In some cases, a polypeptide chain of a multimeric polypeptide of the present disclosure is encoded by SEQ ID NO:142. In some cases, a polypeptide chain of a multimeric polypeptide of the present disclosure is encoded by SEQ ID NO:143. In some cases, a polypeptide chain of a multimeric polypeptide of the present disclosure is encoded by SEQ ID NO:144. In some cases, a polypeptide chain of a multimeric polypeptide of the present disclosure is encoded by SEQ ID NO:145. In some cases, a polypeptide chain of a multimeric polypeptide of the present disclosure is encoded by SEQ ID NO:146. In some cases, a polypeptide chain of a multimeric polypeptide of the present disclosure is encoded by SEQ ID NO:147. In some cases, a polypeptide chain of a multimeric polypeptide of the present disclosure is encoded by SEQ ID NO:148. In some cases, a polypeptide chain of a multimeric polypeptide of the present disclosure is encoded by SEQ ID NO:149. In some cases, a polypeptide chain of a multimeric polypeptide of the present disclosure is encoded by SEQ ID NO:150.

In some cases, a polypeptide chain of a multimeric polypeptide of the present disclosure is encoded by SEQ ID NO:151. In some cases, a polypeptide chain of a multimeric polypeptide of the present disclosure is encoded by SEQ ID NO:152. In some cases, a polypeptide chain of a multimeric polypeptide of the present disclosure is encoded by SEQ ID NO:153. In some cases, a polypeptide chain of a multimeric polypeptide of the present disclosure is encoded by SEQ ID NO:154. In some cases, a polypeptide chain of a multimeric polypeptide of the present disclosure is encoded by SEQ ID NO:155. In some cases, a polypeptide chain of a multimeric polypeptide of the present disclosure is encoded by SEQ ID NO:156. In some cases, a polypeptide chain of a multimeric polypeptide of the present disclosure is encoded by SEQ ID NO:157. In some cases, a polypeptide chain of a multimeric polypeptide of the present disclosure is encoded by SEQ ID NO:158. In some cases, a polypeptide chain of a multimeric polypeptide of the present disclosure is encoded by SEQ ID NO:159. In some cases, a polypeptide chain of a multimeric polypeptide of the present disclosure is encoded by SEQ ID NO:160.

In some cases, a polypeptide chain of a multimeric polypeptide of the present disclosure is encoded by SEQ ID NO:161. In some cases, a polypeptide chain of a multimeric polypeptide of the present disclosure is encoded by SEQ ID NO:162. In some cases, a polypeptide chain of a multimeric polypeptide of the present disclosure is encoded by SEQ ID NO:163. In some cases, a polypeptide chain of a multimeric polypeptide of the present disclosure is encoded by SEQ ID NO:164. In some cases, a polypeptide chain of a multimeric polypeptide of the present disclosure is encoded by SEQ ID NO:165. In some cases, a polypeptide chain of a multimeric polypeptide of the present disclosure is encoded by SEQ ID NO:166. In some cases, a polypeptide chain of a multimeric polypeptide of the present disclosure is encoded by SEQ ID NO:167. In some cases, a polypeptide chain of a multimeric polypeptide of the present disclosure is encoded by SEQ ID NO:168. In some cases, a polypeptide chain of a multimeric polypeptide of the present disclosure is encoded by SEQ ID NO:169. In some cases, a polypeptide chain of a multimeric polypeptide of the present disclosure is encoded by SEQ ID NO:170.

In some cases, a polypeptide chain of a multimeric polypeptide of the present disclosure is encoded by SEQ ID NO:171. In some cases, a polypeptide chain of a multimeric polypeptide of the present disclosure is encoded by SEQ ID NO:172. In some cases, a polypeptide chain of a multimeric polypeptide of the present disclosure is encoded by SEQ ID NO:173. In some cases, a polypeptide chain of a multimeric polypeptide of the present disclosure is encoded by SEQ ID NO:174. In some cases, a polypeptide chain of a multimeric polypeptide of the present disclosure is encoded by SEQ ID NO:175. In some cases, a polypeptide chain of a multimeric polypeptide of the present disclosure is encoded by SEQ ID NO:176. In some cases, a polypeptide chain of a multimeric polypeptide of the present disclosure is encoded by SEQ ID NO:177. In some cases, a polypeptide chain of a multimeric polypeptide of the present disclosure is encoded by SEQ ID NO:178.

Nucleic Acids

The present disclosure provides a nucleic acid comprising a nucleotide sequence encoding a variant CD86 polypeptide of the present disclosure. The present disclosure provides a nucleic acid comprising a nucleotide sequence encoding a CD86 fusion polypeptide of the present disclosure.

The present disclosure provides nucleic acids comprising nucleotide sequences encoding a multimeric polypeptide of the present disclosure. In some cases, the individual polypeptide chains of a multimeric polypeptide of the present disclosure are encoded in separate nucleic acids. In some cases, all polypeptide chains of a multimeric polypeptide of the present disclosure are encoded in a single nucleic acid. In some cases, a first nucleic acid comprises a nucleotide sequence encoding a first polypeptide of a multimeric polypeptide of the present disclosure; and a second nucleic acid comprises a nucleotide sequence encoding a second polypeptide of a multimeric polypeptide of the present disclosure. In some cases, single nucleic acid comprises a nucleotide sequence encoding a first polypeptide of a multimeric polypeptide of the present disclosure and a second polypeptide of a multimeric polypeptide of the present disclosure.

Separate Nucleic Acids Encoding Individual Polypeptide Chains of a Multimeric Polypeptide The present disclosure provides nucleic acids comprising nucleotide sequences encoding a multimeric polypeptide of the present disclosure. As noted above, in some cases, the individual polypeptide chains of a multimeric polypeptide of the present disclosure are encoded in separate nucleic acids. In some cases, nucleotide sequences encoding the separate polypeptide chains of a multimeric polypeptide of the present disclosure are operably linked to transcriptional control elements, e.g., promoters, such as promoters that are functional in a eukaryotic cell, where the promoter can be a constitutive promoter or an inducible promoter.

The present disclosure provides a first nucleic acid and a second nucleic acid, where the first nucleic acid comprises a nucleotide sequence encoding a first polypeptide of a multimeric polypeptide of the present disclosure, where the first polypeptide comprises, in order from N-terminus to C-terminus: a) an epitope (e.g., a T-cell epitope); b) a first MHC polypeptide; and c) an immunomodulatory polypeptide (e.g., a variant CD86 polypeptide of the present disclosure); and where the second nucleic acid comprises a nucleotide sequence encoding a second polypeptide of a multimeric polypeptide of the present disclosure, where the second polypeptide comprises, in order from N-terminus to C-terminus: a) a second MHC polypeptide; and b) an Ig Fc polypeptide. Suitable T-cell epitopes, MHC polypeptides, immunomodulatory polypeptides, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

The present disclosure provides a first nucleic acid and a second nucleic acid, where the first nucleic acid comprises a nucleotide sequence encoding a first polypeptide of a multimeric polypeptide of the present disclosure, where the first polypeptide comprises, in order from N-terminus to C-terminus: a) an epitope (e.g., a T-cell epitope); and b) a first MHC polypeptide; and where the second nucleic acid comprises a nucleotide sequence encoding a second polypeptide of a multimeric polypeptide of the present disclosure, where the second polypeptide comprises, in order from N-terminus to C-terminus: a) an immunomodulatory polypeptide (e.g., a variant CD86 polypeptide of the present disclosure); b) a second MHC polypeptide; and c) an Ig Fc polypeptide. Suitable T-cell epitopes, MHC polypeptides, immunomodulatory polypeptides, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

Nucleic Acid Encoding Two or More Polypeptides Present in a Multimeric Polypeptide The present disclosure provides a nucleic acid comprising nucleotide sequences encoding at least the first polypeptide and the second polypeptide of a multimeric polypeptide of the present disclosure. In some cases, where a multimeric polypeptide of the present disclosure includes a first, second, and third polypeptide, the nucleic acid includes a nucleotide sequence encoding the first, second, and third polypeptides. In some cases, the nucleotide sequences encoding the first polypeptide and the second polypeptide of a multimeric polypeptide of the present disclosure includes a nucleotide sequence encoding a proteolytically cleavable linker interposed between the nucleotide sequence encoding the first polypeptide and the nucleotide sequence encoding the second polypeptide. In some cases, the nucleotide sequences encoding the first polypeptide and the second polypeptide of a multimeric polypeptide of the present disclosure includes an internal ribosome entry site (IRES) interposed between the nucleotide sequence encoding the first polypeptide and the nucleotide sequence encoding the second polypeptide. In some cases, the nucleotide sequences encoding the first polypeptide and the second polypeptide of a multimeric polypeptide of the present disclosure includes a ribosome skipping signal (or cis-acting hydrolase element, CHYSEL) interposed between the nucleotide sequence encoding the first polypeptide and the nucleotide sequence encoding the second polypeptide. Examples of nucleic acids are described below, where a proteolytically cleavable linker is provided between nucleotide sequences encoding the first polypeptide and the second polypeptide of a multimeric polypeptide of the present disclosure; in any of these embodiments, an IRES or a ribosome skipping signal can be used in place of the nucleotide sequence encoding the proteolytically cleavable linker.

In some cases, a first nucleic acid (e.g., a recombinant expression vector, an mRNA, a viral RNA, etc.) comprises a nucleotide sequence encoding a first polypeptide chain of a multimeric polypeptide of the present disclosure; and a second nucleic acid (e.g., a recombinant expression vector, an mRNA, a viral RNA, etc.) comprises a nucleotide sequence encoding a second polypeptide chain of a multimeric polypeptide of the present disclosure. In some cases, the nucleotide sequence encoding the first polypeptide, and the second nucleotide sequence encoding the second polypeptide, are each operably linked to transcriptional control elements, e.g., promoters, such as promoters that are functional in a eukaryotic cell, where the promoter can be a constitutive promoter or an inducible promoter.

The present disclosure provides a nucleic acid comprising a nucleotide sequence encoding a recombinant polypeptide, where the recombinant polypeptide comprises, in order from N-terminus to C-terminus: a) an epitope (e.g., a T-cell epitope); b) a first MHC polypeptide; c) an immunomodulatory polypeptide (e.g., a variant CD86 polypeptide of the present disclosure); d) a proteolytically cleavable linker; e) a second MHC polypeptide; and f) an immunoglobulin (Ig) Fc polypeptide. The present disclosure provides a nucleic acid comprising a nucleotide sequence encoding a recombinant polypeptide, where the recombinant polypeptide comprises, in order from N-terminus to C-terminus: a) a first leader peptide; b) the epitope; c) the first MHC polypeptide; d) the immunomodulatory polypeptide (e.g., a variant CD86 polypeptide of the present disclosure); e) the proteolytically cleavable linker; f) a second leader peptide; g) the second MHC polypeptide; and h) the Ig Fc polypeptide. The present disclosure provides a nucleic acid comprising a nucleotide sequence encoding a recombinant polypeptide, where the recombinant polypeptide comprises, in order from N-terminus to C-terminus: a) an epitope; b) a first MHC polypeptide; c) a proteolytically cleavable linker; d) an immunomodulatory polypeptide (e.g., a variant CD86 polypeptide of the present disclosure); e) a second MHC polypeptide; and f) an Ig Fc polypeptide. In some cases, the first leader peptide and the second leader peptide is a 32-M leader peptide. In some cases, the nucleotide sequence is operably linked to a transcriptional control element. In some cases, the transcriptional control element is a promoter that is functional in a eukaryotic cell.

Suitable MHC polypeptides are described above. In some cases, the first MHC polypeptide is a β2-microglobulin polypeptide; and wherein the second MHC polypeptide is an MHC class I heavy chain polypeptide. In some cases, the β2-microglobulin polypeptide comprises an amino acid sequence having at least 85% amino acid sequence identity to the amino acid sequence set forth in SEQ ID NO:44. In some cases, the MHC class I heavy chain polypeptide is an HLA-A, HLA-B, HLA-C, HLA-E, HLA-F, HLA-G, HLA-K, or HLA-L heavy chain. In some cases, the MHC class I heavy chain polypeptide comprises an amino acid sequence having at least 85% amino acid sequence identity to the amino acid sequence set forth in SEQ ID NO:41. In some cases, the first MHC polypeptide is an MHC Class II alpha chain polypeptide; and wherein the second MHC polypeptide is an MHC class II beta chain polypeptide.

Suitable Fc polypeptides are described above. In some cases, the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In some cases, the Ig Fc polypeptide comprises an amino acid sequence having at least 85% amino acid sequence identity to an amino acid sequence depicted in FIGS. 4A-4C.

Suitable immunomodulatory polypeptides are described above.

Suitable proteolytically cleavable linkers are described above. In some cases, the proteolytically cleavable linker comprises an amino acid sequence selected from: a) LEVLFQGP (SEQ ID NO:86); b) ENLYTQS (SEQ ID NO:87); c) DDDDK (SEQ ID NO:88); d) LVPR (SEQ ID NO:89); and e) GSGATNFSLLKQAGDVEENPGP (SEQ ID NO: 90).

In some cases, a linker between the epitope and the first MHC polypeptide comprises a first Cys residue, and the second MHC polypeptide comprises an amino acid substitution to provide a second Cys residue, such that the first and the second Cys residues provide for a disulfide linkage between the linker and the second MHC polypeptide. In some cases, first MHC polypeptide comprises an amino acid substitution to provide a first Cys residue, and the second MHC polypeptide comprises an amino acid substitution to provide a second Cys residue, such that the first Cys residue and the second Cys residue provide for a disulfide linkage between the first MHC polypeptide and the second MHC polypeptide.

Recombinant Expression Vectors

The present disclosure provides recombinant expression vectors comprising nucleic acids of the present disclosure. In some cases, the recombinant expression vector is a non-viral vector. In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, a non-integrating viral vector, etc.

Suitable expression vectors include, but are not limited to, viral vectors (e.g. viral vectors based on vaccinia virus; poliovirus; adenovirus (see, e.g., L1 et al., Invest Opthalmol Vis Sci 35:2543 2549, 1994; Borras et al., Gene Ther 6:515 524, 1999; L1 and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

In some embodiments, a nucleotide sequence encoding a DNA-targeting RNA and/or a site-directed modifying polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a DNA-targeting RNA and/or a site-directed modifying polypeptide is operably linked to multiple control elements that allow expression of the nucleotide sequence encoding a DNA-targeting RNA and/or a site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator.

The expression vector may also include appropriate sequences for amplifying expression.

Genetically Modified Host Cells

The present disclosure provides a genetically modified host cell, where the host cell is genetically modified with a nucleic acid of the present disclosure.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some cases, the host cell is a mammalian cell that has been genetically modified such that it does not synthesize endogenous MHC 02-M.

Methods of Producing a Multimeric Polypeptide

The present disclosure provides methods of producing a multimeric polypeptide of the present disclosure. The methods generally involve culturing, in a culture medium, a host cell that is genetically modified with a recombinant expression vector comprising a nucleotide sequence encoding the multimeric polypeptide; and isolating the multimeric polypeptide from the genetically modified host cell and/or the culture medium. A host cell that is genetically modified with a recombinant expression vector comprising a nucleotide sequence encoding the multimeric polypeptide is also referred to as an "expression host." As noted above, in some cases, the individual polypeptide chains of a multimeric polypeptide of the present disclosure are encoded in separate recombinant expression vectors. In some cases, all polypeptide chains of a multimeric polypeptide of the present disclosure are encoded in a single recombinant expression vector.

Isolation of the multimeric polypeptide from the expression host cell (e.g., from a lysate of the expression host cell) and/or the culture medium in which the host cell is cultured, can be carried out using standard methods of protein purification.

For example, a lysate may be prepared of the expression host and the lysate purified using high performance liquid chromatography (HPLC), exclusion chromatography, gel electrophoresis, affinity chromatography, or other purification technique. Alternatively, where the multimeric polypeptide is secreted from the expression host cell into the culture medium, the multimeric polypeptide can be purified from the culture medium using HPLC, exclusion chromatography, gel electrophoresis, affinity chromatography, or other purification technique. In some cases, the compositions which are used will comprise at least 80% by weight of the desired product, at least about 85% by weight, at least about 95% by weight, or at least about 99.5% by weight, in relation to contaminants related to the method of preparation of the product and its purification. The percentages can be based upon total protein.

In some cases, e.g., where the multimeric polypeptide comprises an affinity tag, the multimeric polypeptide can be purified using an immobilized binding partner of the affinity tag.

Compositions

The present disclosure provides compositions, including pharmaceutical compositions, comprising a variant CD86 polypeptide of the present disclosure. The present disclosure provides compositions, including pharmaceutical compositions, comprising a multimeric polypeptide of the present disclosure. The present disclosure provides compositions, including pharmaceutical compositions, comprising a nucleic acid or a recombinant expression vector of the present disclosure.

Compositions Comprising a Multimeric Polypeptide

A composition of the present disclosure can comprise, in addition to a multimeric polypeptide of the present disclosure, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can comprise a multimeric polypeptide of the present disclosure, and a pharmaceutically acceptable excipient. In some cases, a subject pharmaceutical composition will be suitable for administration to a subject, e.g., will be sterile. For example, in some embodiments, a subject pharmaceutical composition will be suitable for administration to a human subject, e.g., where the composition is sterile and is free of detectable pyrogens and/or other toxins.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where a multimeric polypeptide of the present disclosure is administered as an injectable (e.g. subcutaneously, intraperitoneally, intramuscularly, and/or intravenously) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The protein-containing formulations may also be provided so as to enhance serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 Ann. Rev. Biophys. Bioeng. 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a multimeric polypeptide of the present disclosure in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising a composition of the present disclosure, e.g., a liquid composition. The container can be, e.g., a syringe, an ampoule, and the like. In some cases, the container is sterile. In some cases, both the container and the composition are sterile.

The present disclosure provides compositions, including pharmaceutical compositions, comprising a variant CD86 polypeptide of the present disclosure. A composition can comprise: a) a variant CD86 polypeptide of the present disclosure; and b) an excipient, as described above for the multimeric polypeptides. In some cases, the excipient is a pharmaceutically acceptable excipient.

Compositions Comprising a Nucleic Acid or a Recombinant Expression Vector

The present disclosure provides compositions, e.g., pharmaceutical compositions, comprising a nucleic acid or a recombinant expression vector of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A composition of the present disclosure can include: a) a subject nucleic acid or recombinant expression vector; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl) methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris (hydroxymethyl)-aminomethane (Tris), etc.). Suitable salts include, e.g., NaCl, $MgCl_2$, KCl, $MgSO_4$, etc.

A pharmaceutical formulation of the present disclosure can include a nucleic acid or recombinant expression vector of the present disclosure in an amount of from about 0.001% to about 90% (w/w). In the description of formulations, below, "subject nucleic acid or recombinant expression vector" will be understood to include a nucleic acid or recombinant expression vector of the present disclosure. For example, in some embodiments, a subject formulation comprises a nucleic acid or recombinant expression vector of the present disclosure.

A subject nucleic acid or recombinant expression vector can be admixed, encapsulated, conjugated or otherwise associated with other compounds or mixtures of compounds; such compounds can include, e.g., liposomes or receptor-targeted molecules. A subject nucleic acid or recombinant expression vector can be combined in a formulation with one or more components that assist in uptake, distribution and/or absorption.

A subject nucleic acid or recombinant expression vector composition can be formulated into any of many possible dosage forms such as, but not limited to, tablets, capsules, gel capsules, liquid syrups, soft gels, suppositories, and enemas. A subject nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a subject nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG)

moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

Methods of Modulating T Cell Activity

The present disclosure provides a method of selectively modulating the activity of an epitope-specific T cell, the method comprising contacting the T cell with a multimeric polypeptide of the present disclosure, where contacting the T cell with a multimeric polypeptide of the present disclosure selectively modulates the activity of the epitope-specific T cell. In some cases, the contacting occurs in vitro. In some cases, the contacting occurs in vivo. In some cases, the contacting occurs ex vivo.

In some cases, e.g., where the target T cell is a $CD8^+$ T cell, the multimeric polypeptide comprises Class I MHC polypeptides (e.g., β2-microglobulin and Class I MHC heavy chain). In some cases, e.g., where the target T cell is a CD4+ T cell, the multimeric polypeptide comprises Class II MHC polypeptides (e.g., Class II MHC α chain; Class II MHC 3 chain).

Where a multimeric polypeptide of the present disclosure includes an immunomodulatory polypeptide that is an activating polypeptide, contacting the T cell with the multimeric polypeptide activates the epitope-specific T cell. In some instances, the epitope-specific T cell is a T cell that is specific for an epitope present on a cancer cell, and contacting the epitope-specific T cell with the multimeric polypeptide increases cytotoxic activity of the T cell toward the cancer cell. In some instances, the epitope-specific T cell is a T cell that is specific for an epitope present on a cancer cell, and contacting the epitope-specific T cell with the multimeric polypeptide increases the number of the epitope-specific T cells.

In some instances, the epitope-specific T cell is a T cell that is specific for an epitope present on a virus-infected cell, and contacting the epitope-specific T cell with the multimeric polypeptide increases cytotoxic activity of the T cell toward the virus-infected cell. In some instances, the epitope-specific T cell is a T cell that is specific for an epitope present on a virus-infected cell, and contacting the epitope-specific T cell with the multimeric polypeptide increases the number of the epitope-specific T cells.

Where a multimeric polypeptide of the present disclosure includes an immunomodulatory polypeptide that is an inhibiting polypeptide, contacting the T cell with the multimeric inhibits the epitope-specific T cell. In some instances, the epitope-specific T cell is a self-reactive T cell that is specific for an epitope present in a self antigen, and the contacting reduces the number of the self-reactive T cells.

Methods of Selectively Delivering A CD86 Polypeptide

The present disclosure provides a method of delivering a costimulatory polypeptide such as CD86, or a reduced-affinity variant of a naturally occurring costimulatory polypeptide such as a CD86 variant disclosed herein, to a selected T cell or a selected T cell population, e.g., in a manner such that a TCR specific for a given epitope is targeted. The present disclosure provides a method of delivering a costimulatory polypeptide such as CD86, or a reduced-affinity variant of a naturally occurring comstimulatory polypeptide such as a CD86 variant disclosed herein, selectively to a target T cell bearing a TCR specific for the epitope present in a multimeric polypeptide of the present disclosure. The method comprises contacting a population of T cells with a multimeric polypeptide of the present disclosure. The population of T cells can be a mixed population that comprises: i) the target T cell; and ii) non-target T cells that are not specific for the epitope (e.g., T cells that are specific for an epitope(s) other than the epitope to which the epitope-specific T cell binds). The epitope-specific T cell is specific for the epitope-presenting peptide present in the multimeric polypeptide, and binds to the peptide HLA complex or peptide MHC complex provided by the multimeric polypeptide. Contacting the population of T cells with the multimeric polypeptide delivers the costimulatory polypeptide (e.g., CD86 or a reduced-affinity variant of CD86) present in the multimeric polypeptide selectively to the T cell(s) that are specific for the epitope present in the multimeric polypeptide.

Thus, the present disclosure provides a method of delivering a costimulatory polypeptide such as CD86, or a reduced-affinity variant of a naturally occurring costimulatory polypeptide such as a CD86 variant disclosed herein, or a combination of both, selectively to a target T cell, the method comprising contacting a mixed population of T cells with a multimeric polypeptide of the present disclosure. The mixed population of T cells comprises the target T cell and non-target T cells. The target T cell is specific for the epitope present within the multimeric polypeptide. Contacting the mixed population of T cells with a multimeric polypeptide of the present disclosure delivers the costimulatory polypeptide(s) present within the multimeric polypeptide to the target T cell.

For example, a multimeric polypeptide of the present disclosure is contacted with a population of T cells comprising: i) a target T cell(s) that is specific for the epitope present in the multimeric polypeptide; and ii) a non-target T cell(s), e.g., a T cell(s) that is specific for a second epitope(s) that is not the epitope present in the multimeric polypeptide. Contacting the population results in selective delivery of the costimulatory polypeptide(s) (e.g., naturally-occurring costimulatory polypeptide (e.g., naturally occurring CD86) or reduced-affinity variant of a naturally occurring costimulatory polypeptide (e.g., a CD86 variant disclosed herein)), which is present in the multimeric polypeptide, to the target T cell. Thus, e.g., less than 50%, less than 40%, less than 30%, less than 25%, less than 20%, less than 15%, less than 10%, less than 5%, or less than 4%, 3%, 2% or 1%, of the non-target T cells bind the multimeric polypeptide and, as a result, the costimulatory polypeptide (e.g., CD86 or CD86 variant) is not delivered to the non-target T cells.

In some cases, the population of T cells is in vitro. In some cases, the population of T cells is in vitro, and a biological response (e.g., T cell activation and/or expansion and/or phenotypic differentiation) of the target T cell population to the multimeric polypeptide of the present disclosure is elicited in the context of an in vitro culture. For example, a mixed population of T cells can be obtained from an individual, and can be contacted with the multimeric polypeptide in vitro. Such contacting can comprise single or multiple exposures of the population of T cells to a defined dose(s) and/or exposure schedule(s). In some cases, said contacting results in selectively binding/activating and/or expanding target T cells within the population of T cells, and results in generation of a population of activated and/or expanded target T cells. As an example, a mixed population of T cells can be peripheral blood mononuclear cells (PBMC). For example, PBMC from a patient can be obtained by standard blood drawing and PBMC enrichment techniques before being exposed to 0.1-1000 nM of a multimeric polypeptide of the present disclosure under standard lymphocyte culture conditions. At time points before, during, and after exposure of the mixed T cell population at a defined dose and schedule, the abundance of target T cells in the in vitro culture can be monitored by specific peptide-MHC multimers and/or phenotypic markers and/or functional activity (e.g. cytokine ELISpot assays). In some cases, upon achieving an optimal abundance and/or phenotype of antigen specific cells in vitro, all or a portion of the population of activated and/or expanded target T cells is administered to the individual (the individual from whom the mixed population of T cells was obtained).

In some cases, the population of T cells is in vitro. For example, a mixed population of T cells is obtained from an individual, and is contacted with a multimeric polypeptide of the present disclosure in vitro. Such contacting, which can comprise single or multiple exposures of the T cells to a defined dose(s) and/or exposure schedule(s) in the context of in vitro cell culture, can be used to determine whether the mixed population of T cells includes T cells that are specific for the epitope presented by the multimeric polypeptide. The presence of T cells that are specific for the epitope of the multimeric polypeptide can be determined by assaying a sample comprising a mixed population of T cells, which population of T cells comprises T cells that are not specific for the epitope (non-target T cells) and may comprise T cells that are specific for the epitope (target T cells). Known assays can be used to detect activation and/or proliferation of the target T cells, thereby providing an ex vivo assay that can determine whether a particular multimeric polypeptide (synTac) possesses an epitope that binds to T cells present in the individual and thus whether the multimeric polypeptide has potential use as a therapeutic composition for that individual. Suitable known assays for detection of activation and/or proliferation of target T cells include, e.g., flow cytometric characterization of T cell phenotype and/or antigen specificity and/or proliferation. Such an assay to detect the presence of epitope-specific T cells, e.g., a companion diagnostic, can further include additional assays (e.g. effector cytokine ELISpot assays) and/or appropriate controls (e.g. antigen-specific and antigen-nonspecific multimeric peptide-HLA staining reagents) to determine whether the multimeric polypeptide is selectively binding/activating and/or expanding the target T cell. Thus, for example, the present disclosure provides a method of detecting, in a mixed population of T cells obtained from an individual, the presence of a target T cell that binds an epitope of interest, the method comprising: a) contacting in vitro the mixed population of T cells with a multimeric polypeptide of the present disclosure, wherein the multimeric polypeptide comprises the epitope of interest; and b) detecting activation and/or proliferation of T cells in response to said contacting, wherein activated and/or proliferated T cells indicates the presence of the target T cell. Alternatively, and/or in addition, if activation and/or expansion (proliferation) of the desired T cell population is obtained using the multimeric polypeptide, then all or a portion of the population of T cells comprising the activated/expanded T cells can be administered back to the individual as a therapy.

In some instances, the population of T cells is in vivo in an individual. In such instances, a method of the present disclosure for selectively delivering a costimulatory polypeptide (e.g., CD86 or a reduced-affinity CD86) to an epitope-specific T cell comprises administering the multimeric polypeptide to the individual.

The epitope-specific T cell to which a costimulatory polypeptide (e.g., CD86 or a reduced-affinity CD86) is being selectively delivered is also referred to herein as a "target T cell." In some cases, the target T cell is a regulatory T cell (Treg). In some cases, the Treg inhibits or suppresses activity of an autoreactive T cell.

In some cases, the target T cell is a cytotoxic T cell. In some cases, the target T cell is a $CD8^+$ cytotoxic T cell. For example, the target T cell can be a cytotoxic T cell specific for a cancer epitope (e.g., an epitope presented by a cancer cell).

Treatment Methods

The present invention provides a method of selectively modulating the activity of an epitope-specific T cell in an individual, the method comprising administering to the individual an amount of the multimeric polypeptide of the present disclosure, or one or more nucleic acids encoding the multimeric polypeptide, effective to selectively modulate the activity of an epitope-specific T cell in an individual. In some cases, a treatment method of the present disclosure comprises administering to an individual in need thereof one or more recombinant expression vectors comprising nucleotide sequences encoding a multimeric polypeptide of the present disclosure. In some cases, a treatment method of the present disclosure comprises administering to an individual in need thereof one or more mRNA molecules comprising nucleotide sequences encoding a multimeric polypeptide of the present disclosure. In some cases, a treatment method of the present disclosure comprises administering to an individual in need thereof a multimeric polypeptide of the present disclosure.

The present disclosure provides a method of selectively modulating the activity of an epitope-specific T cell in an individual, the method comprising administering to the individual an effective amount of a multimeric polypeptide of the present disclosure, or one or more nucleic acids (e.g., expression vectors; mRNA; etc.) comprising nucleotide sequences encoding the multimeric polypeptide, where the multimeric polypeptide selectively modulates the activity of the epitope-specific T cell in the individual. Selectively modulating the activity of an epitope-specific T cell can treat a disease or disorder in the individual. Thus, the present disclosure provides a treatment method comprising administering to an individual in need thereof an effective amount of a multimeric polypeptide of the present disclosure.

In some cases, the immunomodulatory polypeptide is an activating polypeptide, and the multimeric polypeptide activates the epitope-specific T cell. In some cases, the epitope is a cancer-associated epitope, and the multimeric polypeptide increases the activity of a T cell specific for the cancer-associate epitope.

The present disclosure provides a method of treating cancer in an individual, the method comprising administering to the individual an effective amount of a multimeric polypeptide of the present disclosure, or one or more nucleic acids (e.g., expression vectors; mRNA; etc.) comprising nucleotide sequences encoding the multimeric polypeptide, where the multimeric polypeptide comprises a T-cell epitope that is a cancer epitope, and where the multimeric polypeptide comprises a stimulatory immunomodulatory polypeptide. In some cases, an “effective amount” of a multimeric polypeptide is an amount that, when administered in one or more doses to an individual in need thereof, reduces the number of cancer cells in the individual. For example, in some cases, an “effective amount” of a multimeric polypeptide of the present disclosure is an amount that, when administered in one or more doses to an individual in need thereof, reduces the number of cancer cells in the individual by at least 10%, at least 15%, at least 20%, at least 25%, at least 30%, at least 40%, at least 50%, at least 60%, at least 70%, at least 80%, at least 90%, or at least 95%, compared to the number of cancer cells in the individual before administration of the multimeric polypeptide, or in the absence of administration with the multimeric polypeptide. In some cases, an “effective amount” of a multimeric polypeptide of the present disclosure is an amount that, when administered in one or more doses to an individual in need thereof, reduces the number of cancer cells in the individual to undetectable levels. In some cases, an “effective amount” of a multimeric polypeptide of the present disclosure is an amount that, when administered in one or more doses to an individual in need thereof, reduces the tumor mass in the individual. For example, in some cases, an “effective amount” of a multimeric polypeptide of the present disclosure is an amount that, when administered in one or more doses to an individual in need thereof, reduces the tumor mass in the individual by at least 10%, at least 15%, at least 20%, at least 25%, at least 30%, at least 40%, at least 50%, at least 60%, at least 70%, at least 80%, at least 90%, or at least 95%, compared to the tumor mass in the individual before administration of the multimeric polypeptide, or in the absence of administration with the multimeric polypeptide. In some cases, an “effective amount” of a multimeric polypeptide of the present disclosure is an amount that, when administered in one or more doses to an individual in need thereof, increases survival time of the individual. For example, in some cases, an “effective amount” of a multimeric polypeptide of the present disclosure is an amount that, when administered in one or more doses to an individual in need thereof, increases survival time of the individual by at least 1 month, at least 2 months, at least 3 months, from 3 months to 6 months, from 6 months to 1 year, from 1 year to 2 years, from 2 years to 5 years, from 5 years to 10 years, or more than 10 years, compared to the expected survival time of the individual in the absence of administration with the multimeric polypeptide.

In some instances, the epitope-specific T cell is a T cell that is specific for an epitope present on a virus-infected cell, and contacting the epitope-specific T cell with the multimeric polypeptide increases cytotoxic activity of the T cell toward the virus-infected cell. In some instances, the epitope-specific T cell is a T cell that is specific for an epitope present on a virus-infected cell, and contacting the epitope-specific T cell with the multimeric polypeptide increases the number of the epitope-specific T cells.

Thus, the present disclosure provides a method of treating a virus infection in an individual, the method comprising administering to the individual an effective amount of a multimeric polypeptide of the present disclosure, or one or more nucleic acids comprising nucleotide sequences encoding the multimeric polypeptide, where the multimeric polypeptide comprises a T-cell epitope that is a viral epitope, and where the multimeric polypeptide comprises a stimulatory immunomodulatory polypeptide. In some cases, an “effective amount” of a multimeric polypeptide is an amount that, when administered in one or more doses to an individual in need thereof, reduces the number of virus-infected cells in the individual. For example, in some cases, an “effective amount” of a multimeric polypeptide of the present disclosure is an amount that, when administered in one or more doses to an individual in need thereof, reduces the number of virus-infected cells in the individual by at least 10%, at least 15%, at least 20%, at least 25%, at least 30%, at least 40%, at least 50%, at least 60%, at least 70%, at least 80%, at least 90%, or at least 95%, compared to the number of virus-infected cells in the individual before administration of the multimeric polypeptide, or in the absence of administration with the multimeric polypeptide. In some cases, an “effective amount” of a multimeric polypeptide of the present disclosure is an amount that, when administered in one or more doses to an individual in need thereof, reduces the number of virus-infected cells in the individual to undetectable levels.

Thus, the present disclosure provides a method of treating an infection in an individual, the method comprising administering to the individual an effective amount of a multimeric polypeptide of the present disclosure, or one or more nucleic acids comprising nucleotide sequences encoding the multimeric polypeptide, where the multimeric polypeptide comprises a T-cell epitope that is a pathogen-associated epitope, and where the multimeric polypeptide comprises a stimulatory immunomodulatory polypeptide. In some cases, an “effective amount” of a multimeric polypeptide is an amount that, when administered in one or more doses to an individual in need thereof, reduces the number of pathogens in the individual. For example, in some cases, an “effective amount” of a multimeric polypeptide of the present disclosure is an amount that, when administered in one or more doses to an individual in need thereof, reduces the number of pathogens in the individual by at least 10%, at least 15%, at least 20%, at least 25%, at least 30%, at least 40%, at least 50%, at least 60%, at least 70%, at least 80%, at least 90%, or at least 95%, compared to the number of pathogens in the individual before administration of the multimeric polypeptide, or in the absence of administration with the multimeric polypeptide. In some cases, an “effective amount” of a multimeric polypeptide of the present disclosure is an amount that, when administered in one or more doses to an individual in need thereof, reduces the number of pathogens in the individual to undetectable levels. Pathogens include viruses, bacteria, protozoans, and the like.

In some cases, the immunomodulatory polypeptide is an inhibitory polypeptide, and the multimeric polypeptide inhibits activity of the epitope-specific T cell. In some cases, the epitope is a self-epitope, and the multimeric polypeptide selectively inhibits the activity of a T cell specific for the self-epitope.

The present disclosure provides a method of treating an autoimmune disorder in an individual, the method comprising administering to the individual an effective amount of a multimeric polypeptide of the present disclosure, or one or more nucleic acids comprising nucleotide sequences encoding the multimeric polypeptide, where the multimeric polypeptide comprises a T-cell epitope that is a self epitope, and where the multimeric polypeptide comprises an inhibitory immunomodulatory polypeptide. In some cases, an "effective amount" of a multimeric polypeptide is an amount that, when administered in one or more doses to an individual in need thereof, reduces the number self-reactive T cells by at least 10%, at least 15%, at least 20%, at least 25%, at least 30%, at least 40%, at least 50%, at least 60%, at least 70%, at least 80%, at least 90%, or at least 95%, compared to number of self-reactive T cells in the individual before administration of the multimeric polypeptide, or in the absence of administration with the multimeric polypeptide. In some cases, an "effective amount" of a multimeric polypeptide is an amount that, when administered in one or more doses to an individual in need thereof, reduces production of Th2 cytokines in the individual. In some cases, an "effective amount" of a multimeric polypeptide is an amount that, when administered in one or more doses to an individual in need thereof, ameliorates one or more symptoms associated with an autoimmune disease in the individual.

As noted above, in some cases, in carrying out a subject treatment method, a multimeric polypeptide of the present disclosure is administered to an individual in need thereof, as the polypeptide per se. In other instances, in carrying out a subject treatment method, one or more nucleic acids comprising nucleotide sequences encoding a multimeric polypeptide of the present disclosure is/are administering to an individual in need thereof. Thus, in other instances, one or more nucleic acids of the present disclosure, e.g., one or more recombinant expression vectors of the present disclosure, is/are administered to an individual in need thereof.

Formulations

Suitable formulations are described above, where suitable formulations include a pharmaceutically acceptable excipient. In some cases, a suitable formulation comprises: a) a multimeric polypeptide of the present disclosure; and b) a pharmaceutically acceptable excipient. In some cases, a suitable formulation comprises: a) a nucleic acid comprising a nucleotide sequence encoding a multimeric polypeptide of the present disclosure; and b) a pharmaceutically acceptable excipient; in some instances, the nucleic acid is an mRNA. In some cases, a suitable formulation comprises: a) a first nucleic acid comprising a nucleotide sequence encoding the first polypeptide of a multimeric polypeptide of the present disclosure; b) a second nucleic acid comprising a nucleotide sequence encoding the second polypeptide of a multimeric polypeptide of the present disclosure; and c) a pharmaceutically acceptable excipient. In some cases, a suitable formulation comprises: a) a recombinant expression vector comprising a nucleotide sequence encoding a multimeric polypeptide of the present disclosure; and b) a pharmaceutically acceptable excipient. In some cases, a suitable formulation comprises: a) a first recombinant expression vector comprising a nucleotide sequence encoding the first polypeptide of a multimeric polypeptide of the present disclosure; b) a second recombinant expression vector comprising a nucleotide sequence encoding the second polypeptide of a multimeric polypeptide of the present disclosure; and c) a pharmaceutically acceptable excipient.

Suitable pharmaceutically acceptable excipients are described above.

Dosages

A suitable dosage can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A multimeric polypeptide of the present disclosure may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 g to 10 mg per kilogram of body weight per minute.

In some cases, a suitable dose of a multimeric polypeptide of the present disclosure is from 0.01 μg to 100 g per kg of body weight, from 0.1 μg to 10 g per kg of body weight, from 1 g to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a multimeric polypeptide of the present disclosure is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

Those of skill will readily appreciate that dose levels can vary as a function of the specific multimeric polypeptide, the severity of the symptoms and the susceptibility of the subject to side effects. Preferred dosages for a given compound are readily determinable by those of skill in the art by a variety of means.

In some embodiments, multiple doses of a multimeric polypeptide of the present disclosure, a nucleic acid of the present disclosure, or a recombinant expression vector of the present disclosure are administered. The frequency of administration of a multimeric polypeptide of the present disclosure, a nucleic acid of the present disclosure, or a recombinant expression vector of the present disclosure can vary depending on any of a variety of factors, e.g., severity of the symptoms, etc. For example, in some embodiments, a multimeric polypeptide of the present disclosure, a nucleic acid of the present disclosure, or a recombinant expression vector of the present disclosure is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a multimeric polypeptide of the present disclosure, a nucleic acid of the present disclosure, or a recombinant expression vector of the present disclosure, e.g., the period of time over which a multimeric polypeptide of the present disclosure, a nucleic acid of the present disclosure, or a recombinant expression vector of the present disclosure is administered, can vary, depending on any of a variety of factors, e.g., patient response, etc. For example, a multimeric polypeptide of the present disclosure, a nucleic acid of the present disclosure, or a recombinant expression vector of the present disclosure can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Routes of Administration

An active agent (a multimeric polypeptide of the present disclosure, a nucleic acid of the present disclosure, or a recombinant expression vector of the present disclosure) is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intratracheal, intracranial, subcutaneous, intradermal, topical application, intravenous, intraarterial, rectal, nasal, oral, and other enteral and parenteral routes of administration. Routes of administration may be combined, if desired, or adjusted depending upon the multimeric polypeptide and/or the desired effect. A multimeric polypeptide of the present disclosure, or a nucleic acid or recombinant expression vector of the present disclosure, can be administered in a single dose or in multiple doses.

In some embodiments, a multimeric polypeptide of the present disclosure, a nucleic acid of the present disclosure, or a recombinant expression vector of the present disclosure is administered intravenously. In some embodiments, a multimeric polypeptide of the present disclosure, a nucleic acid of the present disclosure, or a recombinant expression vector of the present disclosure is administered intramuscularly. In some embodiments, a multimeric polypeptide of the present disclosure, a nucleic acid of the present disclosure, or a recombinant expression vector of the present disclosure is administered locally. In some embodiments, a multimeric polypeptide of the present disclosure, a nucleic acid of the present disclosure, or a recombinant expression vector of the present disclosure is administered intratumorally. In some embodiments, a multimeric polypeptide of the present disclosure, a nucleic acid of the present disclosure, or a recombinant expression vector of the present disclosure is administered peritumorally. In some embodiments, a multimeric polypeptide of the present disclosure, a nucleic acid of the present disclosure, or a recombinant expression vector of the present disclosure is administered intracranially. In some embodiments, a multimeric polypeptide of the present disclosure, a nucleic acid of the present disclosure, or a recombinant expression vector of the present disclosure is administered subcutaneously.

In some embodiments, a multimeric polypeptide of the present disclosure is administered intravenously. In some embodiments, a multimeric polypeptide of the present disclosure is administered intramuscularly. In some embodiments, a multimeric polypeptide of the present disclosure is administered locally. In some embodiments, a multimeric polypeptide of the present disclosure is administered intratumorally. In some embodiments, a multimeric polypeptide of the present disclosure is administered peritumorally. In some embodiments, a multimeric polypeptide of the present disclosure is administered intracranially. In some embodiments, a multimeric polypeptide is administered subcutaneously.

A multimeric polypeptide of the present disclosure, a nucleic acid of the present disclosure, or a recombinant expression vector of the present disclosure can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, peritumoral, and intravenous routes, i.e., any route of administration other than through the alimentary canal. Parenteral administration can be carried to effect systemic or local delivery of a multimeric polypeptide of the present disclosure, a nucleic acid of the present disclosure, or a recombinant expression vector of the present disclosure. Where systemic delivery is desired, administration typically involves invasive or systemically absorbed topical or mucosal administration of pharmaceutical preparations.

Subjects Suitable for Treatment

Subjects suitable for treatment with a method of the present disclosure include individuals who have cancer, including individuals who have been diagnosed as having cancer, individuals who have been treated for cancer but who failed to respond to the treatment, and individuals who have been treated for cancer and who initially responded but subsequently became refractory to the treatment. Subjects suitable for treatment with a method of the present disclosure include individuals who have an infection (e.g., an infection with a pathogen such as a bacterium, a virus, a protozoan, etc.), including individuals who have been diagnosed as having an infection, and individuals who have been treated for an infection but who failed to respond to the treatment. Subjects suitable for treatment with a method of the present disclosure include individuals who have bacterial infection, including individuals who have been diagnosed as having a bacterial infection, and individuals who have been treated for a bacterial infection but who failed to respond to the treatment. Subjects suitable for treatment with a method of the present disclosure include individuals who have a viral infection, including individuals who have been diagnosed as having a viral infection, and individuals who have been treated for a viral infection but who failed to respond to the treatment. Subjects suitable for treatment with a method of the present disclosure include individuals who have an autoimmune disease, including individuals who have been diagnosed as having an autoimmune disease, and individuals who have been treated for a autoimmune disease but who failed to respond to the treatment.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-89 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A variant CD86 immunomodulatory polypeptide comprising an amino acid sequence having at least 85% amino acid sequence identity to set forth in one of SEQ ID NOs:1, 2, and 4, wherein the variant CD86 immunomodulatory polypeptide has one or more amino acid substitutions relative to set forth in one of SEQ ID NOs:1, 2, and 4, and wherein the variant CD86 immunomodulatory polypeptide exhibits reduced binding affinity to a CD28 polypeptide having an amino acid sequence depicted in one of FIG. 3A-3C, compared to the binding affinity of the CD86 amino acid sequence set forth in one of SEQ ID NOs:1, 2, and 4 for the CD86 polypeptide.

Aspect 2. The variant CD86 polypeptide of aspect 1, wherein the variant comprises a substitution of one or more of N61, D66, W70, H91, F33, Q35, V41, L72, and Y59.

Aspect 3. The variant CD86 polypeptide of aspect 1 or aspect 2, wherein the variant immunomodulatory polypeptide exhibits from less than 10% to less than 50% of the binding affinity exhibited by the CD86 amino acid sequence set forth in SEQ ID NO:1 for the CD28 polypeptide.

Aspect 4. The variant CD86 polypeptide of any one of aspects 1-3, wherein the variant comprises a substitution of H91 with Arg, Asn Asp, Cys, Gln, Glu, Gly, Ile, Leu, Lys, Met, Phe, Pro, Ser, Thr, Trp, Tyr, or Val.

Aspect 5. The variant CD86 polypeptide of any one of aspects 1-3, wherein the variant comprises a substitution of H91 and D66.

Aspect 6. The variant CD86 polypeptide of any one of aspects 1-3, wherein the variant comprises a substitution of H91 and N61.

Aspect 7. The variant CD86 polypeptide of any one of aspects 1-3, wherein the variant comprises a substitution of H91, N61, and D66.

Aspect 8. A multimeric polypeptide comprising: a) a first polypeptide comprising, in order from N-terminus to C-terminus: i) an epitope; ii) a first major histocompatibility complex (MHC) polypeptide; and b) a second polypeptide comprising, in order from N-terminus to C-terminus: i) a second MHC polypeptide; and ii) optionally an immunoglobulin (Ig) Fc polypeptide or a non-Ig scaffold, wherein the multimeric polypeptide comprises one or more immunomodulatory domains, wherein the one or more immunomodulatory domain is: A) at the C-terminus of the first polypeptide; B) at the N-terminus of the second polypeptide; C) at the C-terminus of the second polypeptide; or D) at the C-terminus of the first polypeptide and at the N-terminus of the second polypeptide, wherein at least one of the one or more immunomodulatory domains is a variant CD86 polypeptide of any one of aspects 1-7, and wherein the multimeric polypeptide exhibits reduced binding affinity to a CD28 polypeptide having an amino acid sequence depicted in one of FIG. 3A-3C, compared to the binding affinity of a control multimeric polypeptide comprising an immunomodulatory domain comprising the CD86 amino acid sequence set forth in one of SEQ ID NOs:1, 2, and 4 for the CD28 polypeptide.

Aspect 9. The multimeric polypeptide of aspect 8, wherein: a) the first polypeptide comprises, in order from N-terminus to C-terminus: i) the epitope; ii) the first MHC polypeptide; and iii) the variant CD86 polypeptide; and b) the second polypeptide comprises, in order from N-terminus to C-terminus: i) the second MHC polypeptide; and ii) the Ig Fc polypeptide.

Aspect 10. The multimeric polypeptide of aspect 8, wherein: a) the first polypeptide comprises, in order from N-terminus to C-terminus: i) the epitope; and ii) the first MHC polypeptide; and b) the second polypeptide comprises, in order from N-terminus to C-terminus: i) the variant CD86 polypeptide; ii) the second MHC polypeptide; and iii) the Ig Fc polypeptide.

Aspect 11. The multimeric polypeptide of aspect 8, wherein: a) the first polypeptide comprises, in order from N-terminus to C-terminus: i) the epitope; and ii) the first MHC polypeptide; and b) the second polypeptide comprises, in order from N-terminus to C-terminus: i) the second MHC polypeptide; and ii) the variant CD86 polypeptide.

Aspect 12. The multimeric polypeptide of aspect 8, wherein: a) the first polypeptide comprises, in order from N-terminus to C-terminus: i) the epitope; and ii) the first MHC polypeptide; and b) second polypeptide comprising, in order from N-terminus to C-terminus: i) the variant CD86 polypeptide; and ii) the second MHC polypeptide.

Aspect 13. The multimeric polypeptide of aspect 8, wherein: a) the first polypeptide comprises, in order from N-terminus to C-terminus: i) the epitope; ii) the first MHC polypeptide; and iii) the variant CD86 polypeptide; and b) the second polypeptide comprises the second MHC polypeptide.

Aspect 14. The multimeric polypeptide of aspect 8, wherein the non-Ig scaffold is an XTEN polypeptide, a transferrin polypeptide, an elastin-like polypeptide, a silk-like polypeptide, or a silk-elastin-like polypeptide.

Aspect 15. The multimeric polypeptide of any one of aspects 8-14, wherein the first MHC polypeptide is a β2-microglobulin polypeptide; and wherein the second MHC polypeptide is an MHC class I heavy chain polypeptide.

Aspect 16. The multimeric polypeptide of aspect 15, wherein the β2-microglobulin polypeptide comprises an amino acid sequence having at least 85% amino acid sequence identity to one of the amino acid sequences set forth in FIG. 6.

Aspect 17. The multimeric polypeptide of aspect 15, wherein the MHC class I heavy chain polypeptide is an HLA-A, an HLA-B, or an HLA-C heavy chain.

Aspect 18. The multimeric polypeptide of aspect 15, wherein the MHC class I heavy chain polypeptide comprises an amino acid sequence having at least 85% amino acid sequence identity to the amino acid sequence set forth in one of FIG. 5A-5C.

Aspect 19. The multimeric polypeptide of any one of aspects 8-14, wherein the first MHC polypeptide is an MHC Class II alpha chain polypeptide; and wherein the second MHC polypeptide is an MHC class II beta chain polypeptide.

Aspect 20. The multimeric polypeptide of any one of aspects 8-19, wherein the epitope is a T-cell epitope.

Aspect 21. The multimeric polypeptide of any one of aspects 8-13 and 15-20, wherein multimeric polypeptide comprises an Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect 22. The multimeric polypeptide of aspect 21, wherein the Ig Fc polypeptide comprises an amino acid sequence having at least 85% amino acid sequence identity to an amino acid sequence depicted in FIG. 4A-4C.

Aspect 23. The multimeric polypeptide of any one of aspects 8-22, wherein the first polypeptide and the second polypeptide are non-covalently associated.

Aspect 24. The multimeric polypeptide of any one of aspects 8-22, wherein the first polypeptide and the second polypeptide are covalently linked.

Aspect 25. The multimeric polypeptide of aspect 24, wherein the covalent linkage is via a disulfide bond.

Aspect 26. The multimeric polypeptide of aspect 25, wherein the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the disulfide linkage is between the first and the second Cys residues.

Aspect 27. The multimeric polypeptide of any one of aspects 8-26, comprising a linker interposed between the epitope and the first MHC polypeptide.

Aspect 28. The multimeric polypeptide of any one of aspects 8-26, comprising a linker interposed between the MHC polypeptide and the immunomodulatory polypeptide.

Aspect 29. The multimeric polypeptide of any one of aspects 8-28, comprising 2 variant CD86 polypeptides.

Aspect 30. The multimeric polypeptide of any one of aspects 8-28, comprising 3 variant CD86 polypeptides.

Aspect 31. The multimeric polypeptide of aspect 29 or aspect 30, wherein the 2 or 3 variant CD86 polypeptides are in tandem, and wherein the multimeric polypeptide comprises a linker between the variant CD86 polypeptides.

Aspect 32. The multimeric polypeptide of any one of aspects 8-28, wherein the variant CD86 comprises a substitution of one or more of N61, D66, W70, H91, F33, Q35, V41, L72, and Y59.

Aspect 33. The multimeric polypeptide of any one of aspects 8-28, wherein the variant CD86 comprises a substitution of H91 with Arg, Asn Asp, Cys, Gln, Glu, Gly, Ile, Leu, Lys, Met, Phe, Pro, Ser, Thr, Trp, Tyr, or Val.

Aspect 34. The multimeric polypeptide of aspect 33, wherein the variant CD86 comprises a substitution of H91 and D66.

Aspect 35. The multimeric polypeptide of aspect 33, wherein the variant CD86 comprises a substitution of H91 and N61.

Aspect 36. The multimeric polypeptide of aspect 33, wherein the variant CD86 comprises a substitution of H91, N61, and D66.

Aspect 37. A nucleic acid comprising a nucleotide sequence encoding a recombinant polypeptide, i) wherein the recombinant polypeptide comprises, in order from N-terminus to C-terminus: a) an epitope; b) a first major histocompatibility complex (MHC) polypeptide; c) an immunomodulatory polypeptide; d) a proteolytically cleavable linker or a ribosome skipping signal; e) a second MHC polypeptide; and f) an immunoglobulin (Ig) Fc polypeptide; wherein the immunomodulatory polypeptide is a variant immunomodulatory polypeptide of any one of aspects 1-7; or ii) wherein the recombinant polypeptide comprises, in order from N-terminus to C-terminus: a) an epitope; b) a first MHC polypeptide; c) a proteolytically cleavable linker or a ribosome skipping signal; d) an immunomodulatory polypeptide; e) a second MHC polypeptide; and f) an Ig Fc polypeptide, wherein the immunomodulatory polypeptide is a variant immunomodulatory polypeptide of any one of aspects 1-7.

Aspect 38. The nucleic acid of aspect 37, wherein the first MHC polypeptide is a 02-microglobulin polypeptide; and wherein the second MHC polypeptide is an MHC class I heavy chain polypeptide.

Aspect 39. The nucleic acid of aspect 38, wherein the β2-microglobulin polypeptide comprises an amino acid sequence having at least 85% amino acid sequence identity to one of the amino acid sequences set forth in FIG. 6.

Aspect 40. The nucleic acid of aspect 38, wherein the MHC class I heavy chain polypeptide is an HLA-A, HLA-B, or HLA-C heavy chain.

Aspect 41. The nucleic acid of aspect 40, wherein the MHC class I heavy chain polypeptide comprises an amino acid sequence having at least 85% amino acid sequence identity to the amino acid sequence set forth in any one of FIG. 5A-5C.

Aspect 42. The nucleic acid of aspect 37, wherein the first MHC polypeptide is an MHC Class II alpha chain polypeptide; and wherein the second MHC polypeptide is an MHC class II beta chain polypeptide.

Aspect 43. The nucleic acid of any one of aspects 37-43, wherein the epitope is a T-cell epitope.

Aspect 44. The nucleic acid of any one of aspects 37-43, wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect 45. The nucleic acid of aspect 44, wherein the Ig Fc polypeptide comprises an amino acid sequence having at least 85% amino acid sequence identity to an amino acid sequence depicted in FIGS. 4A-4C.

Aspect 46. The nucleic acid of any one of aspects 37-45, wherein the variant CD86 immunomodulatory polypeptide comprises a substitution of one or more of N61, D66, W70, H91, F33, Q35, V41, L72, and Y59.

Aspect 47. The nucleic acid of any one of aspects 37-46, wherein the multimeric polypeptide comprises a second immunomodulatory polypeptide selected from a CD7, CD30L, CD40, CD70, CD83, HLA-G, MICA, MICB, HVEM, lymphotoxin beta receptor, 3/TR6, ILT3, ILT4, and HVEM.

Aspect 48. The nucleic acid of any one of aspects 37-47, wherein the proteolytically cleavable linker or ribosome skipping signal comprises an amino acid sequence selected from:

```
a)
                                  (SEQ ID NO: 86)
LEVLFQGP;

b)
                                  (SEQ ID NO: 87)
ENLYTQS;

c)
a furin cleavage site;

d)
                                  (SEQ ID NO: 89)
LVPR;

e)
                                  (SEQ ID NO: 90)
GSGATNFSLLKQAGDVEENPGP;
```

-continued f)
(SEQ ID NO: 91)
GSGEGRGSLLTCGDVEENPGP;

g)
(SEQ ID NO: 92)
GSGQCTNYALLKLAGDVESNPGP;
and h)
(SEQ ID NO: 93)
GSGVKQTLNFDLLKLAGDVESNPGP.

Aspect 49. The nucleic acid of aspect 31, wherein the recombinant polypeptide comprises, in order from N-terminus to C-terminus: a) a first leader peptide; b) the epitope; c) the first MHC polypeptide; d) the immunomodulatory polypeptide; e) the proteolytically cleavable linker or ribosome skipping signal; f) a second leader peptide; g) the second MHC polypeptide; and h) the immunoglobulin (Ig) Fc polypeptide.

Aspect 50. The nucleic acid of aspect 49, wherein the first leader peptide and the second leader peptide is a 32-M leader peptide.

Aspect 51. The nucleic acid of any one of aspects 37-50, wherein the nucleotide sequence is operably linked to a transcriptional control element.

Aspect 52. The nucleic acid of aspect 51, wherein the transcriptional control element is a promoter that is functional in a eukaryotic cell.

Aspect 53. The nucleic acid of any one of aspects 37-52, wherein the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the first and the second Cys residues provide for a disulfide linkage between the first MHC polypeptide and the second MHC polypeptide.

Aspect 54. A recombinant expression vector comprising the nucleic acid of any one of aspects 37-52.

Aspect 55. The recombinant expression vector of aspect 54, wherein the vector is a viral vector or a non-viral vector.

Aspect 56. A host cell genetically modified with the recombinant expression vector of any one of aspects 48-55.

Aspect 57. The host cell of aspect 56, wherein the host cell is in vitro.

Aspect 58. The host cell of aspect 57, wherein the host cell is genetically modified such that the cell does not produce an endogenous MHC β2-microglobulin polypeptide.

Aspect 59. A composition comprising: a) a first nucleic acid comprising a nucleotide sequence encoding a first polypeptide comprising, in order from N-terminus to C-terminus: i) an epitope; ii) a first MHC polypeptide; and iii) an immunomodulatory domain, wherein the immunomodulatory domain is a variant CD86 polypeptide of any one of aspects 1-7; and b) a first nucleic acid comprising a nucleotide sequence encoding a second polypeptide comprising, in order from N-terminus to C-terminus: i) a second MHC polypeptide; and ii) an Ig Fc polypeptide.

Aspect 60. A composition comprising: a) a first nucleic acid comprising a nucleotide sequence encoding a first polypeptide comprising, in order from N-terminus to C-terminus: i) an epitope; and ii) a first MHC polypeptide; and b) a first nucleic acid comprising a nucleotide sequence encoding a second polypeptide comprising, in order from N-terminus to C-terminus: i) an immunomodulatory domain, wherein the immunomodulatory domain is a variant CD86 polypeptide of any one of aspects 1-7; ii) a second MHC polypeptide; and iii) an Ig Fc polypeptide.

Aspect 61. The composition of aspect 59 or aspect 60, wherein the first and/or the second nucleic acid is present in a recombinant expression vector.

Aspect 62. A host cell genetically modified with the composition of any one of aspects 59-61.

Aspect 63. A method of producing the multimeric polypeptide of any one of aspects 8-36, the method comprising: a) culturing the host cell of any one of aspects 56-58 and 62 in vitro in a culture medium under conditions such that the host cell synthesizes the multimeric polypeptide; and b) isolating the multimeric polypeptide from the host cell and/or from the culture medium.

Aspect 63. The method of aspect 63, wherein the second polypeptide comprises an affinity tag, and wherein said isolating comprises contacting the multimeric polypeptide produced by the cell with a binding partner for the affinity tag, wherein the binding partner is immobilized, thereby immobilizing the multimeric polypeptide.

Aspect 65. The method of aspect 64, comprising eluting the immobilized multimeric polypeptide.

Aspect 66. A method of selectively activating an epitope-specific T cell, the method comprising contacting the T cell with the multimeric polypeptide of any one of aspects 8-36, wherein said contacting selectively activates the epitope-specific T cell.

Aspect 67. The method of aspect 66, wherein said contacting is in vitro.

Aspect 68. The method of aspect 66, wherein said contacting is in vivo.

Aspect 69. The method of aspect 66, wherein the epitope is a cancer-associated epitope, and wherein said administering selectively increases the activity of a T cell specific for the cancer-associate epitope.

Aspect 70. A method of treating cancer in an individual, the method comprising administering to the individual an effective amount of: a) the multimeric polypeptide of any one of aspects 8-36; or b) one or more recombinant expression vectors comprising nucleotide sequences encoding the multimeric polypeptide of any one of aspects 8-36; or c) one or more mRNAs comprising nucleotide sequences encoding the multimeric polypeptide of any one of aspects 8-36, wherein the epitope is a cancer-associated epitope, and wherein said administering effective to selectively activate a cancer epitope-specific T cell in an individual.

Aspect 71. The method of aspect 70, wherein said administering is subcutaneous.

Aspect 72. The method of aspect 70, wherein said administering is intravenous.

Aspect 73. The method of aspect 70, wherein said administering is peritumoral.

Aspect 74. The method of aspect 70, wherein said administering is systemic.

Aspect 75. The method of aspect 70, wherein said administering is distal to a treatment site.

Aspect 76. The method of aspect 70, wherein said administering is local.

Aspect 77. The method of aspect 70, wherein said administering is at or near a treatment site.

Aspect 78. A composition comprising: a) the multimeric polypeptide of any one of aspects 8-36; and b) a pharmaceutically acceptable excipient.

Aspect 79. A composition comprising: a) the nucleic acid of any one of aspects 37-53 or the recombinant expression vector of aspect 54 or aspect 55; and b) a pharmaceutically acceptable excipient.

Aspect 80. A method of delivering CD86 or a CD86 variant selectively to a target T cell, the method comprising contacting a mixed population of T cells with the multimeric polypeptide of any one of aspects 8-36, wherein the mixed population of T cells comprises the target T cell and non-target T cells, wherein the target T cell is specific for the epitope present within the multimeric polypeptide, and wherein said contacting delivers the CD86 or CD86 variant present within the multimeric polypeptide to the target T cell.

Aspect 81. The method of aspect 80, wherein the population of T cells is in vitro.

Aspect 82. The method of aspect 80, wherein the population of T cells is in vivo in an individual.

Aspect 83. The method of aspect 82, comprising administering the multimeric polypeptide to the individual.

Aspect 84. The method of any one of aspects 80 to 83, wherein the target T cell is a regulatory T cell.

Aspect 85. The method of any one of aspects 80 to 83, wherein the target T cell is a cytotoxic T cell.

Aspect 86. The method of aspect 80, wherein the mixed population of T cells is an in vitro population of mixed T cells obtained from an individual, and wherein said contacting results in activation and/or proliferation of the target T cell, generating a population of activated and/or proliferated target T cells.

Aspect 87. The method of aspect 80, wherein said activation results in increased production of IFN-γ and/or TNF-α by the target T cell.

Aspect 88. The method of aspect 86 or aspect 87, further comprising administering the population of activated and/or proliferated target T cells to the individual.

Aspect 89. A method of detecting, in a mixed population of T cells obtained from an individual, the presence of a target T cell that binds an epitope of interest, the method comprising: a) contacting in vitro the mixed population of T cells with the multimeric polypeptide of any one of aspects 8-36, wherein the multimeric polypeptide comprises the epitope of interest; and b) detecting activation and/or proliferation of T cells in response to said contacting, wherein activated and/or proliferated T cells indicates the presence of the target T cell.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: In Vitro Activity of CD86/synTac

In vitro activity included: effect on cell viability of a target cell population; effect on IFNγ production by $CD8^+$ T cells; and effect on production of TNF-α by $CD8^+$ T cells.

A CD86/synTac comprising CD86 ectodomain, a CD86/synTac comprising a CD86 IgV domain, and a CD86/synTac comprising a CD86 IgV domain with an H91A substitution, were constructed. The effects of 3.17 nM, 10.01 nM, 31.7 nM, and 100 nM of each CD86/synTac on cell viability, IFNγ production by CD8' T cells, and production of TNF-α by $CD8^+$ T cells, was tested. For comparison, an antibody to CD3/CD28 was used.

Figure 12A:
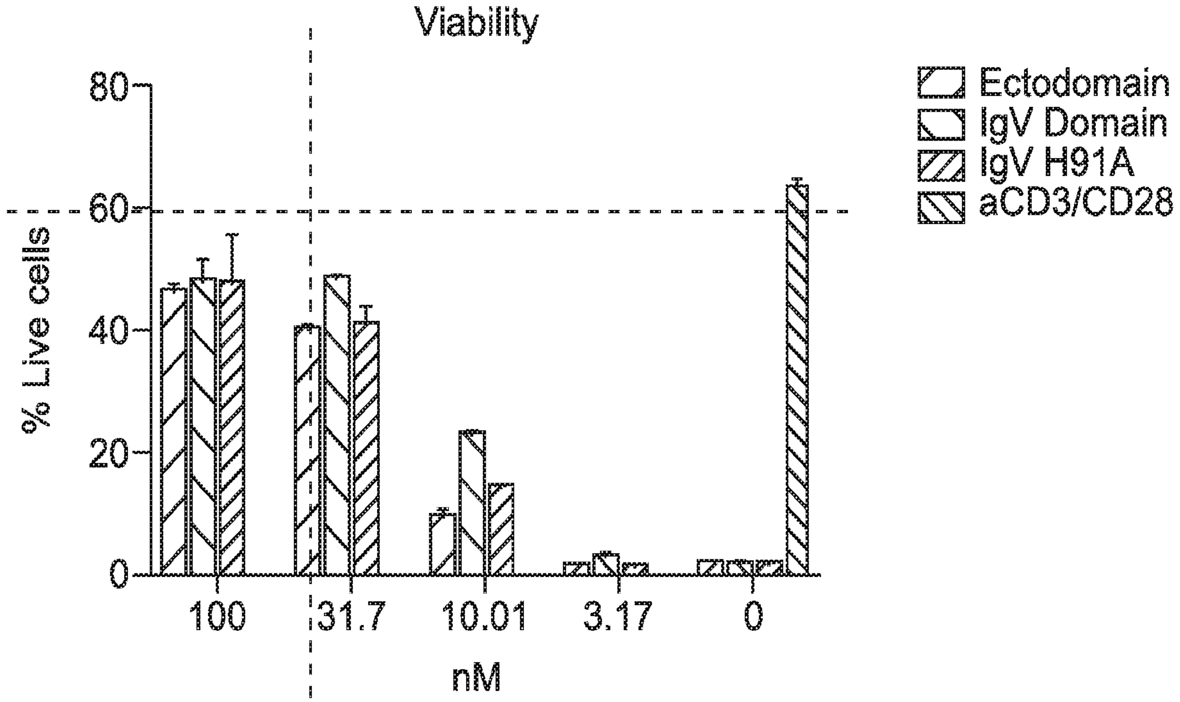
FIG. 12A-12C provide comparisons among the effect of a CD86/synTac including a full-length CD86 ectodomain, a CD86/synTac including a "minimal" CD86 IgV domain, and a CD86/synTac including a "minimal" CD86 IgV domain comprising an H91A substitution, on cell viability (FIG. 12A), production of IFN-γ (FIG. 12B), and production of TNF-α (FIG. 12C).
Figure 12B:
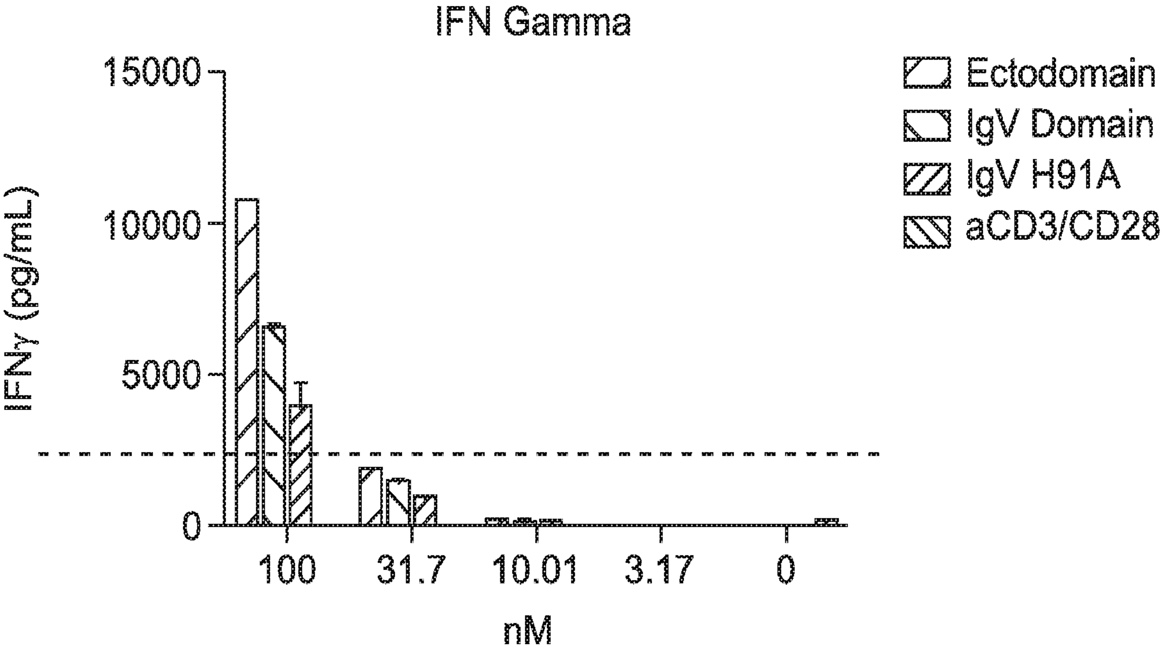
Figure 12C:
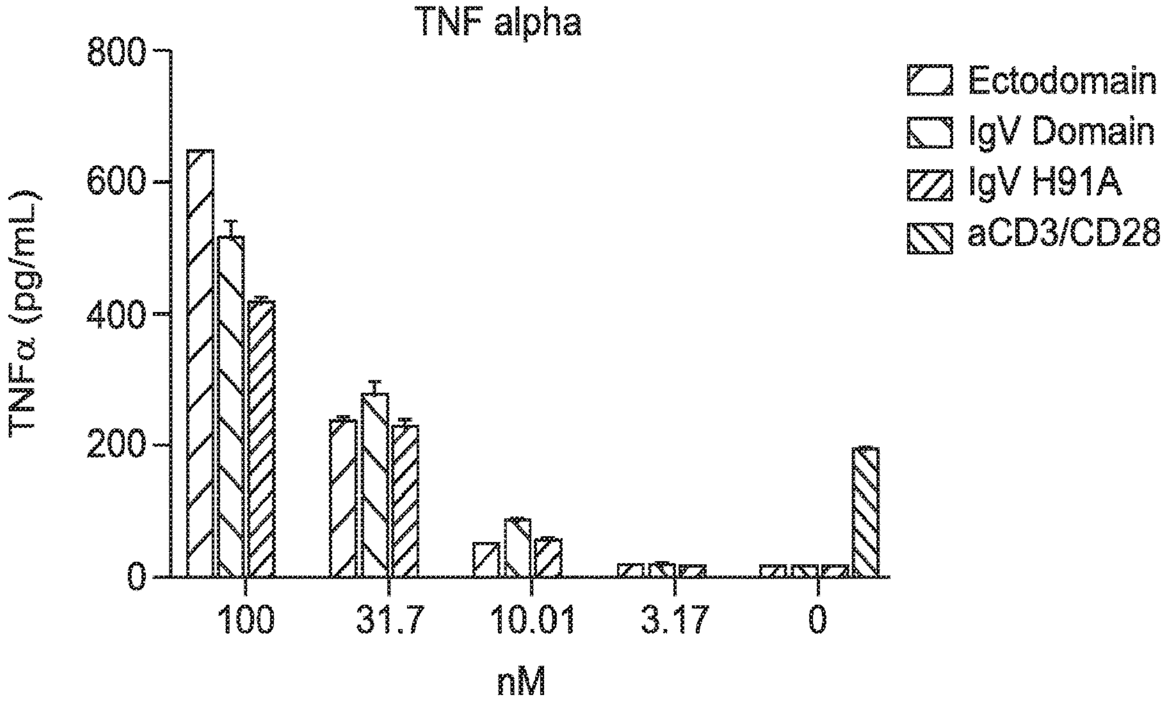

As shown in FIG. 12A all three constructs induced viability of $CD8^+$ T cells. As shown in FIG. 12B, all three constructs induced IFNγ production at 100 nM, with the construct including the CD86 ectodomain resulting in production of over 10,000 pg/mL IFNγ. As shown in FIG. 12C, all three constructs induced production of TNF-α, with the CD86 ectodomain resulting in production of over 600 pg/mL TNFα, and the other two constructions inducing somewhat less TNFα production.

FIG. 12A-12C provide comparisons among the effect of a CD86/synTac including a full-length CD86 ectodomain, a CD86/synTac including a "minimal" CD86 IgV domain, and a CD86/synTac including a "minimal" CD86 IgV domain comprising an H91A substitution, on cell viability (FIG. 12A), production of IFN-γ (FIG. 12B), and production of TNF-α (FIG. 12C).

Figure 13A:
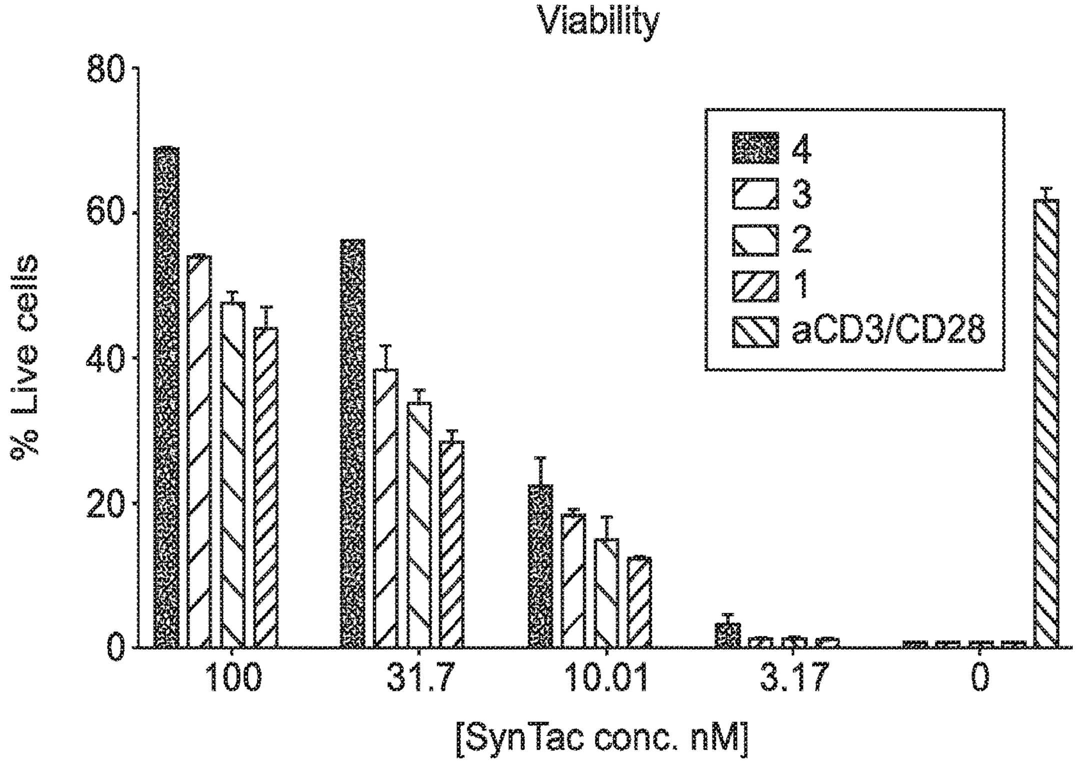
FIG. 13A-13F depict the effect of linker length of the L2 linker (linker between the costimulatory domain and MHC polypeptide) on cell viability (FIG. 13A), IFNγ production by $CD8^+$ T cells (FIG. 13B), and TNF-α production by $CD8^+$ T cells (FIG. 13C); and the effect of linker length of the L3 linker (linker between co-stimulatory domain repeats) on cell viability (FIG. 13D), IFNγ production by $CD8^+$ T cells (FIG. 13E), and TNF-α production by $CD8^+$ T cells (FIG. 13F).
Figure 13B:
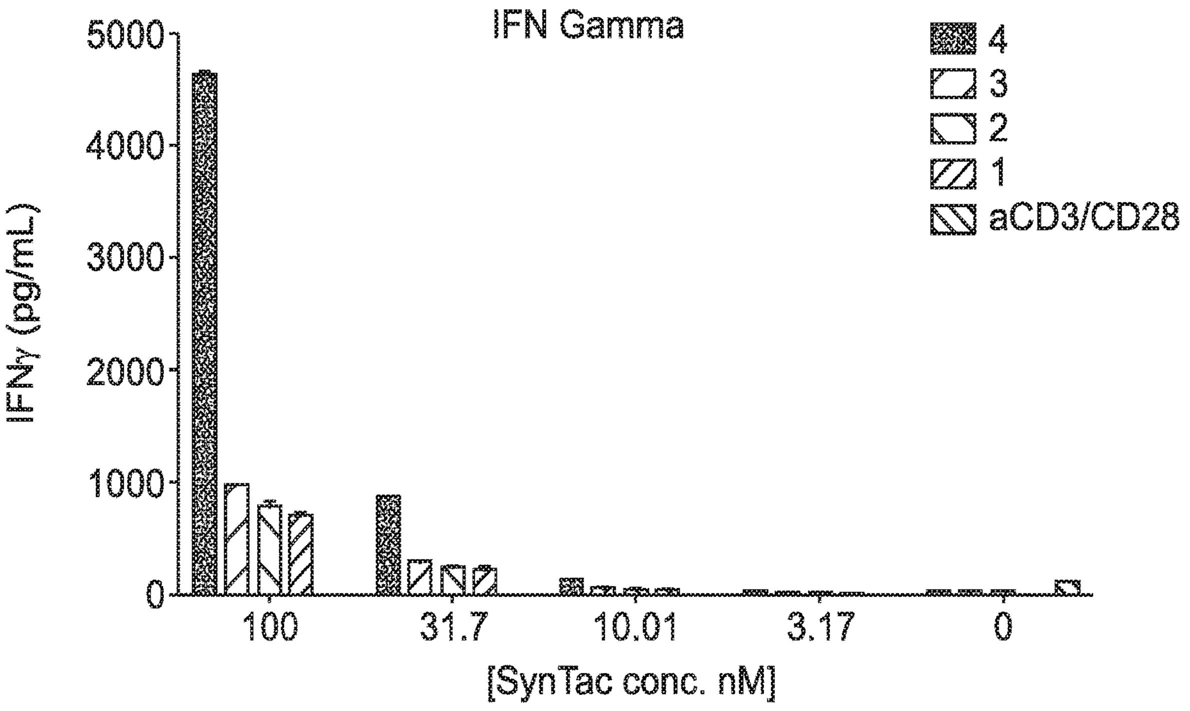
Figure 13C:
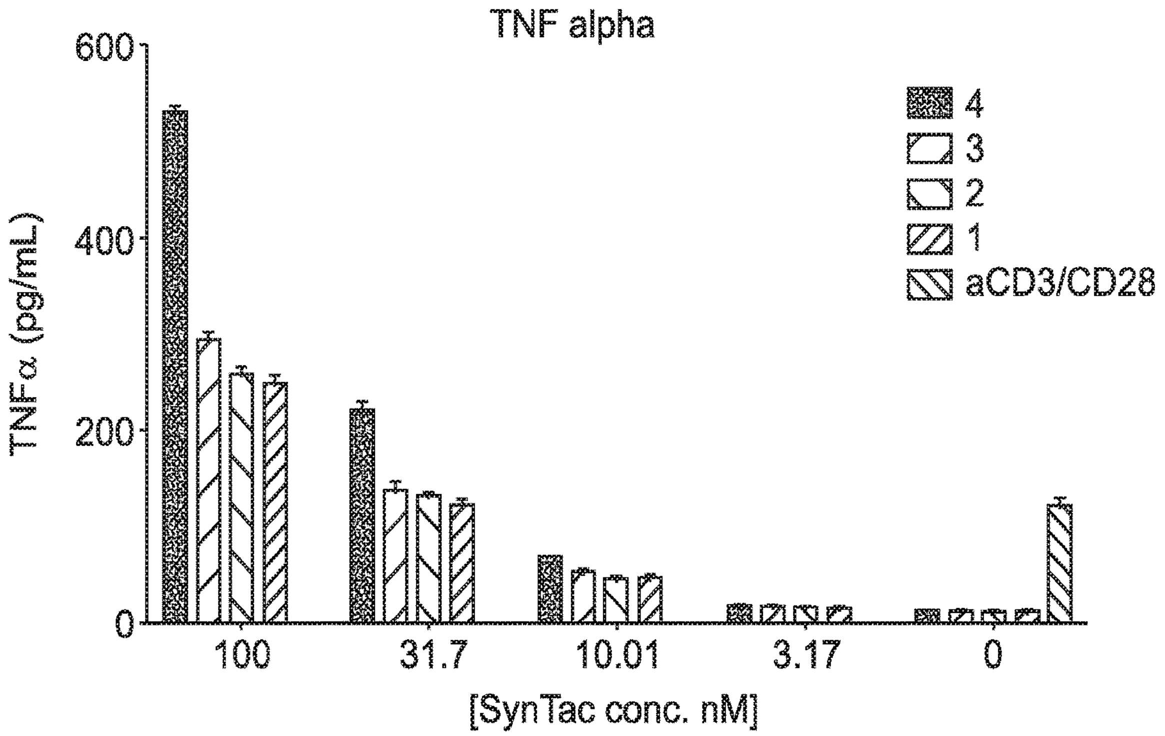
Figure 13D:
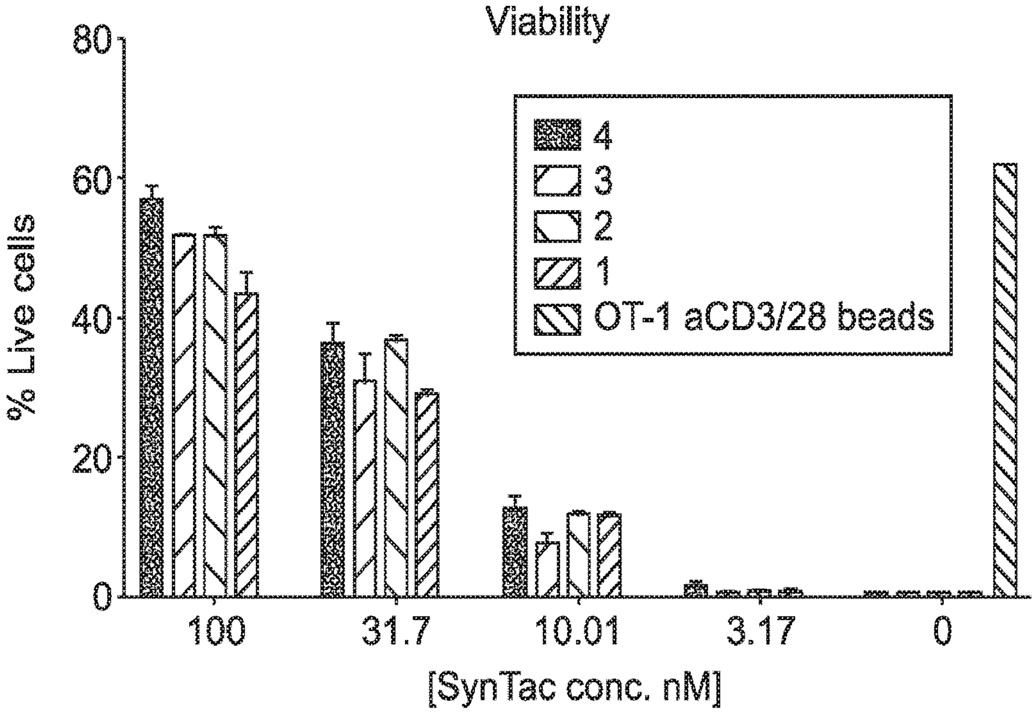
Figure 13E:
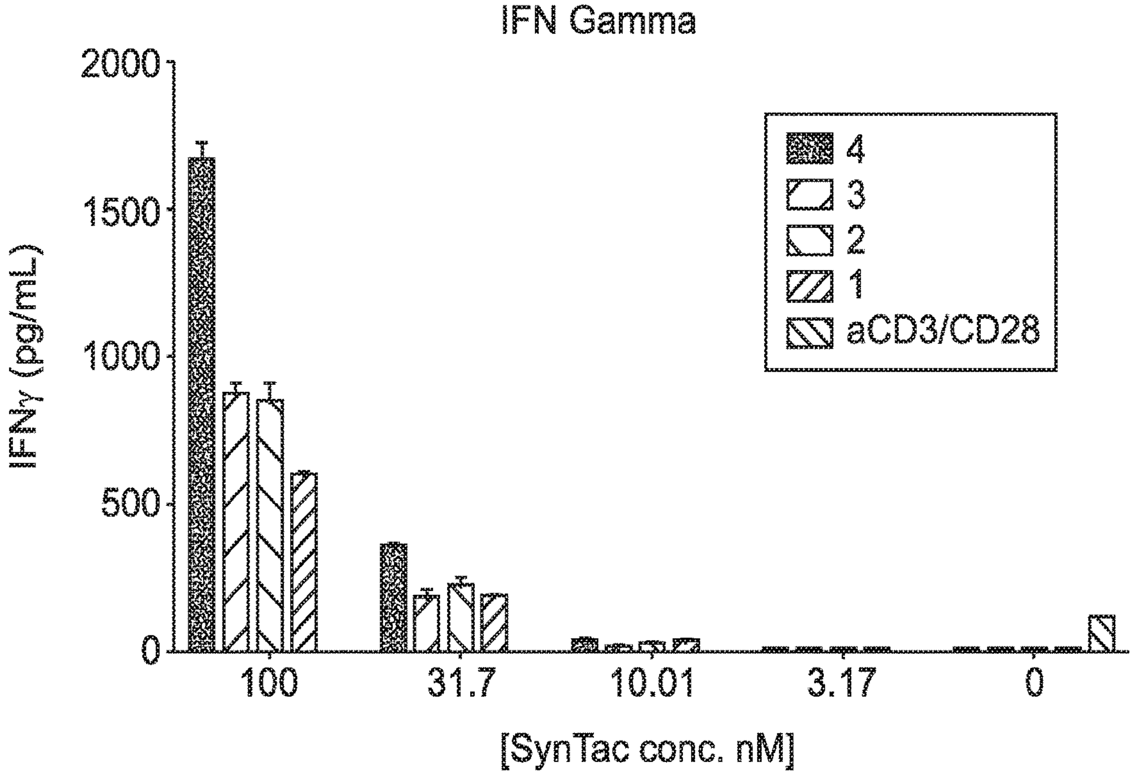

The effects of the linker length on cell viability of a target cell population, on IFNγ production by $CD8^+$ T cells, and production of TNF-α by $CD8^+$ T cells, were analyzed. Effects of the length of the linker between the costimulatory domain and MHC polypeptide (L2), and the length of the linker between co-stimulatory domain (CD86) repeats (L3), were assessed. The linkers were (Gly-Gly-Gly-Gly-Ser)x (SEQ ID NO:190), with x being 1, 2, 3, or 4. As shown in FIG. 13A-13C, the longer the L2 linker, the more pronounced the effect on target cell viability (FIG. 13A), IFNγ production by $CD8^+$ T cells (FIG. 13B), and production of TNF-α by $CD8^+$ T cells (FIG. 13C). Similar results were observed with the L3 linker.

Figure 13F:
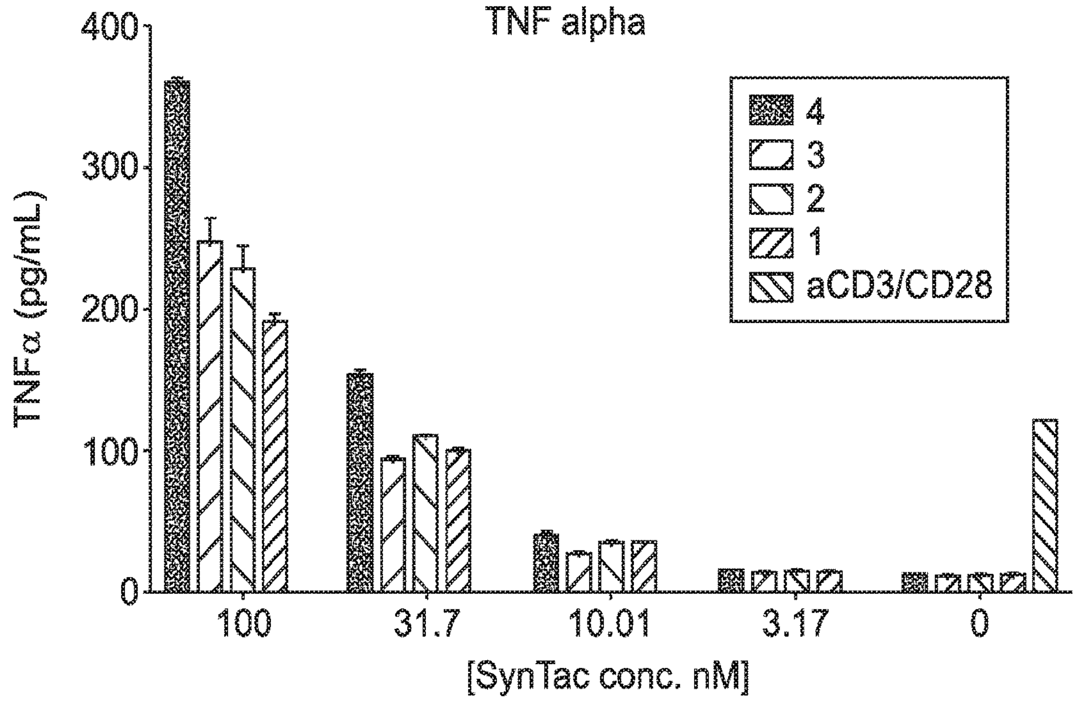

FIG. 13A-13F depict the effect of linker length of the L2 linker (linker between the costimulatory domain and MHC polypeptide) on cell viability (FIG. 13A), IFNγ production by $CD8^+$ T cells (FIG. 13B), and TNF-α production by $CD8^+$ T cells (FIG. 13C); and the effect of linker length of the L3 linker (linker between co-stimulatory domain repeats) on cell viability (FIG. 13D), IFNγ production by $CD8^+$ T cells (FIG. 13E), and TNF-α production by $CD8^+$ T cells (FIG. 13F).

Figure 14A:
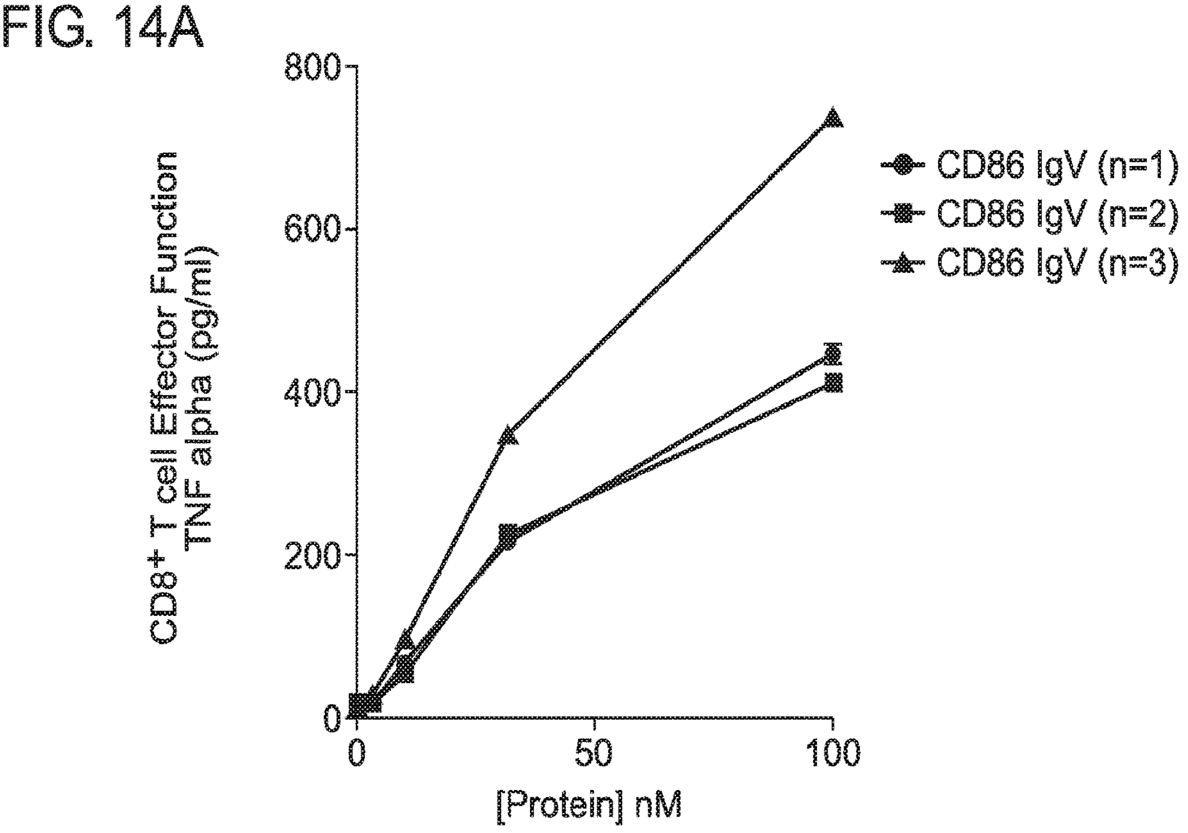
FIG. 14A-14D depict the effect of the number of costimulatory repeats on TNF-α production by $CD8^+$ T cells (FIG. 14A), on cell viability (FIG. 14B), on IFN-γ production (FIG. 14C), and on TNF-α production (FIG. 14D).
Figure 14B:
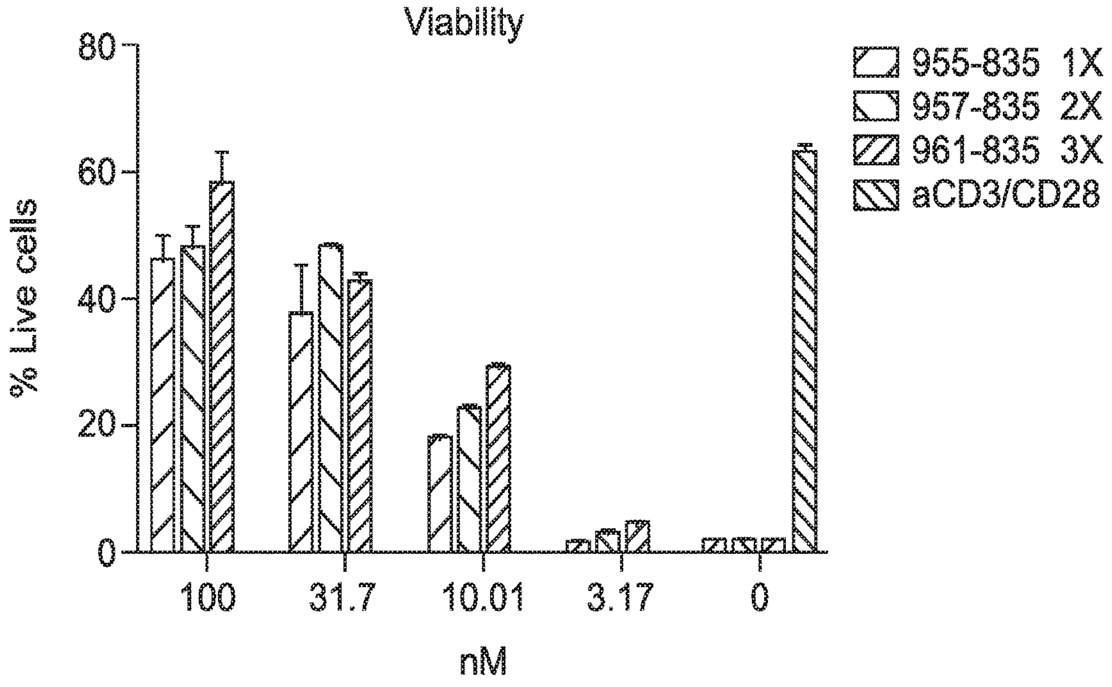
Figure 14C:
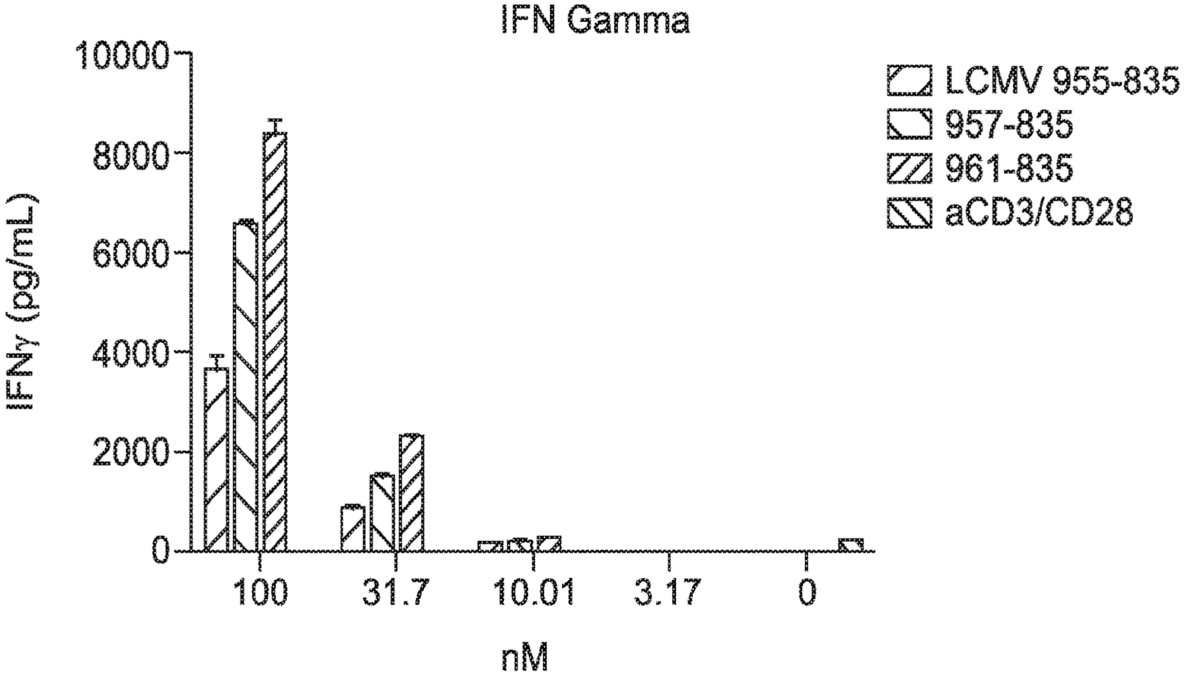

The effects of the number of CD86 repeats on cell viability of a target cell population, on IFNγ production by $CD8^+$ T cells, and production of TNF-α by $CD8^+$ T cells, were analyzed. As shown in FIG. 14A, the number of CD86 repeats had an effect on cell viability at 10 nM, but less of an effect at 31.7 nM and 100 nM. A CD86/synTac with 3 CD86 repeats induced more IFNγ production by $CD8^+$ T cells than did CD86/synTacs with 2 copies of CD86, or with 1 copy of CD86 (FIG. 14B). Similarly, A CD86/synTac with 3 CD86 repeats induced more TNF-α production by $CD8^+$ T cells than did CD86/synTacs with 2 copies of CD86, or with 1 copy of CD86 (FIG. 14C).

Figure 14D:
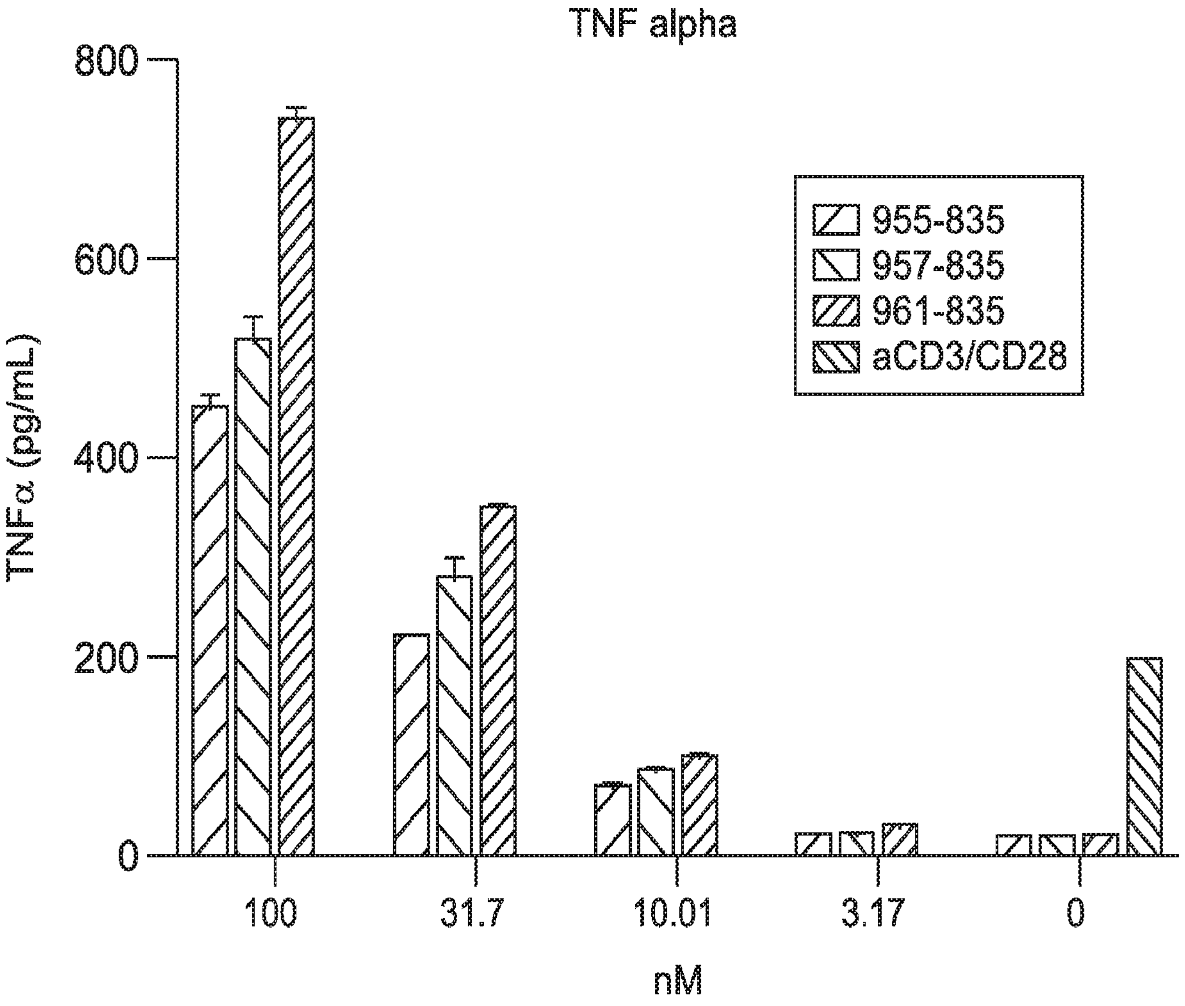

FIG. 14A-14D depict the effect of the number of costimulatory repeats on TNF-α production by $CD8^+$ T cells (FIG. 14A), on cell viability (FIG. 14B), on IFN-γ production (FIG. 14C), and on TNF-α production (FIG. 14D).

Figure 15:
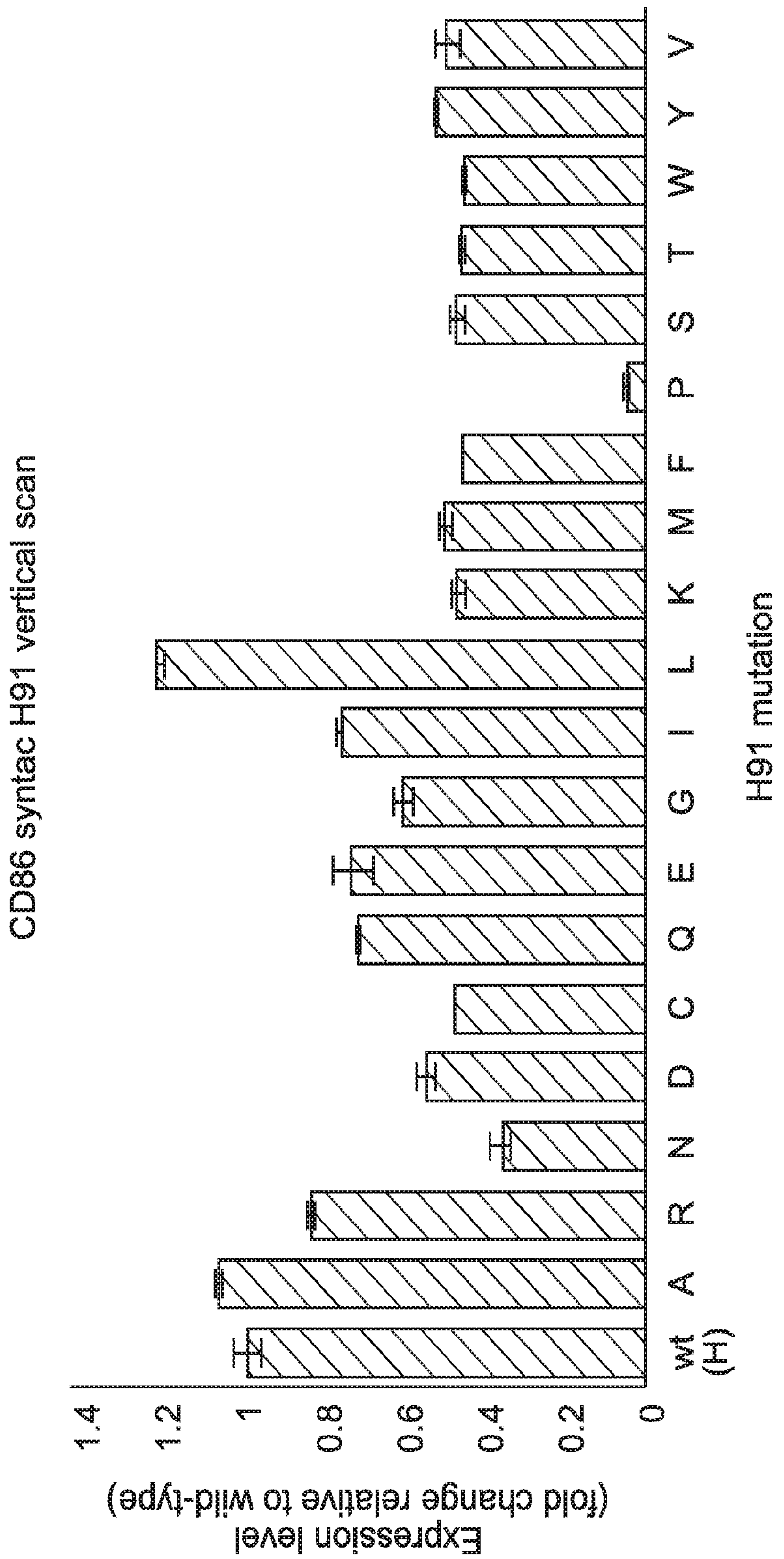
FIG. 15 depicts expression levels of CD86/synTacs comprising amino acid substitutions at H91.
Figure 16:
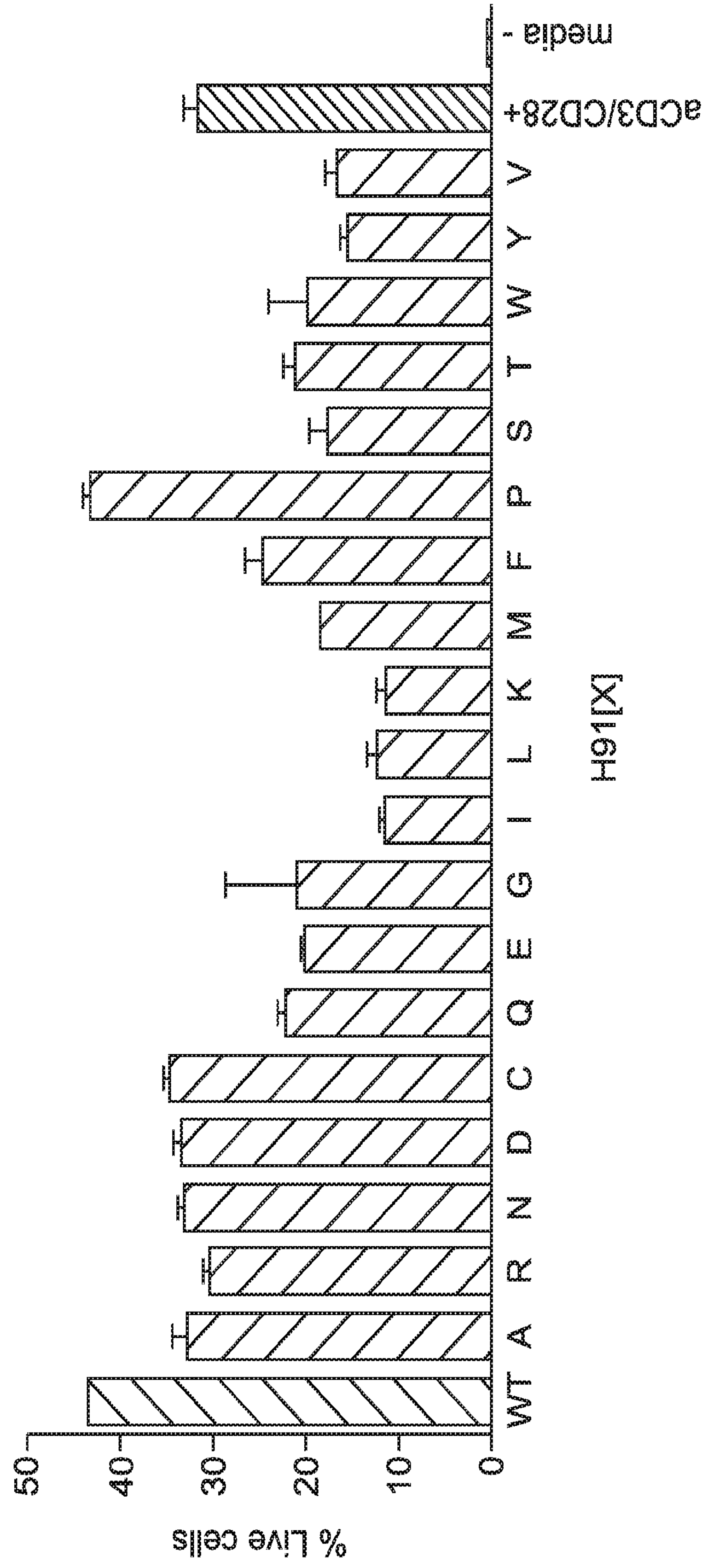
FIG. 16 depicts in vitro effect of CD86/synTacs comprising amino acid substitutions at H91 on the viability of antigen-specific $CD8^+$ T cells.

CD86/synTacs were generated, in which amino acid H91 was substituted with 19 different amino acids. Each of the variant CD86/synTacs was produced in a mammalian cell line. Expression levels, relative to a CD86/synTac with wild-type CD86, are shown in FIG. 15. The effect of each of the variant CD86/synTacs on the viability of antigen-specific CD86+ T cells was determined. Each variant CD86/synTac was incubated with target cells at 3.17 nM for two days. The results are shown in FIG. 16.

Example 2: In Vivo Activity of CD86/synTac

The in vivo efficacy of CD86/synTacs was assessed.

Figure 17B:
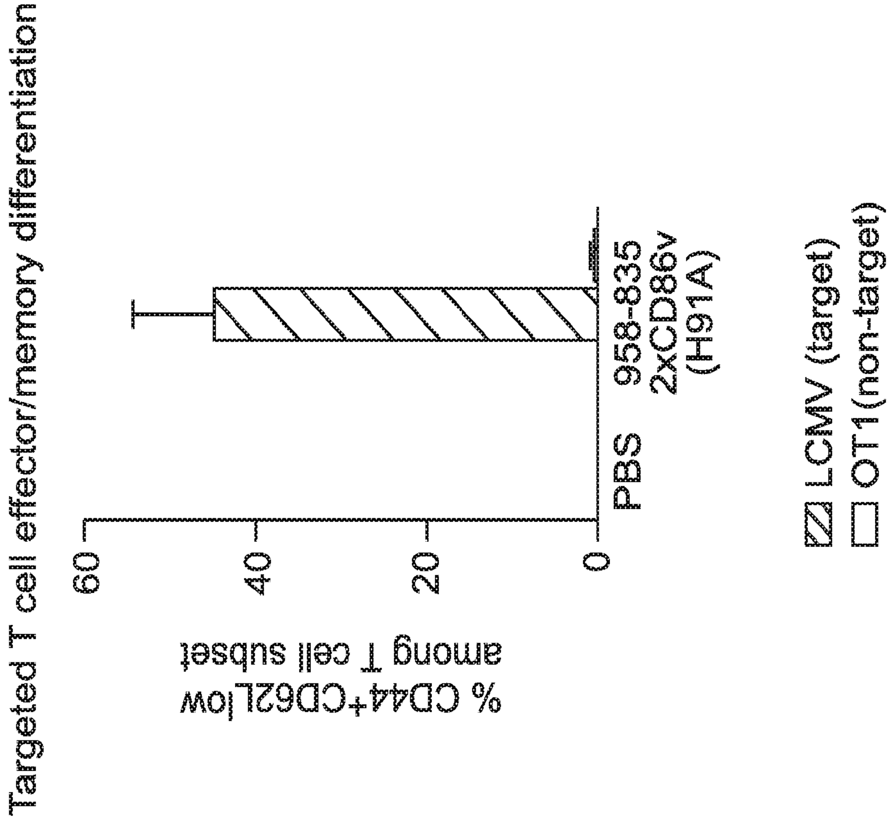
FIG. 17A-17B depict in vivo effects of a CD86/synTac of the present disclosure on targeted T cell proliferation (FIG. 17A) and targeted T cell effector/memory differentiation (FIG. 17B).
Figure 17A:
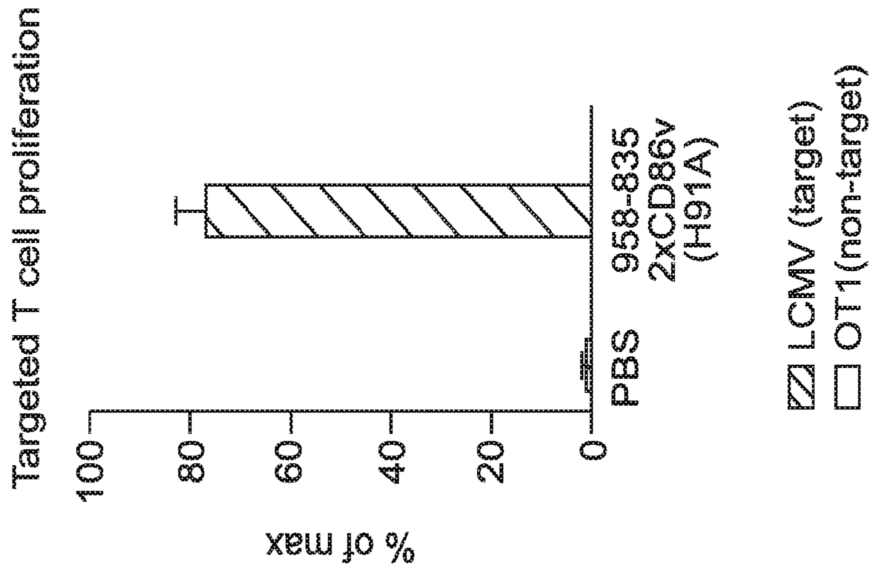

The effect of CD86/synTac on antigen-specific target cells (specific for lymphocytic choriomeningitis virus (LCMV)) or non-antigen-specific target cells (specific for ovalbumin (OT1)) was assessed. The CD86/synTac included two copies of CD86 IgV domain with an H91A substitution. As shown in FIG. 17A, the CD86/synTac induced proliferation of antigen-specific target cells. As shown in FIG. 17B, the CD86/synTac induced target T cell (T cells specific for LCMV) effector/memory differentiation.

FIG. 17A-17B depict in vivo effects of a CD86/synTac of the present disclosure on targeted T cell proliferation (FIG. 17A) and targeted T cell effector/memory differentiation (FIG. 17B).

Figure 18A:
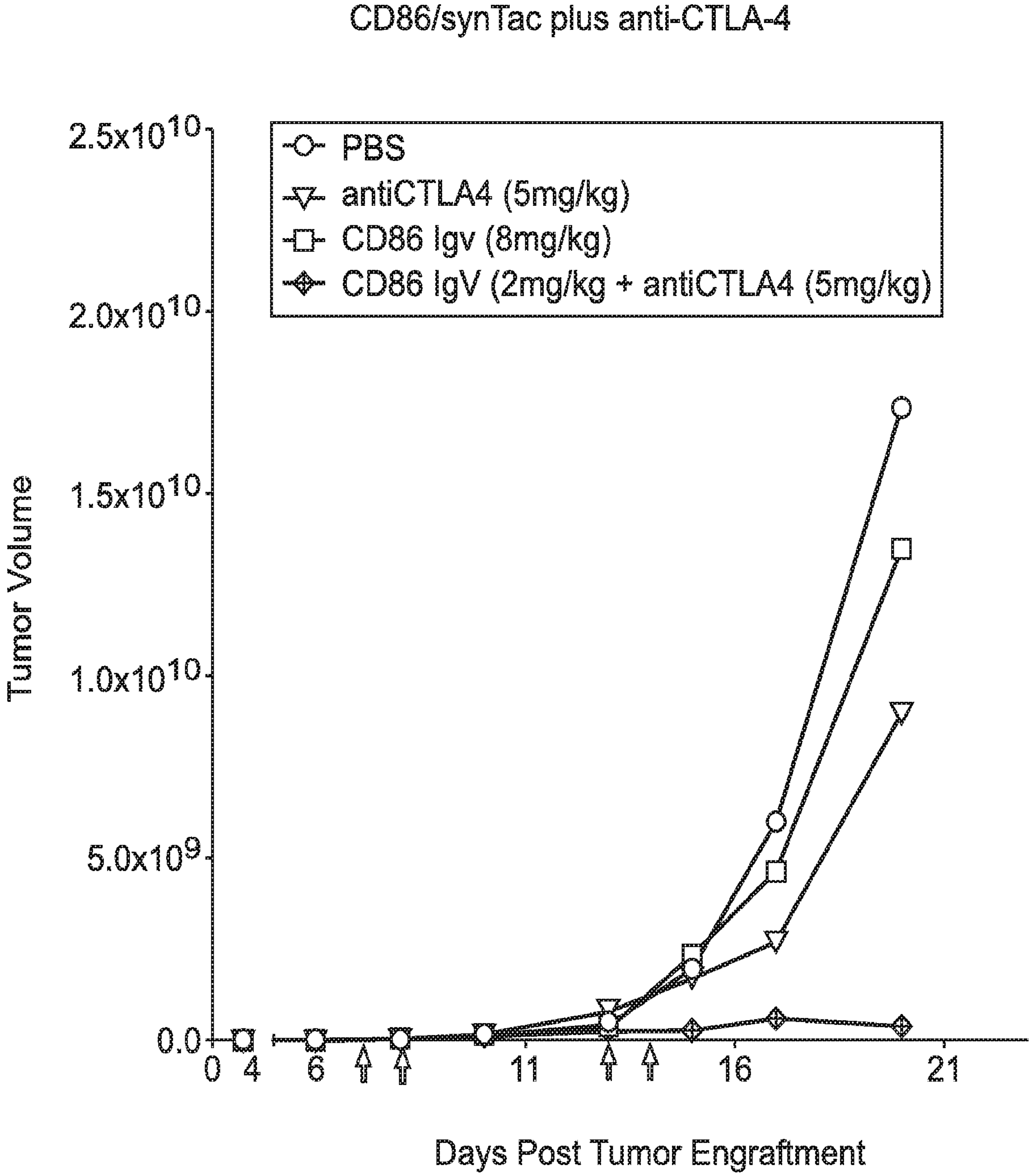
FIG. 18A-18B depict: in vivo effects of a CD86/synTac of the present disclosure, with or without co-administration of an anti-CTLA4 antibody, on tumor volume (FIG. 18A); and in vivo resistance of mice previously treated with CD86/cynTac plus anti-CTLA4 antibody to tumor re-challend (FIG. 18B).
Figure 18B:
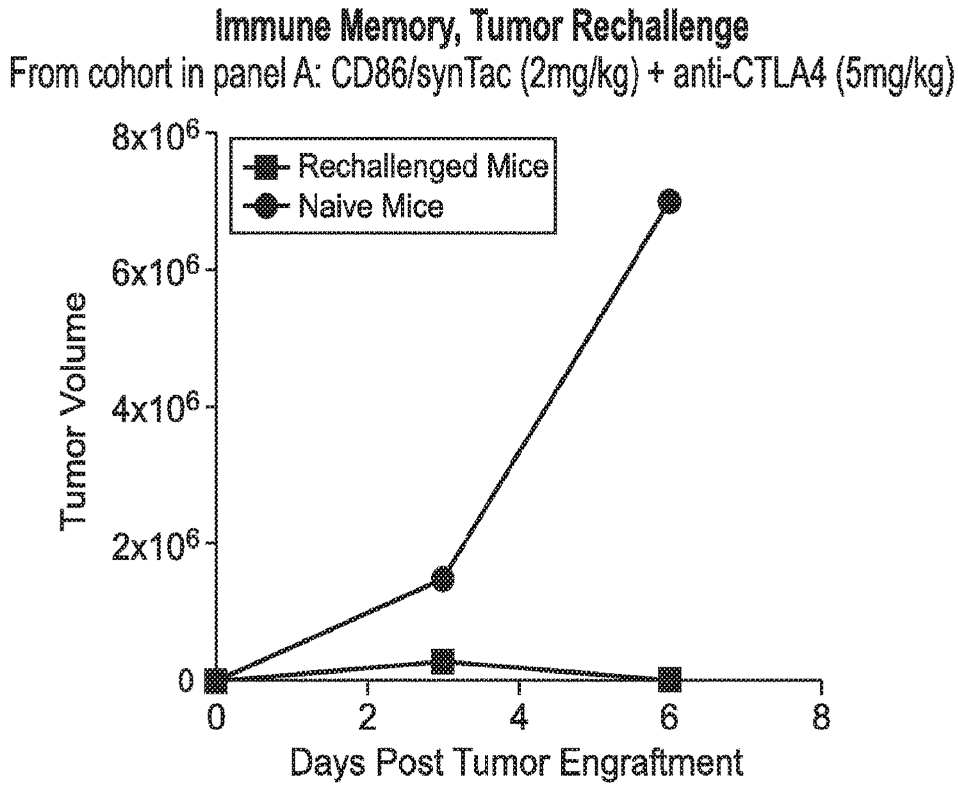

The effect of CD86/synTac (8 mg/kg), an anti-CTLA4 antibody (100 μg/mouse), or CD86/synTac (2 mg/kg)+anti-CTLA4 antibody (100 mg/kg), on human papilloma virus-positive (HPV+) lung carcinoma was assessed. As shown in FIG. 18A, CD86/synTac and anti-CTLA4 antibody synergistically reduced tumor volume. Naïve or previously-treated mice (mice treated with CD86/synTac (2 mg/kg)+anti-CTLA4 antibody (100 mg/kg)) were rechallenged with tumor. The results are shown in FIG. 18B. As shown in FIG. 18B, the tumor volume of the rechallenged mice was controlled by the CD86/synTac+anti-CTLA4 antibody treatment, indicating induction of immune memory; in contrast, naïve mice did not exhibit immune memory.

FIG. 18A-18B depict in vivo effects of a CD86/synTac of the present disclosure, with or without co-administration of an anti-CTLA4 antibody on tumor volume.

Example 3: Pharmacokinetic (PK) and Pharmacodynamic (PD) Studies on CD86/synTac

Figure 19:
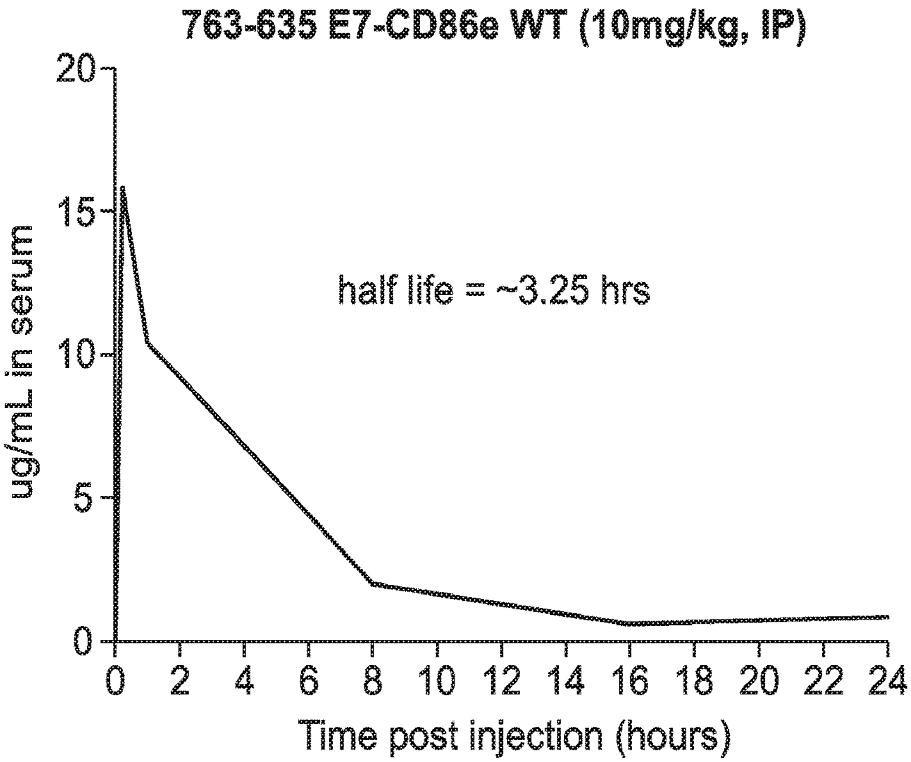
FIG. 19 depicts in vivo half life of a CD86/synTac of the present disclosure.

CD86/synTac was injected IP into a C57BL/6 mouse at 10 mg/kg, and serum was collected at various time points after injections. The CD86/synTac included wild-type CD86 ectodomain. The results, depicted in FIG. 19, show that the in vivo serum half-life of the CD86/synTac is about 3.25 hours.

Figure 20:
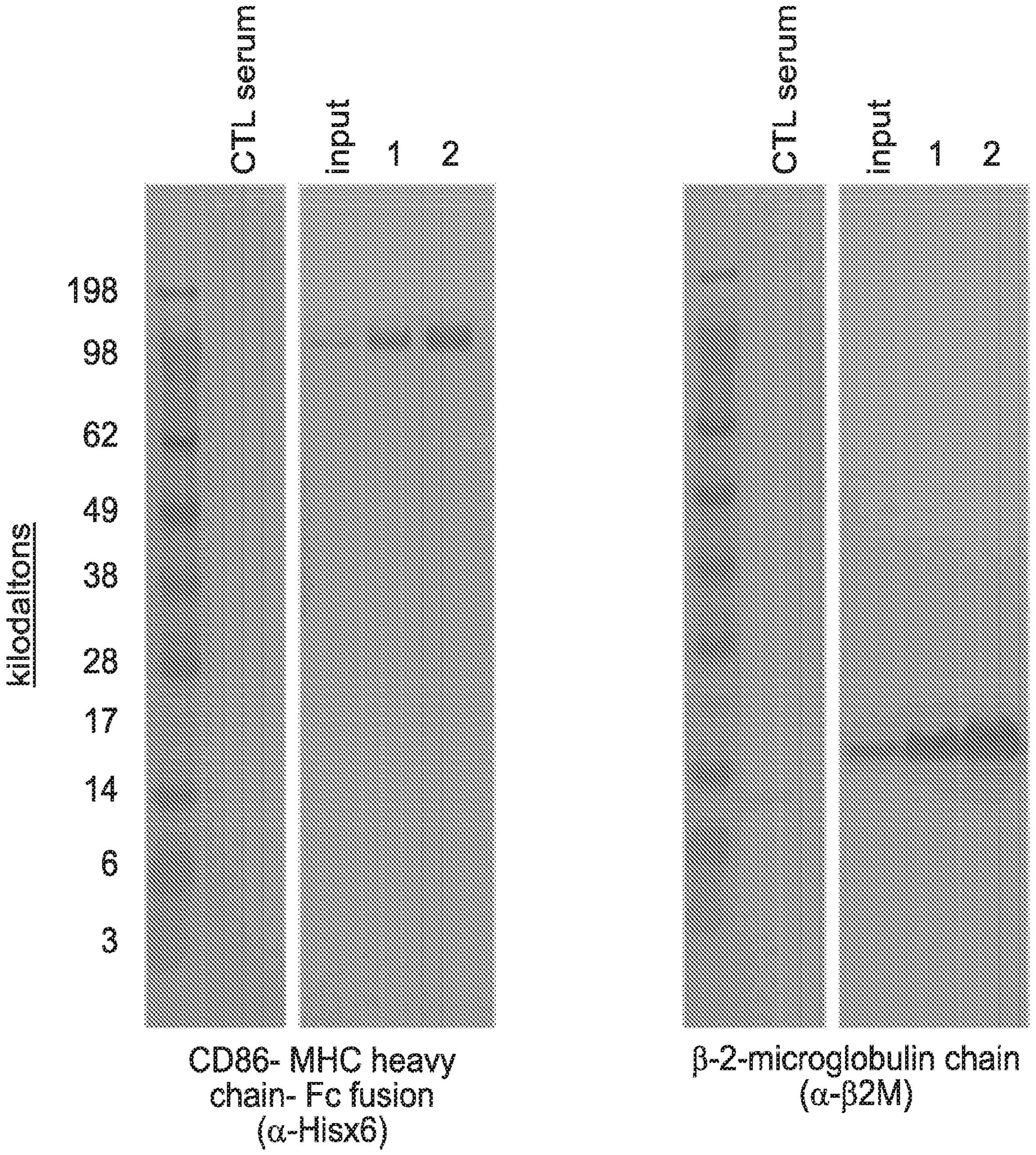
FIG. 20 depicts in vivo stability of a CD86/synTac of the present disclosure.

A CD86/synTac, which included a $(His)_6$ (SEQ ID NO:81) tag, was injected IP into a C57BL/6 mouse at 10 mg/kg, and serum was collected after two hours. 100 ng of the protein, or the equivalent of 40 L of serum, from two samples was subjected to sodium dodecyl sulfate-polyacrylamide gel electrophoresis, transferred to a membrane, and probed with an anti-$(His)_6$ antibody or an anti-β-2M antibody. The results, depicted in FIG. 20, show that CD86/synTac remains stable and intact for at least 2 hours in vivo.

Figure 21:
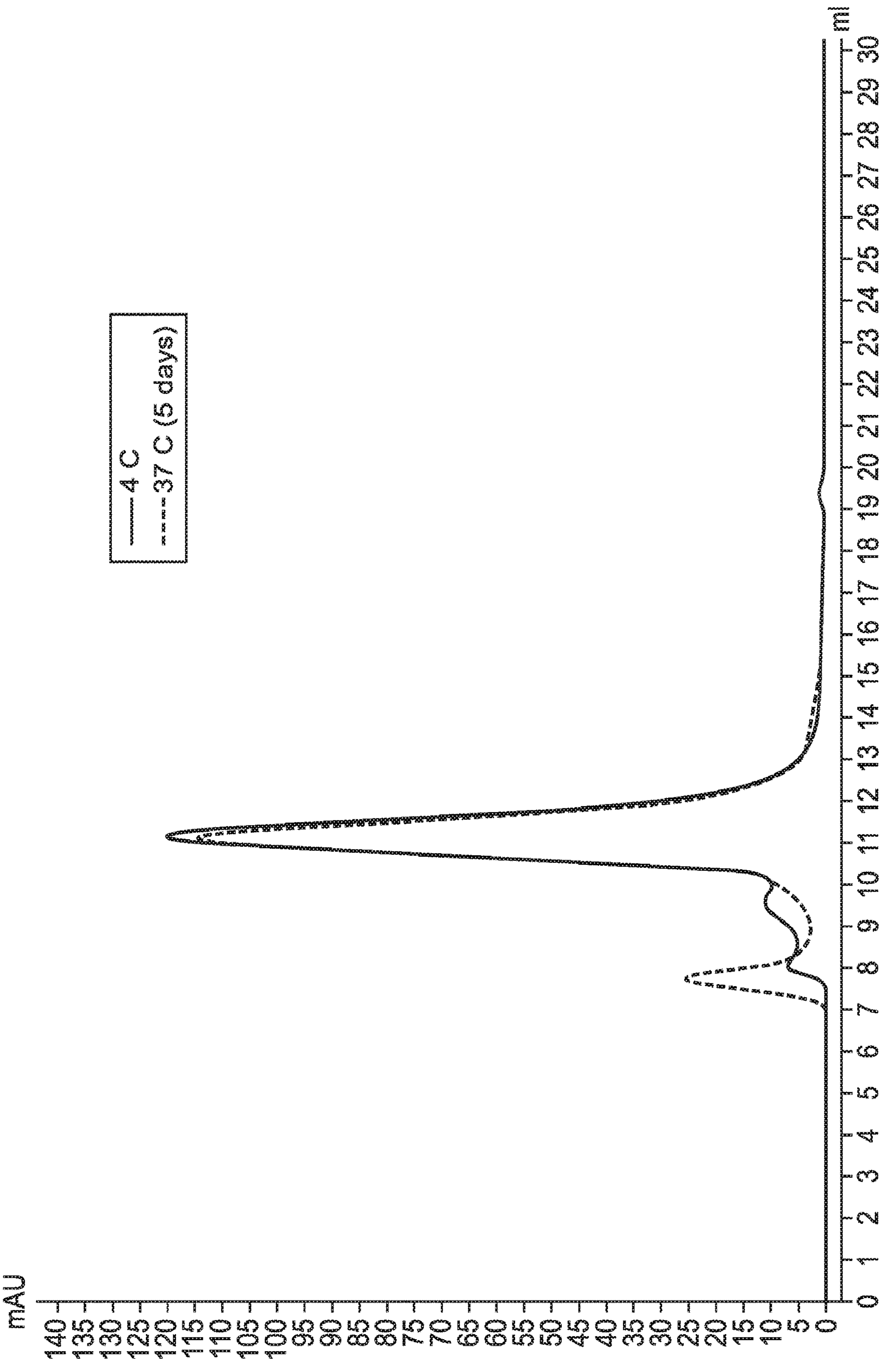
FIG. 21 depicts stability of a CD86/synTac of the present disclosure at 37° C. and at 4° C.

CD86/synTac was kept at 4° C. or 37° C. for 5 days. 0.5 mg of each sample (at 10 mg/ml) was analyzed by size exclusion chromatography. As shown in FIG. 21, CD86/synTac is stable and intact for at least 5 days at 4° C. or 37° C.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A heterodimer comprising:
a) a first polypeptide comprising:
i) a peptide epitope;
ii) a first major histocompatibility complex (MHC) polypeptide, wherein the first MHC polypeptide is a beta-2 microglobulin (β2M) polypeptide; and
b) a second polypeptide comprising:
i) a second MHC polypeptide, wherein the second MHC polypeptide is an MHC class I heavy chain polypeptide; and
wherein the first and/or the second polypeptide comprises one or more immunomodulatory polypeptides,
optionally, wherein the heterodimer comprises an immunoglobulin (Ig) Fc polypeptide or a non-Ig scaffold,
wherein at least one of the one or more immunomodulatory polypeptides is a variant CD86 polypeptide comprising an amino acid sequence having at least 98% amino acid sequence identity to the amino acid sequence set forth in SEQ ID NO:2
wherein the variant CD86 polypeptide comprises
a substitution of H91 with Ala, Arg, Asn, Asp, Cys, Gln, Glu, Gly, Ile, Leu, Lys, Met, Phe, Pro, Ser, Thr, Trp, Tyr, or Val, based on the numbering of the amino acid sequence set forth in SEQ ID NO:2;
and
wherein the variant CD86 polypeptide binds to a CD28 polypeptide having the amino acid sequence depicted in SEQ ID NO:30, and wherein the variant CD86 polypeptide exhibits reduced binding affinity to the CD28 polypeptide, compared to the binding affinity of the CD86 amino acid sequence set forth in SEQ ID NO:2 for the CD28 polypeptide,
wherein one or more independently selected linkers may be interposed between the components of the first polypeptide and one or more independently selected linkers may be interposed between the components of the second polypeptide, and
wherein, when the heterodimer comprises two or more immunomodulatory polypeptides, a peptide linker may be interposed between the immunomodulatory polypeptides.

2. The heterodimer of claim 1, wherein the variant CD86 polypeptide binds to the CD28 polypeptide comprising the amino acid sequence set forth in SEQ ID NO:30 with an affinity that is at least 25% less than the binding affinity of a control CD86 polypeptide comprising the amino acid sequence set forth in SEQ ID NO:2 for the CD28 polypeptide.

3. The heterodimer of claim 1, wherein the variant CD86 polypeptide binds to the CD28 polypeptide comprising the amino acid sequence set forth in SEQ ID NO:30 with an affinity that is at least 50% less than the binding affinity of a control CD86 polypeptide comprising the amino acid sequence set forth in SEQ ID NO:2 for the CD28 polypeptide.

4. The heterodimer of claim 1, wherein:
a1) the first polypeptide comprises, in order from N-terminus to C-terminus:
i) the peptide epitope;
ii) an optional peptide linker; and
ii) the β2M polypeptide; and
b1) the second polypeptide comprises, in order from N-terminus to C-terminus:
i) the one or more immunomodulatory polypeptides;
ii) an optional peptide linker;
iii) the MHC class I heavy chain polypeptide;
iv) an optional peptide linker; and
v) an Ig Fc polypeptide; or
a2) the first polypeptide comprises, in order from N-terminus to C-terminus:
i) the peptide epitope;
ii) an optional peptide linker; and
iii) the β2M polypeptide; and
2) the second polypeptide comprises, in order from N-terminus to C-terminus:
i) the MHC class I heavy chain polypeptide; and
ii) an optional peptide linker;
iii) an Ig Fc polypeptide;
iv) an optional peptide linker; and
v) the one or more immunomodulatory polypeptides,
wherein, when the heterodimer comprises two or more immunomodulatory polypeptides, a peptide linker may be interposed between the immunomodulatory polypeptides.

5. The heterodimer of claim 4, wherein the first polypeptide and the second polypeptide are non-covalently associated.

6. The heterodimer of claim 4, wherein the heterodimer comprises a disulfide bond that joins a Cys residue in the β2M polypeptide to a Cys residue in the MHC class I heavy chain polypeptide.

7. The heterodimer of claim 4, wherein: i) the first polypeptide comprises a linker between the epitope and the β2M polypeptide, wherein the linker comprises a first Cys residue, and ii) the second MHC polypeptide comprises an amino acid substitution to provide a second Cys residue, and wherein the heterodimer comprises a disulfide linkage between the first and the second Cys residues.

8. The heterodimer of claim 4, comprising 2 or more of the variant CD86 polypeptides, wherein the 2 or more variant CD86 polypeptides are in tandem.

9. The heterodimer of claim 4, wherein the variant CD86 comprises a substitution of H91 with Ala.

10. The heterodimer of claim 4, wherein the variant CD86 comprises a) a substitution of H91 and D66 based on the numbering of the amino acid sequence set forth in SEQ ID NO:2; or b) a substitution of H91 and N61 based on the numbering of the amino acid sequence set forth in SEQ ID NO:2; or c) a substitution of H91, N61, and D66 based on the numbering of the amino acid sequence set forth in SEQ ID NO:2.

11. A protein comprising two of the heterodimers of claim 4.

12. The protein of claim 11, wherein the two heterodimers are joined by one or more disulfide bonds between the respective Ig Fc polypeptides.

13. One or more nucleic acids comprising nucleotide sequences encoding the first and the second polypeptide according to claim 4.

14. One or more expression vectors comprising the one or more nucleic acids of claim 13.

15. A host cell genetically modified with the one or more expression vectors of claim 14.

16. A method of selectively modulating the activity of an epitope-specific T cell, the method comprising contacting the T cell with the heterodimer of claim 4, wherein said contacting selectively modulates the activity of the epitope-specific T cell.

17. A method of selectively modulating the activity of an epitope-specific T cell, the method comprising contacting the T cell with the protein of claim 12, wherein said contacting selectively modulates the activity of the epitope-specific T cell.

18. A method of selectively modulating the activity of a T cell that binds to an epitope in an individual, the method comprising administering to the individual the heterodimer of claim 4 to selectively modulate the activity of the T cell in the individual.

19. A method of selectively modulating the activity of a T cell that binds to an epitope in an individual, the method comprising administering to the individual the protein of claim 12 to selectively modulate the activity of the T cell in the individual.

20. A composition comprising:

a) the heterodimer of claim 4; and b) a pharmaceutically acceptable excipient.

21. A composition comprising:

a) the protein of claim 12; and b) a pharmaceutically acceptable excipient.

22. The heterodimer of claim 1, wherein the variant CD86 polypeptide comprises an amino acid sequence having at least 99% amino acid sequence identity to the amino acid sequence set forth in SEQ ID NO:2.

* * * * *